(12) United States Patent
Kaur Brar et al.

(10) Patent No.: US 11,999,977 B2
(45) Date of Patent: Jun. 4, 2024

(54) IN SITU ENZYMATIC DEGRADATION OF HYDROCARBON-POLLUTED SOILS

(71) Applicant: INSTITUT NATIONAL DE LA RECHERCHE SCIENTIFIQUE, Quebec (CA)

(72) Inventors: Satinder Kaur Brar, Quebec (CA); Tayssir Guedri, Quebec (CA); Tarek Rouissi, Quebec (CA)

(73) Assignee: INSTITUT NATIONAL DE LA RECHERCHE SCIENTIFIQUE (CA)

( * ) Notice: Subject to any disclaimer, the term of this patent is extended or adjusted under 35 U.S.C. 154(b) by 556 days.

(21) Appl. No.: 16/777,081

(22) Filed: Jan. 30, 2020

(65) Prior Publication Data
US 2020/0239343 A1   Jul. 30, 2020

(30) Foreign Application Priority Data

Jan. 30, 2019  (CA) .................................. CA 3031942

(51) Int. Cl.
| | |
|---|---|
| *C12N 9/02* | (2006.01) |
| *C12N 9/16* | (2006.01) |
| *C12N 9/20* | (2006.01) |
| *C12N 11/06* | (2006.01) |
| *C12N 11/18* | (2006.01) |

(52) U.S. Cl.
CPC ............ *C12N 9/0077* (2013.01); *C12N 9/16* (2013.01); *C12N 9/20* (2013.01); *C12N 11/06* (2013.01); *C12N 11/18* (2013.01)

(58) Field of Classification Search
CPC ........... C12N 9/0077; C12N 9/16; C12N 9/20
See application file for complete search history.

(56) References Cited

PUBLICATIONS

Miri. Production of a recombinant alkane hydroxylase (AlkB2) from Alcanivorax borkumensis. Biotechnol Lett. Apr. 2010;32(4):497-502. Epub Dec. 2, 2009.*
Kadri. Nanoencapsulation and release study of enzymes from Alkanivorax borkumensis in chitosan-tripolyphosphate formulation. Biochemical Engineering Journal. vol. 137, Sep. 15, 2018, pp. 1-10.*
Dang Vu, K., Tyagi, R.D., Brar, S.K., Valero, J.R., Surampalli, R.Y., 2009. *Starch industry wastewater for production of biopesticides—Ramifications of solids concentrations*. Environ. Technol. 30, 393-405.
Abbassi, B.E., Shquirat, W.D., 2008. Kinetics of indigenous isolated bacteria used for ex-situ bioremediation of petroleum contaminated soil. Water. Air. Soil Pollut. 192, 221-226.
Abraham, W.R., Meyer, H., Yakimov, M., 1998. *Novel glycine containing glucolipids from the alkane using bacterium Alcanivorax borkumensis*. Biochim. Biophys. Acta BBA—Lipids Lipid Metab. 1393, 57-62.
Ahmad, Z., Arshad, M., Asghar, H.N., Sheikh, M.A., Crowley, D.E., 2016. Isolation, screening and functional characterization of biosurfactant producing bacteria isolated from crude oil contaminated site. Int. J. Agric. Biol. 18.
Aichberger, H., Hasinger, M., Braun, R., Loibner, A.P., 2005. Potential of preliminary test methods to predict biodegradation performance of petroleum hydrocarbons in soil. Biodegradation 16, 115-125.
Ajun, W., Yan, S., Li, G., Huili, L., 2009. Preparation of aspirin and probucol in combination loaded chitosan nanoparticles and in vitro release study. Carbohydr. Polym. 75, 566-574.
Alcalde, M., Ferrer, M., Plou, F.J., Ballesteros, A., 2006. *Environmental biocatalysis: from remediation with enzymes to novel green processes*. Trends in Biotechnology 24, 281-287.
Andreoni, V., Cavalca, L., Rao, M.A., Nocerino, G., Bernasconi, S., Dell'Amico, E., Colombo, M., Gianfreda, L., 2004. *Bacterial communities and enzyme activities of PAHs polluted soils*. Chemosphere 57, 401-412.
Anwar, M.Z., Kim, D.J., Kumar, A., Patel, S.K., Otari, S., Mardina, P., Jeong, J.-H., Sohn, J.-H., Kim, J.H., Park, J.T., 2017. *SnO 2 hollow nanotubes: a novel and efficient support matrix for enzyme immobilization*. Sci. Rep. 7, 15333.
Aparna, A., Srinikethan, G., Hedge, S., 2011. Effect of addition of biosurfactant produced by *Pseudomonas* ssp. on biodegradation of crude oil. Int. Proc. Chem. Biol. Environ. Eng. 71-75.
Horowitz, A., Atlas, R.M., 1977. Response of microorganisms to an accidental gasoline spillage in an arctic freshwater ecosystem. Appl. Environ. Microbiol. 33, 1252-1258.
Choo, D.-W., Kurihara, T., Suzuki, T., Soda, K., Esaki, N., 1998. A cold-adapted lipase of an Alaskan psychrotroph, *Pseudomonas* sp. strain B11-1: gene cloning and enzyme purification and characterization. Appl. Environ. Microbiol. 64, 486-491.
Chenier, et al. Impact of Seasonal Variations and Nutrient Inputs on Nitrogen Cycling and Degradation of Hexadecane by Replicated River Biofilms, Applied And Environmental Microbiology, vol. 69, No. 9, Sep. 2003, p. 5170-5177.
Austin, R.N., Groves, J.T., 2011. *Alkane-oxidizing metalloenzymes in the carbon cycle*. Metallomics 3, 775-787.
Bahreini, E., Aghaiypour, K., Abbasalipourkabir, R., Mokarram, A.R., Goodarzi, M.T., Saidijam, M., 2014. *Preparation and nanoencapsulation of l-asparaginase II in chitosan-tripolyphosphate nanoparticles and in vitro release study*. Nanoscale Res. Lett. 9, 340.
Basuki, W., Syahputra, K., Suryani, A.T., Pradipta, I., 2015. *Biodegradation of Used Engine Oil by Acinetobacter junii TBC 1.2*. Indones. J. Biotechnol. 16.
Bisht, D., Yadav, S.K., Darmwal, N.S., 2013. An oxidant and organic solvent tolerant alkaline lipase by P. aeruginosa mutant: downstream processing and biochemical characterization. Braz. J. Microbiol. 44, 1305-1314.

(Continued)

Primary Examiner — Yong D Pak
(74) *Attorney, Agent, or Firm* — David Meibos; Maywood IP Law

(57) ABSTRACT

The present invention provides crude enzyme extracts, cocktails and compositions from *Alkanivorax borkumensis* and methods for the enzymatic treatment and bioremediation of petroleum hydrocarbon polluted ecosystems.

23 Claims, 31 Drawing Sheets

(56) References Cited

PUBLICATIONS

Boniolo, F.S., Rodrigues, R.C., Prata, A.M.R., López, M.L., Jacinto, T., da Silveira, M.M., Berbert-Molina, M.A., 2012. Oxygen supply in Bacillus thuringiensis fermentations: bringing new insights on their impact on sporulation and δ-endotoxin production. Appl. Microbiol. Biotechnol. 94, 625-636.

Bookstaver, M., Godfrin, M.P., Bose, A., Tripathi, A., 2015. *An insight into the growth of Alcanivorax borkumensis under different inoculation conditions*. J. Pet. Sci. Eng. 129, 153-158.

Borkar, P.S., Bodade, R.G., Rao, S.R., Khobragade, C.N., 2009. Purification and characterization of extracellular lipase from a new strain: Pseudomonas aeruginosa SRT 9. Braz. J. Microbiol. 40, 358-366.

Calvo, P., Remuñan-López, C., Vila-Jato, J.L., Alonso, M.J., 1997. Chitosan and chitosan/ethylene oxide-propylene oxide block copolymer nanoparticles as novel carriers for proteins and vaccines. Pharm. Res. 14, 1431-1436.

Carvalho et al., Adaptation of *Rhodococcus erythropolis* DCL14 to growth on *n-alkanes*, alcohols and terpenes, Appl Microbiol Biotechnol (2005) 67: 383-388.

Chebbi, A., Hentati, D., Zaghden, H., Baccar, N., Rezgui, F., Chalbi, M., Sayadi, S., Chamkha, M., 2017. Polycyclic aromatic hydrocarbon degradation and biosurfactant production by a newly isolated *Pseudomonas* sp. strain from used motor oil-contaminated soil. Int. Biodeterior. Biodegrad. 122, 128-140.

Chiou, S.-H., Wu, W.-T., 2004. Immobilization of Candida rugosa lipase on chitosan with activation of the hydroxyl groups. Biomaterials 25, 197-204.

Colombo, J.C., Cabello, M., Arambarri, A.M., 1996. Biodegradation of aliphatic and aromatic hydrocarbons by natural soil microflora and pure cultures of imperfect and lignolitic fungi. Environ. Pollut. 94, 355-362.

Costa et al., Modeling and comparison of dissolution profiles, European Journal of Pharmaceutical Sciences 13 (2001) 123-133.

Cyplik, P., Schmidt, M., Szulc, A., Marecik, R., Lisiecki, P., Heipieper, H.J., Owsianiak, M., Vainshtein, M., Chrzanowski, \Lukasz, 2011. *Relative quantitative PCR to assess bacterial community dynamics during biodegradation of diesel and biodiesel fuels under various aeration conditions*. Bioresour. Technol. 102, 4347-4352.

Dados, A., Omirou, M., Demetriou, K., Papastephanou, C., Ioannides, I.M., 2014. *Rapid remediation of soil heavily contaminated with hydrocarbons: a comparison of different approaches*. Ann. Microbiol. 65, 241-251.

Das, N., Chandran, P., 2010. Microbial degradation of petroleum hydrocarbon contaminants: an overview. Biotechnol. Res. Int. 2011.

Das, K., Mukherjee, A.K., 2007. Crude petroleum-oil biodegradation efficiency of Bacillus subtilis and Pseudomonas aeruginosa strains isolated from a petroleum-oil contaminated soil from North-East India. Bioresour. Technol. 98, 1339-1345.

Dastgheib, S.M.M., Amoozegar, M.A., Khajeh, K., Ventosa, A., 2011. *A halotolerant Alcanivorax sp. strain with potential application in saline soil remediation*. Appl. Microbiol. Biotechnol. 90, 305-312.

Davis, C., Cort, T., Dai, D., Illangasekare, T.H., Munakata-Marr, J., 2003. *Effects of heterogeneity and experimental scale on the biodegradation of diesel*. Biodegradation 14, 373-384.

Dou, J., Liu, X., Hu, Z., 2008. Substrate interactions during anaerobic biodegradation of BTEX by the mixed cultures under nitrate reducing conditions. J. Hazard. Mater. 158, 264-272.

Dutta, T.K., Harayama, S., 2001. Biodegradation ofn-alkylcycloalkanes and n-alkylbenzenes via new pathways in *Alcanivorax* sp. strain MBIC 4326. Appl. Environ. Microbiol. 67, 1970-1974.

Dzionek, A., Wojcieszyńska, D., Guzik, U., 2016. *Natural carriers in bioremediation: A review*. Electron. J. Biotechnol. 23, 28-36.

El-Bakry, M., Gea, T., Sánchez, A., 2016a. Inoculation effect of thermophilic microorganisms on protease production through solid-state fermentation under non-sterile conditions at lab and bench scale (SSF). Bioprocess Biosyst. Eng. 39, 585-592.

Faustorilla, M.V., Chen, Z., Dharmarajan, R., Naidu, R., 2017. Determination of Total Petroleum Hydrocarbons in Australian Groundwater through the Improvised Gas Chromatography—Flame Ionization Detection Technique. J. Chromatogr. Sci. 1-9.

Flores-Flores, T.C., Gutiérrez-Rojas, M., Revah, S., Favela-Torres, E., 2011. Comparative study for oxygenases produced by Aspergillus niger, ATCC 9642, in solid-state and submerged fermentation. Rev. Mex. Ing. Quím. 10, 189-207.

Freijer, J.I., De Jonge, H., Bouten, W., Verstraten, J.M., 1996. Assessing mineralization rates of petroleum hydrocarbons in soils in relation to environmental factors and experimental scale. Biodegradation 7, 487-500.

Gan, Q., Wang, T., 2007. Chitosan nanoparticle as protein delivery carrier-systematic examination of fabrication conditions for efficient loading and release. Colloids Surf. B Biointerfaces 59, 24-34.

Gan, Q., Wang, T., Cochrane, C., McCarron, P., 2005. Modulation of surface charge, particle size and morphological properties of chitosan-TPP nanoparticles intended for gene delivery. Colloids Surf. B Biointerfaces 44, 65-73.

Garcia-Ochoa, F., Gomez, E., 2009. Bioreactor scale-up and oxygen transfer rate in microbial processes: an overview. Biotechnol. Adv. 27, 153-176.

Gianfreda, L., Rao, M.A., 2004. Potential of extra cellular enzymes in remediation of polluted soils: a review. Enzyme Microb. Technol. 35, 339-354.

Gill, J., Orsat, V., Kermasha, S., 2017. Optimization of encapsulation of a microbial laccase enzymatic extract using selected matrices. Process Biochem.

Glieder, A., Farinas, E.T., Arnold, F.H., 2002. Laboratory evolution of a soluble, self-sufficient, highly active alkane hydroxylase. Nat. Biotechnol. 20, 1135-1139.

Gogoi, B.K., Dutta, N.N., Goswami, P., Mohan, T.K., 2003. A case study of bioremediation of petroleum-hydrocarbon contaminated soil at a crude oil spill site. Adv. Environ. Res. 7, 767-82.

Golyshin, P.N., Martins Dos Santos, V.A.P., Kaiser, O., Ferrer, M., Sabirova, Y.S., Lünsdorf, H., Chernikova, T.N., Golyshina, O.V., Yakimov, M.M., Pühler, A., Timmis, K.N., 2003. *Genome sequence completed of Alcanivorax borkumensis, a hydrocarbon-degrading bacterium that plays a global role in oil removal from marine systems*. J. Biotechnol. 106, 215-220.

Gupta, R., Beg, Q., Khan, S., Chauhan, B., 2002. An overview on fermentation, downstream processing and properties of microbial alkaline proteases. Appl. Microbiol. Biotechnol. 60, 381-395.

Guzik, U., Hupert-Kocurek, K., Wojcieszyńska, D., 2014. Immobilization as a strategy for improving enzyme properties-application to oxidoreductases. Molecules 19, 8995-9018.

Haines, J.R., Alexander, M., 1974. *Microbial degradation of high-molecular-weight alkanes*. Appl. Microbiol. 28, 1084.

Hamed, T.A., Bayraktar, E., Mehmetoğlu, T., Mehmetoğlu, Ü, 2003. *Substrate interactions during the biodegradation of benzene, toluene and phenol mixtures*. Process Biochem. 39, 27-35.

Haritash, A.K., Kaushik, C.P., 2009. Biodegradation aspects of Polycyclic Aromatic Hydrocarbons (PAHs): A review. J. Hazard. Mater. 169, 1-15.

Hassanshahian, M., Emtiazi, G., Caruso, G., Cappello, S., 2014. Bioremediation (bioaugmentation/biostimulation) trials of oil polluted seawater: a mesocosm simulation study. Mar. Environ. Res. 95, 28-38.

Ijah, U.J.J., 1998. Studies on relative capabilities of bacterial and yeast isolates from tropical soil in degrading crude oil. Waste Manag. 18, 293-299.

Ivshina, I.B., Kuyukina, M.S., Krivoruchko, A. V., Elkin, A.A., Makarov, S.O., Cunningham, C.J., Peshkur, T.A., Atlas, R.M., Philp, J.C., 2015. *Oil spill problems and sustainable response strategies through new technologies*. Environ. Sci. Process. Impacts 17, 1201-1219.

Jo, M.- S., Rene, E.R., Kim, S.-H., Park, H.-S., 2008. An analysis of synergistic and antagonistic behavior during BTEX removal in batch system using response surface methodology. J. Hazard. Mater. 152, 1276-1284.

Jonassen, H., Kjøniksen, A.L., Hiorth, M., 2012a. *Stability of chitosan nanoparticles cross-linked with tripolyphosphate*. Biomacromolecules 13, 3747-3756.

(56) References Cited

PUBLICATIONS

Breuil et al., Stimulation of Lipase Production During Bacterial Growth on Alkanes, Journal of Bacteriology, vol. 133, No. 2, Feb. 1978, 601-606.

Kanaly et al., Biodegradation of High-Molecular-Weight Polycyclic Aromatic Hydrocarbons by Bacteria, J. of Bacteriology, Apr. 2000, vol. 182, No. 8, Apr. 2000, p. 2059-2067.

Hsu, Y.- L., Wu, W.- T., 2002. *A novel approach for scaling-up a fermentation system.* Biochem. Eng. J. 11, 123-130.

Chandrashekhar, H., Rao, J.V., 2010. An Overview of fermenter and the design considerations to enhance its productivity. Pharmacologyonline 1, 261-301.

Mathur, A.K., Majumder, C.B., 2010. Kinetics modelling of the biodegradation of benzene, toluene and phenol as single substrate and mixed substrate by using Pseudomonas putida. Chem. Biochem. Eng. Q. 24, 101-109.

Kadri, T., Magdouli, S., Rouissi, T., Brar, S.K., Daghrir, R., Lauzon, J.-M., 2018. Bench-scale production of enzymes from the hydrocarbonoclastic bacteria Alcanivorax borkumensis and biodegradation tests. J. Biotechnol.

Sadighi, A., Faramarzi, M.A., 2013. Congo red decolorization by immobilized laccase through chitosan nanoparticles on the glass beads. J. Taiwan Inst. Chem. Eng. 44, 156-162.

Kadri, T., Rouissi, T., Magdouli, S., Brar, S.K., Hegde, K., Khiari, Z., Daghrir, R., Lauzon, J.-M., 2018. Production and characterization of novel hydrocarbon degrading enzymes from Alcanivorax borkumensis. Int. J. Biol. Macromol. 112, 230-240.

Ndao, A., Sellamuthu, B., Gnepe, J.R., Tyagi, R.D., Valero, J.R., 2017. Pilot-scale biopesticide production by *Bacillus thuringiensis* subsp. kurstaki using starch industry wastewater as raw material. J. Environ. Sci. Health Part B 52, 623-630.
Kanwar, L., Gogoi, B.K., Goswami, P., 2002. Production of a Pseudomonas lipase in n-alkane substrate and its isolation using an improved ammonium sulfate precipitation technique. Bioresour. Technol. 84, 207-211.
Priya, A., Mandal, A.K., Ball, A.S., Manefield, M., Lal, B., Sarma, P.M., 2015. Mass culture strategy for bacterial yeast co-culture for degradation of petroleum hydrocarbons in marine environment. Mar. Pollut. Bull. 100, 191-199.
Karamalidis, A.K., Evangelou, A.C., Karabika, E., Koukkou, A.I., Drainas, C., Voudrias, E.A., 2010. Laboratory scale bioremediation of petroleum-contaminated soil by indigenous microorganisms and added Pseudomonasaeruginosa strain Spet. Bioresour. Technol. 101, 6545-6552.
Sharma, A., Kumar, P., Rehman, M.B., 2014. Biodegradation of diesel hydrocarbon in soil by bioaugmentation of Pseudomonas aeruginosa: A laboratory scale study. Int. J. Environ. Bioremediation Biodegrad. 2, 202-212.
De Lourdes Moreno, M., Pérez, D., García, M.T., Mellado, E., 2013. Halophilic bacteria as a source of novel hydrolytic enzymes. Life 3, 38-51.
Rampino, A., Borgogna, M., Blasi, P., Bellich, B., Cesàro, A., 2013. Chitosan nanoparticles: preparation, size evolution and stability. Int. J. Pharm. 455, 219-228.
Margaritis, A., Zajic, J.E., 1978. Mixing, mass transfer, and scale-up of polysaccharide fermentations. Biotechnol. Bioeng. 20, 939-1001.
Nkem, B.M., Halimoon, N., Yusoff, F.M., Johari, W.L.W., Zakaria, M.P., Medipally, S.R., Kannan, N., 2016. Isolation, identification and diesel-oil biodegradation capacities of indigenous hydrocarbon-degrading strains of Cellulosimicrobium cellulans and Acinetobacter baumannii from tarball at Terengganu beach, Malaysia. Mar. Pollut. Bull. 107, 261-268.
Peng, C., Lee, J.-W., Sichani, H.T., Ng, J.C., 2015. Toxic effects of individual and combined effects of BTEX on Euglena gracilis. J. Hazard. Mater. 284, 10-18.
Naether, D.J., Slawtschew, S., Stasik, S., Engel, M., Olzog, M., Wick, L. Y., Timmis, K.N., Heipieper, H.J., 2013. Adaptation of the Hydrocarbonoclastic Bacterium Alcanivorax borkumensis SK2 to Alkanes and Toxic Organic Compounds: a Physiological and Transcriptomic Approach. Appl. Environ. Microbiol. 79, 4282-4293.
Salvachúa, D., Prieto, A., Martínez, A.T., Martínez, M.J., 2013. Characterization of a novel dye-decolorizing peroxidase (DyP)-type enzyme from Irpex lacteus and its application in enzymatic hydrolysis of wheat straw. Appl. Environ. Microbiol. 79, 4316-4324.
Lee, D.- W., Powers, K., Baney, R., 2004. Physicochemical properties and blood compatibility of acylated chitosan nanoparticles. Carbohydr. Polym. 58, 371-377.
Bamard, E., Bulle, C., Deschênes, L., 2011. Method development for aquatic ecotoxicological characterization factor calculation for hydrocarbon mixtures in life cycle assessment. Environ. Toxicol. Chem. 30, 2342-2352.
Koukaras, E.N., Papadimitriou, S.A., Bikiaris, D.N., Froudakis, G.E., 2012a. Insight on the formation of chitosan nanoparticles through ionotropic gelation with tripolyphosphate. Mol. Pharm. 9, 2856-2862.
Topakas, E., Vafiadi, C., Christakopoulos, P., 2007. Microbial production, characterization and applications of feruloyl esterases. Process Biochem. 42, 497-509.
Suja, F., Rahim, F., Taha, M.R., Hambali, N., Razali, M.R., Khalid, A., Hamzah, A., 2014. Effects of local microbial bioaugmentation and biostimulation on the bioremediation of total petroleum hydrocarbons (TPH) in crude oil contaminated soil based on laboratory and field observations. Int. Biodeterior. Biodegrad. 90, 115-122.
Rojo, F., 2009. Degradation of alkanes by bacteria. Environ. Microbiol. 11, 2477-2490.
Graham, D.W., Smith, V.H., Cleland, D.L., Law, K.P., 1999. Effects of nitrogen and phosphorus supply on hexadecane biodegradation in soil systems. Water. Air. Soil Pollut. 111, 1-18.
Zaak, H., Siar, E.-H., Kornecki, J.F., Fernandez-Lopez, L., Pedrero, S.G., Virgen-Ortíz, J.J., Fernandez-Lafuente, R., 2017. Effect of immobilization rate and enzyme crowding on enzyme stability under different conditions. The case of lipase from Thermomyces lanuginosus immobilized on octyl agarose beads. Process Biochem. 56, 117-123.
Liu, H., Yao, J., Yuan, Z., Shang, Y., Chen, H., Wang, F., Masakorala, K., Yu, C., Cai, M., Blake, R.E., Choi, M.M.F., 2014. Isolation and characterization of crude-oil-degrading bacteria from oil-water mixture in Dagang oilfield, China. Int. Biodeterior. Biodegrad. 87, 52-59.
Li, H., Liu, Y.H., Luo, N., Zhang, X. Y., Luan, T.G., Hu, J.M., Wang, Z.Y., Wu, P.C., Chen, M.J., Lu, J.Q., 2006. Biodegradation of benzene and its derivatives by a psychrotolerant and moderately haloalkaliphilic *Planococcus* sp. strain ZD22. Res. Microbiol. 157, 629-636.
Zhang, H., Oh, M., Allen, C., Kumacheva, E., 2004. Monodisperse chitosan nanoparticles for mucosal drug delivery. Biomacromolecules 5, 2461-2468.
Kennedy, J., O'leary, N.D., Kiran, G.S., Morrissey, J.P., O'Gara, F., Selvin, J., Dobson, A.D.W., 2011. Functional metagenomic strategies for the discovery of novel enzymes and biosurfactants with biotechnological applications from marine ecosystems. J. Appl. Microbiol. 111, 787-799.
Van Beilen, J.B., Funhoff, E.G., 2007. Alkane hydroxylases involved in microbial alkane degradation. Appl. Microbiol. Biotechnol. 74, 13-21.
Van Beilen, J.B., Marín, M.M., Smits, T.H.M., Röthlisberger, M., Franchini, A.G., Witholt, B., Rojo, F., 2004. Characterization of two alkane hydroxylase genes from the marine hydrocarbonoclastic bacterium Alcanivorax borkumensis. Environ. Microbiol. 6, 264-273.
Patel, J.G., Kumar, J.N., Kumar, R.N., Khan, S.R., 2016. Biodegradation capability and enzymatic variation of potentially hazardous polycyclic aromatic hydrocarbons-anthracene and pyrene by Anabaena fertilissima. Polycycl. Aromat. Compd. 36, 72-87.
Jonassen, H., Kjøniksen, A.L., Hiorth, M., 2012b. Effects of ionic strength on the size and compactness of chitosan nanoparticles. Colloid Polym. Sci. 290, 919-929.
Knaul, J.Z., Hudson, S.M., Creber, K.A., 1999. Improved mechanical properties of chitosan fibers. J. Appl. Polym. Sci. 72, 1721-1732.

(56) References Cited

PUBLICATIONS

Vasco-Correa, J., Zapata, A.D.Z., 2017. Enzymatic extraction of pectin from passion fruit peel (*Passiflora edulis f. flavicarpa*) at laboratory and bench scale. LWT-Food Sci. Technol. 80, 280-285.
Jaeger, K.-E., Ransac, S., Dijkstra, B.W., Colson, C., van Heuvel, M., Misset, O., 1994. Bacterial lipases. FEMS Microbiol. Rev. 15, 29-63.
Van Gestel, K., Mergaert, J., Swings, J., Coosemans, J., Ryckeboer, J., 2003. Bioremediation of diesel oil-contaminated soil by composting with biowaste. Environ. Pollut. 125, 361-368.
Kumar, A., Kim, I.-W., Patel, S.K., Lee, J.-K., 2018. Synthesis of Protein-Inorganic Nanohybrids with Improved Catalytic Properties Using Co 3 (PO 4) 2. Indian J. Microbiol. 58, 100-104.
Federation, W.E., Association, A.P.H., others, 2005. Standard methods for the examination of water and wastewater. Am. Public Health Assoc. APHA Wash. DC USA. (book).
Izrael-Zivkovic, L.T., Gojgic-Cvijovic, G.D., Gopcevic, K.R., Vrvic, M.M., Karadzic, I.M., 2009. Enzymatic characterization of 30 kDa lipase from Pseudomonas aeruginosa ATCC 27853. J. Basic Microbiol. 49, 452-462.
Liu, W., Luo, Y., Teng, Y., Li, Z., Ma, L.Q., 2010. Bioremediation of oily sludge-contaminated soil by stimulating indigenous microbes. Environ. Geochem. Health 32, 23-29.
Lubna Tahir, M.I.A., 2013. Production and Characterization of Esterase in Lantinus tigrinus for Degradation of Polystyrene. Pol. J. Microbiol. Pol. Tow. Mikrobiol. Pol. Soc. Microbiol. 62, 101-8.
Lu, L., Zeng, G., Fan, C., Ren, X., Wang, C., Zhao, Q., Zhang, J., Chen, M., Chen, A., Jiang, M., 2013. Characterization of a laccase-like multicopper oxidase from newly isolated *Streptomyces* sp. C1 in agricultural waste compost and enzymatic decolorization of azo dyes. Biochem. Eng. J. 72, 70-76.
Miastkowska, M., Sikora, E., Ogonowski, J., Zielina, M., \Ludzik, A., 2016. The kinetic study of isotretinoin release from nanoemulsion. Colloids Surf. Physicochem. Eng. Asp. 510, 63-68.
Margesin, R., Hämmerle, M., Tscherko, D., 2007. Microbial activity and community composition during bioremediation of diesel-oil-contaminated soil: effects of hydrocarbon concentration, fertilizers, and incubation time. Microb. Ecol. 53, 259-269.
Bradford, M.M., 1976. A rapid and sensitive method for the quantitation of microgram quantities of protein utilizing the principle of protein-dye binding. Anal. Biochem. 72, 248-254.
Yakimov, M.M., Golyshin, P.N., Lang, S., Moore, E.R., Abraham, W.-R., Lunsdorf, H., Timmis, K.N., 1998. *Alcanivorax borkumensis* gen. nov., sp. nov., a new, hydrocarbon-degrading and surfactant-producing marine bacterium. Int. J. Syst. Evol. Microbiol. 48, 339-348.
Martínez-Martínez, M., Lores, I., Peña-García, C., Bargiela, R., Reyes-Duarte, D., Guazzaroni, M.-E., Peláez, A.I., Sánchez, J., Ferrer, M., 2014. Biochemical studies on a versatile esterase that is most catalytically active with polyaromatic esters. Microb. Biotechnol. 7, 184-191.
Qiao, N., Shao, Z., 2010. Isolation and characterization of a novel biosurfactant produced by hydrocarbon-degrading bacterium Alcanivorax dieselolei B-5. J. Appl. Microbiol. 108, 1207-1216.
Prim, N., Sánchez, M., Ruiz, C., Pastor, F.J., Diaz, P., 2003. Use of methylumbeliferyl-derivative substrates for lipase activity characterization. J. Mol. Catal. B Enzym. 22, 339-346.
Li, P., Wang, L., Feng, L., 2013. Characterization of a novel Rieske-type alkane monooxygenase system in *Pusillimonas* sp. strain T7-7. J. Bacteriol. 195, 1892-1901.
Thenmozhi, R., Nagasathya, A., Thajuddin, N., 2011. Studies on biodegradation of used engine oil by consortium cultures. Adv. Environ. Biol. 1051-1058.
Boopathy, R., 2000. Factors limiting bioremediation technologies. Bioresour. Technol. 74, 63-67.
Margesin, R., Labbe, D., Schinner, F., Greer, C.W., Whyte, L.G., 2003. Characterization of hydrocarbon-degrading microbial populations in contaminated and pristine alpine soils. Appl. Environ. Microbiol. 69, 3085-3092.

Pulicharla, R., Marques, C., Das, R.K., Rouissi, T., Brar, S.K., 2016. Encapsulation and release studies of strawberry polyphenols in biodegradable chitosan nanoformulation. Int. J. Biol. Macromol. 88, 171-178.
Xu, R., Zhou, Q., Li, F., Zhang, B., 2013. Laccase immobilization on chitosan/poly (vinyl alcohol) composite nanofibrous membranes for 2, 4-dichlorophenol removal. Chem. Eng. J. 222, 321-329.
Korsmeyer, R.W., Gurny, R., Doelker, E., Buri, P., Peppas, N.A., 1983. Mechanisms of solute release from porous hydrophilic polymers. Int. J. Pharm. 15, 25-35.
Admon, S., Green, M., Avnimelech, Y., 2001. Biodegradation kinetics of hydrocarbons in soil during land treatment of oily sludge. Biorernediation J. 5, 193-209.
Laemmli, U.K., 1970. Cleavage of structural proteins during the assembly of the head of bacteriophage T4. Nature 227, 680-685.
Laxman Pachapur, V., Jyoti Sarma, S., Kaur Brar, S., Le Bihan, Y., Ricardo Soccol, C., Buelna, G., Verma, M., 2015. Co-culture strategies for increased biohydrogen production. Int. J. Energy Res. 39, 1479-1504.
López-León, T., Carvalho, E.L.S., Seijo, B., Ortega-Vinuesa, J.L., Bastos-González, D., 2005. Physicochemical characterization of chitosan nanoparticles: electrokinetic and stability behavior. J. Colloid Interface Sci. 283, 344-351.
Luo, Y., Zhang, B., Cheng, W.- H., Wang, Q., 2010. Preparation, characterization and evaluation of selenite-loaded chitosan/TPP nanoparticles with or without zein coating. Carbohydr. Polym. 82, 942-951.
Maletić, S., Dalmacija, B., Rončević, S. jan. 2013. Petroleum Hydrocarbon Biodegradability in Soil-Implications for Bioremediation. Ed. Vladimir Kutcherov 43.
Malik, Z., Ahmed, S., 2012. Degradation of petroleum hydrocarbons by oil field isolated bacterial consortium. Afr. J. Biotechnol. 11, 650-658.
Miles, A.A., Misra, S.S., Irwin, J.O., 1938. The estimation of the bactericidal power of the blood. Epidemiol. Infect. 38, 732-749.
Mishra, S., Sarma, P.M., Lal, B., 2004. Crude oil degradation efficiency of a recombinant Acinetobacter baumannii strain and its survival in crude oil-contaminated soil microcosm. FEMS Microbiol. Lett. 235, 323-331.
Mishra, S., Singh, S.N., 2012. Microbial degradation of n-hexadecane in mineral salt medium as mediated by degradative enzymes. Bioresour. Technol. 111, 148-154.
106. Namkoong, W., Hwang, E.- Y., Park, J.- S., Choi, J.-Y., 2002. Bioremediation of diesel-contaminated soil with composting. Environ. Pollut. 119, 23-31.
Obayori, O.S., Salam, L.B., Ogunwumi, O.S., 2014. Biodegradation of fresh and used engine oils by Pseudomonas aeruginosa LP5. J. Bioremediation Biodegredation 5, 1.
Parakulsuksatid, P., 2000. Utilization of a Microbubble Dispersion to Increase Oxygen Transfer in Pilot-Scale Bakerâ s Yeast Fermentation Unit (PhD Thesis). Virginia Tech.
Patel, S.K., Choi, S.H., Kang, Y.C., Lee, J.K., 2016. Large-scale aerosol-assisted synthesis of biofriendly Fe 2 O 3 yolk-shell particles: a promising support for enzyme immobilization. Nanoscale 8, 6728-6738.
Patel, S.K., Otari, S.V., Kang, Y.C., Lee, J.-K., 2017. Protein-inorganic hybrid system for efficient his-tagged enzymes immobilization and its application in L-xylulose production. RSC Adv. 7, 3488-3494.
Rončević, S., Dalmacija, B., Ivančev-Tumbas, I., Tričković, J., Petrović, O., Klašnja, M., Agbaba, J., 2005. Kinetics of degradation of hydrocarbons in the contaminated soil layer. Arch. Environ. Contam. Toxicol. 49, 27-36.
Ryu, H.-W., Joo, Y.-H., An, Y.-J., Cho, K.-S., 2006. Isolation and characterization of psychrotrophic and halotolerant *Rhodococcus* sp. YHLT-2. J. Microbiol. Biotechnol. 16, 605-612.
Schneiker, S., dos Santos, V.A.M., Bartels, D., Bekel, T., Brecht, M., Buhrmester, J., Chernikova, T.N., Denaro, R., Ferrer, M., Gertler, C., Goesmann, A., Golyshina, O.V., Kaminski, F., Khachane, A.N., Lang, S., Linke, B., McHardy, A.C., Meyer, F., Nechitaylo, T., Pühler, A., Regenhardt, D., Rupp, O., Sabirova, J.S., Selbitschka, W., Yakimov, M.M., Timmis, K.N., Vorhölter, F.- J., Weidner, S.,

(56) References Cited

PUBLICATIONS

Kaiser, O., Golyshin, P.N., 2006. Genome sequence of the ubiquitous hydrocarbon-degrading marine bacterium Alcanivorax borkumensis. Nat. Biotechnol. 24, 997-1004.

Schoefs, O., Perrier, M., Samson, R., 2004. Estimation of contaminant depletion in unsaturated soils using a reduced-order biodegradation model and carbon dioxide measurement. Appl. Microbiol. Biotechnol. 64, 53-61.

Schultz, N., Hobley, T.J., Syldatk, C., 2007. Spectrophotometric assay for online measurement of the activity of lipase immobilised on micro-magnetic particles. Biotechnol. Lett. 29, 365-371.

Setti, L., Lanzarini, G., Pifferi, P.G., Spagna, G., 1993. Further research into the aerobic degradation of n-alkanes in a heavy oil by a pure culture of a *Pseudomonas* sp. Chemosphere 26, 1151-1157.

Shu, X.Z., Zhu, K.J., 2002. Controlled drug release properties of ionically cross-linked chitosan beads: the influence of anion structure. Int. J. Pharm. 233, 217-225.

Shu, X.Z., Zhu, K.J., 2000. A novel approach to prepare tripolyphosphate/chitosan complex beads for controlled release drug delivery. Int. J. Pharm. 201, 51-58.

Ueno, A., Hasanuzzaman, M., Yumoto, I., Okuyama, H., 2006. Verification of degradation of n-alkanes in diesel oil by Pseudomonas aeruginosa strain WatG in soil microcosms. Curr. Microbiol. 52, 182-185.

Volke-Sepulveda, T.L., Gutiérrez-Rojas, M., Favela-Torres, E., 2003. Biodegradation of hexadecane in liquid and solid-state fermentations by Aspergillus niger. Bioresour. Technol. 87, 81-86.

Wu, Y., Yang, W., Wang, C., Hu, J., Fu, S., 2005. Chitosan nanoparticles as a novel delivery system for ammonium glycyrrhizinate. Int. J. Pharm. 295, 235-245.

Xu, Y., Du, Y., 2003. Effect of molecular structure of chitosan on protein delivery properties of chitosan nanoparticles. Int. J. Pharm. 250, 215-226.

Zeynalov, E., Nagiev, T., 2015. Enzymatic catalysis of hydrocarbons oxidation "in vitro" (review).

Zhang, S., Wu, G., Liu, Zhixiang, Shao, Z., Liu, Ziduo, 2014. Characterization of EstB, a novel cold-active and organic solvent-tolerant esterase from marine microorganism Alcanivorax dieselolei B-5 (T). Extremophiles 18, 251-259.

Higuchi, "Theoretical Analysis of Rate of Release of Solid Drugs Dispersed in Solid Matrices", Journal of Pharmaceutical Sciences (1963), vol. 52, No. 12, pp. 1145-1149.

Costa et al., Environmental strategies to remove volatile aromatic fractions (BTEX) from petroleum industry wastewater using biomass, Bioresource Technology 105 (2012) 31-39.

\* cited by examiner (g)

Table 26.
Analytical results obtained in soils

| # Sample | Depth (in ft) | Injection well setup | Initial characterization ||||||| Drill testing #1 |||
|---|---|---|---|---|---|---|---|---|---|---|---|
| | | | F18-01 | F18-02 | F18-03 | F18-04 | F18-05 | F18-07 | | F18-08 | F18-09 | Average reduction compared to previous characterization (all wells) |
| | 0 | | | | | | | | | | | |
| 1 | 2 | | | | | | | | | | | |
| 2 | 4 | | | | | | | | | | | |
| 3 | 6 | | | | | | | | | | | |
| | 8 | | | | | | | | | | | |
| | 10 | | | | | | | | | | | |
| | 12 | | 7,300 | 9,400 | 600 | 6,700 | 6,600 | 6,100 | | 5,000 | 8,300 | -5% |
| 4 | 14 | | 3,200 | 4,400 | 11,000 | 7,100 | 8,700 | 7,200 | | 9,900 | 4,200 | -6% |
| 5 | 16 | | 1,100 | 5,200 | 7,200 | 1,300 | 15,000 | 16,000 | | 6,800 | 5,350 | 36% |
| 6 | 18 | | 340 | 1,500 | 1,600 | <100 | 3,400 | 8,700 | | 180 | 110 | 97% |
| | 19–20 | | | | | | 310 | 320 | | <100 | <100 | >99% |

Notes:
bold — Positive = measured reduction
grey — Negative = measured increase

IN SITU ENZYMATIC DEGRADATION OF HYDROCARBON-POLLUTED SOILS

FIELD OF THE INVENTION

The present invention relates to compositions and methods for the remediation of polluted systems, particularly by enzymatic treatment.

BACKGROUND OF THE INVENTION

Petroleum hydrocarbons are an important energy resource used by industry and the population as a whole. At the same time, petroleum hydrocarbons are the main cause of soil and water contamination.

Several methods have been applied for the remediation of polluted systems. Enzymatic treatment is among the most promising methods with many advantages. Enzymes are catalysts with narrow specificity (chemo-, region and stereo-selectivity) or broad, therefore, they can be applied over a wide range of compounds as well as their mixtures. They can produce extensive transformations of the structural and toxicological properties of contaminants, and even their complete conversion into harmless final inorganic products. In addition, enzymes may have advantages over traditional technologies and also with respect to sanitation using microorganisms.

Against such a background, there is a need to develop natural enzymatic solutions for treating contaminants in polluted ecosystems.

Embodiments of this invention provide for compositions and methods for the remediation of petroleum hydrocarbons polluted systems, such as soil or water.

SUMMARY OF THE INVENTION

A main aspect intended to be addressed by the present invention is to provide a composition comprising one or more enzymes obtained from a culture of Alkanivorax borkumensis (A. borkumensis).

In some implementations, the composition is a crude cell culture supernatant.

In accordance with an alternative aspect, the composition comprises a mixture of at least two enzymes obtained from a culture of Alkanivorax borkumensis (A. borkumensis).

According to a more particular aspect, the enzymes comprises lipolytic enzymes and/or oxidative enzymes.

In some implementations, the enzymes are obtained from an extracellular culture medium.

In some implementations, the enzymes are selected from: hydrolase, lipase and mixtures thereof.

In some implementations, the enzymes comprise an intracellular enzyme obtained from a supernatant of sonicated cells of A. Borkumensis.

In some implementations, the intracellular enzyme is alkane hydroxylase.

In some implementations, the A. borkumensis comprises Alakanivorax borkumensis strain SK2 (DSM 11573).

In some implementations, the composition comprises three enzymes selected from: hydrolase, lipase and alkane hydroxylase.

In some implementations, the composition comprises enzymes having between about 30 and about 100 kDa molecular weight.

In some implementations, the composition comprises enzymes having between about 35 and about 70 kDa molecular weight.

In some implementations, the composition comprises enzymes having between about 40 kDa and about 52 kDa molecular weight.

In some implementations, the composition comprises three enzymatic activities selected from: lipase, esterase and alkane hydroxylase.

In some implementations, the composition retains more than 70% of its original activity after one month when stored at low temperature between $-20\pm1$ and $4\pm1°$ C.

In some implementations, the composition comprises a concentration of esterase from about 10 U/mL to about A 500 U/mL.

In some implementations, the composition comprises a concentration of esterase from about 35 U/mL to about 70 U/mL.

In some implementations, the composition comprises a concentration of lipase from about 10 to about 250 U/mL.

In some implementations, the composition comprises a concentration of lipase from about 40 U/mL to about 75 U/mL.

In some implementations, the composition comprises a concentration of alkane hydroxylase from about 1 U/mL to about 1000 U/mL.

In some implementations, the composition comprises a concentration of alkane hydroxylase from about 5 U/mL to about 15 U/mL.

In some implementations, the composition is in liquid form.

In some implementations, the composition is in dry form.

In some implementations, the composition is lyophilized.

In some implementations, the composition further comprises a biosurfactant produced from A. borkumensis and obtained from a culture supernatant thereof.

In accordance with another aspect, there is provided a formulation comprising one or more enzyme selected from the group consisting of: hydrolase, lipase and alkane hydroxylase from A. borkumensis, in admixture with chitosan.

In some implementations, the formulation further comprises a polyanion to form nanoparticles with chitosan.

In some implementations, the polyanion is tripolyphosphate (TPP) to form chitosan-TPP nanoparticles (CSNP).

In some implementations, the one or more enzyme is entrapped into the chitosan-TPP nanoparticles (CSNP).

In some implementations, the formulation comprises an enzyme to CSNP ratio of between 1:1 to 7:1.

In some implementations, the enzyme-to-CSNP ratio is of about 5:1.

In some implementations, the CSNP have a particle size between 50 nm and 600 nm.

In some implementations, the alkane hydroxylase and lipase immobilized on the CSNP exhibit more than a two-fold increase in vitro half-life in comparison with free enzyme.

In some implementations, the alkane hydroxylase and lipase immobilized on the CSNP maintain more than about 70% of initial activity after 5 days.

In some implementations, the alkane hydroxylase is released from the CSNP between about 37% and about 80% after about one week.

In accordance with another aspect, there is provided a use of a composition as defined herein, for treating a petroleum-hydrocarbon polluted-system.

In accordance with another aspect, there is provided a use of a formulation as defined herein as described herein, for treating a petroleum-hydrocarbon polluted-system.

In some implementations, the petroleum-hydrocarbon polluted-system is water or soil.

In some implementations, the petroleum-hydrocarbon comprises $C_{10}$-$C_{50}$ hydrocarbons, BTX or PAH or polychlorinated organic compounds, or mixtures thereof.

In accordance with a further aspect, there is provided a method for treating a petroleum-hydrocarbon polluted-system, comprising the steps of: a) contacting the composition as defined herein, or a formulation as defined herein, with a petroleum-hydrocarbon polluted-medium to form an inoculated medium; and b) incubating the inoculated medium for at least about 24 hours at a temperature of at least about 8° C. to achieve biodegradation of at least a portion of the hydrocarbons.

In some implementations, the method is used for the bioremediation of petroleum hydrocarbon-contaminated soil or water.

In some implementations, the petroleum-hydrocarbon comprises $C_{10}$-$C_{50}$ hydrocarbons, BTX, PAH, polychlorinated organic compounds, or mixtures thereof.

In some implementations, the treating of the petroleum-hydrocarbon polluted-system comprises removing between about 30% and about 80% of total petroleum hydrocarbons (TPH).

In accordance with an alternative aspect, there is provided a method for producing a composition as defined herein. The method comprises the steps of: a) growing *A. borkumensis* cells in a medium comprising from 0.5% to 12% (v/v) of petroleum-derived hydrocarbons; b) recovering a crude culture medium; c) sonicating the medium; and d) centrifuging to recover a supernatant comprising said enzymes.

In accordance with another aspect, there is provided a method for producing a composition as defined herein. The method comprises the steps of: obtaining a crude culture medium comprising *A. borkumensis* cells grown on a medium comprising from about 0.5% (v/v) to about 12% (v/v) of petroleum-derived hydrocarbons; sonicating the crude culture medium to obtain a sonicated crude culture medium; and centrifuging the sonicated crude culture medium to recover a supernatant comprising the enzymes.

In some implementations, the method further comprises incubating the cells under conditions comprising about 2% to about 10% of salt to achieve production of a biosurfactant.

In some implementations, the salt is NaCl.

In some implementations, wherein the medium comprises petroleum-derived hydrocarbons at a concentration of 3% (v/v), the petroleum-derived hydrocarbon being selected from the group consisting of hexane, hexadecane, motor oil, and mixtures thereof.

In some implementations, the source of hydrocarbon is synthetic or non-synthetic.

DETAILED DESCRIPTION OF THE INVENTION

Description of the Figures

FIG. 33. Table 26 showing the results of verification drilling conducted near the injection well (at 1 m distance).

ABBREVIATIONS AND DEFINITIONS

Abbreviations

Figure 1:
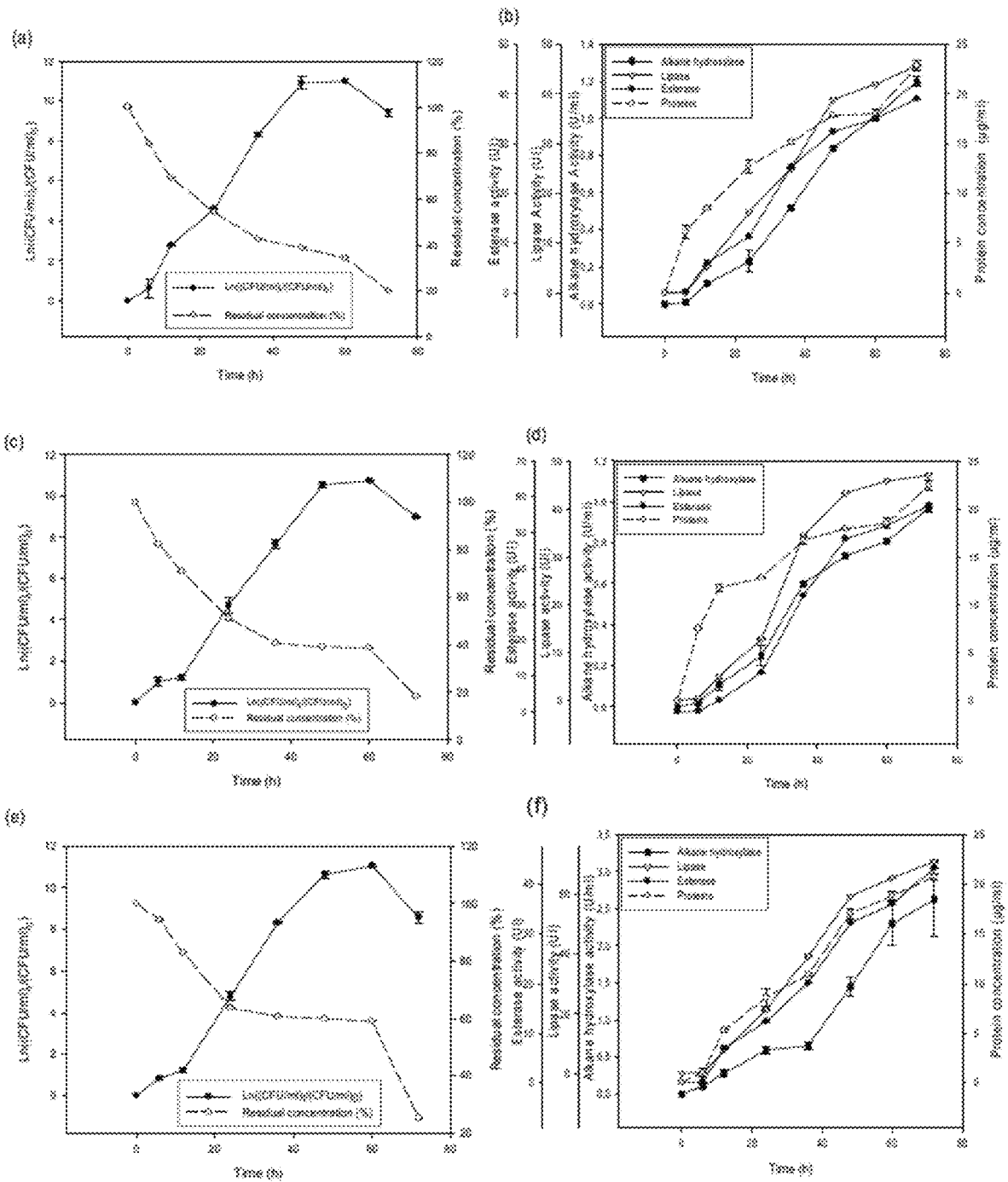
FIG. 1. Colony forming units of *Alkanivorax borkumensis* grown on different substrates and residual concentration profile of the different substrates: hexane (a); hexadecane (c); and motor oil (e). Kinetics of production of alkane hydroxylase, lipase and esterase and concentration of crude protein produced by *A. borkumensis* grown on different substrates: Hexane (b); Hexadecane (d) and; Motor oil (f).

BTEX Benzene Toluene Ethylene Xylene
CFU/mL Colony forming units per mL
CSNPs Chitosan nanoparticles
Da Dalton
DDW Double distilled water
DMSO Dimethyl sulphoxyde
DO Dissolved oxygen
ENZ-CS/TPP Enzyme-chitosan/tripolyphosphate
EE Encapsulation efficiency
FTIR Fourier Transform Infrared Spectroscopy
$K_L a$ Volumetric oxygen transfer coefficient
MW Molecular weight
NADPH Nicotinamide adenine dinucleotide phosphate
OTR Oxygen transfer rate
OUR Oxygen uptake rate
PAGE Polyacrylamide gel electrophoresis
PAH Polyaromatic hydrocarbons
PBS Phosphate buffer saline
PH Petroleum hydrocarbons
p-NP p-nitrophenol
p-NPP p-nitrophenyl palmitate
SD Standard deviation
SEM Scanning electron microscopy
TPP Sodium tripolyphosphate
UV Ultraviolet

Definitions

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

The terms "about" or "around" as used herein refers to a margin of + or −10% of the number indicated. For sake of precision, the term about when used in conjunction with, for example: 90% means 90%+/−9% i.e. from 81% to 99%. More precisely, the term about refers to + or −5% of the number indicated, where for example: 90% means 90%+/−4.5% i.e. from 86.5% to 94.5%. When used in the context of a pH, the term about means +/−0.5 pH unit.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps.

The term "crude" or "crude extract" is used herein to indicate that the enzymes are present in a physical milieu in their natural mixtures or ratio (depending on theirs substrates or growth conditions) and are not submitted to enrichment or extraction processes prior to use. For example, a "crude extract" or "crude enzymes" may be substantially or unpurified with respect to the complex cellular milieu in which it is produced or secreted. In some circumstances, bacteria byproducts or debris may form part of a crude composition (for example containing many other substances) or buffer system, which may for example contain other components.

The term "carrier" refers to a diluent, adjuvant, excipient, or vehicle with which the compounds of the present invention may be administered. Sterile water or aqueous saline solutions and aqueous dextrose and glycerol solutions may be employed as carrier, particularly for injectable solutions. Suitable pharmaceutical carriers are described in "Remington's Pharmaceutical Sciences" by E. W. Martin.

The term "effective amount" means an amount effective, at dosages and for periods of time necessary, to achieve the desired degradation treatment or depolluting result. An "effective amount" of an enzyme composition or crude extract, in reference to decreasing organic pollutants, means an amount capable of decreasing, to some extent, the concentration or content of targeted hydrocarbon. The term includes an amount capable of invoking a degradation of polluting hydrocarbon. Particularly, the term effective amount means a decrease by 10%, 20%, 30%, 40%, 50%, 60%, 70%, 80%, 90%, 95%, 98% and/or 99% of the original hydrocarbon content.

The terms "petroleum hydrocarbons" also referred to often as "total petroleum hydrocarbons" or TPH is a term used for any mixture of hydrocarbons that are found in crude oil. There are several hundred of these compounds, but not all occur in any one sample. Crude oil is used to make petroleum products which can contaminate the environment. Because there are so many different chemicals in crude oil and in other petroleum products, it is not practical to measure each one separately. However, it is useful to measure the total amount of TPH at a site. In our present context, chemicals that occur in TPH include without being limiting: $C_{10}$ to $C_{50}$ hydrocarbons, hexane, benzene, toluene, xylenes (also known as BTX), naphthalene, and fluorene, other constituents of gasoline, jet fuels, mineral oils, and of other petroleum products such as polyaromatic hydrocarbons (PAH) or polychlorinated organics such as polychlorinated aromatics (such as PCB).

DETAILED DESCRIPTION OF PARTICULAR ASPECTS OF THE INVENTION

This work is a complete study where the crude enzymes produced by the hydrocarbonoclastic bacteria *Alcanivorax borkumensis* and their application for the degradation of hydrocarbons have been investigated. Firstly, the capacity of the strain *Alcanivorax borkumensis* to grow on different petroleum substrates and the capacity of the enzyme to degrade different petroleum hydrocarbons was studied. Then the immobilization of the enzyme on different matrices for better performance was carried out. Later, the possibility of scaling up the production of enzymes for industrial usage was investigated. Finally, the application of the enzymes in the controlled conditions of soil columns, which represent the best imitation of the field was performed.

Composition

A main aspect intended to be addressed by the present invention is to provide a composition comprising one or more enzymes obtained from a culture of *Alkanivorax borkumensis* (*A. borkumensis*).

According to a particular embodiment, the composition is a crude cell culture supernatant. Particularly, the composition comprises a mixture of at least two enzymes obtained from a culture of *Alkanivorax borkumensis* (*A. borkumensis*). More particularly, the composition comprises a mixture of three enzyme activities obtained from a culture of *Alkanivorax borkumensis* (*A. borkumensis*).

According to a particular embodiment, the strain of *A. borkumensis* comprises *Alakanivorax borkumensis* strain SK2 (DSM 11573).

According to a particular embodiment, the enzymes comprises lipolytic enzymes and/or oxidative enzymes, particularly, the enzymes are obtained from extracellular culture medium; and more particularly the enzymes are selected from: hydrolase, lipase and mixtures thereof.

In accordance with an alternative embodiment, the mixture of enzymes comprise an intracellular enzyme obtained from a supernatant of sonicated cells of *A. Borkumensis*; and, in particular, the intracellular enzyme is alkane hydroxylase.

According to a particular embodiment, the mixture comprises three enzyme proteins and/or enzymatic activities selected from: hydrolase/esterase, lipase and alkane hydroxylase.

Particularly, the mixture comprises enzymes having between about 30 and about 100 kDa molecular weight; more particularly between about 35 and about 70 kDa molecular weight; or most particularly between about 40 kDa and about 52 kDa molecular weight.

In accordance with an alternative embodiment, the enzyme mixture retains more than 70% of its original activity after one month when stored at low temperature between −20±1 and 4±1° C.

In accordance with an alternative embodiment, the enzyme mixture comprises a concentration of esterase from about 10 U/mL to about b 500 U/mL; more particularly from about 35 U/mL to about 70 U/mL; most particularly from about 10 to about 250 U/mL.

In accordance with an alternative embodiment, the enzyme mixture comprises a concentration of lipase from about 40 U/mL to about 75 U/mL.

In accordance with an alternative embodiment, the enzyme mixture comprises a concentration of alkane hydroxylase from about 1 U/mL to about 1000 U/mL; more particularly from about 5 U/mL to about 15 U/mL.

In accordance with an alternative embodiment, the composition is in liquid form or in dry form, particularly dried by lyophilization.

Biosurfactant

As hydrocarbons are mostly insoluble in water, bacterial cultures producing biosurfactant plays a key role in the solubilization and/or emulsification of hydrocarbons. These mechanisms lead to desorption and, by increasing the availability of hydrocarbons in the aqueous phase, ultimately enhance the biodegradation rate. Moreover, biosurfactants are an alternative to chemical surfactant because of their properties as eco-friendly, least toxic, biodegradable and exhibiting high specificity.

*Alcanivorax borkumensis* produces an effective biosurfactant when cultivated on 3% (v/v) motor oil as a sole carbon source. The biosurfactant showed quite stable behaviour under harsh conditions of temperature, pH and salt with effective emulsification index. Furthermore, this biosurfactant offered stable emulsions with a wide range of hydrocarbons.

Biosurfactant produced on the same media with 3% motor oil was screened and results revealed that parafilm test was positive, surface tension can be reduced to 34.27 dynes/cm, that hexane, hexadecane, and diesel can be emulsified with an emulsification index of 59%, 85% and 83%, respectively and that the biosurfactant was quite stable at harsh conditions of temperature, pH and NaCl. Batch tests indicated that these biosurfactants significantly affected the desorption in soil and that alkane hydroxylase and lipase enzymes maintained their catalytic activity even after 20 days.

Thus, according to an alternative embodiment, the enzyme mixture further comprises a biosurfactant produced from *A. borkumensis* and obtained from a culture supernatant thereof.

Method of Production

In accordance with an alternative embodiment, there is provided a method for producing a composition as defined in any one of claims 1 to 24, comprising the steps of: a) growing *A. borkumensis* cells in a medium comprising from 0.5% to 12% (v/v) of petroleum-derived hydrocarbons; b) recovering a crude culture medium; c) sonicating said medium; and d) centrifuging to recover a supernatant comprising said enzymes.

According to a particular embodiment, the method further comprises the incubation of the cells under conditions comprising about 1 to about 10% of salt to achieve production of a biosurfactant. Particularly, the salt is NaCl.

Growth Substrates

The study of the growth of *Alcanivorax borkumensis* in shake flasks, on model petroleum substrates, hexane, hexadecane and motor oil showed high cell growth reaching 7×10⁸ CFU/mL with interesting alkane hydroxylase, lipase and esterase production with maximal values of 2.62 U/mL, 71 U/mL and 57.5 U/mL, respectively. The degradation results of hexane, hexadecane and motor oil during 72 h of the strain incubation showed 80%, 82% and 75%, respectively. The usage of the crude enzyme for the degradation of hexadecane, motor oil, BTEX and petroleum contaminated soils with different concentrations varying from 5000 to 7000 mg/L for hexadecane, from 30 to 70 mg/L for BTEX, from 500 to 1000 mg/L for motor oil and from 2000 to 6000 mg/L for TPH in soil, showed 73.75% degradation for 5000 mg/L of hexadecane, 82.80% degradation for 1000 mg/L of motor oil, 64.70% degradation for 70 mg/L of BTEX and 88.52% degradation for 6000 mg/kg of contaminated soil.

Thus, in accordance with an alternative embodiment, the culture medium is supplied with a source of hydrocarbon at a concentration of between 2 and 10% (v/v), the hydrocarbon being selected from: hexane, hexadecane, motor oil or a mixture thereof. Particularly, the source of hydrocarbon is synthetic or non-synthetic.

Formulation

The crude alkane hydroxylase and lipase enzymes from *Alcanivorax borkumensis* were targeted to be entrapped into chitosan nanoparticles by ionotropic gelation method to increase the stability and the half-life of the enzymes. For an optimal loading efficiency, enzyme-chitosan/tripolyphosphate ratio was investigated. The optimal ratio with the best entrapment efficiency that was maintained for both alkane hydroxylase and lipase was 5:1 with an efficiency of 58.37% and 67.14%, respectively. The half-life of the immobilized enzymes increased by two folds compared to the free one with 70% of activity maintained after 5 days.

In accordance with an alternative embodiment, there is provided a formulation comprising one or more enzyme selected from the group consisting of: hydrolase, lipase and alkane hydroxylase from *A. borkumensis*, in admixture with chitosan.

In accordance with a further embodiment, the formulation further comprises a polyanion, for forming nanoparticles. Particularly, the polyanion is tripolyphosphate (TPP).

In accordance with an alternative embodiment, the one or more enzyme is entrapped into said chitosan-TPP nanoparticles (CSNP) thus forming a nanoparticulate formulation. Particularly, the enzyme to CSNP ratio is between 1:1 to 7:1; more particularly about 5:1.

According to an alternative embodiment, the nanoparticles have a particle size between 50 nm and 600 nm.

In accordance with an alternative embodiment, once the alkane hydroxylase and lipase are immobilized on the CSNP, they exhibit more than a two-fold increase in vitro half-life in comparison with free enzyme. In particular, the alkane hydroxylase and lipase immobilized on the CSNP maintain more than about 70% of their initial activity after storage for 5 days.

According to a particular embodiment, the alkane hydroxylase is released from the CSNP by about 37% to about 80% after about one week in the field, under biodegradation conditions.

Use and Method for Treating Polluted Systems

In accordance with an alternative embodiment, there is provided a use of the composition, or formulation, each as defined herein, for the treatment or bioremediation of a petroleum-hydrocarbon polluted-system.

According to a particular embodiment, there is provided a method for treating a petroleum-hydrocarbon polluted-system, comprising the steps of: a) contacting the composition as defined herein, or a formulation as defined herein, with a petroleum-hydrocarbon polluted-medium to form an inoculated medium; and b) incubating said inoculated medium for at least about 24 hours at a temperature of at least about 8° C. to achieve biodegradation of at least a portion of said hydrocarbon.

In particular, the petroleum-hydrocarbon polluted-system may be water or soil.

In accordance with a particular embodiment, the petroleum-hydrocarbon may comprise $C_{10}$-$C_{50}$ hydrocarbons, BTX, PAH, polychlorinated organic compounds, or mixtures thereof.

In accordance with a particular embodiment, the estimated biodegradation in the soil can reach between 30 and 80% of TPH removal.

Scale-Up

Later on, the production of enzymes from *Alcanivorax borkumensis* was scaled-up in 5 L and 150 L bioreactors under controlled conditions using 5% (v/v) of motor oil as a substrate. Compared with the 5 L bioreactor, the 150 L fermenter showed better oxygen transfer rate which had an effect on the cell growth that doubled, and enzymes production that increased (more than 4 times for alkane hydroxylase). In fact, the cell count of *Alcanivorax borkumensis* increased from $3 \times 10^{10}$ CFU/mL to $8.6 \times 10^{10}$ CFU/mL. And both bioreactors showed significant and higher alkane hydroxylase and lipase activities of 55.6 U/mL and 208.30 U/mL, respectively in 5 L fermenter and 222.49 U/mL and 325 U/mL, respectively in 150 L fermenter. These studies results corroborate the feasibility of industrial-scale operation of enzymes production using motor oil as a substrate.

On Site Studies

Soil columns were carried out to study the biodegradation of $C_{10}$-$C_{50}$ in soil contaminated with a high concentration of diesel (19,500 mg/kg) using the crude enzyme of *Alcanivorax borkumensis* cultivated on 3% (v/v) of motor oil. The effects of the enzyme concentration, treatment time and oxidant on the bioremediation of $C_{10}$-$C_{50}$ were investigated. The enzyme concentration X formulated with 40 U/mL of lipase and 10 U/mL of alkane hydroxylase, showed the highest conversion of 57.36% after 12 weeks of treatment with the best degradation rate of 0.0218/day.

The following examples are put forth to provide those of ordinary skill in the art with a complete disclosure and description of how to make and use the present invention and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXAMPLES

Production, Characterization and Performance Study of the Enzymes Produced by the Strain *Alcanivorax Borkumensis* for the Elimination of Petroleum Hydrocarbons Example 1—Production, Characterization of Novel Hydrocarbon-Degrading Enzymes from *Alcanivorax borkumensis*

This study investigates the production of alkane hydroxylase, lipase and esterase by the marine hydrocarbon degrading bacteria *Alkanivorax borkumensis*. The focus of this study is the remediation of petroleum hydrocarbons, hexane, hexadecane and motor oil as a model substrate. *A. borkumensis* showed an interesting growth on these substrates with a high cell count. Growth on motor oil showed highest alkane hydroxylase and lipase production of 2.62 U/mL and 71 U/mL, respectively, while growth on hexadecane showed the highest esterase production of 57.5 U/mL. The percentage of hexane, hexadecane and motor oil degradation during *A. borkumensis* growth after 72 h, was around 80%, 81.5% and 75%, respectively. Zymogram showed two different bands with a molecular weight of approx. 52 and 40 kDa, respectively with lipase and esterase activity. Alkane hydroxylase reached optimum activity at pH 8.0 and 70±1° C. for hexane and hexadecane and 75±1° C. for motor oil. Lipase and esterase showed optimum activity at 35±1° C. and 40±1° C., respectively and pH 7.0. The crude enzymes showed higher stability in a wide range of pH, but they were not thermostable at higher temperatures.

Materials and Methods

All chemical reagents of the highest purity, such as pyruvic acid, hexane, hexadecane, Bradford reagent, NADPH (Nicotinamide adenine dinucleotide phosphate) and DMSO (Dimethyl sulfoxide) among others, were procured from Sigma-Aldrich, Fisher Scientific or VWR (Mississauga, Ontario, Canada). The strain, *A. borkumensis* was purchased from Deutsche Sammlung von Mikroorganismen und Zellkulturen GmbH, DSMZ (Braunschweig, Germany). The composition of motor oil used in this study is (in mg/l): 69.8 of $C_{10}$-$C_{50}$, 1.83 of naphthalene, 44 of benzene, 30 of toluene, 44 of ethyl-benzene and 84 of xylene.

Bacterial Strain

*Alcanivorax borkumensis* strain SK2 (DSM 11573) was used in this study. *A. borkumensis* was subcultured and streaked on agar plates, incubated for 72 h at 30±1° C. and then preserved at 4.0±1° C. for future use. Standard growth media consisted of (per liter of distilled water): 23 g NaCl, 0.75 g KCl, 1.47 g $CaCl_2 \cdot 2H_2O$, 5.08 g $MgCl_2 \cdot 6H_2O$, 6.16 g $MgSO_4 \cdot 7H_2O$, 0.89 g $Na_2HPO_4 \cdot 2H_2O$, 5.0 g $NaNO_3$, and 0.03 g $FeSO_4 \cdot 7H_2O$ (Yakimov et al., 1998). The media was supplied with either hexane, hexadecane or motor oil at a concentration of 3% (v/v) as the carbon and energy source and the growth was monitored at 30±1° C., 150 rpm for 72 h. Agar plates were prepared with the same media and agar was added in a concentration of 18 g $L^{-1}$. Experiments were conducted in replicates. Cell growth was monitored by measuring the Colony Forming Units per mL (CFU/mL).

Inoculum Preparation

For inoculum preparation, a loopful of *A. borkumensis* from the agar plates was employed to inoculate a 250 mL Erlenmeyer flask containing 50 mL of sterilized medium. The flask was incubated on an incubator-shaker at 150 rpm and 30±1° C. for 24 h and the actively growing cells from these flasks were used at a concentration of 3% (v/v) as inoculum for the production of *A. borkumensis* in shake flasks.

Polyacrylamide Gel Electrophoresis (PAGE) and Zymography

A native PAGE composed of 12% resolving and 4% stacking gel was performed according to the method described by Laemmli, (1970) to identify the enzymes with lipase/esterase activities by activity staining (zymogram). About 50 µL of the crude enzyme produced by *A. borkumensis* was loaded on the native PAGE gel without denaturing the sample. The electrophoresis was performed at a constant voltage of 85 V in Tris-glycine buffer (pH-8.3) at 25° C.

Activity staining for putative lipase/esterase was performed according to the method described by Prim et al., (2003). In brief, the native PAGE gel after electrophoresis was washed in distilled water and soaked in 2.5% Triton X-100 at room temperature followed by a wash in 50 mM Tris-HCl buffer (pH-8.0). The washed gel was immersed in 100 µM 4-methylumbelliferone butyrate (substrate) solution in the same buffer. A visible activity band was observed after 10 minutes by exposing the gel to UV light.

Zymogram for alkane hydroxylase was performed as described by Flores-Flores et al., (2011). The enzyme activity was tested using the crude extract and by submerging the gel in a reaction mixture composed by 10 mL of 50 mM Tris buffer pH 8.5 added with 0.4 µm $mL^{-1}$ of NADH, 6.25 mL of o-dianisidine reagent ((20 mg 3,3'-dimetoxibenzidine dissolved in 3 mL 0.025 M hydrochloride acid, added with agitation to 50 mL of 50 mM Tris buffer pH 8.5 and brought up to 100 mL with the same buffer)) and 1 mL of substrate (hexadecane) and incubating the gel at room temperature with gentle agitation until the activity bands appeared. The protein loaded was 63.5 µg per lane.

Protein and Enzymes Assays

Cells of each sampling were centrifuged at 4° C. for 10 min at 5000×g. The supernatant was used for total protein estimation and enzymatic assays. Total protein concentration was determined according to the standard Bradford method, Bradford (1976).

Alkane Hydroxylase Assay

For cell disruption, *A. borkumensis* cell pellet (1 g), was re-suspended in phosphate buffer (1 mL, 0.1 M, pH 8.0). The mixture was sonicated by using two frequencies of ultrasounds (22 kHz and 30 kHz) for 6 min at 4° C. and centrifuged at 13 000×g for 20 min. The supernatant was used as a crude intracellular enzyme extract.

Alkane hydroxylase activity was measured as described by Glieder et al., (2002). Briefly, the crude enzyme assay was carried out in sodium phosphate buffer (0.1 M, pH 8.0) with either hexane, hexadecane or motor oil as a substrate (0.5-1 mM) and dimethyl sulfoxide (DMSO; 1%, v/v). The reaction was initiated by addition of NADPH (200 µM), and the oxidation of NADPH was monitored at 340 nm.

The enzymatic assay was performed on the crude enzyme produced by *A. borkumensis* grown in three different substrates: hexane, hexadecane and motor oil. One unit is defined as the amount of enzyme required for consumption of 1 nmol of NADPH per min.

Lipase Assay

Extracellular lipase activity was performed by the titrimetric method according to Lopes et al., (2011) by using an olive oil emulsion composed of 25 mL of olive oil and 75 mL of 7% Arabic gum solution which was emulsified in liquefier for 2 minutes. About 5 mL of olive oil emulsion was then added to 0.1 M phosphate buffer (pH 7.0) and 1 mL of the enzymatic suspension (10 mg/mL) and incubated at 37° C. for 30 minutes under shaking. Subsequently, the emulsion was immediately disrupted by the addition of 15 mL of a mixture of acetone-ethanol (1:1 v/v). The released fatty acids were titrated with 0.05 M NaOH. One unit of lipase activity was defined as the amount of enzyme which liberated 1 µmol of fatty acids per minute.

Esterase Assay

Extracellular esterase activity was measured by the titrimetric method according to Lopes et al., (2011) by using olive oil as a substrate. The reaction mixture is composed of 5 mL of olive oil, 2 mL of 0.1 M phosphate buffer (pH 7.0) and 1 mL of the enzymatic extract (10 mg/mL). The mixture was incubated at 37° C. for 30 minutes under shaking and it was immediately disrupted by adding 15 mL of the acetone-ethanol mixture (1:1 v/v). The released fatty acids were titrated with 0.05 M NaOH. One unit of esterase activity was defined as the amount of enzyme which liberated 1 µmol of fatty acids per minute.

Effect of Temperature on Alkane Hydroxylase, Lipase, Esterase Activity and Stability To study the effect of temperature, the alkane hydroxylase assay was performed at different temperatures between 25±1° C. and 85±1° C., using hexane, hexadecane or motor oil as a substrate as described in section "Alkane hydroxylase assay".

For thermal stability, the enzyme was incubated at different temperatures from 50±1° C. to 75±1° C. for 5 h and the residual activity was measured every hour by alkane hydroxylase assay. The enzyme without incubation was used as a positive control.

Similarly, the optimum temperature for lipase and esterase enzymes was studied at different temperature ranges (25-60±1° C.) at constant pH (7.0). For the thermal stability studies, lipase and esterase were incubated at different temperatures from 25±1° C. to 50±1° C. for 5 h and the residual activity was measured.

Effect of pH on Alkane Hydroxylase, Lipase and Esterase Activity, and Stability

The activity of alkane hydroxylase at different pH between 3.0 and 10 was investigated at 70±1° C. for 10 min, using hexane, hexadecane or motor oil as a substrate. The effect of pH on enzyme stability was investigated by measuring the residual activity of the enzyme after incubation at various pH (3.0-10) for one hour at room temperature.

Also, the effect of pH on the esterase and lipase activities was studied at 37±1° C., pH values varied between 5 and 9. For enzyme stability measurements, the enzymes were incubated at various pH (5.0-9.0) for one hour at room temperature and the respective residual enzymes were measured.

The following buffer system was used to maintain various pH: 100 mM citrate-phosphate, pH 3.0; 100 mM glycine-HCl, pH 4.0 and 5.0; 100 mM sodium acetate, pH 6.0; 100 mM phosphate-buffer, pH 7.0; 100 mM Tris-HCl, pH 8.0, and 100 mM glycine-NaOH, pH 9.0 and 10.

Gas Chromatography-Flame Ionization Detector (GC-FID) Analysis

GC-FID was used to test the efficiency of degradation of the different substrates studied in this work: hexane, hexadecane and motor oil with the crude alkane hydroxylase produced by *A. borkumensis* during its growth.

One drop of lube oil taken at different intervals of *A. borkumensis* fermentation (6 h, 12 h, 24 h, 36 h, 48 h, 60 h, 72 h) grown on hexane, hexadecane and motor oil, was diluted with hexane to 2 mL and analyzed by a Hewlett-Packard 6890/5973 gas chromatograph coupled to flame ionization detector. The gas chromatograph was equipped with a 30 m length, 0.25 mm internal diameter, and 0.11 µm film thickness capillary column ($C_{10}$-$C_{50}$) (Make: Agilent). Helium was used as carrier gas. The temperature program consisted of a heating rate of 8° C./min from 80° C. to 340° C. with a hold time of 6 min.

Substrates Biodegradation Kinetics

The kinetics of different substrates was investigated using different models. Petroleum hydrocarbon half-life ($T_{1/2}$) was calculated according to Dados et al., (2014) using the following equation 1:

$$T_{1/2} = \ln 2/K \quad (1)$$

Where K represents the biodegradation rate constants using the single first-order kinetic (SFO) model given in equation 2:

$$C = C_0 e^{-kt} \quad (2)$$

The overall and specific substrate biodegradation rate constants for *A. borkumensis* were calculated using the modified Hockey-Stick model (FOCUS 2006). The following equations 3 and 4 related to this method were used:

$$C = C_0 \text{ for } t \leq t_b \quad (3)$$

$$C = C_0 e^{-K(t-t_b)} \text{ for } t > t_b \quad (4)$$

Hexane, hexadecane and motor oil half-life (T %) was calculated using equation 5:

$$T_{1/2} = t_b + \ln 2/K \quad (5)$$

In both mathematical models, C is the concentration of the different substrates at a given time (t), $C_0$ is the initial concentration of the different substrates in the sandy soil sample, K is the biodegradation rate constant of the different substrates and $t_b$ is the breakpoint at the time at which rate constant changes and biodegradation starts.

Results

Growth of *A. borkumensis* and Enzymes Production

The growth curves of *A. borkumensis* on three different culture substrates (hexane, hexadecane and motor oil) used as a sole source of carbon and energy, are shown in FIGS. 1 (*a*), (*c*) and (*e*). The best growth was obtained between 48 h and 60 h for the three different media with 6×10$^8$ CFU/mL for hexane-based media, 4.8×10$^8$ CFU/mL for hexadecane-based media and 7×10$^8$ CFU/mL for motor oil-based media. The analysis of the residual concentration of the tested substrates by GC-FID as a function of incubation time is shown in FIGS. 1 (*a*), (*c*) and (*e*) and allowed calculating degradation rates of 80% for hexane, 82% for hexadecane and 75% for motor oil after 72 h.

*A. borkumensis* also showed higher protein synthesis and enzymes production throughout the cultivation time on the three different liquid culture media that were optimized in this study. The fermentation time course for alkane hydroxylase, lipase and esterase production by *A. borkumensis* (FIGS. 1 (*b*), (*d*) and (*f*)) indicated that the maximum protein synthesis and the maximum alkane hydroxylase, lipase and esterase activity were obtained after 72 h of cultivation on the three different substrates, when cells were in the stationary phase, and its production was not growth associated. The concentration of crude protein produced by *A. borkumensis* grown on hexane, hexadecane and motor oil presented no large difference using the three substrates. After 72 h of fermentation, around 23 µg/mL was obtained for hexane, 22.5 µg/mL for hexadecane and 20.75 µg/mL for motor oil. Motor oil substrate was found to be the best medium for the production of *A. borkumensis* crude alkane hydroxylase with an activity of 2.62 U/mL obtained after 72 h of liquid fermentation.

The degradation of motor oil and other relative compounds is not only performed by alkane hydroxylase, but also by other enzymes that can interfere in the entire degradation. In this regard, the determination of the lipase and esterase activities was performed.

A high lipase activity was observed when using motor oil as a substrate with a value of 71 U/mL compared to hexadecane (47 U/mL) and hexane (45.8 U/mL), respectively. Also, important esterase activities were observed during the fermentation of *A. borkumensis* on the three different substrates with the highest activity found in motor oil (43.3 U/mL) and a lower activity was found on hexadecane (57.5 U/mL) and hexane (39 U/mL).

Enzymes Characterization

The present study corroborates with previous studies demonstrating that *A. borkumensis* is an efficient hydrocarbon-degrading microorganism. This efficiency depends on the properties of the involved key enzymes, such as alkane hydroxylase, lipase and esterases.

Native PAGE and Zymography

Figure 2:
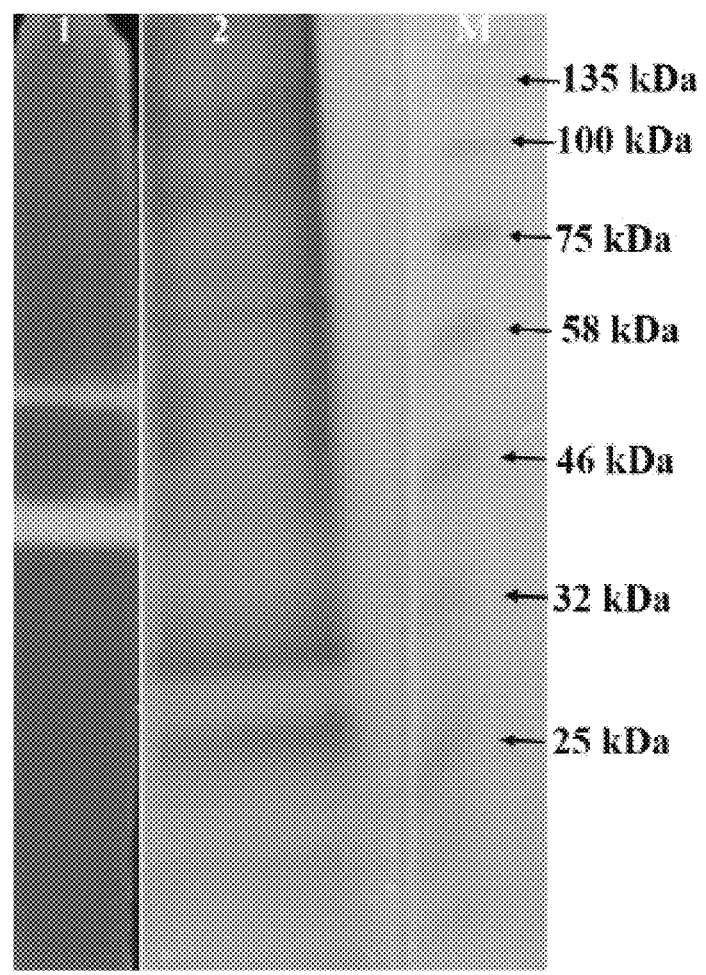
FIG. 2. Lane 1: Zymogram of the crude enzyme as observed in UV light; Lane 2: Coomassie staining of the crude enzyme on native PAGE; M: Molecular weight marker.

FIG. 2 shows the zymogram of the crude enzyme extract of *A. borkumensis*. The activity staining and Coomassie staining of the sample run on the different lanes of the native PAGE showed two distinct bands corresponding to the size of approx. 52 and 40 kDa, respectively with lipase/esterase activity. For alkane hydroxylase zymogram, seven trials were carried out, but the method used showed a lower resolution and no bands were obtained. This method is usually applied for oxygenase enzyme and no conventional method was found in the literature corresponding to the migration of alkane hydroxylase enzyme since the study of this enzyme is new which may suggest the modification and the adaptation of the protocol to alkane hydroxylase properties.

Effect of Temperature on the Activity and Stability of Alkane Hydroxylase

Figure 3:
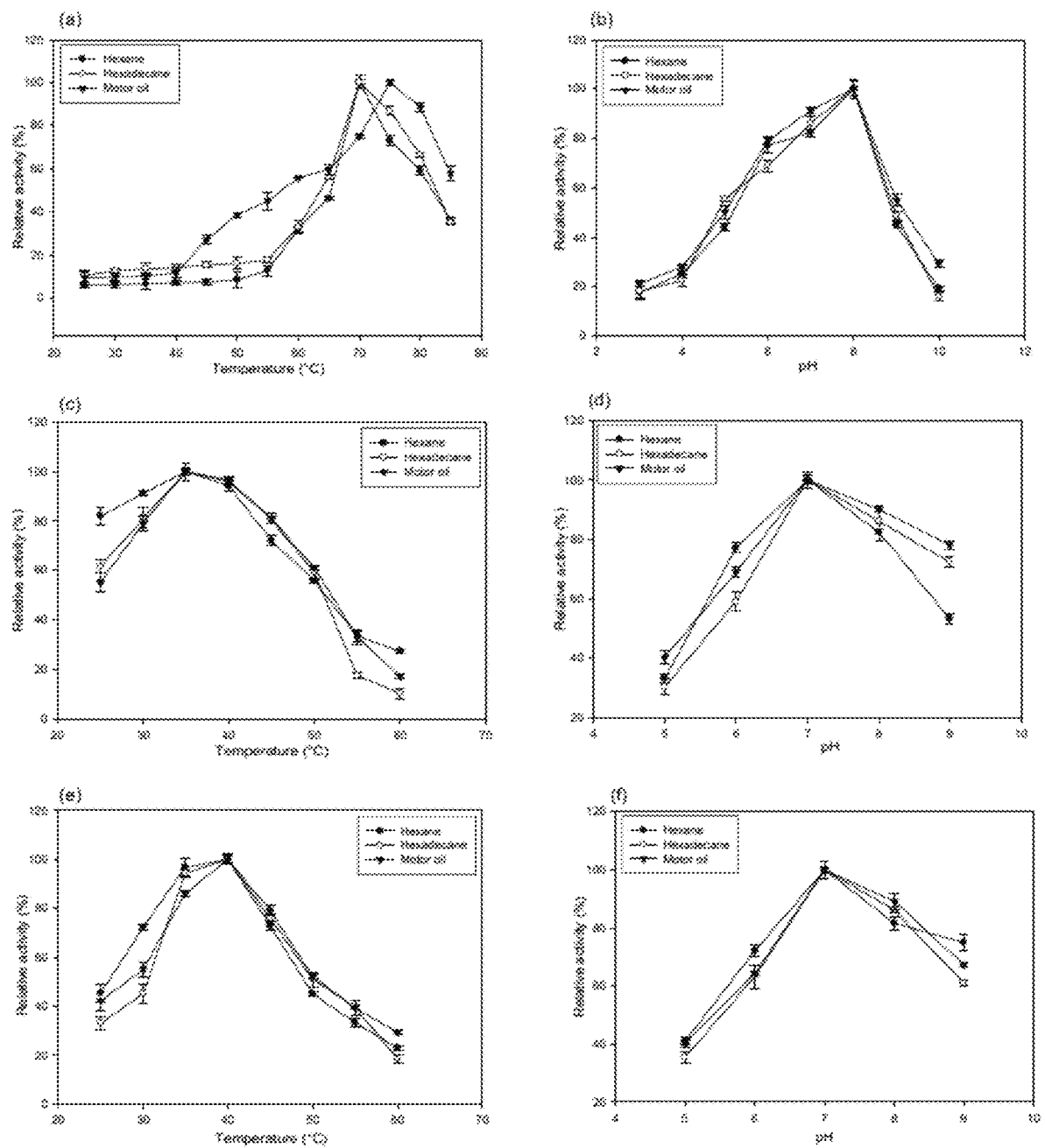
FIG. 3. Effect of temperature (a, c, e) and pH (b, d, f) on the activity of the crude alkane hydroxylase (a, b); lipase (c, d); and esterase (e, f) from *A. borkumensis* grown on Hexane, on Hexadecane, and on Motor oil.
Figure 4:
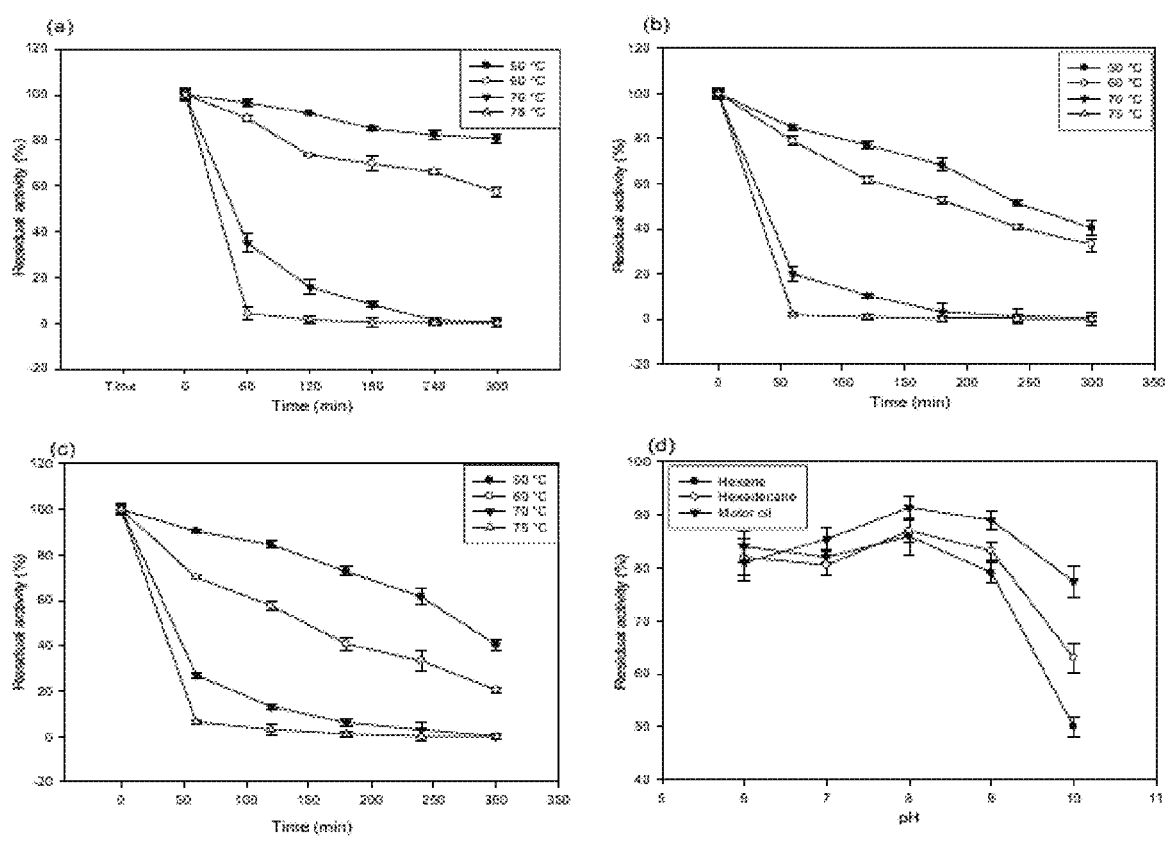
FIG. 4. Effect of temperature (a, b, c) and pH (d) on the stability of the crude alkane hydroxylase from *A. borkumensis* grown on (a) Hexane; (b) Hexadecane and; (c) Motor oil.

The temperature profile of alkane hydroxylase activity from *A. borkumensis* grown on hexane, hexadecane, and motor oil is presented in FIG. 3 (*a*). The *A. borkumensis* crude enzyme extract had an optimum activity at 70±1° C. in presence of hexane and hexadecane, while activity decreased slightly above 70±1° C. For motor oil, the maximum was reached at 75±1° C., with a slight decrease above 75±1° C. The relative activities at 65±1° C. and 75±1° C. were about 46% and 73%, respectively for hexane and 56% and 86.6%, respectively for hexadecane. For motor oil, the relative activities at 80±1° C. and 70±1° C. were about 75% and 88.4%, respectively. The thermal stability profiles of alkane hydroxylase at a temperature range between 50±1° C. and 75±1° C. for the three different substrates hexane, hexadecane, and motor oil are shown in FIGS. 4 (*a*), (*b*) and (*c*), respectively. Profiles showed a high stability at temperatures below 50±1° C. for the three different substrates but were inactivated at higher temperatures.

After 60 min of incubation at 75±1° C., 95.7%, 98% and 93.7% of the initial activities were lost for hexane, hexadecane, and motor oil, respectively. *A. borkumensis* alkane hydroxylases were stable at 50±1 and 60±1° C. after 5 h of incubation for hexane, hexadecane, and motor oil. At low temperatures (−20±1 and 4±1° C.), the crude enzyme preparation retained more than 70% of its activity after one month.

Effect of pH on the Activity and Stability of Alkane Hydroxylase

The pH profile of alkane hydroxylase activity from *A. borkumensis* grown on three different substrates: hexane, hexadecane and motor oil are presented in FIG. 3 (*b*).

The pH stability of *A. borkumensis* alkane hydroxylase assayed in the range of 5.0-9.0 on the three different substrates is shown in FIG. 4 (*d*). Figures showed that the crude alkane hydroxylase was highly stable over a broad pH range, maintaining more than 75% of its original activity between pH 6.0 and 9.0 for hexane, hexadecane and also for motor oil.

For the three different substrates, the crude enzyme was active within pH 6.0 and 8.0, with an optimum at pH 8.0. A sharp decline in activity was observed above pH 9.0. The relative activities at pH 6.0 and 7.0 were about 77% to 80% for hexane substrate, 70% to 75% for hexadecane substrate and around 80% to 88% for motor oil.

Effect of Temperature on the Activity and Stability of Lipase

Figure 5:
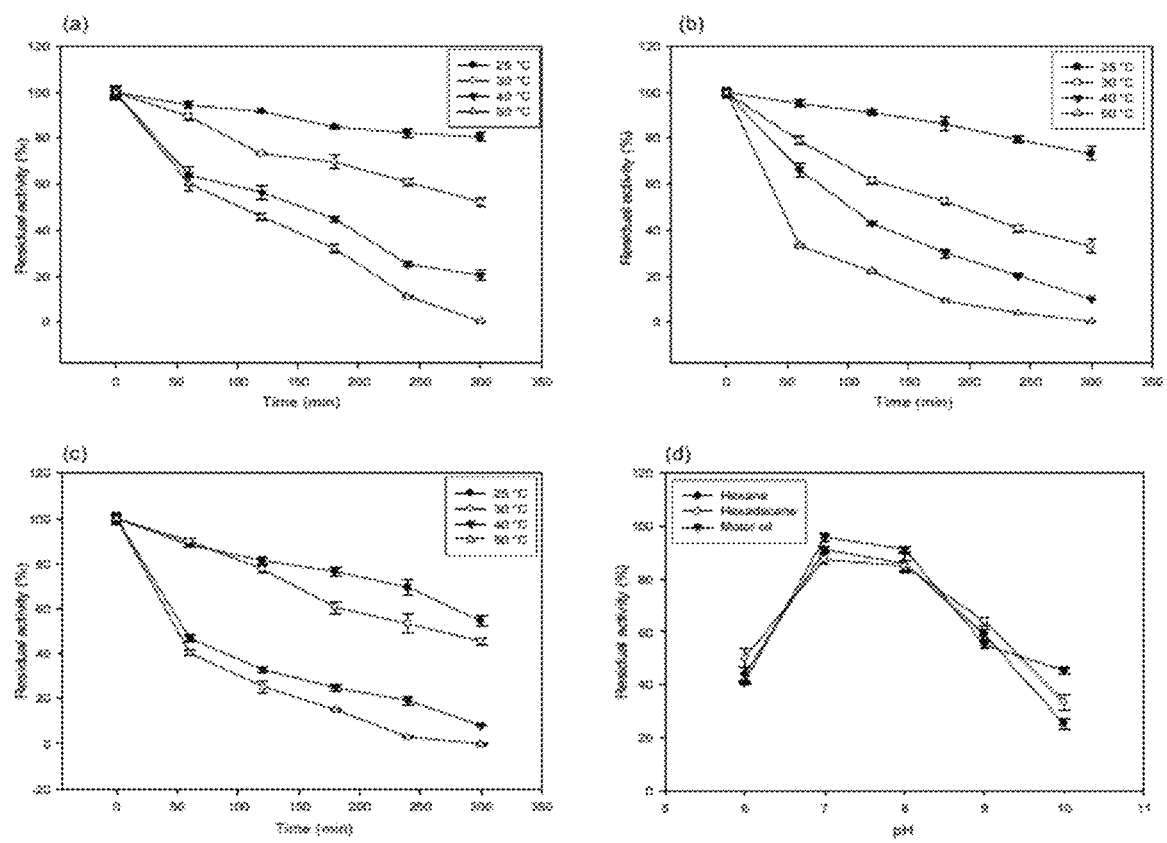
FIG. 5. Effect of temperature (a, b, c) and pH (d) on the stability of the crude lipase from *A. borkumensis* grown on (a) Hexane; (b) Hexadecane and; (c) Motor oil.

The temperature profile of lipase activity from *A. borkumensis* grown on hexane, hexadecane, and motor oil is presented in FIG. 5 (*c*). The *A. borkumensis* crude extract had an optimum at 35±1° C. for the three different substrates hexane, hexadecane and motor oil. The enzymatic activities at 30±1° C. and 40±1° C. were so close to the optimal activity with relative activities values of about 91.2% and 94.3%, respectively for hexane, 81.3% and 96.7%, respectively for hexadecane and 79.10% and 96% for motor oil.

Figure 6:
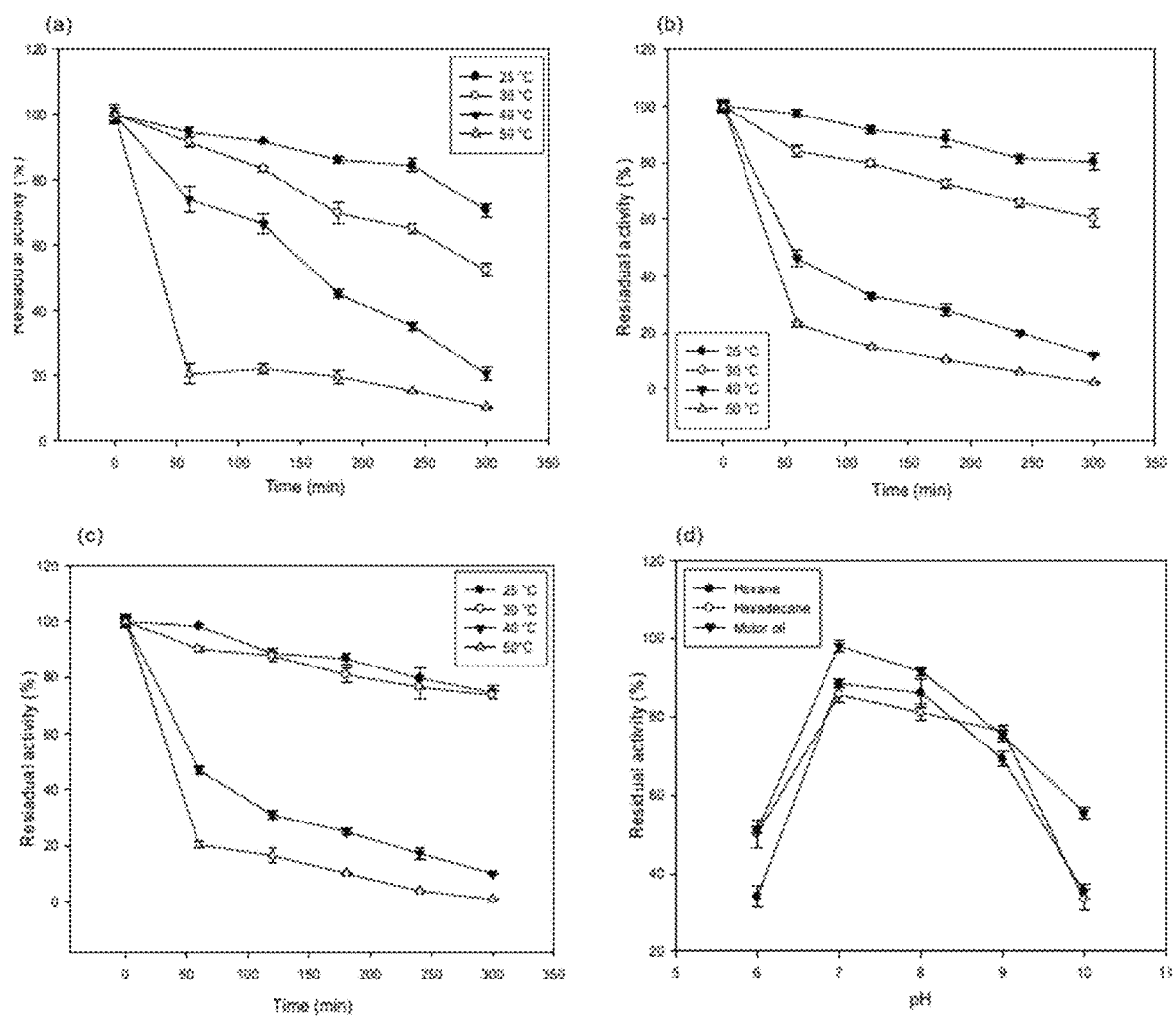
FIG. 6. Effect of temperature (a, b, c) and pH (d) on the stability of the crude esterase from *A. borkumensis* grown on (a) Hexane; (b) Hexadecane and; (c) Motor oil.

The thermal stability profiles of lipase at a temperature range between 25±1° C. and 50±1° C. for the three different substrates hexane, hexadecane and motor oil are shown in FIGS. 6 (*a*), (*b*) and (*c*), respectively. Lipase was highly stable at 25±1° C. with residual activities around 80.6% for hexane, 73.3% for hexadecane and 54.5% for motor oil after 5 hours incubation. In contrast, at 50±1° C., the enzyme was inactivated and loses the entire activity after 5 hours of incubation.

Effect of pH on the Activity and Stability of Lipase

The pH profile of lipase activity from *A. borkumensis* grown on three different substrates is shown in FIG. 5 (*d*). For hexane, hexadecane and motor oil, the crude enzyme was active in the pH range of 6.0-8.0, with an optimum at pH 7.0. The relative activities at pH 6.0 and 8.0 were about 77.1% and 82.4%, respectively for hexane substrate, 59%, and 86.2%, respectively for hexadecane substrate and around 69% to 90.1%, respectively for motor oil.

The pH stability of lipase assayed in the range of 6.0-10 on three different substrates is presented in FIG. 5 (*d*). Profiles showed that the crude extracellular lipase was highly stable in a large pH range, maintaining more than 50% of its original activity in the pH range of 7.0 to 9.0 for hexane, hexadecane and also for motor oil.

Effect of Temperature on the Activity and Stability of Esterase

The temperature profile of esterase activity from *A. borkumensis* grown on hexane, hexadecane, and motor oil is presented in FIG. 6 (*e*). The *A. borkumensis* crude extract had an optimum activity at 40±1° C. for the three different substrates. The relative activities at 35±1° C. and 45±1° C. were around 96.7% and 72.9%, respectively for hexane, 94.3%, and 76%, respectively for hexadecane and 86% and 79% for motor oil.

The thermal stability profiles of esterase at a temperature range between 25±1° C. and 50±1° C. for the three different substrates hexane, hexadecane, and motor oil are shown in FIGS. 6 (*a*), (*b*) and (*c*), respectively. Similar to lipase, esterase was highly stable at 25±1° C. with residual activities of around 70.6% for hexane, 80% for hexadecane and 74% for motor oil after 5 hours' incubation. At 50±1 00 the enzyme loose more than 90% after 5 hours of incubation.

Effect of pH on the Activity and Stability of Esterase

The pH profile of esterase enzymatic activity from *A. borkumensis* grown on three different substrates is shown in FIG. 6 (*d*). For hexane, hexadecane and motor oil the crude enzyme was active in the pH range of 6.0-9.0 with a relative activity higher than 60%. The optimum activity was obtained at pH 7.0. The relative activities at pH 6.0 and 8.0 were about 72% to 81.6% for hexane, 63 to 86% for hexadecane and finally 64.3 to 89% for motor oil.

The pH stability of esterase assayed in the range of 6.0-10 on the three different substrates is presented in FIG. 6 (*d*). Profiles showed that the extracellular esterase was stable in a large pH range, maintaining more than 69% of its original activity in the pH range of 7.0 to 9.0 for hexane, hexadecane and also for motor oil.

The analysis of esterase activity in *A. borkumensis* has revealed that maximum activity is obtained at 40±1° C. and pH 8.0 for the different substrates.

Hexane, Hexadecane and Motor Oil Degradation Efficiency

*Alcanivorax borkumensis* was tested for its biodegradation potential when growing on hexane, hexadecane and motor oil. In experiments, where the media was supplemented with different hydrocarbon sources, *A. borkumensis* showed higher biodegradation potential, with $T_{1/2}$ values of 40.65 h for hexane, 52.20 h for hexadecane and 40.65 h for motor oil. The biodegradation pattern exhibited by this strain consisted of two sequential first-order curves that were characterized by drastic changes in the biodegradation rates after 6 h of experimentation (FIGS. 7 (*a*), (*b*) and (*c*)); these could be described by the modified Hockey-Stick kinetic model. The biodegradation kinetic parameters obtained for the three different substrates are presented in Table 1. The results shown in FIGS. 7 (*a*), (*b*) and (*c*) suggested that the biodegradation time for *A. borkumensis* grown on hexane and motor oil (40.65 h for both substrates) was lesser than when the strain was grown on hexadecane (52.2 h). *A. borkumensis* was able to mineralize up to 80% of the initial concentration of hexane, 81.5% of the hexadecane and 75% of the motor oil.

TABLE 1

Biodegradation kinetic parameters obtained by the Hockey-Stick modified method in media enriched with hexane, hexadecane and motor oil.

| Sample | K (h$^{-1}$) | R$^{2a}$ | $t_b^b$ (h) | $T_{1/2}$ (h) |
|---|---|---|---|---|
| Hexane | 0.02 | 0.96 | 6 | 40.65 |
| Hexadecane | 0.015 | 0.79 | 6 | 52.20 |
| Motor oil | 0.02 | 0.91 | 6 | 40.65 |

$t_b$: breakpoint at the time that biodegradation starts; K, overall biodegradation rate of the substrate; $T_{1/2}$: substrates half life.
$^a$Coefficient of determination of the modified Hockey-Stick model.
$^b$Constant rate from T = $t_b$.

Discussion

Growth of *A. borkumensis* and Enzymes Production

As shown in FIG. 1 (a, c, e), growth on the different substrates (hexane, hexadecane and motor oil) shows typically four phases: an initial lag phase, an exponential growth phase, stationary phase (maximum growth), and a death phase, which is the result of the toxic effects of the octanol product of degradation (Naether et al., 2013). Since *A. borkumensis* is a natural producer of surfactants, almost all the substrates used were in the aqueous phase which discarded the supposition of having a biphasic media with cells present in the liquid-liquid interface. The high growth obtained for the three different media between 48 h and 60 h reflects the capacity of *A. borkumensis* to use theses substrates, allowing degradation at an active stage. Thus, hydrocarbons are processed and degraded inside the cells. These results are in accordance with Boopathy (2000) who reported that in some cases, substances originating from crude oil had stimulatory activity. In contrast, Kanaly and Harayama, (2000) have reported that petroleum hydrocarbons showed toxic properties which inhibit development and metabolic activity of microorganism in most cases. Thus, at high concentrations of test substrates (around 3% v/v) which correlates with their concentrations detected in the contaminated soils/waters, *A. borkumensis* was able to grow and utilize these xenobiotics as the sole source of carbon and energy. In accordance with our results, Bookstaver et al., (2015) reported around 6.93×10$^8$ of counted cells of *A. borkumensis* in the organic nitrogen free broth with octane layer. To the best of our knowledge, this is the only work reported on *A. borkumensis*, most of the other reports pertain to genetic fields (Golyshin et al., 2003; Van Beilen et al., 2004; Naether et al., 2013). The obtained results open the horizon to use *A. borkumensis* for the degradation of recalcitrant compounds and permit to classify this strain among reported xenobiotic-degrading strains, such as *Pseudomonas*, *Mycobacterium*, *Haemophilus*, *Rhodococcus*, *Paenibacillus*, and *Ralstonia* (De Carvalho et al., 2005; Haritash and Kaushik, 2009).

More studies on *A. borkumensis* need to be done to cope with bioremediation of petroleum contaminated sites which may lead to more studies on its alkane oxidation system. *A. borkumensis* SK2 is known to possess an AlkB1 alkane hydroxylase that can oxidize medium chain alkanes in the range C5 to C12 and an alkane hydroxylase AlkB2, that oxidizes medium-chain alkanes in the range C8 to C16. It has been also claimed that *A. borkumensis* SK2 is able to degrade a large range of alkanes up to C32 and branched aliphatic, as well as isoprenoid hydrocarbons (e.g., phytane), alkylarenes and alkylcycloalkanes (Dutta and Harayama, 2001). Consequently, hexane can be degraded by the alkane hydroxylase AlkB1, hexadecane can be degraded by the alkane hydroxylase AlkB2 and the motor oil can be degraded by both AlkB1 and AlkB2, since it contains a mixture of $C_{10}$-$C_{50}$ other that monoaromatic and polyaromatic hydrocarbons. The genome also includes 11 genes coding for different lipases/esterases of unknown specificity. Two of these esterases were purified and functionally characterized (Schneiker et al., 2006). This allows the strain to grow on hexane, hexadecane and motor oil at high concentrations.

The difference of residual concentration obtained for the three substrates (80% for hexane, 82% for hexadecane and 75% for motor oil, after 72 h of growth), is attributed to the dissimilarity of chain-length of the tested substrates as reported by (Rojo, 2009; Van Beilen and Funhoff, 2007). Thus, linear alkanes are lipophilic substances which easily enter through the cell membrane and are more easily degraded.

Owing to the high degradation rate, *A. borkumensis* can be considered among the potential candidates in the bioremediation, such as for *P. aeruginosa* which exhibited a degradation rate of 94% in the presence of n-alkane (Karamalidis et al., 2010) and *Pseudomonas aeruginosa* that showed a degradation capability of 66% in the presence of diesel after 30 days (Sharma et al., 2014).

In this study, results showed that motor oil is the best substrate for the production of *A. borkumensis* crude alkane hydroxylase (FIGS. 1 (*b*, *d*, *f*)). Likewise, a higher activity of alkane hydroxylase was observed by Glieder et al., (2002) in the presence of octane, hexane, cyclohexane and pentane, major compounds present in the motor oil.

Most of the degradation reported is a cooperative action of multitude enzymes as reported by Kennedy et al., (2011) and Zeynalov and Nagiev, (2015). Besides, the lipase and esterase activity were tested as a valuable tool to monitor oil biodegradation in freshly diesel oil-contaminated soils (Margesin et al., 2002, 2003). In this regard, important lipase activities and high esterase activities were observed during the growth of *A. borkumensis* of the three different substrates. Similar results were reported by Margesin et al., (2007), for the induction of soil lipase activity in oil-contaminated sites and in the presence of inorganic nutrients. Therefore, the induction of soil lipase activity is a valuable indicator of oil biodegradation and permits a faster and accurate assessment of the decontamination treatment after an oil spill (Margesin et al., 2002, 2003). Moreover, Martinez-Martinez et al., (2014) suggested that multifunctional esterase-like proteins from the alp hydrolase family that can hydrolyze both C—C and C—O bonds may exist in nature at much higher levels than previously reported. From an ecological perspective, such proteins may contribute to global carbon cycling processes for complex substrates, including recalcitrant organic pollutants.

Enzymes Characterization

Native PAGE and Zymography

*A. borkumensis* is known for degradation of petroleum-derived aliphatic and aromatic hydrocarbons. However, recent studies on the genome sequencing of *A. borkumensis* SK2 revealed that the genome has 11 genes coding for different lipases/esterases (Schneiker et al., 2006). There are also reports that lipases and esterases are actively involved in the degradation of petroleum hydrocarbons (Margesin et al., 2007; Martinez-Martinez et al., 2014). Thus, as shown in FIG. 2, zymogram showed two distinct bands of approx. 52 and 40 kDa, respectively with lipase/esterase activity. The fact that both lipase and esterase can hydrolyze the substrate, 4-methylumbelliferone butyrate, it is difficult to distinguish the active enzyme between lipase and esterase. Further, scarce literature is available on the molecular characterization of lipase and esterase from *Alcanivorax* family. However, from the available reports from the sequence data in the NCBS database for *A. borkumensis*, the molecular weight of lipase and esterase genes are in the range of 35-52 kDa (based on the amino acid length) (*Alcanivorax borkumensis* SK2, complete genome, NCBI). In addition, there are few reports on other related bacteria, viz. *Alcanivorax dieselolei* B-5(T), *Marinobacter lipolyticus* and *Pseudomonas* sp., which has lipase/esterase enzymes with a molecular weight in the range of 43-45 kDa (Izrael-Zivkovic et al., 2009; de Lourdes Moreno et al., 2013; Zhang et al., 2014). The molecular weight of the active protein bands in our study is in accordance with the size range of lipase/esterase reported earlier for *Alcanivorax* sp. and other phylogenetically related bacteria. The investigation showed that two different lipase/esterase are strongly induced and produced in presence of hexadecane in the growth medium. However, further detailed investigations, such as N-terminal sequencing and MALDI-TOF are necessary to characterize these enzymes.

Crude Alkane Hydroxylase Characterization

The small difference of relative activities of alkane hydroxylase between substrates at different temperatures (FIG. 3 (*a*)), may be due to the structure of each one of them. For the thermal stability profiles of alkane hydroxylase produced from *A. borkumensis*, FIGS. 3 (*a*), (*b*) and (*c*), high stabilities were shown at temperatures below 50±1° C. but were inactivated at higher temperatures. Similarly, Li et al., (2013) studied the alkane monooxygenase produced by the bacterium *Pusillimonas* sp. and found that the optimal reaction condition for this enzyme is pH 7.5 at 30° C. Also, this monooxygenase system showed better cold tolerance, with activity retained at temperatures as low as 0° C.

As shown in FIG. 3 (*b*), alkane hydroxylase was active within pH 6.0 and 8.0, with an optimum at pH 8.0 for the three different substrates. A similar study was done by Lu et al., (2013b) reported a pH of 8.0 in laccase-like multicopper oxidase produced by *Streptomyces* sp. C1 in the presence of ABTS (2,2'-azino-bis (3-ethylbenzothiazoline-6-sulphonic acid)) and guaiacol as substrates. However, Salvachúa et al., (2013) have found that acidic pH was required to reach high activities for other oxidative enzymes, such as peroxidase (DyP)-Type form.

Crude Lipase Characterization

The temperature profiles of lipase activity and stability (FIG. 3 (*c*), FIG. 4 (*a*), FIG. 4 (*b*) and FIG. 4 (*c*)) show that the crude enzyme is highly active at 35±1° C. and has an important stability at 25±1° C., and this is for the three different substrates. This is related to the cells' growth temperature range (Feller et al., 1990), which is defined to be 30° C. In this regard, Margesin et al., (2003) have found that lipase enzyme was active at pH 7.25 and temperature of 30° C. This activity was considered as a valuable tool to monitor oil biodegradation in freshly diesel oil-contaminated soils, most probably due to a high content of available aliphatic compounds. On the other side, at 50±1° C., the enzyme loses the entire activity after 5 hours of incubation. This is probably due to the thermal denaturation of the enzyme. The temperature stability of lipolytic is of high importance, particularly for applications in industry (Choo et al., 1998). Although some studies have investigated the effects of high temperatures on the activity of esterase and lipase isolated from *Acinetobacter*, no study was reported on the effects of temperatures on the activity of lipolytic enzymes of *A. borkumensis*.

This same enzyme was highly active at pH 7.0 for hexane, hexadecane and motor oil (FIG. 3 (*d*)) and stable in a wide range of pH from 7.0 to 9.0 (FIG. 5 (*d*)). Similarly, Bisht et al., (2013) have identified an extracellular alkaline lipase from a mutant strain of *P. aeruginosa* with a maximum activity at pH 8.0 with a considerable stability in pH range 7.0-11.0. Moreover, lipase from *P. aeruginosa* SRT9 and *Burholderia* sp. had shown maximum lipase activity at pH 6.9 and 8.5, respectively (Park et al., 2007; Borkar et al., 2009). These characteristics provided a clear indication for their industrial use as effective agents to degrade hydrocarbons even at a high range of pH.

Crude Esterase Characterization

Esterases were reported to degrade alkanes and aromatic rings in different bacterial and fungal isolates (Lubna Tahir, 2013; Ueda et al., 1982). In our study, The analysis of esterase activity in *A. borkumensis* has revealed that maximum activity is obtained at 40±1° C. and pH 8.0 for the different substrates (FIGS. 3 (*f*) and (*e*)) and the highest stability is achieved at 25±1° C. and in a wide range pH from 7.0 to 9.0 (FIG. 6 (*a*), FIG. 6 (*b*), FIG. 6 (*c*) and FIG. 6 (*d*)). As mentioned previously for lipase, also esterase activity is used as a biological indicator to monitor total petroleum hydrocarbons biodegradation and both hydrolases (lipases and esterase) were induced in the presence of hydrocarbons (Margesin et al., 2007). Our results were in agreement with Lubna Tahir, (2013) who found that temperature of a 45±1° C. enhanced the high esterase activity in *Lentinus tigrinus*. Besides, a basic pH was required to reach a high activity (Lubna Tahir, 2013; Ueda et al., 1982). Thus, the role of pH is highly important and may be related to the stability of the enzyme (Ueda et al., 1982). All these observations proved the role of assay conditions (e.c. pH and temperature) in maintaining higher enzymatic activities (Topakas et al., 2007). These insights could have larger implications on the future of bioinspired oil spill remediation. Thus, this study can be further exploited by applying *A. borkumensis* enzymes for the bioremediation of real contaminated sites, which is being explored at the laboratory scale.

Moreover, in all the previous results, we noticed that the profile of lipase enzyme and esterase showed the same kinetics and behavior during incubation time under different pH and temperatures. This proved that both enzymes exhibited a synergetic action (Breuil et al., 1978).

Hexane, Hexadecane and Motor Oil Degradation Efficiency

The substrate degradation capacity of *A. borkumensis* was evaluated by calculating the different degradation rates and kinetic constants. Differences between biodegradation rates may be due to the type and the bioavailability of the hydrocarbons. In fact, it has been demonstrated that different bacterial species have different dissipation potentials depending on those two factors (Cyplik et al., 2011).

Figure 7:
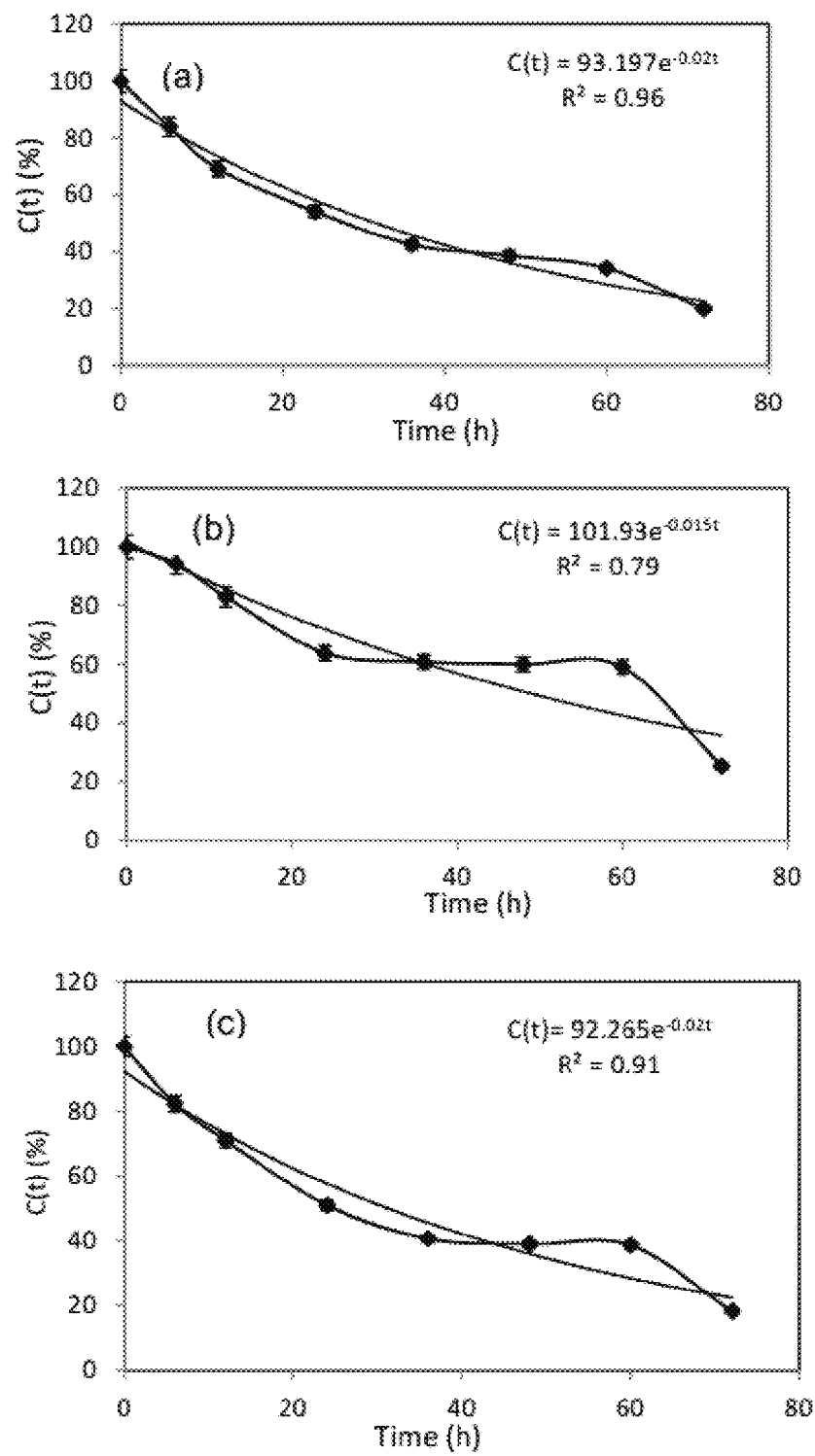
FIG. 7. Biodegradation of hexane (a), hexadecane (b) and motor oil (c) by *A. borkumensis*. Lines represent Exponential equation estimates of the first-order kinetic model of the samples where $R^2$ is the correlation coefficient, C(t) is the residual concentration in (%) of the different substrates at a given time (t).

The Hockey-Stick model is commonly used to describe dissipation patterns with a lag-phase where the concentration of the pollutant is not constant but declines very slowly up to a point where the biodegradation process starts (FOCUS 2006). In this study, *A. borkumensis* exhibited this pattern when grown on hexane, hexadecane and motor oil at a high correlation ($R^2$=0.96, 0.79 and 0.91, respectively; FIGS. 7 (*a*), (*b*) and (*c*)).

These results are similar to those found for the remediation of soil heavily contaminated with hydrocarbons by *Pseudomonas* sp. (Dados et al., 2014) or other microbial consortia (Liu et al., 2010; Nikolopoulou and Kalogerakis, 2009).

Conclusions

The growth of *Alcanivorax borkumensis* was investigated on various substrates, hexane, hexadecane and motor oil that could exist in the marine environment during an oil spill situation. *Alcanivorax borkumensis* showed excellent growth on the three different substrates with the production of high activities of alkane hydroxylase, lipase, and esterase enzymes. A higher percentage of hexane, hexadecane and motor oil removal during *Alkanivorax bokumensis* growth were obtained (80%, 81.5%, and 75%, respectively).

The best production of alkane hydroxylase and lipase was found when using motor oil as a substrate while the best esterase production was reached when using hexadecane as a substrate. Zymogram of the crude enzyme extract of the studied strain showed two distinct bands corresponding to the size of approx. 52 and 40 kDa, respectively with lipase/esterase activity. Crude alkane hydroxylase was shown to have optimum activity at pH 8.8 and temperature 70±1° C. for hexane and hexadecane and temperature 75±1° C. for motor oil. Characterization of lipase and esterase showed optimum activity pH 7.0 and temperatures 35±1° C. and 40±1° C., respectively. All the enzymes possessed stability in a wide range of pH, but they were not thermostable at high temperatures.

Kinetics of *Alcanivorax borkumensis* showed higher biodegradation efficiency in terms of time and hydrocarbon removal. Moreover, *A. borkumensis* responded to the same kinetic models when growing on different hydrocarbons, but faster biodegradation rate was observed on hexane and motor oil than hexadecane.

Example 2—Ex-Situ Biodegradation of Petroleum Hydrocarbons Using *Alcanivorax borkumensis* Enzymes Abstract Bioremediation for degradation of hydrocarbons is a widely used alternative for the recovery of contaminated sites. The current study aimed to use *Alcanivorax borkumensis* crude enzyme preparation as an agent for enhanced microbial hydrocarbons biodegradation in contaminated water and soil. The inoculum and hydrocarbons concentration have a remarkable effect on the biodegradation with the crude enzymes. The high enzymatic production reaching 145.71 U/mg for alkane hydroxylase, 3628.57 U/mg for lipase and 2200 U/mg for esterase led to a significant degradation efficiency of the different concentrations of petroleum hydrocarbon substrates reaching 73.75% for 5000 mg/L of hexadecane, 82.80% for 1000 mg/L of motor oil, 64.70% for 70 mg/L of BTEX and 88.52% for 6000 mg/kg of contaminated soil. The study suggested that *Alcanivorax borkumensis* is a potential hydrocarbon-degrading bacterium with higher enzymatic capacities for bioremediation of hydrocarbon-polluted environment.

Materials and Methods

All chemical reagents of the highest purity, such as hexadecane, BTEX (Benzene, Toluene, Ethylene, Xylene), NADPH (nicotinamide adenine dinucleotide phosphate) and DMSO (Dimethyl sulfoxide) among others, were procured from Sigma-Aldrich, Fisher Scientific or VWR (Mississauga, Ontario, Canada). The strain, *Alcanivorax borkumensis* was purchased from DSMZ (Braunschweig, Germany).

Soil and Motor Oil Characteristics

The contaminated soil used in this study was provided by TechnoRem Inc from a confidential site in Quebec. This soil was chosen due to its intense contamination with total petroleum hydrocarbons. The soil comprised 59% of 1 mm sized particles, 38% of particles with a size range between 250 μm and 500 μm and 3% of very fine particles with a size less than 250 μm.

The chemical characteristics of the heavily contaminated soil used during this study are presented in Tables 2, 3 and 4.

TABLE 2

Soil characteristics.

| Parameters | Units | Soil | Soluble fraction |
|---|---|---|---|
| Total solids | % | 75.36 ± 0.93 | — |
| Moisture content | % | 24.17 ± 0.45 | |
| pH | — | 7.80 ±0.10 | — |
| Density | g cm$^{-3}$ | 1.15 ± 0.02 | — |
| Total carbon (C) | gC/100 g | 0.38 ± 0.02 | 98.00 mg/L |
| Total nitrogen (N) | gN/100 g | 0.06 ± 0.002 | 1.61 mg/L |
| C/N ratio | — | 6.33 | — |
| Oil content | % | 13.87 ± 0.81 | — |

TABLE 3

Initial content and soluble fractions of metals in contaminated soil and applicable norms in Quebec for commercial and industrial uses

| Metals | Initial content (mg/kg of dry soil) | Soluble fraction (mg/L) | Norms [a]MEF C criteria (mg/kg) |
|---|---|---|---|
| Aluminum (Al) | 2018.34 ± 20.00 | 1.95 ± 0.20 | — |
| Arsenic (As) | 5.42 ± 0.50 | 0.05 ± 0.02 | 50.00 ± 4.20 |
| Cadmium (Cd) | 0.45 ± 0.02 | BDL | 20.00 ± 1.20 |
| Chromium (Cr) | 101.43 ± 5.10 | 0.01 ± 0.01 | 800.00 ± 9.50 |
| Copper (Cu) | 18.26 ± 1.20 | 0.15 ± 0.01 | 500.00 ± 10.45 |
| Iron (Fe) | 17812.66 ± 34.66 | 2.67 ± 0.50 | — |
| Manganese (Mn) | 435.26 ± 7.30 | 1.71 ± 0.20 | 2200.00 ± 21.02 |
| Molybdenum (Mo) | 0.52 ± 0.05 | 0.06 ± 0.01 | 40.00 ± 2.40 |
| Nickel (Ni) | 114.18 ± 2.00 | 0.03 ± 0.01 | 500.00 ± 4.50 |

TABLE 3-continued

Initial content and soluble fractions of metals in contaminated soil and applicable norms in Quebec for commercial and industrial uses

| Metals | Initial content (mg/kg of dry soil) | Soluble fraction (mg/L) | Norms [a]MEF C criteria (mg/kg) |
|---|---|---|---|
| Lead (Pb) | 6.69 ± 0.30 | 0.05 ± 0.02 | 1000.00 ± 13.50 |
| Zinc (Zn) | 50.17 ± 1.80 | 0.20 ± 0.07 | 1500.00 ± 8.30 |
| Σ metals | 20563.42 ± 15.00 | | — |

[a]MEF, Ministry of Environment and Fauna;
BDL: below detection level

TABLE 4

Initial content of polyaromatic hydrocarbons (PAH) and $C_{10}$-$C_{50}$ in contaminated soil and regulatory limits in Quebec for commercial and industrial uses

| Composition | Units | Soil | Norm [a]MEF C criteria |
|---|---|---|---|
| Acenaphtene | mg/kg | 0.9 ± 0.02 | 100 |
| Acenaphtylene | mg/kg | 0.5 ± 0.01 | 100 |
| Anthracene | mg/kg | 0.1 ± 0.01 | 100 |
| Benzo (a) anthracene | mg/kg | <0.10 | 10 |
| Benzo (a) pyrene | mg/kg | <0.10 | 10 |
| Benzo (e) pyrene | mg/kg | <0.10 | 10 |
| Benzo (b) fluoranthene | mg/kg | <0.10 | 10 |
| Benzo (j) fluoranthene | mg/kg | <0.10 | 10 |
| Benzo (k) fluoranthene | mg/kg | <0.10 | 10 |
| Benzo (b + j + k) fluoranthene | mg/kg | <0.10 | 10 |
| Benzo (c) phénanthrene | mg/kg | <0.10 | 10 |
| Benzo (g, h, i) perylene | mg/kg | <0.10 | 10 |
| Chrysene | mg/kg | <0.10 | 10 |
| Dibenzo (a, h) anthracene | mg/kg | <0.10 | 10 |
| Dibenzo (a, i) pyrene | mg/kg | <0.10 | 10 |
| Dibenzo (a, h) pyrene | mg/kg | <0.10 | 10 |
| Dibenzo (a, l) pyrene | mg/kg | <0.10 | 10 |
| Diméthyl-7,12 benzo (a) anthracene | mg/kg | <0.10 | 10 |
| Fluoranthene | mg/kg | 0.20 ± 0.02 | 100 |
| Fluorene | mg/kg | 2.20 ± 0.05 | 100 |
| Indeno (1,2,3-cd) pyrene | mg/kg | <0.10 | 10 |
| Methyl-3 cholanthrene | mg/kg | <0.10 | 10 |
| Naphtalene | mg/kg | 8.80 ± 0.80 | 50 |
| Phenanthrene | mg/kg | 3.30 ± 0.40 | 50 |
| Pyrene | mg/kg | 0.20 ± 0.010 | 100 |
| Methyl-1 naphtalene | mg/kg | 13.80 ± 0.50 | 10 |
| Méthyl-2 naphtalene | mg/kg | 21.10 ± 1.50 | 10 |
| Dimethyl-1,3 naphtalene | mg/kg | 25.50 ± 1.40 | 10 |
| Trimethyl-2,3,5 naphtalene | mg/kg | 6.40 ± 0.70 | 10 |
| Σ PAH | mg/kg | <84.70 | |
| Petroleum hydrocarbons $C_{10}$-$C_{50}$ | mg/kg | 6020.00 ± 10.42 | 3500 |

[a]MEF, Ministry of Environment and Fauna

Total solids (TS) and moisture content were measured using the protocol 2540B of Federation et al., (2005) which consists of heating the clean dish to 103±1 to 105±1° C. for 1 h. Later, it was stored and cooled in the desiccator. And finally, it was weighed immediately before use. To determine the elemental concentration of carbon and nitrogen, the sample was first dried at 60±1° C. for 8 h and placed into a glass vial. Two sub-samples (2-3 mg each) were analyzed using a Leco-932 CHNS Analyzer in CHN mode. In CHN mode, samples are combusted in the presence of pure $O_2$ and the combustion gases are measured to determine initial elemental concentrations of C, H, and N.

Oil content was determined by adding n-hexane to the soil (1:1 w/v) and then centrifuging at 10,000×g for 30 minutes to recover the pellet. Once again, n-hexane was added to the pellet (1:1 w/v) and then centrifuged at the same speed and time to recover the pellet. Finally, n-hexane was dried at room temperature and the oil content (supernatant) was weighed. Metals content was determined using inductively coupled plasma optical emission spectrometry (ICP-OES). Samples digestion was fulfilled following the method MENVIQ.89.12/213.Mét 1.3. All the analyses were performed in triplicates.

The method used to determine the PAHs is MA. 400-HAP 1.1, which consists of: extracting PAHs using dichloromethane or hexane after adding recovery standards ("surrogates"). Later, the extract was concentrated to a small volume under a nitrogen stream and purified on a silica gel-alumina column. The final volume of purified extract was concentrated to meet the target detection limits. Finally, the extract was concentrated and then analyzed by chromatography gas phase coupled to a mass spectrometer (GC-MS) operating in the mode selective ion acquisition ("SIM") was used. The method used to determine the $C_{10}$-$C_{50}$ was MA. 400-HYD. 1.1, which consists of extracting aqueous samples with hexane using a mechanical stirrer. Solid samples are first dried with acetone and then extracted with hexane with the aid of an extraction system "mixer painting". As for organic liquids, they are directly diluted in hexane. Thereafter, silica gel is added to the extract to adsorb polar substances and then the supernatant was analyzed by gas chromatography coupled to flame ionization detector.

The composition of motor oil in this study comprised: 69.8 mg/L of $C_{10}$-$C_{50}$, 1.83 mg/L of naphthalene, 44 mg/L of benzene, 30 mg/L of toluene, 44 mg/L of ethyl-benzene and 84 mg/L of xylene.

Bacterial Strain

Aerobic bacterial strain, *Alcanivorax borkumensis* SK2 (DSM 11573) which has the capability to degrade petroleum hydrocarbons was used in all the experiments in this study. The strain was stored at 4° C. on agar plates coated with a film of hexadecane.

Culture Conditions

The initial culture of *A. borkumensis* strain was grown aerobically in batch culture in 250-mL Erlenmeyer flasks for 72 h at 30±1° C. and 150 rpm in synthetic sea water medium SM1 in order to mimic the conditions of an oil spill in the environment (high carbon concentration and nitrogen limitation). This medium was supplemented each time with a different substrate used as a sole carbon and energy source: 3% hexadecane, 3% motor oil and 3% BTEX. SM1 contained (per liter of distilled water): 23 g NaCl, 0.75 g KCl, 1.47 g $CaCl_2 \cdot 2H_2O$, 5.08 g $MgCl_2 \cdot 6H_2O$, 6.16 g $MgSO_4 \cdot 7H_2O$, 0.89 g $Na_2HPO_4 \cdot 2H_2O$, 5.0 g $NaNO_3$, and 0.03 g $FeSO_4 \cdot 7H_2O$. To prevent precipitation, four separate solutions were prepared and later mixed together after autoclaving when the solutions had cooled to room temperature; the first solution contained $Na_2HPO_4$ and $NaNO_3$ (the pH value of medium was adjusted to 7.5 by the addition of a 10% solution of NaOH), the second solution contained NaCl, KCl, and $CaCl_2$, the third solution contained $MgCl_2$ and $MgSO_4$, and the fourth solution contained $FeSO_4$. Bacto agar (Difco, Fisher Scientific, Mississauga, Ontario) (15 g/L) was added to the first solution for the preparation of solid media (Yakimov et al., 1998). About 3% (v/v) and 10% of sub-cultures were used to inoculate the different media which contained the same carbon source (3% (v/v) of hexadecane, 3% (v/v) of motor oil or 3% (v/v) of BTEX) as a sole source of carbon and energy. For Colony Forming Units per mL (CFU/mL), the solution was serially diluted and plated on agar medium plates which were incubated for 72 h at 30° C. (Miles et al., 1938).

For enzymes recovery, the bacterial culture was centrifuged at 12,000×g for 30 minutes at 4° C., and the supernatant containing the extracellular enzymes was recovered and stored at −20° C. for further biodegradation experiments. *A. borkumensis* cell pellet (1 g) frozen at −20° C. was re-suspended in phosphate buffer (1 mL, 0.1 M, pH 8.0). The mixture was sonicated by using two frequencies of ultrasounds (22 kHz and 30 kHz) for 6 min at 4° C. and centrifuged at 13 000×g for 20 min. The supernatant was used as a crude intracellular enzyme extract.

Biodegradation Using the Crude Enzymes Mixture

The performance of the extracellular and intracellular crude enzymes from *A. borkumensis* was evaluated in batch tests in Milli-Q water. The test solutions contained 50 mL Milli-Q water, 10 mg/mL of an equal mixture of intracellular and extracellular crude enzyme and the different petroleum hydrocarbons concentrations: 5000, 6000 and 7000 mg/L of hexadecane, 30 mg/L, 50 mg/L and 70 mg/L of BTEX compounds mixture (1:1:1:1:1:1), 500, 750 and 1000 mg/L of motor oil, and 2000, 4000 and 6000 mg/mL of contaminated soil. The control tests are only composed of Milli-Q water at different concentrations of the different substrates without the enzyme mixture. The solutions were incubated at 30° C. for 7 days with shaking at 100 rpm in an incubator shaker. All experiments were carried out in triplicates.

Sampling Strategy and Parameters Assayed

At the beginning ($T_0$) and at the end ($T_7$) of the experimental period, sub-samples of enzymatic degradation were taken. Measures of enzymes activities (alkane hydroxylase, lipase, and esterase) and concentrations of different petroleum hydrocarbons (hexadecane, BTEX and motor oil) were carried out. All experiments were performed in triplicates.

Proteins and Enzymatic Assays

Total Protein Assay

Both intracellular and extracellular protein concentration was determined according to the Bradford method (Bradford, 1976), and the specific activity (units per mg of proteins) for both the intracellular and the extracellular enzymes was determined.

Alkane Hydroxylase Assay

Alkane hydroxylase activity was measured at 25° C. using a cofactor (NADPH) depletion assay to determine relative activities. The intracellular enzyme was diluted into phosphate buffer (0.1 M, pH 8), the substrate (0.5-1 mM), and dimethyl sulfoxide (DMSO; 1%, vol/vol). Substrates were added to the buffer using stock solutions in DMSO. The reaction was initiated by addition of NADPH (200 µM), and the oxidation of NADPH was monitored at 340 nm (Glieder et al., 2002). One unit is defined as the amount of enzyme required for consumption of 1 nmol of NADPH per min. Hexadecane, BTEX, and motor oil were used as substrates.

Lipase Assay

Extracellular lipase activity was performed by the titrimetric method according to Lopes et al., (2011) by using an olive oil emulsion composed of 25 mL of olive oil and 75 mL of 7% Arabic gum solution which was emulsified in liquefier for 2 minutes. About 5 mL of olive oil emulsion was then added to 0.1M phosphate buffer (pH 7.0) and 1 mL of the enzymatic suspension (10 mg/mL) and incubated at 37° C. for 30 minutes under shaking. Subsequently, the emulsion was immediately disrupted by the addition of 15 mL of a mixture of acetone-ethanol (1:1 v/v). The released fatty acids were titrated with 0.05M NaOH. One unit of lipase activity was defined as the amount of enzyme which liberated 1 µmol of fatty acids per minute.

Esterase Assay

Extracellular esterase activity was measured by the titrimetric method according to Lopes et al. (Lopes et al., 2011) by using olive oil as a substrate. The reaction mixture is composed of 5 mL of olive oil, 2 mL of 0.1M phosphate buffer (pH 7.0) and 1 mL of the enzymatic extract (10 mg/mL). The mixture was incubated at 37° C. for 30 minutes under shaking and it was immediately disrupted by adding 15 mL of the acetone-ethanol mixture (1:1 v/v). The released fatty acids were titrated with 0.05M NaOH. One unit of esterase activity was defined as the amount of enzyme which liberated 1 µmol of fatty acids per minute.

Gas Chromatography

GC analysis of petroleum hydrocarbons biodegradation was performed using Hewlett-Packard 6890/5973 with flame ionization detector (FID). Analyses were carried out with helium as the carrier gas at a flow rate of 2 mL/min on a DB-1 column (30 m, 0.53 mm i.d., 1.0 mm film thickness). Oven temperature was programmed from 60° C. 260° C. at a rate of 4° C./min. Split/Splitless injector and detector (FID) temperatures were 260° C. and 260° C., respectively, and 1 mL of the sample was injected (Ryu et al., 2006).

Statistical Analysis

All the experiments were performed in replicates and an average of 3 replicates was calculated along with the standard deviation.

Results and Discussion

Dynamics of Petroleum Hydrocarbons Degradation with Crude Enzymes

Figure 8:
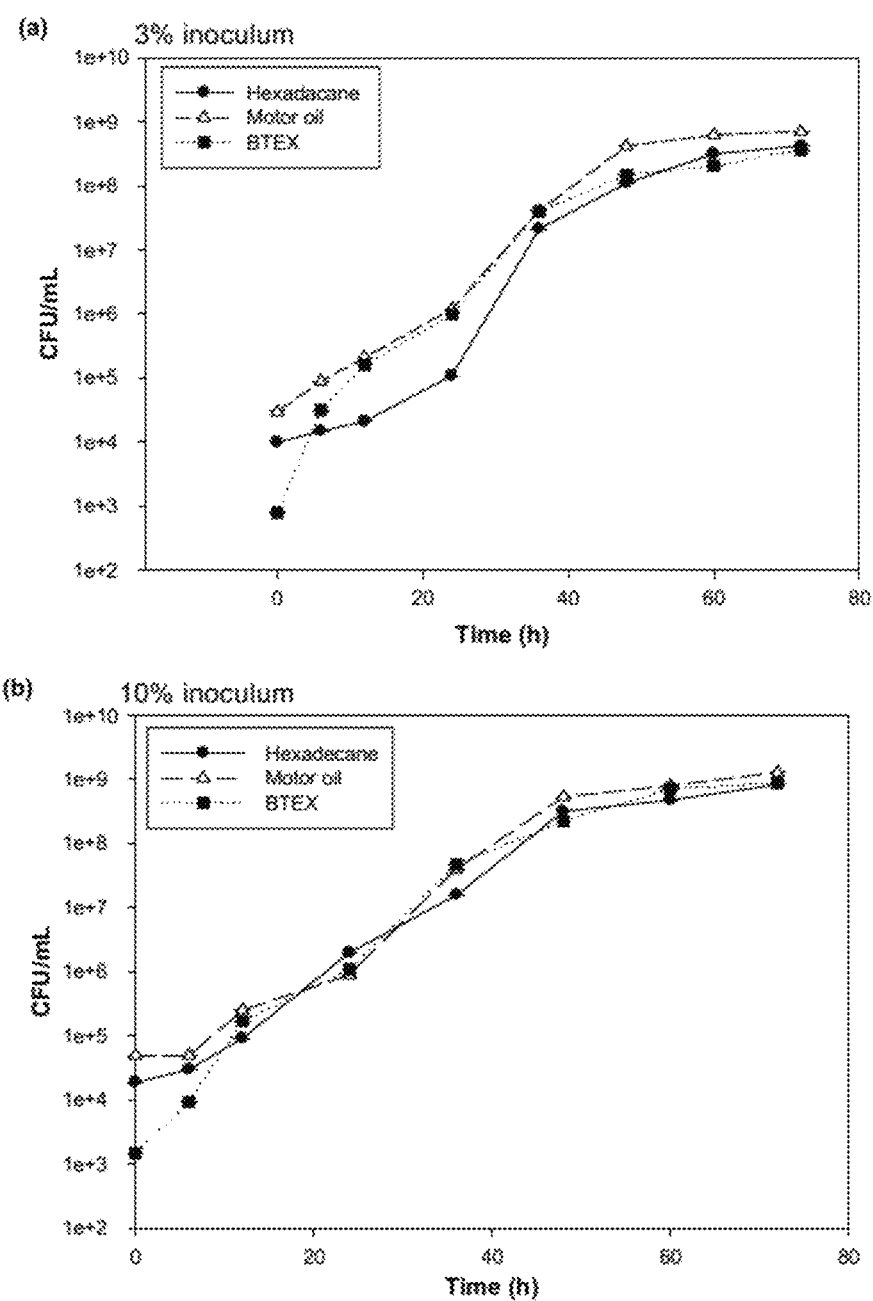
FIG. 8. Colony forming units per mL of *Alcanivorax borkumensis* using different substrates and inoculated with (a) 3% (v/v) and (b) 10% (v/v).

The present study deals with the enzymatic degradation of *A. borkumensis* which was grown in the presence of xenobiotic petroleum hydrocarbons being reported to be toxic substances, such as hexadecane, motor oil, and BTEX. Overall, degrading capacities of crude enzymes produced were also tested in the presence of contaminated soil which contains a range of contaminants as described in Table 2. The bacterial strain was able to use the various tested substrates as sole carbon source and energy for its growth and proliferation which was confirmed by cell count. FIG. 8 shows that the cell number reached $4.2 \times 10^8$ CFU/mL and $8.4 \times 10^8$ CFU/mL in the case of hexadecane with 3% and 10% (v/v) inoculum, respectively. In the case of BTEX, the cell count reached $3.7 \times 10^8$ CFU/mL and $8.9 \times 10^8$ CFU/mL with 3% and 10% (v/v) inoculum, respectively. And finally, in the case of motor oil, the cell count was $7.1 \times 10^8$ CFU/mL and $13 \times 10^8$ CFU/mL with 3% and 10% (v/v) inoculum, respectively. The crude enzyme was isolated after 72 hours of bacterial growth.

Enzymatic degradation can be affected by many parameters, such as the hydrocarbons present in the contaminated site, the concentration of the pollutant, the environmental compartment in which the process is being carried out and the enzymes adaptation (Bamard et al., 2011; Singh and Celin, 2010). In the current study the influence of substrate concentration on the degradation rate of *A. borkumensis*, was very representative. Herein, the percentage of removal was correlated with the concentration of hydrocarbons and with the specific activity of each of the studied enzymes over the time period.

Hexadecane used in this study is part of the aliphatic fraction of crude oil and it is one of the most important components of diesel (Chénier et al., 2003). This compound is present at many oil-contaminated sites and its biodegradability has been well characterized (Graham et al., 1999). For these reasons, hexadecane is used in this study as a model molecule to study aliphatic hydrocarbon biodegradation since it has been always considered as a model (Schoefs et al., 2004). The concentrations adopted in our research (5000 mg/L, 6000 mg/L, and 7000 mg/L) were based on the concentration of $C_{10}$-$C_{50}$ that has been found in the characterized contaminated soil (Table 3).

Figure 9:
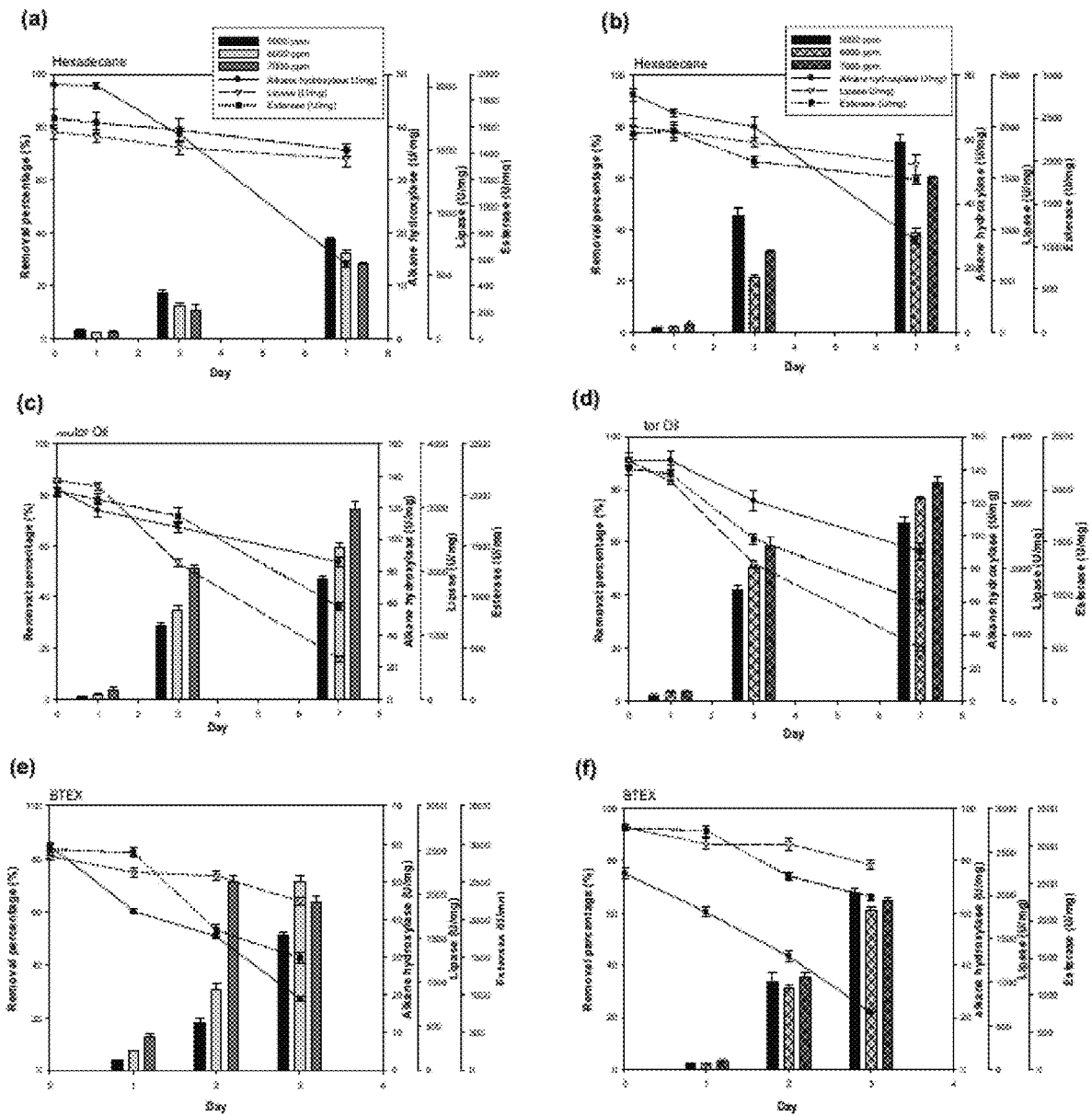
FIG. 9. Specific enzyme activity and removal percentage of different petroleum hydrocarbons using the crude enzyme produced by *A. borkumensis* at different inoculum size 3% (v/v) (not scratched histograms) and 10% (v/v) (scratched histograms).

The removal percentage of $C_{18}H_{34}$ decreased from 73.75% to 59.74% after 7 days of enzymatic degradation, while increasing the concentration of hexadecane from 5000 to 7000 mg/L when using 10% (v/v) of inoculum concentration. As shown in FIG. 9, the specific activity of alkane hydroxylase, lipase and esterase was quite stable after 7 days of degradation using 7000 mg/L hexadecane and 10% (v/v) inoculum. This specific activity decreased from 73.80, 2000, 2320 U/mg, respectively after extraction of the crude enzymes (initial activity) to 28.57, 1628, 1781.48 U/mg, respectively after 7 days of degradation. These findings are in agreement with Maletić et al., (2013) who reported that hydrocarbon degradation is ultimately dependent on their concentration. Most of the previous studies on hexadecane biodegradation have used an initial concentration lower than 1 g/L and have been carried out for up to 45 days (Haines and Alexander, 1974; Hanstveit, 1992). Setti et al., (1993) reported 86.4% of hexadecane mineralization at an initial concentration of 12 g/L by *Pseudomonas* sp. after 31 days of biodegradation. Colombo et al., (1996) reported that several fungal strains were able to biodegrade up to 80% of aliphatic hydrocarbons after 90 days, using a contaminated soil with a concentration of 10% crude oil which contains 16.5 mg of aliphatic hydrocarbons per g of soil. Moreover, Volke-Sepulveda et al., (2003) found that an initial concentration of 45 g/L of hexadecane was totally mineralized after 31 days of culture using a solid-state fermentation.

Moreover, as noticed from FIG. 9, the enzyme specific activity considerably increased while increasing the inoculum, from 48, 1642.85, and 1666.66 U/mg to 73.80, 2000 and 2320 U/mg for alkane hydroxylase, lipase, and esterase, respectively. This increase in enzymes activity had a significant effect on hexadecane degradation. In fact, as observed in FIG. 10, the degradation percentage increased almost twice (from 37.70 to 73.75) when using 5000 mg/L of hexadecane and from 32.40 to 38.50 when using 6000 mg/L of hexadecane and also almost two time degradation increase was observed when using 7000 mg/L of hexadecane (from 28.31 to 59.74), after 7 days of degradation with enzymes produced by the inoculated *A. borkumensis*.

Peng et al., (2015) has stated that the BTEX mixture is the most toxic TPH component for living cells. The BTEX degradation abilities of the enzymes produced by *A. borkumensis* inoculated with 3% (v/v) and 10% (v/v), were evaluated during 3 days using a BTEX mixture containing 30 mg/L, 50 mg/L and 70 mg/L of each of the six compounds (benzene, toluene, ethylbenzene, o-xylene, m-xylene and p-xylene (1:1:1:1:1:1)) in the enzymatic preparation.

Figure 10:
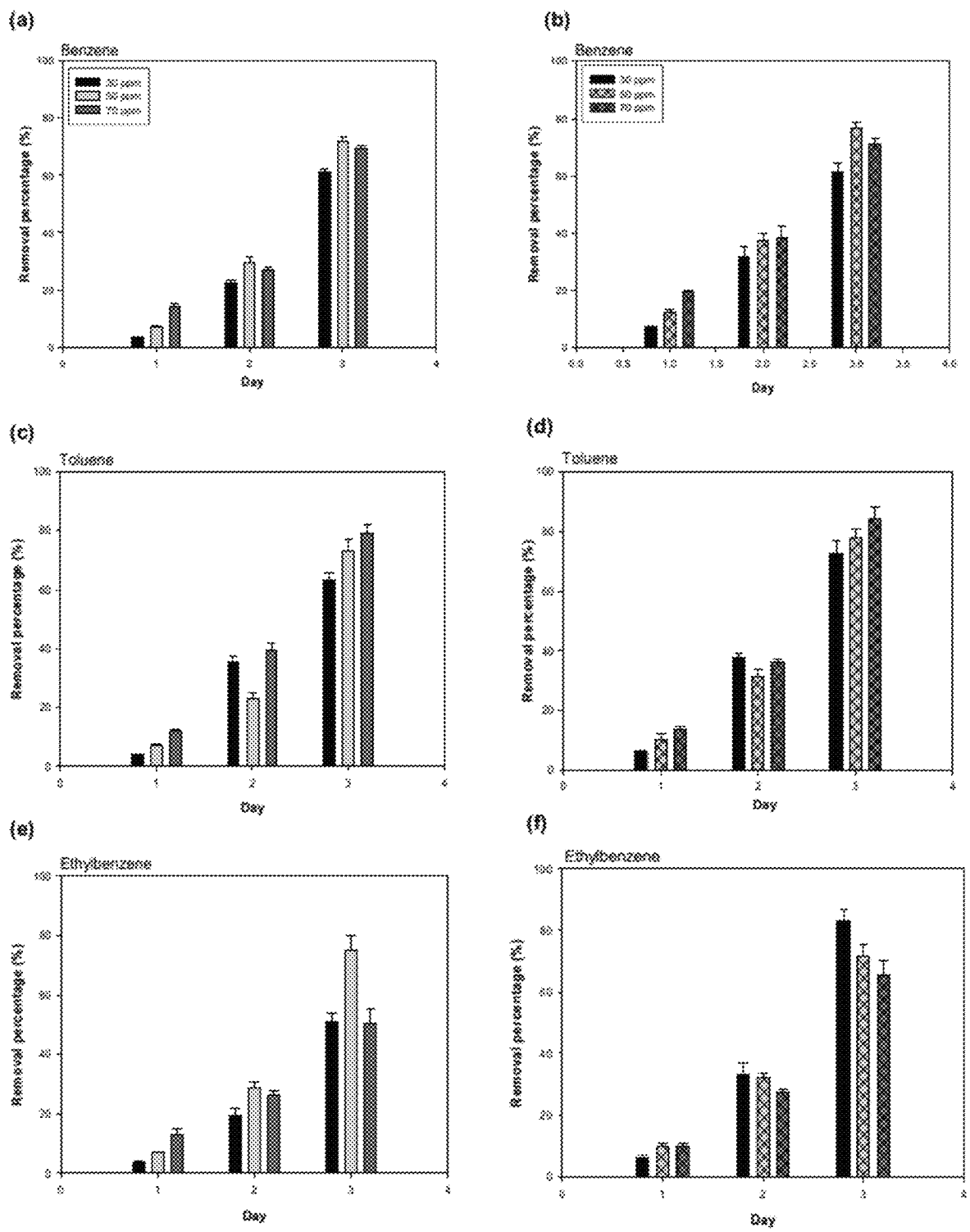
FIG. 10. Removal percentage of different BTEX compounds during 3 days using the crude enzyme produced by *A. borkumensis* at different inoculum sizes 3% (v/v) (not scratched histograms) and 10% (v/v) (scratched histograms).
Figure 10:
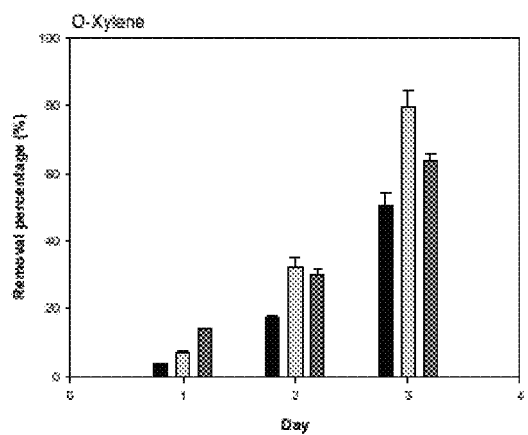
Figure 10:
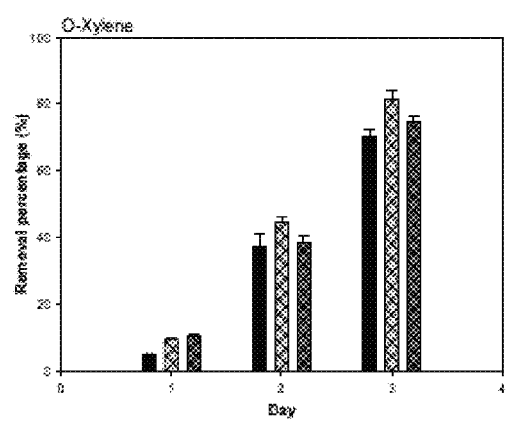
Figure 10:
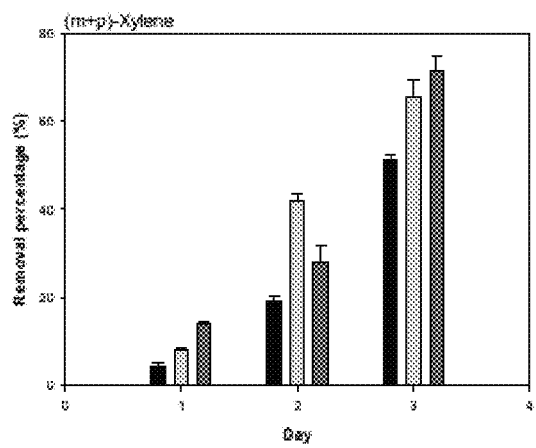
Figure 10:
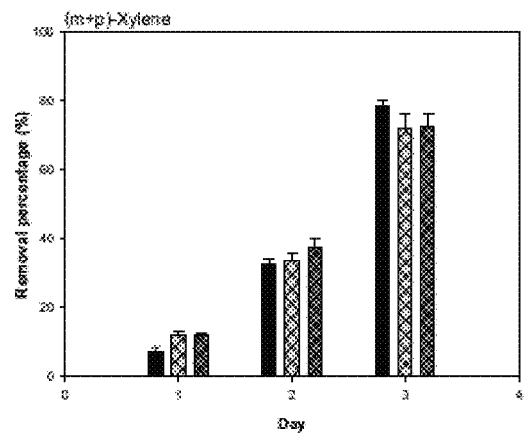

As shown in FIG. 9, the activity of the initial enzyme obtained after extraction from the culture broth with 3% (v/v) inoculum measured for the mixture of 70 mg/L of BTEX were 59.45, 2432.43 and 2928 U/mg for alkane hydroxylase, lipase, and esterase, respectively. The enzyme activity increased to 75, 2785.71 and 3243.24 U/mg for alkane hydroxylase, lipase, and esterase, respectively while increasing the inoculum concentration to 10% (v/v). Also, as shown in FIG. 10 the removal percentage of benzene, ethylbenzene and o-xylene decreased from 72.22%, 74.8%, 79.3% to 69.5%, 50.25% and 63.71%, respectively while increasing substrate concentration from 50 mg/L to 70 mg/L using 3% (v/v) inoculum concentration. However, in the presence of higher inoculum concentration (10% (v/v)), the degradation decreased from 76.48%, 71.69%, 81.2% to 71.22%, 65.45%, 74.8% respectively. These observations were in agreement with Li et al., (2006) who showed an inhibitory effect of higher benzene concentration (more than 80 mg/L) in the presence of *Planococcus* sp. strain ZD22. Similarly, Hamed et al., (2003) reported that the specific growth rate of *P. putida* in batch systems has been set up to be a decreasing function of benzene and toluene concentrations. BTEX compounds upon reaching certain concentrations can inhibit the microbes and their enzymatic activity due to complex micro- and macro-level interactions (Jo et al., 2008). Furthermore, Mathur and Majumder, (2010) claimed that at higher initial concentrations (>150 mg/L benzene and >200 mg/L toluene), the degradation rate was lower. The removal efficiency could also be attributed to the simple structure and the molecular composition of BTEX (Fedorak and Westlake, 1981; Horowitz and Atlas, 1977). In the case of toluene and as shown in FIG. 10, about 84.22% of removal percentage was obtained at an initial concentration of 70 mg/L on day 3. Thus, toluene had been claimed as the most easily biodegradable among the six compounds of BTEX. In the current study, the mixture of different BTEX compounds (benzene, toluene, ethylbenzene, and xylene) together is seen to affect one another. For example, they can interact synergistically or antagonistically as reviewed by Dou et al., (2008). Herein, the interaction between BTEX components in this study seems to be synergistic since a high removal percentage (up to 60%) is reached while using the mixture of the above contaminants in a time period of 3 days.

Other xenobiotic components were tested in the current study for their removal efficiency, such as motor oil which showed a potential degradation (FIG. 9). As mentioned earlier in this study, this compound was characterized and it is composed of (in mg/L): 69.8 $C_{10}$-$C_{50}$, 1.83 naphthalene, ≤44 benzene, ≤30 toluene, ≤44 ethyl-benzene, and ≤84 xylene. Thus, *A. burkumensis* grew well on engine oil producing high crude enzymes activities which was confirmed in FIG. 9 by the specific activity of the enzymes. This activity increased from 131.81 to 145.71 U/mg for alkane hydroxylase and from 3434.78 to 3628.57 U/mg for lipase and from 2043.47 to 2200 U/mg for esterase when using 1000 mg/L motor oil as substrate and increasing the inoculum concentration. This increase in enzymes activity led to an increase in removal from around 74% to around 83% after 7 days of enzymatic degradation. As discussed earlier, the biodegradation carried out by *A. burkomensis* seemed to be concentration dependent as observed with BTEX. These results are advantageous compared with *Pseudomonas aeruginosa* which was able to utilize 81% of used engine oil within 4 weeks compared to 7 days in the current study (Thenmozhi et al., 2011). Likewise, Basuki et al., (2015) reported the removal of 35 out of 47 components of used oil by *Acinetobacter junii* TBC 1.2. Besides, *Pseudomonas aeruginosa* LP5 degraded more than 90% of all oil types within 21 days. The incomplete degradation obtained (between 59-83%) can be further improved by extending the fermentation time to more than 7 days.

In the current study, the degradation efficiency varied largely between the different compounds, hexadecane, BTEX or motor oil reflecting a complexity in the structure and chain-length of the different studied substrates. These observations substantiated the findings of Das and Chandran, (2010) who stated that all the mechanisms of biodegradation and the degradative enzymes produced are dependent on the physical and chemical properties of hydrocarbons.

These results are advantageous compared to similar strains that presented higher degradation capacities. *Acinetobacter baumannii* isolated from crude oil exhibited 62.8% of TPH biodegradation after 7 days (Mishra et al., 2004). *Cellulosimicrobium cellulans* exhibited hydrocarbon degradability of 18.86% after 15 days (Nkem et al., 2016). Similarly, Ijah, (1998) reported more than 52% obtained in 16 days.

Biodegradation Kinetics of Contaminated Soil

Figure 11:
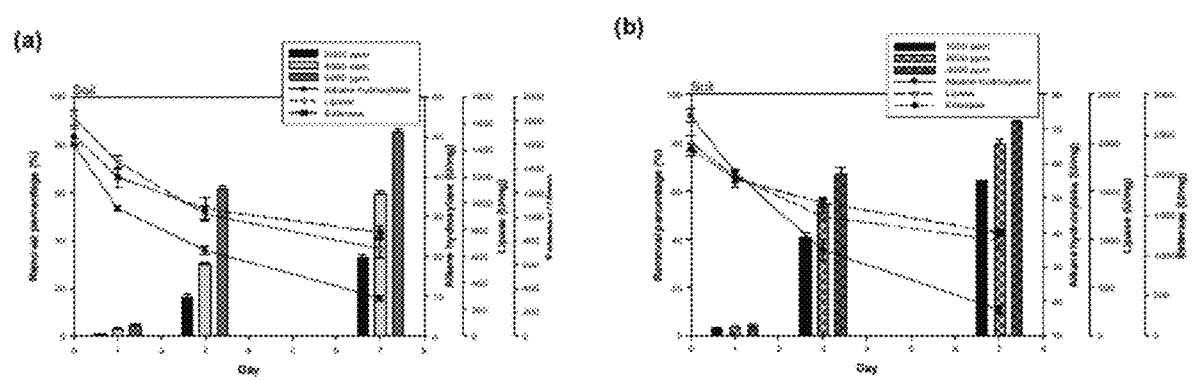
FIG. 11. Specific enzyme activity and removal percentage of petroleum hydrocarbons in the soil using the crude enzyme produced by *A. borkumensis* at different inoculum size 3% (v/v) (not scratched histograms) and 10% (v/v) (scratched histograms).

The crude enzyme used for the degradation of the contaminated soil was produced with *A. borkumensis* using hexadecane as the sole carbon source (since it is the standard carbon source). The specific activity obtained during the degradation of 6000 mg/kg of petroleum hydrocarbons in soil was studied when using both 3% and 10% (v/v) inoculum. In the case of 10% (v/v) inoculum and 7 days degradation period, this specific activity decreased from 73.8 to 17.47 U/mg for alkane hydroxylase, from 2000 to 994.26 U/mg for lipase and from 2320 to 1286 U/mg for esterase and it was associated with a high removal percentage reaching 88.52%. The higher removal percentage of contaminated soil was observed after 7 days of culture with 64.23%, 79.59% and 88.52% of degradation calculated with an initial concentration of contaminated soil of 2000 mg/L, 4000 mg/L, and 6000 mg/L, respectively. In the $3^{rd}$ day, 40.67%, 54.43% and 67.29% were observed with 10% (v/v) inoculum in the case of 2000 mg/L, 4000 mg/L and 6000 mg/L of contaminated soil, respectively (FIG. 11). This rapid degradation rate on the 3rd day is likely due to the consumption of the easily degradable compounds of low molecular weight found in the soil.

Based on a first order model, degradation constant (k) and half-life ($t_{1/2}$) were determined. Table 5 presents the kinetic parameters calculated for the removal of TPH in the soil as well as the hydrocarbons consumption data (i.e. global consumption rate; maximum consumption rate). The half-life was around 5.12 days. This indicates that it would take about 10 days to achieve complete biodegradation of the carbon source by applying the tested inoculum and enzymes. According to the analysis, the estimated biodegradation in the soil reached around 64% of TPH removal. The calculated global consumption rate (GCR) was about 566.14±42.1 mg $kg^{-1}$ $d^{-1}$ for contaminated soil with 6170.7 $mg^{-1}$ $kg^{-1}$ of TPH while the maximum consumption was 363.4 $mg^{-1}$ $kg^{-1}$.

TABLE 5

Biodegradation constant and half-life for total petroleum hydrocarbons removal in soil, after 7 days assay.

| | Biodegradation (%) | GCR$^a$ (mg kg$^{-1}$ d$^{-1}$) | MCR$^b$ (mg kg$^{-1}$ d$^{-1}$) | k$^c$ (d$^{-1}$) | Half life time (day) |
|---|---|---|---|---|---|
| Contaminated soil | 64.23 ± 0.45 | 566.14 ± 42.10 | 363.40 ± 32.50 | 0.16 | 5.12 |

$^a$Global Consumption Rate (GCR) was calculated considering the initial and residual hydrocarbon content after 7 days.

$^b$Maximum Consumption Rate (MCR).

$^c$Biodegradation constant was calculated as:

$C = C_0 e^{-kt}(t)$

Where:

C = Total petroleum hydrocarbon concentration at "t" time.

$C_0$ = initial concentration of petroleum hydrocarbon.

k = Biodegradation constant represented as the slope of Ln C/C$_0$ vs time (days).

$^a$Global Consumption Rate (GCR) calculated as:

$$GCR = \frac{[TPH_{final}] - [TPH_{initial}]}{t_0 - t_{final}}$$

Where:

GCR: Global consumption rate.

TPH$_{final}$ = Total petroleum hydrocarbon concentration at the end of the assay.

TPH$_{initial}$ = Initial total petroleum hydrocarbon concentration.

$t_0$ = initial time.

$t_{final}$ = final experimental time.

$^b$Maximum Consumption Rate (MCR) calculated as:

$$MCR = \frac{[TPHr]_n - [TPHr]_{n-1}}{t_{n-1} - t_n}$$

Where:

MCR: Maximum consumption rate determined between each sampling interval.

[TPH$_r$]$_n$ = Residual total petroleum hydrocarbon concentration at tn.

[TPH$_r$]$_{n-1}$ = = Residual total petroleum hydrocarbon concentration at tn − 1.

Herein, the degradation rate using enzymes from *A. borkumensis* was very important compared to other reported strains. In fact, Diaz-Ramirez, (2000) evaluated the biodegradation of hydrocarbons using a bacterial consortium and has found around 62% of removal within 30 days. In the contaminated soil, the biotransformation of hydrocarbons was probably due to degradation of short-chain compounds (low molecular weight) and medium-sized alkanes. Herein, the higher content of petroleum hydrocarbons C10-C50 (6020 mg kg-1) activated the capacity of biodegradation in the selected microorganism. The biodegradation pathway initially involved the degradation of short to medium chain aliphatics (C10) presented by methyl naphthalene up to 25 mg kg-1. Similarly, Marquez-Rocha et al. (2001), reported the degradation of medium-sized hydrocarbons (>C12) contained in the diesel, together with the short-chain compounds. To make the process wholesome, ecotoxicological studies should be carried out and special attention should be put on the effects of hydrocarbons on the physicochemical properties of the soil.

Conclusion

Crude enzyme extracted from *Alacanivorax borkumensis* showed high efficiency in terms of removal of hydrocarbons. This study confirms the alternative of using bacterial enzymes for the bioremediation of hydrocarbons. High enzymatic activity reaching 145.71 U/mg for alkane hydroxylase, 3628.57 U/mg for lipase and 2200 U/mg for esterase was obtained leading to more than 80% removal of different compounds with different concentrations namely BTEX, motor oil, hexadecane and contaminated soil, in a short period of time (3 days for BTEX and 7 days for the remaining compounds). Thus, *Alacanivorax borkumesis* derived enzymes may be used as a powerful approach for the clean-up of environments polluted with petroleum compounds in both aquatic and terrestrial ecosystem.

Study of the Immobilization of *Alcanivorax borkumensis* Enzymes for Better Performance Example 3—Nanoencapsulation and Release Study of Enzymes from *Alkanivorax borkumensis* in Chitosan-Tripolyphosphate Formulation Abstract The crude alkane hydroxylase and lipase enzymes from the hydrocarbonoclastic bacterium, *Alcanivorax borkumensis* were entrapped into chitosan nanoparticles (CSNPs) by ionotropic gelation method. For optimal loading efficiency, enzyme-chitosan/tripolyphosphate (ENZ-CS/TPP) ratio was investigated. Fourier transform infrared spectra and morphology by scanning electron microscopy were used to explore and confirm alkane hydroxylase and lipase loaded into CSNPs. Seven consecutive ratios were investigated. Entrapment efficiency increased by increasing the ratio enzyme-chitosan/TPP. The optimal ratio with the best entrapment efficiency that was maintained for both alkane hydroxylase and lipase was 5:1. Particle size and zeta potential of the optimal ENZ-CSNPs was 473 nm and +21.8, respectively. Entrapment efficiency for alkane hydroxylase loaded CSNPs and lipase loaded CSNPs was 58.37% and 67.14%, respectively.

The immobilized alkane hydroxylase and lipase exhibited more than two folds increase in vitro half-life in comparison with the free enzymes maintaining around 70% of initial activity after 5 days. This study leads to a better understanding of how to prepare CSNPs, how to achieve high encapsulation efficiency and how to prolong the release of enzymes from CSNPs.

Materials and Methods

Materials

All chemical reagents of highest purity, such as high molecular weight chitosan (100-300 kDa), sodium tripolyphosphate (TPP), acetic acid (99.7%), hexadecane (99%), nicotinamide adenine dinucleotide phosphate (NADPH), Dimethyl sulfoxide (DMSO), p-nitrophenol (p-NP) and p-nitrophenyl palmitate (p-NPP) were purchased from Fisher Scientific or Sigma-Aldrich (Ontario, Canada). Phosphate buffer saline (PBS) and other reagents used were of analytical grade. The strain, *Alcanivorax borkumensis* was purchased from DSMZ (Braunschweig, Germany). Double distilled water (DDW) was produced in the laboratory using Milli-Q/Milli-Ro Millipore system (Massachusetts, USA).

Bacterial Strain

*Alcanivorax borkumensis* strain SK2 (DSM 11573) was used in this study. *A. borkumensis* was sub-cultured and streaked on agar plates, incubated for 72 h at 30±1° C. and then preserved at 4±1° C. for future use. Standard media consisted of (per liter of distilled water): 23 g NaCl, 0.75 g KCl, 1.47 g $CaCl_2 \cdot 2H_2O$, 5.08 g $MgCl_2 \cdot 6H_2O$, 6.16 g $MgSO_4 \cdot 7H_2O$, 0.89 g $Na_2HPO_4 \cdot 2H_2O$, 5 g $NaNO_3$, and 0.03 g $FeSO_4 \cdot 7H_2O$ (Yakimov et al., 1998). The media was supplied with 3% (v/v) hexadecane as the carbon and energy source and the growth was monitored at 30±1° C., 150 rpm for 72 h. Agar plates were prepared with the same media and agar was added at 18 g/L.

Figure 12:
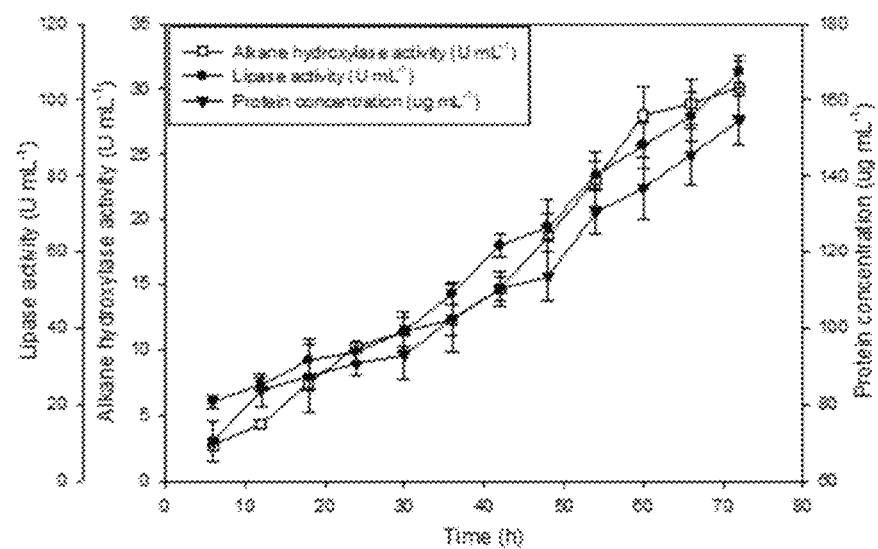
FIG. 12. Profiles of protein concentration, alkane hydroxylase activity and lipase activity during fermentation of *Alcanivorax borkumensis* using (a) 3% (v/v) Hexadecane as a substrate.

The enzymes used in this work were produced in the controlled conditions of a 5 L bioreactor using 5% (v/v) of motor oil as a sole carbon source for the growth of *Alcanivorax borkumensis*. All the details of this fermentation are explained in our previous work (unpublished data). Results of protein concentration, alkane hydroxylase activity and lipase activity obtained during the fermentation time are presented in FIG. 12.

Total Protein Assay

Total protein concentration was determined according to the (Bradford, (1976) method. The principle of this assay is that the binding of protein molecules to Coomassie dye under acidic conditions results in a color change from brown to blue.

Sonication

*Alcanivorax borkumensis* cell pellet (1 g) frozen at −20° C. was re-suspended in phosphate buffer (1 mL, 0.1 M, pH 8.0). The mixture was sonicated by using two frequencies of ultrasounds (22 kHz and 30 kHz) for 6 min at 4° C. and centrifuged at 13 000×g for 20 min. The supernatant was used as a crude intracellular enzyme extract.

Alkane Hydroxylase Assay

Alkane hydroxylase activity was measured using a cofactor (NADPH) depletion assay to determine relative activities. The supernatant containing the enzyme was diluted into phosphate buffer (0.1 M, pH 8), alkane substrate (0.5-1 mM), and dimethyl sulfoxide (DMSO; 1%, v/v). Alkanes were added to the buffer using alkane stock solutions in DMSO. The reaction was initiated by addition of NADPH (200 μM), and the oxidation of NADPH was monitored at 340 nm (Glieder et al., 2002). The alkane substrate used was hexadecane.

Lipase Assay

The lipase activity assay was conducted based on the spectrophotometric method described by Schultz et al., (2007) with some modifications. The stoichiometric release of p-nitrophenol (p-NP) was measured from cleavage of p-nitrophenyl palmitate (p-NPP). p-NPP stock solution at concentration 100 mM was prepared in acetone and 30 µl was added to 2.82 mL of measuring buffer (0.1 M sodium phosphate, 10% v/v acetone, 4% v/w Triton X-100, 0.2% w/v gum arabic, pH 8.0). The prepared solution was incubated for 5 minutes in 60° C. water bath. Subsequently, it was cooled to 29° C., added to a pre-warmed cuvette (29° C.), containing 150 µl of the lipase solution and placed into the temperature-controlled spectrophotometer (Spectrophotometer CARY 300 UV-VIS). No mixing and no agitation were carried out. The measurements were conducted at 410 nm.

Preparation of the Chitosan Nanoparticles

Chitosan nanoparticles (CSNPs) were generated based on the ionotropic gelation technique, which exploits the electrostatic interaction between cations (amine group of chitosan) and a polyanion (TPP) (Pulicharla et al., 2016).

Firstly, chitosan (CS) at a concentration of 2.5 mg/mL was dissolved in 2% acetic acid solution, and the pH was adjusted to 5.5 using 0.5 M NaOH. CS solution was constantly stirred for 1 h, with the speed ranging between 200 and 300 rpm. TPP stock solution was prepared by dissolving TPP in deionized water to obtain its final concentration at 0.25 mg/mL. Subsequently, CS and TPP solutions were filtered via a 0.45 µm membrane. A mixture of intracellular and extracellular enzymes of 10 mg/mL concentration (1:1 w/w) was added to chitosan solution and stirred for 15 minutes at ambient temperature. Later, the TPP solution was added dropwise to enzyme-chitosan (ENZ-CS) solution, with different ratios (1:1 to 7:1). All the suspensions were stirred for 1 hour at 250 rpm. Afterward, 0.03% (v/v) of glutaraldehyde was added to all solutions and stirred for an extra hour at the ambient temperature. Finally, the suspensions were ultracentrifuged at 47,815×g for 2 h at 4° C. The supernatant was separated and used to estimate the entrapment efficiency by measuring the unbound proteins. The pellet containing nanoparticles (NPs) was suspended in deionized water and used for further analysis.

Encapsulation Efficiency

As mentioned earlier, the encapsulation efficiency (EE) was established by measuring the concentration of free enzyme in the supernatant, separated after ultracentrifugation. EE was calculated using the Equation (1):

$$EE = \frac{\text{Total enzyme activity used in formulation} - \text{activity of the free enzyme}}{\text{Total enzyme activity used in formulation}} * 100 \qquad \text{Eq. (1)}$$

Characterization of Enzyme-Loaded Chitosan Nanoparticles:

Particle Size and Zeta Potential

The dynamic light scattering technique (25° C., detection angle 90°) was used to determine the particle size, size distribution (polydispersity index (PDI)) and zeta potential of nanoparticles. All measurements were performed using Zetasizer (Malvern Instruments, US). The average particle size was approximated as the z-average diameter. The width of the distribution was defined as the PDI.

All measurements were performed in triplicate, and the results were reported as a mean±standard deviation.

Fourier Transform Infrared Spectroscopy

The characterization of the bonding between generated nanoparticles with encapsulated enzymes was analyzed by Fourier Transform Infrared Spectroscopy (FTIR) in transmission mode (Cary 670 FTIR Spectrometer). This technique helps to identify possible functional groups, which are responsible for nanoparticles stabilization. Spectra were performed at resolution 4 cm$^{-1}$, in the range of 4000-400 cm$^{-1}$ with 100 scans.

Morphological Observations

The morphology and size of the generated nanoparticles were investigated using scanning electron microscopy (SEM) (Carl ZeissEVO®50). The SEM samples were prepared by placing small drops of the diluted solution of nanoparticles on the aluminum foil and then dried at room temperature. The foil was fixed on the SEM instrument and coated with gold metal using a sputter coater.

In Vitro Enzyme Release Study

Encapsulated crude enzyme release from the nanoparticles complex was performed in two solutions: double distilled water (DDW) (pH 7) and phosphate buffer saline (PBS) solution (pH 7.4). Enzyme-loaded CS nanoparticles were suspended in each of these solutions. Later, they were incubated at ambient temperature. At specific time points, the samples of nanoparticles were collected and centrifuged for 30 minutes, 25,000×g, 4° C. The supernatant was separated to measure the free alkane hydroxylase and lipase activities.

Stability of the Free and Immobilized Enzymes

Double distilled water was used for measuring the stability of the free and immobilized alkane hydroxylase and lipase. Solutions of the immobilized and free enzyme were slowly homogenized and incubated at room temperature to measure the stability of both enzymes in time. Samples were drawn at 1, 5, 10, 15, 25 and 30 days for the determination of relative activity of enzymes.

Statistical Analyses

Data in this study were summarized as the mean±standard error (SD). Release profiles of enzymes from chitosan nanoparticles in both DDW and PBS were statistically evaluated using analysis of variance (ANOVA). Data from the three replicates of enzymes release were expressed as the mean±standard deviation.

Results and Discussion

Optimization of ENZ-CS and TPP Mass Ratio

Enzyme-loaded Chitosan nanoparticles (ENZ-loaded CSNPs) containing embedded alkane hydroxylase and lipase were prepared by ionotropic gelation technique (Calvo et al., 1997). Based on the electrostatic interaction between the positively charged amino group of CS and oppositely charged phosphate of TPP. This technique was slightly modified by including glutaraldehyde at the end of the reaction, where the Schiff base reaction led to the higher stability of the nanoparticles by polymer crosslinking.

The choice of adding TPP into the protein-CS solution rather than adding TPP into CS solution was based on a previous study of Bahreini et al., (2014) on enzyme encapsulation. In this study, both methods were tested and resulted in higher entrapment efficiency when adding TPP prior to mixing enzyme with chitosan, but no significant differences were observed in the particle size and zeta potential. This observation can be explained by possible interactions of the enzyme molecules with CS polymer before the addition of the cross-linker (Bahreini et al., 2014).

CS-TPP mass ratio was stated as a key parameter that influences the TPP and ENZ-CS cross-linking efficacy for nanoparticles formation. In fact, Jonassen et al., (2012a) and Koukaras et al., (2012a) have reported that the long-term physical stability of chitosan nanoparticles cross-linked with TPP is affected by the ionic strength, the chitosan concentration, and the chitosan/TPP ratio employed in the particle preparation. Thus, an optimization study of ENZ-CS/TPP ratio was carried out to obtain higher encapsulation efficiency. In fact, the nanoparticles formation started spontaneously after adding TPP to the ENZ-CS solution; the rapidity of their reaction is due to the molecular linkage between the positively charged chitosan amino groups and oppositely charged TPP phosphate ions (Rampino et al., 2013).

Figure 13:
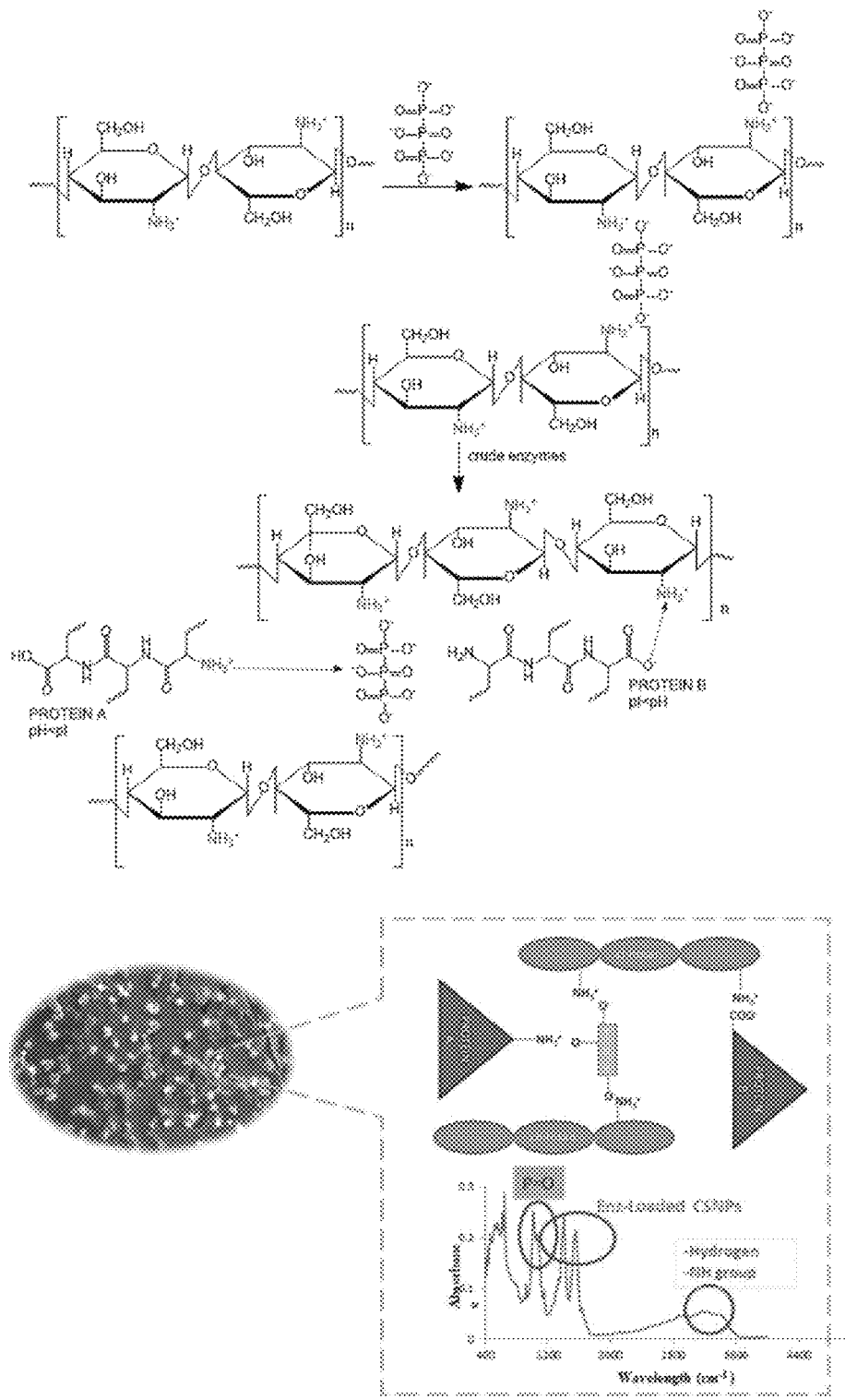
FIG. 13. Hypothesis of the mechanism of immobilization of enzymes in chitosan nanoparticles.

Thus, chitosan mixed with the crude enzyme and TPP mass ratio varied from 1:1 to 7:1 as given in Table 6.

occurred due to the reduction of chitosan —$NH_3^+$ groups caused by further enzyme loading (Bahreini et al., 2014). The crude enzyme was used for nanoparticle loading thus the enzyme solution contained a mixture of proteins, which possess various physicochemical features (i.e. pI, structure). Hence, during cross-linking, the negatively charged groups on protein surface was neutralized by positively charged amine groups of chitosan as shown in FIG. 13 (protein A situation). Additionally, —$NH3^+$ groups on the enzyme

TABLE 6

Parameters for optimization of CS -TFP mass ratio.

| Chitosan/Sodium tripolyphosphate ratio | Particle size (nm) | Zeta potential (mV) | PDI | pH of chitosan solution (SD ± 0.05) | pH of the formulation (SD ± 0.05) |
| --- | --- | --- | --- | --- | --- |
| 1:1 | 720.4 ± 8.2 | +36.7 ± 2.0 | 0.55 ± 0.12 | 550 | 5.89 |
| 2:1 | 814.1 ± 4.5 | +34.2 ± 3.0 | 0.56 ± 0.08 | 550 | 5.66 |
| 3:1 | 1032 ± 9.8 | +31.5 ± 4.0 | 0.50 ± 0.06 | 550 | 5.67 |
| 4:1 | 999.4 ± 5.6 | +24.6 ± 3.0 | 1.00 ± 0.21 | 550 | 5.7 |
| 5:1 | 473.6 ± 7.3 | +21.8 ± 2.0 | 1.00 ± 0.09 | 550 | 5.81 |
| 6:1 | 433.6 ± 4.5 | +21.1 ± 3.0 | 1.00 ± 0.11 | 550 | 5.83 |
| 7:1 | 1104.0 ± 8.7 | +20.4 ± 2.0 | 0.50 ± 0.08 | 550 | 5.64 |

| Chitosan/Sodium tripolyphosphate ratio | Free Alkane hydroxylase activity (U) | Alkane hydroxylase activity in the supernatant (U) | Specific activity of the encapsulated alkane hydroxylase (U/µg proteins) | % of encapsulation of alkane hydroxylase | Free lipase activity (U) | Lipase activity in supernatant (U) | Specific activity of the encapsulated lipase (U/µg proteins) | % of encapsulation of lipase |
| --- | --- | --- | --- | --- | --- | --- | --- | --- |
| 1:1 | 115.6 ± 2.1 | 58.9 ± 1.1 | 1.9 ± 0.1 | 49.0 | 254.4 ± 1.4 | 140.2 ± 2.4 | 3.9 ± 0.1 | 44.8 |
| 2:1 | 154.1 ± 3.3 | 83.7 ± 0.8 | 2.5 ± 0.1 | 45.7 | 310.3 ± 2.7 | 163.0 ± 3.7 | 5.3 ± 0.2 | 47.4 |
| 3:1 | 173.6 ± 2.9 | 86.74 ± 1.2 | 2.9 ± 0.3 | 50.0 | 405 3 ± 5.8 | 208.1 ± 4.6 | 6.6 ± 0.2 | 48.6 |
| 4:1 | 185.0 ± 2.0 | 79.2 ± 0.7 | 3.9 ± 0.4 | 57.2 | 433.7 ± 5.0 | 187.0 ± 3.5 | 8.5 ± 0.6 | 54.5 |
| 5:1 | 192.7 ± 1.7 | 80.2 ± 1.3 | 3.9 ± 0.6 | 58.3 | 449.8 ± 5.6 | 164.2 ± 2.7 | 11.7 ± 0.4 | 67.1 |
| 6:1 | 198.2 ± 2.4 | 179.7 ± 1.8 | 0.5 ± 0.04 | 9.3 | 507.7 ± 6.5 | 459.4 ± 8.5 | 1.5 ± 0.1 | 9.5 |
| 7:1 | 202.4 ± 1.8 | 204.1 ± 1.5 | 0.0 | 0.0 | 515.0 ± 7.3 | 507.3 ± 6.6 | 0.2 ± 0.03 | 1.5 |

The ENZ-CS/TPP ratio of 5:1 showed the highest alkane hydroxylase and lipase encapsulation with 58.3% for alkane hydroxylase and 67.1% for lipase. Moreover, the calculation of the specific activity of the encapsulated alkane hydroxylase and lipase confirmed the results with the best encapsulation shown for the ratio 5:1 with 3.9 U/µg and 11.7 U/ug, respectively. The ratio 4:1 for the encapsulated alkane hydroxylase showed the same specific activity as the ratio 5:1 (3.9 U/µg). Further decrease in ENZ-CS/TPP ratio led to the aggregation of the particles and high reaction response rate. The higher the volume of TPP, the more turbid the solution became, indicating a shift to higher particle size (Jonassen et al., 2012a). Comparable results were found by Zhang et al., (2004) who reported an optimum ratio of 5:1 resulting in the finest particle size, while Koukaras et al., (2012b) reported an optimum of 4:1.

Low ratios of 1:1 to 4:1 showed the appearance of high turbidity, due to the increased aggregation of nanoparticles and a shift to higher particle size. Jonassen et al., (2012b) confirmed the high turbidity when switching from a particle size of 720.4 nm to 1032 nm. Thus, these ratios were discarded. Nanoparticle aggregation takes place under some conditions, such as inappropriate homogenization speed, or a higher concentration of cross-linker (Gan and Wang, 2007).

Furthermore, with the decrease in ENZ-CS/TPP mass ratio from 7:1 to 1:1, zeta potential increased from +21.1 to +36.7 mV, respectively, and pH of the resulting formulation ranged from 5.64 to 5.89. The diminution of zeta potential surface might be counteracted by polyanionic TPP molecules (FIG. 13, protein B situation). This results in compression of the proteins inside the particles and on their surface. The nanoparticles, as potential protein carriers, must be able to ionically hold the active molecules. Thus, the sufficient zeta potential value is essential for these nanoparticles. Particles with zeta potential between 20-25 mV exhibit relative stability (Lee et al., 2004). On the other hand, alkane hydroxylase encapsulation increased from 0% to 58.7% with decreasing ENZ-CS/TPP ratio from 7:1-5:1 and increased lipase encapsulation from 1.5% to 67.1% for the same ratios. And even further decrease in ENZ-CS/TPP ratio resulted in no significant change in the encapsulation of ENZ and in fact increased the particle size.

The immobilization of lipase on $SnO_2$ hollow nanotubes investigated by Anwar et al., (2017) showed an efficiency of 89%. Also, lipase nanohybrid synthesized using cobalt chloride studied by Kumar et al., (2018) exhibited 181% higher activity compared to the free lipase. Moreover, Gill et al., (2017) reported 59% and 70% of laccase encapsulation efficiency when using alginate and silica incorporated into alginate, respectively as supports. Patel et al., (2016) demonstrated the improvement of the immobilization efficiency of laccase, from 83.5% to 90.2%, when using glutaraldehyde as a crosslinker.

Fourier Transform InfraRed Spectrometry Study

Figure 14:
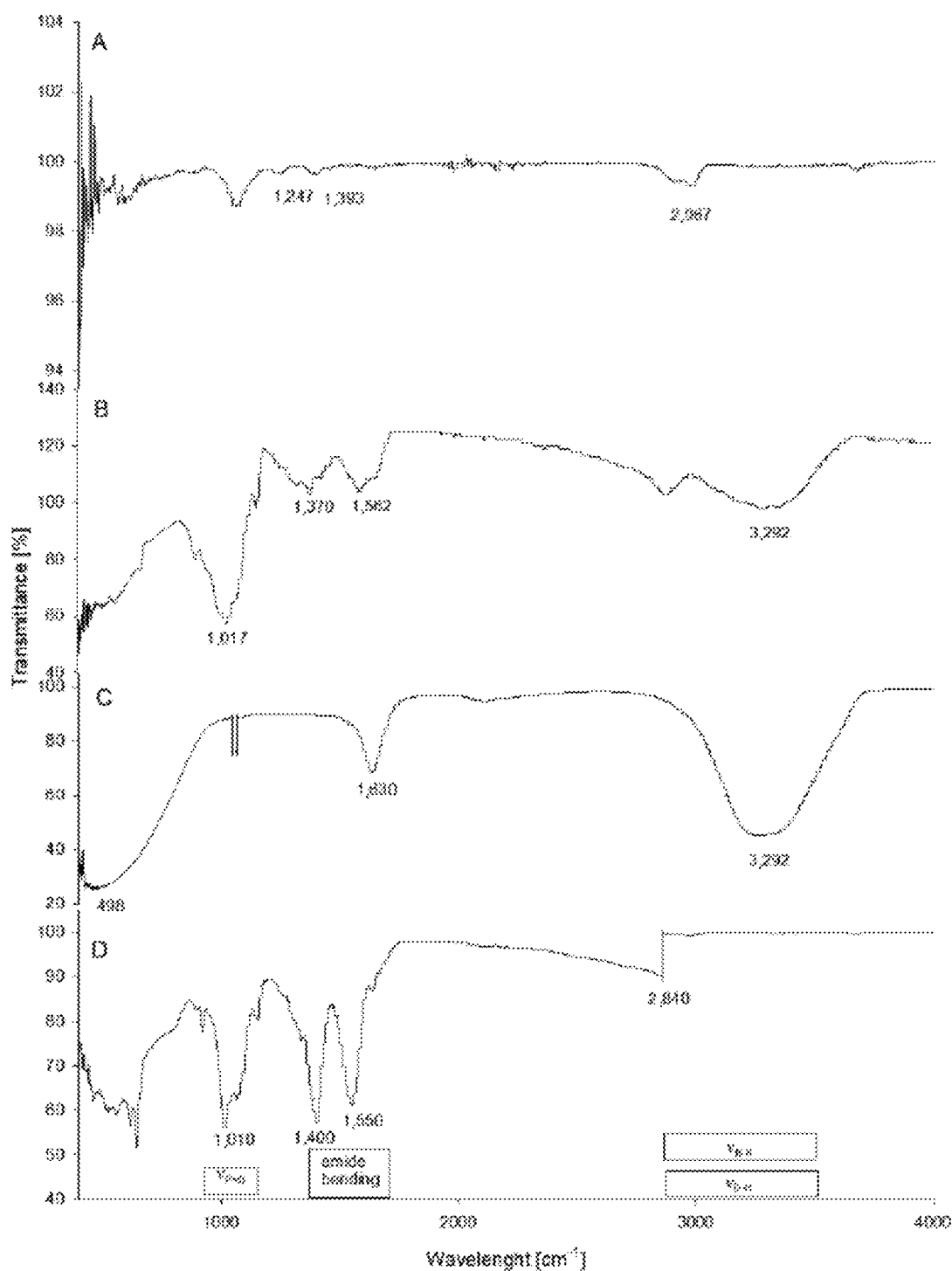
FIG. 14. FTIR spectra of (A) Crude enzyme, (B) Chitosan, (C) Non-encapsulated enzyme, and (D) ENZ-loaded CSNPs.

The FTIR spectra for the enzyme (A), CS (B), CS blank NPs (C), and ENZ-loaded CSNPs (D) are shown in FIG. 14. The peaks at 2,967 $cm^{-1}$ in the enzyme spectrum (A) and at 3,292 cm$^{-1}$ in the CS spectrum (B) relate to the stretching of O—H and N—H bonds. In the CSNPs spectrum (C), the peak at 3,292 cm$^{-1}$ becomes much more intense; pointing out the —NH$_3^+$ interactions with negatively charged TPP. A corresponding peak in the ENZ-loaded CSNPs (D) at 2840 cm$^{-1}$ becomes wider; this effect is attributable to the participation of the enzyme in hydrogen bonding and —NH group interactions (Wu et al., 2005).

In CS blank NPs, the 1,562 cm$^{-1}$ peak of —NH$_2$ bending vibration shifts to 1,630 cm$^{-1}$ and became sharper. This can be a hydrogen bond and amide bond linkage in chitosan with phosphoric groups of TPP; inter- and intra-molecular interactions are enhanced in CS blank NPs (Knaul et al., 1999). A shift from 1,017 cm$^{-1}$ to a peak at 1,051 cm$^{-1}$ in CS blank NPs to a sharper peak at 1010 cm$^{-1}$ in ENZ-loaded CS NPs corresponds to the stretching vibration of the P=O groups.

Two high-intensity peaks at 1,550 cm$^{-1}$ (amide I bending) and 1,400 cm$^{-1}$ (amide II bending) in ENZ-loaded CSNPs correspond to the small intensity peaks at 1,393 and 1,247 cm$^{-1}$ in the enzyme spectra and to the peaks at 1,562 cm$^{-1}$ and 1,370 cm$^{-1}$ in CS spectra. These results prove successful loading of the enzyme in CSNPs and also indicates some interactions between CS with TPP and the crude enzyme (Xu and Du, 2003).

Morphology Study

Figure 15:
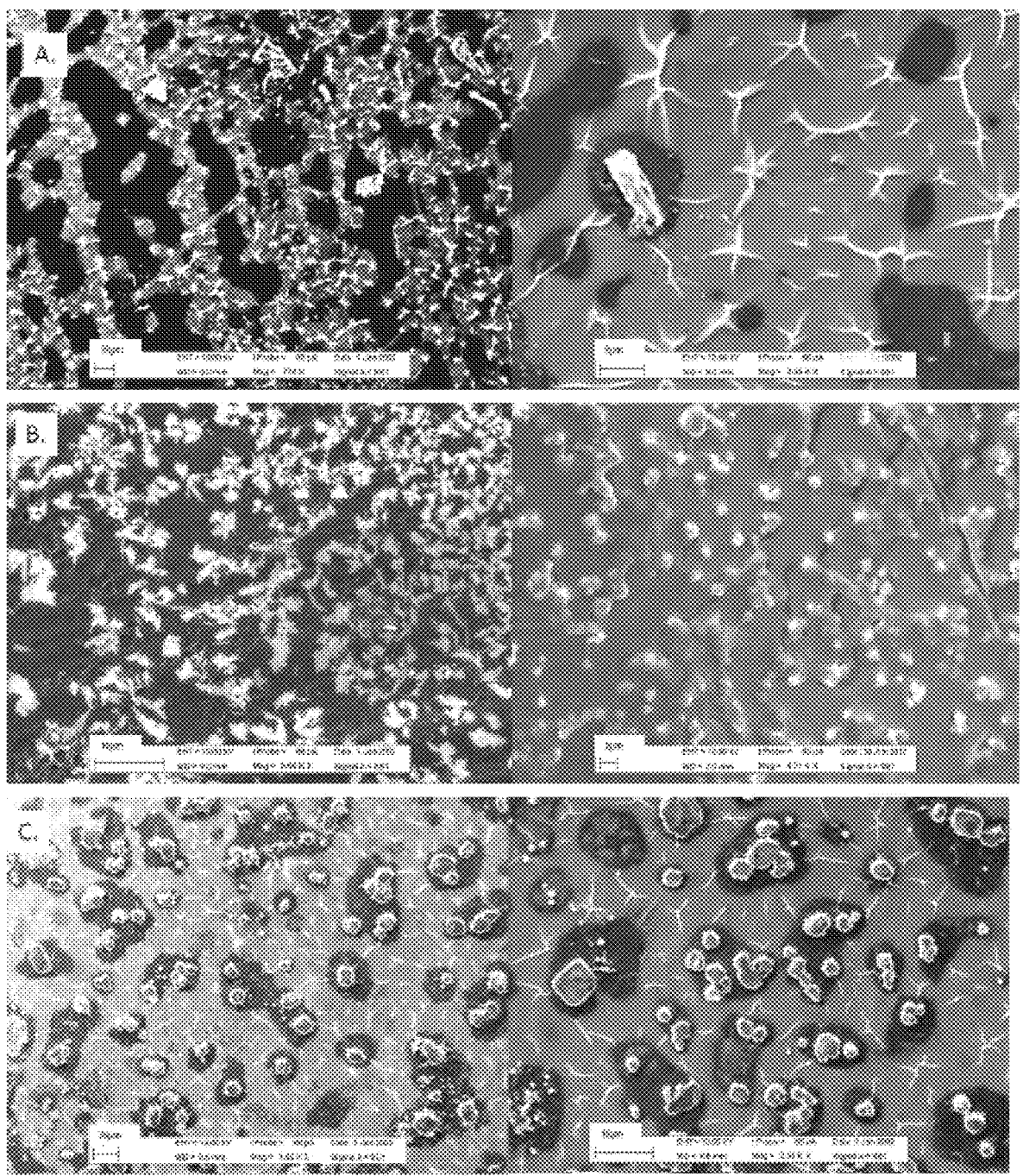
FIG. 15. Scanning electron microscopy images of CSNPs (A), ENZ-loaded CSNPs (B) and; a non-encapsulated enzyme (C). Particles size shown in SEM is 203 nm for CSNPs and 430 nm for ENZ-loaded CSNPs.

FIG. 15 shows the morphological characteristics of CSNPs (A), ENZ-loaded CSNPs (B) and the supernatant of chitosan solution containing the non-encapsulated enzymes (C). From the SEM images, it can be noticed that CSNPs (A) have a spherical morphology with some irregularities on the surface (white needle-like structures). ENZ-loaded CSNPs (B) are also spherical, however, their surface smoothens. In both cases, the particles aggregate, which may have been generated during the drying step (Luo et al., 2010). As for the morphology of the supernatant (C), it shows the same rough spherical morphology as FIG. 15 (A) with non-regular spheres in between which are obviously the enzymes. Furthermore, the nanometric size estimated through DLS (Dynamic Light Scattering) of the enzymatic preparation is correlated to the average particle size revealed by SEM which is ~430 nm.

Figure 16:
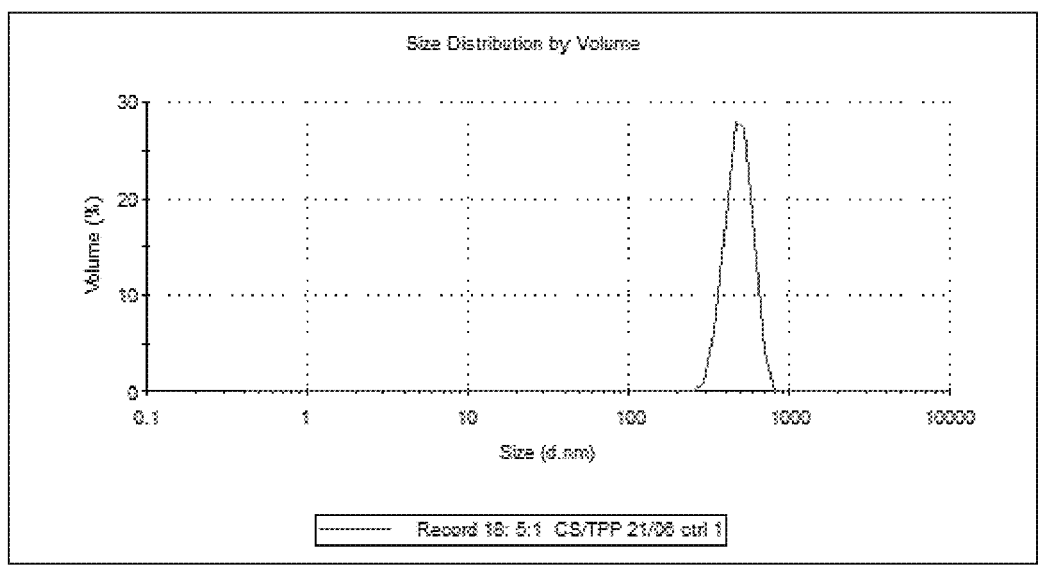
FIG. 16. Particles size distribution of enzyme loaded optimum chitosan nanoformulation (CS/TPP 5:1 mass ratio).

In FIG. 15 (A), a fairly uniform particle size distribution (the average size is ~203 nm) and the smooth border around the CS blank NPs was noticed. In FIG. 15 (B), ENZ-loaded CSNPs showed an asymmetrical, but smoothened spherical shape that is obviously induced by the presence of the enzyme. It can also be noted that the size of the core of the ENZ-loaded CSNPs (the average size is ~430 nm; FIG. 16) is approximately 2-fold larger than the particle size of CSNPs. Consequently, it could be assumed that the significantly increased size of the ENZ-loaded CSNPs estimated through SEM and also through DLS is due to the enzymes that coated the surface. The protein effect on the nanoparticle size and their shape due to the chitosan-protein ionic interaction has been previously reported by Rampino et al., (2013). Furthermore, in another study of Sadighi and Faramarzi, (2013), it was discovered that laccase immobilization on the surface of CSNPs induced a change in the nanoparticles' morphology. Unloaded chitosan nanoparticles were reported as polyhedron shaped, however, due to the bovine serum albumin incorporation in CS, the particles became spherical and smooth surfaced which is comparable to this study (Gan et al., 2005).

In Vitro Alkane Hydroxylase and Lipase Release Study

Figure 17:
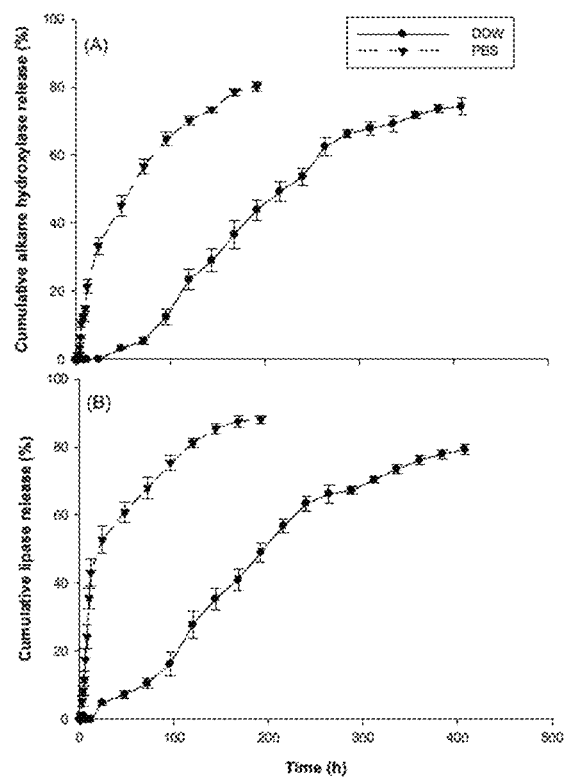
FIG. 17. Alkane hydroxylase (A); and lipase (B) release profiles from the ENZ-loaded CSNPs in two different solutions: double distilled water and phosphate buffer saline.

FIG. 17 shows alkane hydroxylase and lipase release profiles from the ENZ-loaded CSNPs in two different solutions (DDW and PBS) that have approximately the same pH as the ones that can be found in petroleum contaminated water and soil. Alkane hydroxylase loaded CSNPs incubated in DDW (pH 7) (FIG. 17 (A)) showed no release until the first 24 h. A release of 3.2% was shown starting from 48 h, 36.7% release for one week, and 74.3% release for 17 days. Alkane hydroxylase release in PBS was negligible after 3 hours (1.2%), 33.4% release during 24 h, 45.2% release during 48 h and 80.3% release after 8 days only. Further increase in release time resulted in no significant change ($p>0.05$).

Lipase loaded CSNPs incubated in DDW (pH 7) (FIG. 17 (B)) showed no release until the first 24 hours with 4.8% release. A 41% release was shown for one week, and 79.3% release after 17 days. Alkane hydroxylase release in PBS with started after 2 hours (1.3%). 52.8% release was shown during 24 h, 60.9% release during 48 h, and 88.1% release after 8 days only. After 8 days no significant change in the release was shown ($p>0.05$). Several factors influence the burst release of enzyme from CSNPs such as pH of the solution and ionic strength of PBS (Bahreini et al., 2014).

Firstly, pH is a crucial parameter in the stability and release of the protein from the CS matrix. The $pK_a$ value of CS is 6.5, thus the —NH$_2$ groups of CS are protonated at lower pH (—NH$_3^+$). However, when pH is higher than its $pK_a$ the amine group is converted to non-ionized state. This results in the reduction of the cross-linking area with negatively charged TPP molecules (Mao et al., 2001; Shu and Zhu, 2000). Moreover, with the increase of pH, the increased permeation of water occurs (Ajun et al., 2009). Hence, at neutral pH of this study, the CSNPs may undergo elongation due to the diffusion, which leads to an extension of particle size and release of protein.

The CS-TPP interaction may also be influenced by the ionic strength of the media. The presence of NaCl in PBS buffer at lower or moderate concentrations resulted in enhancement of the CSNPs swelling, which attenuated the CS-TPP interaction and disintegrated NPs (López-León et al., 2005). Hence, the CSNPs increase their volume by swelling and then their structure collapses which lead to the biomolecule release. This may be the reason for the faster release of enzymes in PBS solution than in DDW solution.

Kinetics of the Release Study

The ENZ release from CSNPs was fitted to the most common kinetic models to determine the release characteristics. The parameters of the release study for various mathematical models are presented in Table 7. Based on the higher linearity of the plots ($R^2>0.97$), the best model that fits the alkane hydroxylase release in DDW is a zero-order kinetic model. This results in their slow release from CS matrix, however, the release does not depend on the concentration of the initial enzyme (Costa and Lobo, 2001; Miastkowska et al., 2016). This result can be confirmed by diffusional release exponent value (n~1). In the case of the release of alkane hydroxylase in PBS, it followed the Higuchi kinetic model ($R^2>0.93$) (Higuchi, 1963). The results suggested that the discharge of the biomolecule is based on the Fick's diffusion law (Costa and Lobo, 2001). Hence, the release of the biomolecule depends on the diffusion rate throughout the CS matrix in both cases.

TABLE 7

Kinetic model parameters fitting into the enzyme release study.

| | | | Alkane hydrosylase | | lipase | |
|---|---|---|---|---|---|---|
| Model | Equation | Parameter | DDW | PBS | DDW | PBS |
| Zero order | $Q_t = Q_0 + K_0 t$ | $R^2$ | 0.979 | 0.903 | 0.978 | 0.803 |
| First order | $\ln Q_t = \ln Q_0 + K_1 t$ | $R^2$ | 0.732 | 0.598 | 0.807 | 0.478 |
| Higuchi | $Q_t = Q_0 + K_H t^{1/2}$ | $R^2$ | 0.932 | 0.983 | 0.953 | 0.932 |
| Korsmeyer-Peppas | $Q_t = Q_0 + K_{KP} t^n$ | $n\ R^2$ | 0.993 0.977 | 0.561 0.976 | 0.895 0.981 | 0.434 0.941 |

$Q_t$ - the activsty of enzymes released in time t;
$Q_0$ - initial activity of enzymes:
$K_0$ - zero-order kinetic constant;
$K_1$ - first order kinetic constant;
$K_H$ - Higuchi kinetic constant.
t - time.

The lipase release in DDW and PBS followed the Korsmeyer-Peppas model (Korsmeyer et al., 1983). In DDW, the diffusional release exponent value was between 0.5 and 1, thus the lipase discharge is non-Fickian (anomalous transport). However, in PBS the n value decreased (n<0.5), which suggests that lipase release depended on the diffusion (Fick's first law).

As can be observed, the kinetic model depends on the media in which CS-ENZ particles are present. As discussed earlier, PBS has higher ionic strength than DDW, which results in CS particles swelling and faster release than in solutions with low ionic strength (Shu and Zhu, 2002). Hence, the release kinetic model changes with the alteration of the media. Furthermore, alkane hydroxylase and lipase do not follow the same release model. This suggests that the interaction between the media and CSNPs differs due to the variable structure or overall charge (pI).

In Vitro Half-Life of Free and Immobilized Enzymes

Figure 18:
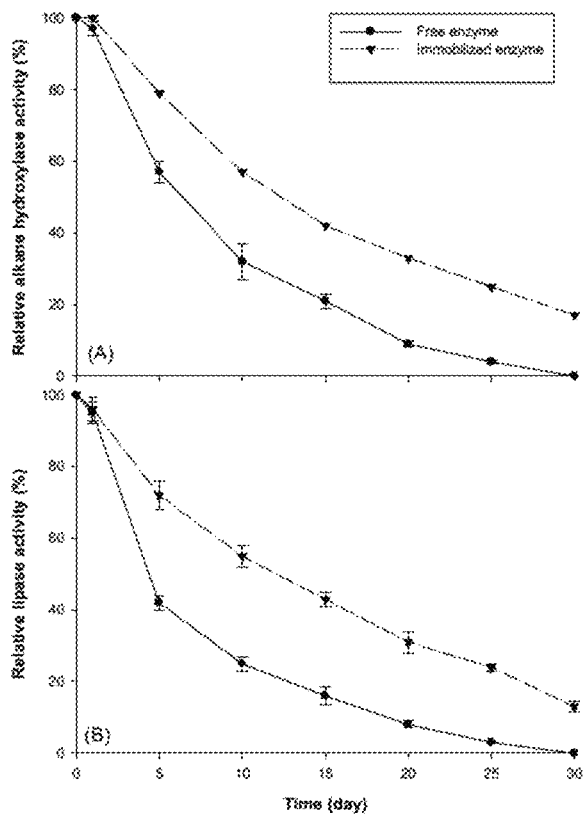
FIG. 18. In-vitro half-life of the free and immobilized alkane hydroxylase (A) and; lipase (B).

In general, the free enzymes are not stable and rapidly lose their activity (Zaak et al., 2017). Gradual and faster depletion of catalytic activity with time and recovery problems after reactions limited the applications of free enzymes. Thus, different immobilization technologies were investigated to overcome these barriers (Guzik et al., 2014). The higher half-life of the enzyme reflects their stability and is one of the main standards to estimate the performance of the enzyme. Consequently, immobilized enzymes are considered more performant compared to the free enzyme. FIG. 18 (A) and FIG. 18 (B) exhibit the profiles feature of the free and immobilized alkane hydroxylase and lipase. Both enzymes were kept at room temperature for up to 30 days and their activities were determined periodically to evaluate their half-life. The results demonstrated that both alkane hydroxylase-loaded CSNPS and lipase-loaded CSNPs had longer half-life than the free enzymes in a one-month study period. Moreover, the deactivation constant $k_d$ is lower for both immobilized enzymes than that for the free enzymes (Table 8) which were also reported in previous studies (Patel et al., 2017d).

TABLE 8

Half-life of the free and immobilized enzymes.

| | Free lipase | Immobilized lipase | Free alkane hydroxylase | Immobilized alkane hydroxylase |
|---|---|---|---|---|
| Half-life (day) | 4.62 | 11.60 | 5.96 | 11.95 |
| Deactivation constant $k_d$ (day$^{-1}$) | 0.15 | 0.06 | 0.12 | 0.06 |

During the first 5 days of incubation, free alkane hydroxylase lost 43% of its activity while immobilized alkane hydroxylase lost only 21% of the activity. Lipase free enzyme lost 58% of activity after the first 5 days while the immobilized form of lipase maintained 72% of its activity. After 30 days, free alkane hydroxylase and also free lipase lost 100% of their catalytic activity, while immobilized alkane hydroxylase and lipase maintained 17% and 13% of the initial activity, respectively.

Same results were found for oxidoreductase type of enzymes, such as laccase immobilized on polymeric nanofibers with 60% residual activity of the immobilized enzyme and almost no activity for the free laccase after 10 days (Xu et al., 2013). Chiou and Wu, (2004) observed that the activity of lipase decreased more than 50% in 5 days, while the lipase immobilized to wet chitosan beads did not show any activity reduction up to 30 days at 25° C. (Chiou and Wu, 2004).

Conclusion

A successful nanoencapsulation of alkane hydroxylase and lipase produced from the hydrocarbonoclastic bacteria *Alcanivorax borkumensis* in chitosan polymer has been achieved with homogeneously nanosized particle formation. To the best of our knowledge, this is the first report about immobilization of enzymes produced from *Alkanivorax borkumensis* and also first report on nanoencapsulation of lipase and alkane hydroxylase using chitosan. Different enzyme-chitosan/tripolyphosphate ratios were studied and (5:1) was maintained for the best entrapment efficiency for both alkane hydroxylase and lipase with a particle size and a zeta potential of 473 nm and +21.8, respectively. Entrapment efficiency for alkane hydroxylase loaded chitosan nanoparticles CSNPs and lipase loaded chitosan nanoparticles was 58.3% and 67.1%, respectively. Interestingly, the half-life catalytic activity of the immobilized enzymes was very important, even after 30 days compared to the free enzymes. This in vitro study would provide an interesting impetus for the future in vivo study of the formulation of crude enzymes from *A. borkumensis* for the degradation of petroleum hydrocarbons in the field.

Scaling-Up the Production of *Alcanivorax borkumensis* Enzymes

Example 4—Bench-Scale Production of Enzymes from the Hydrocarbonoclastic Bacteria *Alcanivorax borkumensis* and Biodegradation Tests Abstract This study investigates motor oil (3, 5, 7.5 and 10% (v/v)) as a sole carbon source for the production of *Alcanivorax borkumensis* in shake flasks and a 5 L bench-scale fermenter in comparison to the standard media. Shake flask studies showed a significant and higher cell growth (p=0.000038), lipase (p=0.006900) and alkane hydroxylase production (p=0.000921) by *Alcanivorax borkumensis* when motor oil was used as the substrate. Based on Tukey post-hoc tests, 5% motor oil concentration was selected as the optimal substrate concentration. The 5 L fermenter experiments conducted using motor oil at 5% (v/v) concentration, under controlled conditions exhibited significant and higher alkane hydroxylase and lipase activities (55.6 U mL$^{-1}$ (p=0.018418) and 208.30 U mL$^{-1}$ (p=0.020087), respectively) as compared with those of motor oil at 3% (v/v) and n-hexadecane at 3% (v/v) concentration which was used as control. Cell growth was significantly higher when motor oil (3 or 5%) was used as a substrate (p=0.024705).

Enzymatic degradation tested on two different polycyclic aromatic hydrocarbons (PAHs) contaminated groundwaters showed 37.4% removal after 5 days with a degradation rate of 196.6 µg L$^{-1}$ day$^{-1}$ and 82.8% removal after 10 days with a degradation rate of 217.54 µg L$^{-1}$ day$^{-1}$ for the 1$^{st}$ site and an almost complete biodegradation with 95% removal and 499.02 µg L$^{-1}$ day$^{-1}$ removal rate after only 5 days for the 2$^{nd}$ site.

Materials and Methods

All chemical reagents of the highest purity, such as n-hexadecane, NADPH (nicotinamide adenine dinucleotide phosphate), DMSO (Dimethyl sulfoxide) and p-nitrophenyl palmitate among others, were procured from Sigma-Aldrich, Fisher Scientific or VWR (Mississauga, Ontario, Canada). The strain, *Alcanivorax borkumensis* was ordered from DSMZ (Braunschweig, Germany).

Bacterial Strain

The strain used in this study was *Alcanivorax borkumensis* SK2 (DSM 11573). *A. borkumensis* was sub-cultured and streaked on agar plates with an agar concentration of 18 g L$^{-1}$, incubated for 72 h at 30±1° C. and then kept at 4.0±1° C. for future use. The composition of the culture media (per liter of distilled water) is as follows: 23 g NaCl, 0.75 g KCl, 1.47 g CaCl$_2$·2H$_2$O, 5.08 g MgCl$_2$·6H$_2$O, 6.16 g MgSO$_4$·7H$_2$O, 0.89 g Na$_2$HPO$_4$·2H$_2$O, 5.0 g NaNO$_3$, and 0.03 g FeSO$_4$·7H$_2$O (Yakimov et al., 1998). 3% (v/v) n-hexadecane was used as the sole carbon and energy source and considered as a control in this study. The pH value of medium was adjusted to 7.5 with 10% solution of NaOH, and the growth was conducted in a shaking incubator at 30±1° C., 150 rpm for 72 h. Motor oil at different concentrations (3%, 5%, 7.5% and 10% v/v) was also studied as a carbon and energy source.

Motor oil was characterized using Agilent 7890B gas chromatograph (GC) on a VF-5MS-FS column (0.25 mm diameter, 30 m long and 0.25 µm film thickness) coupled to an Agilent, model 5977 A. The mass spectrometer detector operated with a mass range between m/z 60 and 130. The GC column temperature was first kept at 40° C. for 4 min and then heated at a rate of 1° C. min$^{-1}$ up to 52° C. and maintained at this temperature for 18 min. The injection temperature was 40° C. Helium was used as the carrier gas with a column flow rate of 1 mL min$^{-1}$. The composition (in mg L$^{-1}$) is as follows: 69.8 of C$_{10}$-C$_{50}$, 1.83 of naphthalene, 44 of benzene, 530 of toluene, 44 of ethyl-benzene and s 84 of xylene.

Inoculum Preparation

A loopful of *A. borkumensis* from the agar plates was utilized to inoculate a 500 mL Erlenmeyer flask with a working volume of 100 mL. The flask was then incubated at 150 rpm and 30±1° C. for 24 h. A 3% (v/v) inoculum from this flask (first stage) was then used to inoculate 500 mL Erlenmeyer flasks with 100 mL of media containing different motor oil concentrations (3%, 5%, 7.5%, 10% v/v) and 3% (v/v) n-hexadecane. The flasks were shaken and incubated for 24 h. The cells from these flasks were used as inoculum (second stage or pre-culture) for the production of *A. borkumensis* in shake flasks or in the 5 L fermenter.

Fermentation in Erlenmeyer Flasks

Erlenmeyer flasks containing 100 mL of sterilized media with different motor oil concentrations (3%, 5%, 7.5%, 10% v/v) and with 3% (v/v) n-hexadecane and inoculated with 3% (v v$^{-1}$) of pre-culture were prepared, as given earlier. The flasks were incubated in a shaker-incubator for 72 h at 30±1° C., 150 rpm. The colony forming units per mL (CFU mL$^{-1}$), alkane hydroxylase and lipase activity was determined as described in the following sections. Experiments were performed in triplicates. From the results obtained, the optimum motor oil concentrations with the best *A. borkumensis* growth were selected for further fermenter tests.

Fermentation Procedure in 5 L Computer-Controlled Bioreactor

In order to have an evaluation of the impacts of Carbon source on the growth of *A. bokumensis* and on the production of enzymes, the fermentation was performed in a 5 L stirred tank fermenter (Biostat B plus, Sartorius Stedim Biotech, Germany). The working volume was 3 L. Among other accessories, this tank fermenter is equipped with a programmable logic control (PLC) board to monitor dissolved oxygen (DO), anti-foam, pH, impeller speed, temperature, and aeration rate. The calibration of the polarographic pH-electrode (Mettler Toledo, USA) was done using two buffers of pH 4 and pH7 (VWR, Canada). Sodium thiosulfate water was used to calibrate the oxygen probe to zero while air saturated water was used to calibrate it to 100%. The calibration was done before the sterilization cycle. The anti-foaming component that was used in this study is propylene glycol (Sigma-Canada). Then, the fermenter and the medium were sterilized and cooled down. N2 gas and air were sparged to recalibrate the DO probe to zero and 100%, respectively. The agitation rate was varied from 250 to 400 rpm. The temperature was kept at 30±1° C. during fermentation. This was accomplished by circulating water inside the fermenter jacket. The pH value was also maintained at 7.5±0.1 by pumping 4 M NaOH and 3 M H$_2$SO$_4$. During this step, the dissolved oxygen and the pH were continuously controlled by a polarographic dissolved oxygen probe and a pH sensor, respectively. Three media were used: standard medium with 3% (v/v) of n-hexadecane, motor oil at 3% (v/v) and motor oil at 5% (v/v). All the three fermenters were then inoculated with 3% (v/v) inoculum. Sampling was carried out every 6 hours to determine the colony forming units per mL. A part of each sample, a cell-free supernatant obtained by centrifugation at 8000 rpm for 10 min and 4° C. was used to determine protein concentration. Extracellular enzymes activity of lipase was calculated using the supernatant extracted by centrifuging the culture at 8000 rpm for 10 min at a temperature of 4° C.

The pellet with the biomass was resuspended in phosphate buffer (pH 8.0) and then ultrasonicated to recover intracellular alkane hydroxylase crude enzymes as described in the following sections.

Analysis Parameters

Determination of Volumetric Oxygen Transfer Coefficient ($K_La$), Oxygen Transfer Rate (OTR) and Oxygen Uptake Rate (OUR)

The volumetric oxygen transfer coefficient, ($k_La$), measurement was based on the dynamic method (Hatch, 1974; Stanbury et al., 2013), in which the air input was interrupted and, then reinstated. When the aeration was off, the dissolved oxygen decreased and when the aeration was on, the dissolved oxygen increased. All these values were recorded. The $k_La$ was calculated from the mass balance on DO, immediately after each sampling of the fermentation broth. During the batch fermentation, the mass balance for the DO concentrations can be expressed as follows:

$$\frac{dC_L}{dt} = OTR - OUR \quad (1)$$

Where $dC_L/dt$ is the accumulation oxygen rate in the liquid phase

OTR is the oxygen transfer rate from the gas phase to the liquid phase:

$$OTR = k_La(C^* - C_L) \quad (2)$$

OUR is the oxygen uptake rate by the microorganism:

$$OUR = Q_{O_2}X \quad (3)$$

$K_La$ is the volumetric oxygen transfer coefficient
$C^*$ is the oxygen concentration at saturation
$C_L$ is the dissolved oxygen concentration in the medium
$Q_{O2}$ is the specific oxygen uptake rate of the microorganism employed
X is the biomass concentration The DO electrode in the medium was calibrated at 30±1° C. and then shifted to air-saturated distilled water at a known temperature and ambient pressure to transform the concentration of oxygen in the broth from percentage air saturation to mmol $O_2$ $L^{-1}$. This reading was used with the known saturation concentration of oxygen at saturation in distilled water (0.07559 mmol $L^{-1}$) (100%), to determine the saturation concentration of oxygen in the media at 30° C.

Total Cell Count

The viable cells count was determined by counting colonies grown on agar medium with different dilutions. For all counts, the average of triplicate plates was used for each tested dilution and the results were expressed as colony forming units per mL (CFU $mL^{-1}$).

Total Protein and Enzyme Assays

Total Protein Assay

Total protein concentration was determined according to the Bradford method (Bradford, 1976).

Sonication

*Alcanivorax borkumensis* cell pellet was suspended in 1 mL of 0.1 M of phosphate buffer, pH 8.0. Two different ultrasound frequencies of 22 kHz and 30 kHz were used to sonicate the mixture for 6 min (the 30 s off and 30 s on) at 4±1° C. The mixture was then centrifuged at 13 000×g for 20 min to extract the intracellular crude enzyme.

Alkane Hydroxylase Assay

Alkane hydroxylase activity was measured by determining NADPH depletion. The assay mixture was composed of the supernatant containing the enzyme, the phosphate buffer (0.1 M, pH 8), the alkane substrate (0.5-1 mM), and the dimethyl sulfoxide (DMSO; 1%, vol/vol). Alkanes were added to the buffer using alkane stock solutions in DMSO. The reaction starts by adding NADPH (200 μM), and the oxidation of NADPH was estimated spectrophotometrically at 340 nm (Glieder et al., 2002). One unit of enzyme activity is defined as the amount of enzyme required for consumption of 1 nmol of NADPH per min. The alkane hydroxylase substrate used was n-hexadecane.

Exolipase Assay

Lipase activity was evaluated by spectrophotometer using p-nitrophenyl palmitate as the substrate (M. Thoner, Diploma-Thesis, University of Bochum, Bochum, Germany, 1973). The substrate solution was prepared as follows: 30 mg of p-nitrophenyl palmitate diluted in 10 mL of isopropanol was mixed with a solution composed of 90 mL of 0.05 M Sorensen phosphate buffer, pH 8.0, 207 mg of sodium deoxycholate and 100 mg of gum Arabic. 2.4 mL of this pre-warmed substrate solution (37° C.) was mixed with 0.1 mL of the enzyme. After 15 min of incubation at 37° C., the enzyme activity was evaluated at 410 nm against an enzyme-free control. One unit of enzyme activity is defined as the amount of enzyme needed to liberate 1 nmol of p-nitrophenol per minute.

Evaluation of PAHs Biodegradation Capacity and Kinetics

Biodegradation

To test the efficiency of the crude enzyme produced by *Alcanivorax borkumensis* grown in the 5 L fermenter using 5% (v/v) of motor oil as a substrate, the lyophilized extracellular and intracellular crude enzyme (which was stored at −20° C.) was used at a concentration of 1 mg $mL^{-1}$ (this concentration is a 50-50 mixture of the extracellular and intracellular enzyme) for the degradation of groundwater (GW) contaminated with petroleum hydrocarbons which was procured from TechnoRem Inc. from two different confidential sites located near to Montreal city (Quebec, Canada). The initial composition of the contaminated water is presented in Table 9. Degradation tests were performed in hermetically sealed 1 L glass bottles, in order to avoid evaporation, and they were incubated in an incubator shaker at 30° C. and 100 rpm. Samples were taken after 5 and 10 days for degradation analyses. GC-MS was used to quantify the PAH compounds before and after enzymatic degradation using the method MA. 400-HAP 1.1.

TABLE 9

Biodegradation of Contaminated Ground Water with produced enzymes.

| | Initial concentration | Enzymatic treatment | | Initial concentration | Enzymatic treatment | |
|---|---|---|---|---|---|---|
| Compounds | 1st site (ppb) | After 5 days (ppb) | After 10 days (ppb) | 2nd site (ppb) | After 5 days (ppb) | After 10 days (ppb) |
| Acenaphtene | 76.0 | 30.2 | 11.8 | 32.9 | 18.5 | 5.9 |
| Acenaphthylene | — | — | 37.4 | — | — | 8.0 |

TABLE 9-continued

Biodegradation of Contaminated Ground Water with produced enzymes.

| | Initial concentration | Enzymatic treatment | | Initial concentration | Enzymatic treatment | |
|---|---|---|---|---|---|---|
| Compounds | $1^{st}$ site (ppb) | After 5 days (ppb) | After 10 days (ppb) | $2^{nd}$ site (ppb) | After 5 days (ppb) | After 10 days (ppb) |
| Anthracene | 29.4 | 13.7 | 6.6 | 7.96 | 7.5 | 7.6 |
| Benzo(a)anthracene | 13.0 | 11.1 | 10.5 | <7.50 | 1.30 | 4.0 |
| Benzo (b) fluoranthene | <22.4 | <19.8 | <22.0 | <22.40 | <3.70 | <10.10 |
| Benzo(j)fluoranthene | <10.7 | <10.7 | <10.0 | <10.70 | <0.60 | <3.90 |
| Benzo [k] fluoranthene | <8.2 | <8.0 | <8.4 | <8.20 | <2.60 | <7.0 |
| Benzo (c) phenanthrene | — | 14.4 | 7.1 | — | <0 40 | <0.80 |
| Benzo (g,h,i) peylene | <8.9 | 4.6 | 4.4 | <8.90 | 0.70 | 2.7 |
| Benzo(a)pyrene | <7.15 | 6.5 | 4.3 | <7.15 | <1.0 | 6.0 |
| Benzo(e)pyrene | <6.4 | 6.7 | 5.9 | <6.40 | <0.90 | <7.30 |
| Chrysene | 11.2 | 8.3 | 5.3 | <8.55 | 1.10 | 3.7 |
| Dibenzo(a,h)anthracene | <8.9 | <8.0 | 4.9 | 1.61 | <0.65 | 0.8 |
| Dibenzo (a,h) pyrene | — | — | 1.0 | — | <0.25 | <0.30 |
| Dibenzo (a,i) pyrene | <18.5 | 8.9 | 3.8 | <18.15 | <0.90 | <1.05 |
| Dibenzo(a,l) pyrene | — | — | <1.9 | — | <0.55 | <0.50 |
| Dimethyl-1,3 naphtalene | — | — | — | — | — | — |
| Dimethyl-7,12benzo(a) anthracene | — | — | — | — | <0.30 | — |
| Fluoranthene | 64.9 | 45.1 | 5.0 | 52.2 | 8.8 | 14.0 |
| Fluorene | 93.2 | 40.4 | 17.2 | 20.3 | 25.0 | 6.7 |
| Indeno(1,2,3-cd)pyrene | <7.15 | 6.4 | 5.4 | <7.15 | <0.75 | 3.0 |
| Naphtalene | 2170 | 1320 | 291 | 786 | 37.6 | 49.4 |
| Phenanthrene | 146 | 76.1 | 26.6 | 38.6 | 25.9 | 3.1 |
| Pyrene | 33.4 | 31.9 | 3.5 | <8.55 | 5.6 | 14.1 |
| Trimethyl-2,3,5 naphtalene | — | — | — | — | — | — |
| Methyl-1 naphtalene | — | — | — | — | — | — |
| Methyl-2 naphtalene | — | — | — | — | — | — |
| Methyl-3 chloranthrene | — | — | — | — | — | <0.30 |
| Σ PAHs | 2627.1 | 1644.1 | 451.7 | 959.57 | 132 | 129 |
| Removal percentage PAHs (%) | | 37.4 | 82.8 | | 95.0 | 95.1 |

Kinetic Study

The rate of the total PAHs degradation was determined using the first-order kinetic model (Eq (1)). This choice was based on some previous kinetic studies on the biodegradation of petroleum hydrocarbons (Abbassi and Shquirat, 2008).

$$S = S_0 e^{-kt} \quad \text{Eq (1)}$$

Applying the Natural Logarithm of Eq (1):

$$\ln \frac{S}{S_0} = -kt \quad \text{Eq (2)}$$

Where:

S0: initial PAHs concentration,

S: final PAHs concentration, k: specific degradation rate constant, t: degradation time.

Statistical Analysis

All the experiments were performed in triplicates. Data presented are the mean values with standard deviation (±SD). To evaluate the statistical significance of the measured values of cell growth and enzymes production in shake flask and in the fermenter, ANOVA test has been carried out with 95% confidence level using Statistica, version 7.0 (StatSoft, USA) and the results which have p<0.05 were considered as significant. Also, Tukey HSD test has been implemented for the multiple comparisons to emphasize the results obtained using ANOVA.

Results and Discussion

Shake Flask Optimization

Figure 19:
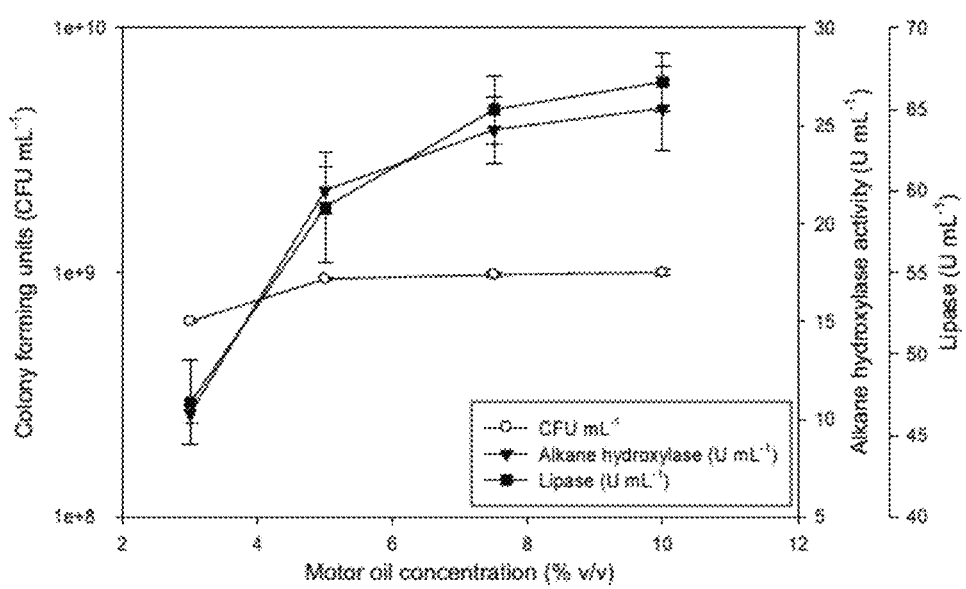
FIG. 19. Effects of different motor oil concentration (% v/v) on the growth of *Alcanivorax borkumensis* and production of alkane hydroxylase and lipase.

The fermentation experiment at different motor oil concentrations (3%, 5%, 7.5% and 10% (v/v)) was conducted in shake flasks using an inoculum volume of pre-culture at 3% (v/v) and the results of cell count, alkane hydroxylase activity and lipase activity at the end of fermentation are presented in FIG. 19. The control in this experiment was the standard medium. The results showed a significant increase in the total cell count (p=0.000038) and in the production of lipase (p=0.006900) and alkane hydroxylase (p=0.000921) when motor oil is used as a substrate in comparison to the standard medium. In contrast, total protein and protease production were not affected by the increase in motor oil concentration (p=0.115 and p=0.2128, respectively).

For the cell count, the increase was approximately uniform with approximately 1.5 times more colony forming units per mL than the control when the concentration of motor oil increased from 3% to 5% (v/v). Further increase in motor oil concentrations (from 7.5% to 10% v/v) generated a flat growth with 1.05 and 1.02 increase in total cell count when increasing the concentration of motor oil from 5% to 7.5% (v/v) and from 7.5% to 10% (v/v), respectively.

Furthermore, Tukey post-hoc analysis showed that the highest significant cell growth was observed with 5, 7.5 and 10% motor oil and that no significant difference was observed between the three different motor oil concentrations.

Mishra and Singh, (2012) studied the growth of three different hydrocarbonoclastic bacteria (P. aeruginosa PSA5, O. intermedium P2 and Rhodococcus sp. NJ2) using 1% (v/v) n-hexadecane and found that the duplication started immediately after incubation with an exponential phase achieved between day 2 and day 4. The authors also observed that the degradation of n-hexadecane was lower when growing *Rhodococcus* sp. NJ2 in comparison with *P. aeruginosa* PSA5 and *O. intermedium* P2, despite a higher bacterial growth.

Chebbi et al., (2017) demonstrated that the newly isolated *Pseudomonas* sp. strain from motor oil-contaminated soil was able to use both motor oil and n-hexadecane, among other hydrocarbons as a sole carbon and energy source.

As a result of the significant increase in cell growth, considerable increases in enzymes activities were noticed when increasing the concentration of motor oil. For example, when the concentration of the added motor oil increased, alkane hydroxylase activity increased in parallel from 10.3±0.5 U mL$^{-1}$ (3% motor oil) to 21.7±1.2 U mL$^{-1}$ (5% motor oil). For lipase, the enzymatic activity increased from 47±2.6 U mL$^{-1}$ to 59±3.4 U mL$^{-1}$, when the motor oil concentration increased from 3 to 5%, respectively. When the motor oil concentration increased to 7.5 and 10%, the lipase activity increased to 65 and 66.7 U mL$^{-1}$, respectively. Tukey post-hoc analysis showed that the highest significant alkane hydroxylase and lipase production was observed with 5, 7.5 and 10% motor oil and that no significant difference was observed between the three different motor oil concentrations.

(OTR) for the three different media: standard media, motor oil 3% v/v and motor oil 5% v/v (which is the optimal concentration obtained from flask experiments based on cell growth, alkane hydroxylase and lipase production). Results are presented in FIG. 20 and the maximum values of these studied parameters are presented in Table 10, with constant values of pH and temperature (7.5 and 30° C., respectively). Determination of these environmental variables is important in scale-up during fermentation (Hsu and Wu, 2002). Agitation rate between 250-500 rpm and air flow rate between 2.5-3.5 L/min were varied to control the DO value and maintain it above the critical required level (>25% saturation based on previously reported works). During the first stage of fermentation (from 0-42 h depending on the media), a decrease in the DO values was detected. Therefore, a higher agitation from 250 to 500 rpm and a higher aeration rate reaching 3.5 L min$^{-1}$ was adopted to maintain high dissolved oxygen greater than 60%. This decrease was followed by an increase, until the end of the fermentation. Thus, the agitation and the aeration were preserved at the same level. The values of oxygen uptake rate (OUR), oxygen transfer rate (OTR) and oxygen transfer coefficient ($k_L a$) are presented in FIG. 20.

TABLE 10

Maximum values of fermentation process parameters in different media.

| Parameters | 3% (v v$^{-1}$) n-Hexadecane | 3% (v v$^{-1}$) Motor Oil | 5% (v v$^{-1}$) Motor Oil |
|---|---|---|---|
| Max. $k_L a$ (h$^{-1}$)$^a$ | 187 ± 4.40 (40 h) | 167.82 ± 7.35 (62 h) | 187.09 ± 10.93 (55 h) |
| Max. OTR (mmol O$_2$ L$^{-1}$ h$^{-1}$)$^a$ | 0.87 ± 0.06 | 0.78 ± 0.06 | 0.87 ± 0.09 |
| Max. OUR (mmol O$_2$ L$^{-1}$ h$^{-1}$)$^a$ | 0.16 ± 0.01 | 0.43 ± 0.05 | 0.21 ± 0.01 |
| Max. specific growth rate (μmax h$^{-1}$)$^a$ | 0.29 ± 0.02 | 0.1236 ± 0.01 | 1.4746 ± 0.09 |
| Max. total cell count (×10$^{10}$ CFU mL$^{-1}$)$^b$ | 0.71 ± 0.08 (72 h) | 2.90 ± 0.39 (60 h) | 3 ± 0.47 (60 h) |
| Max. protein concentration (μg mL$^{-1}$)$^b$ | 154.60 ± 6.30 | 347.60 ± 12.30 | 295.80 ± 12.20 |
| Max. alkane hydroxylase activity (U mL$^{-1}$)$^b$ | 30.10 ± 2.10 | 42.95 ± 3.20 | 55.6 ± 3.80 |
| Max. lipase activity (U mL$^{-1}$)$^b$ | 107.33 ± 4.50 | 236.48 ± 21.50 | 208.30 ± 14.00 |

$^a$The presented values are the mean values obtained from two separate experiments conducted for each fermentation condition.
$^b$The values are the mean of three determinations of two separate experiments conducted for each fermentation condition. The presented values are the mean ± SD. Different letters within the same row indicate the significant differences among these values determined by one-factor analysis of variance (Turkey HSD test, p ≤ D0.05).

These results can be explained by the increase in viscosity and a relative increase in the degree of heterogeneity at a higher motor oil concentration which may cause limitation of oxygen transfer, especially in shake flasks, causing a slowdown in *Alcanivorax borkumensis* growth, and later enzymes production. Increase in osmotic pressure across the bacterial membrane due to increased motor oil concentration could also contribute towards inhibition of growth, and enzymatic production (Dang Vu et al., 2009).

Consequently, motor oil concentration in the range of 3% to 5% (v/v) is the most advantageous for *A. borkumensis* growth and synthesis of enzymes. At higher concentration, the media became less advantageous for microbial growth and enzymes synthesis. This result will be taken into account for the next work when choosing substrates to study the fermentation of *A. borkumensis* in a 5 L bioreactor.

Fermentation Parameters

Profiles of fermentation parameters, namely, dissolved oxygen concentration DO (% saturation), agitation (rpm), aeration (L min$^{-1}$), volumetric oxygen transfer coefficient ($k_L a$), oxygen uptake rate (OUR) and oxygen transfer rate The decrease in DO observed is in coincidence with the exponential growth phase of *A. borkumensis* which required higher OUR. On the other side, the increase in DO and decrease in OUR is the consequence of the stationary growth phase reached by *A. borkumensis* at a lower oxygen rate.

The maximum values of $k_L a$ observed for different media were in the following order: 187.07 h$^{-1}$ (Motor oil 5% v/v) >187 h$^{-1}$ (n-hexadecane 3% v/v) >167.82 h$^{-1}$ (motor oil 3% v/v) (Table 10). These variations in $k_L a$ values depend on several factors, namely aeration and agitation degree, rheological properties of the media and the concentration of antifoam (Stanbury et al., 2013).

Figure 20:
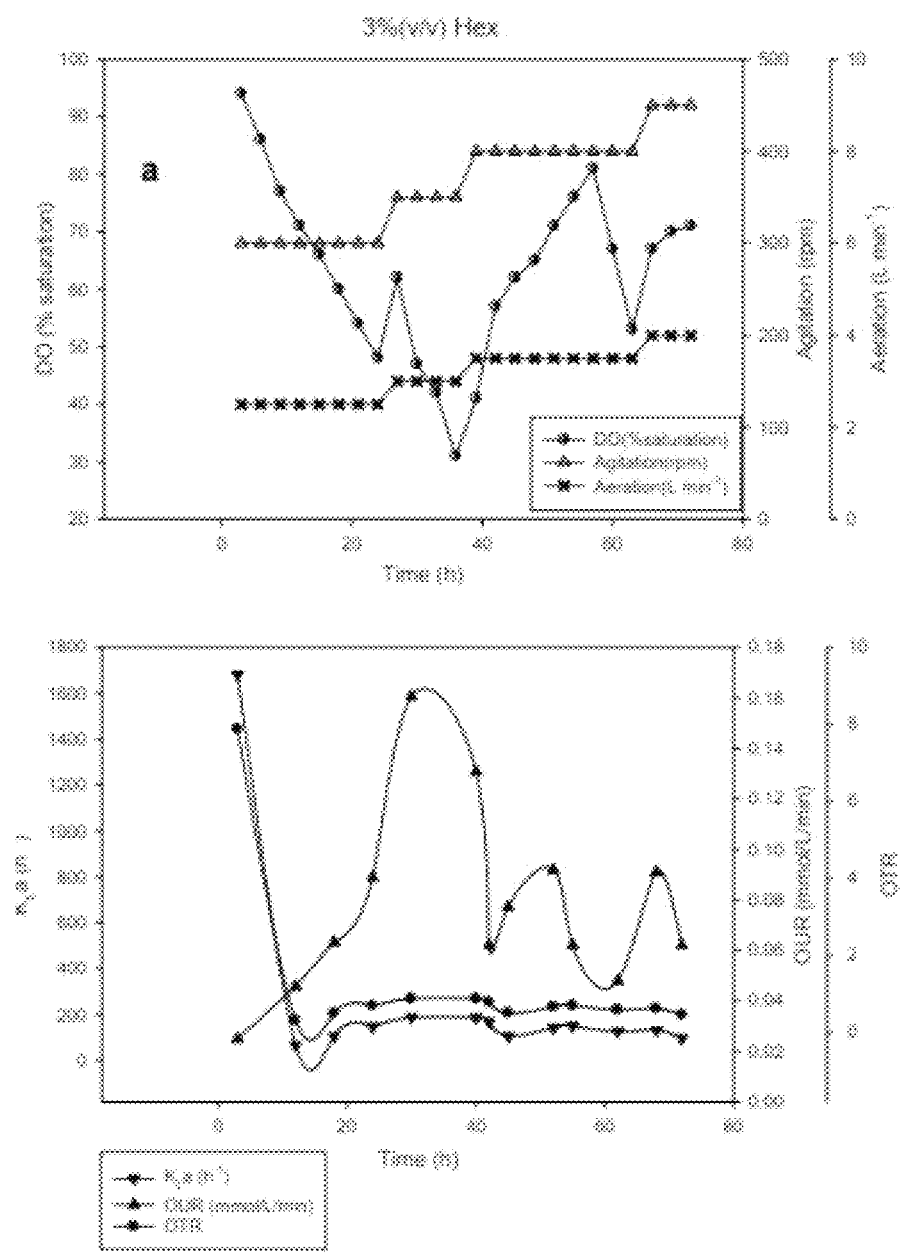
FIG. 20. Fermentation parameters of (a) 3% (v/v) n-Hexadecane, (b) 3% (v/v) Motor oil and (c) 5% (v/v) Motor oil.
Figure 20:
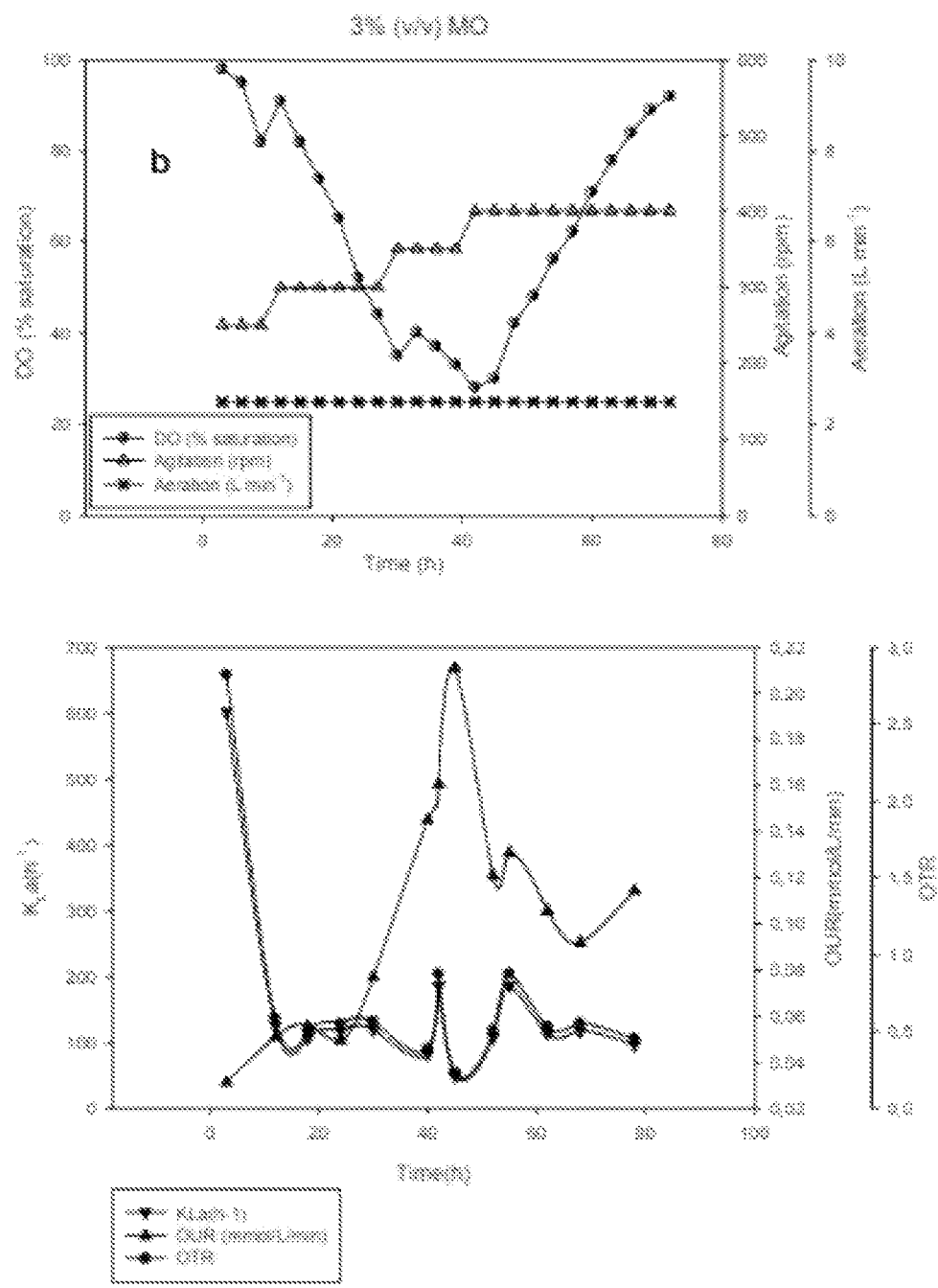
Figure 20:
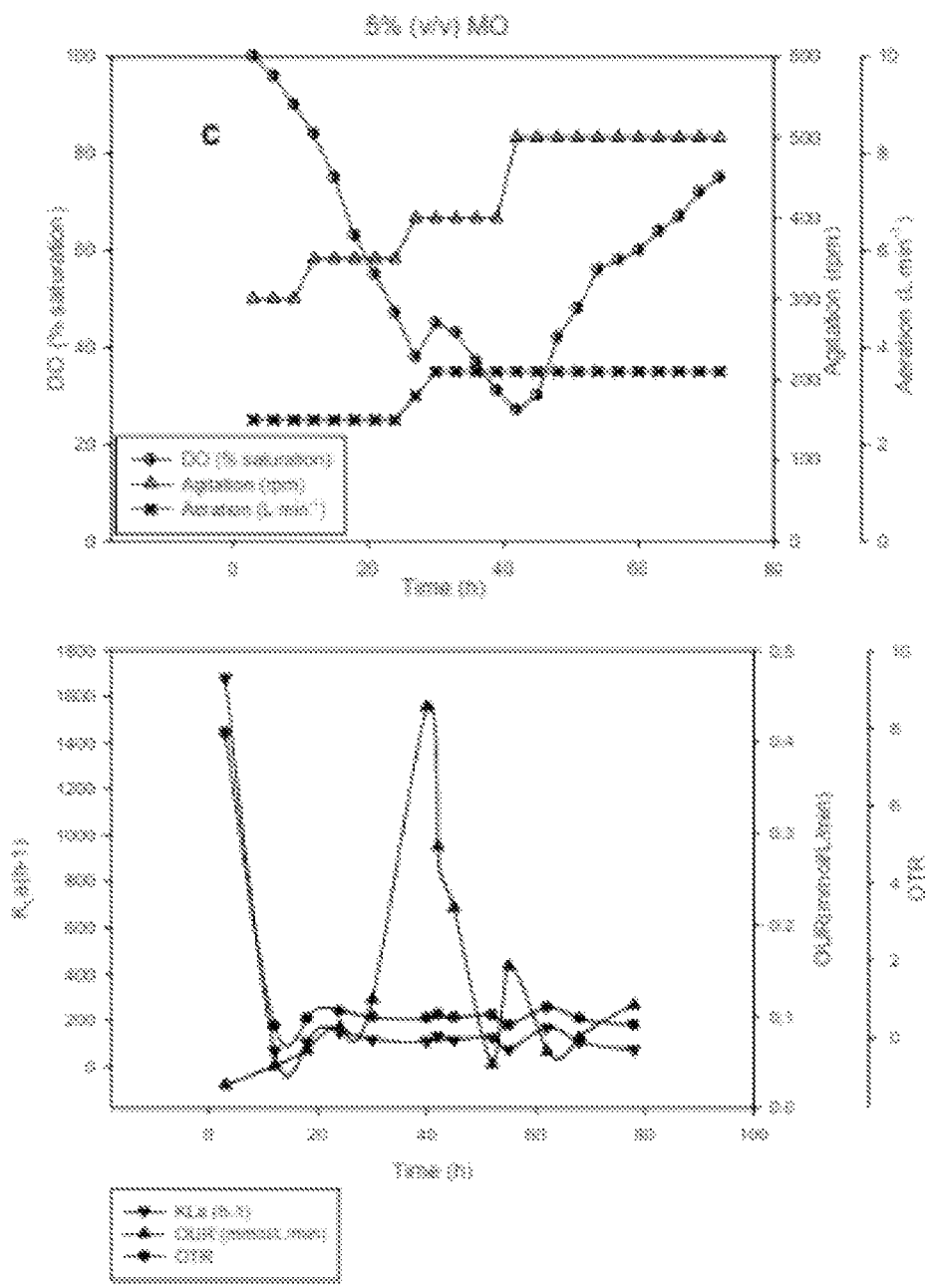

FIG. 20 shows that agitation speed, in the case of 3% v/v n-hexadecane and 3% v/v motor oil were almost the same with a slight difference and less than that of 5% v/v motor oil. Nevertheless, $k_L a$ values for the three different media were very close. The possible reason for this could be attributed to the different rheological characteristics of the three media (Dang Vu et al., 2009).

*Alcanivorax borkumensis* Growth and Enzyme Production During Fermentation

Scale-up studies are important to establish the enzymes production ability to be used later for bioremediation before considering it for deployment in actual contaminated sites (Priya et al., 2015). Moreover, the role of enzymes as biocatalysts in degrading and detoxifying contaminants is substantial (Sharma et al., 2014). Therefore, determining enzyme activity is crucial and can be used as an indicator of the activity and metabolism in a petroleum-contaminated soil. Thus, through this study, the enzyme activity of the intracellular alkane hydroxylase which is an enzyme that oxidizes alkanes and enable microorganisms to use hydrocarbons as a source of carbon and energy (Glieder et al., 2002) and also the extracellular lipase, which degrades lipids in glycerol and fatty acid (Jaeger et al., 1994) was established.

Figure 21:
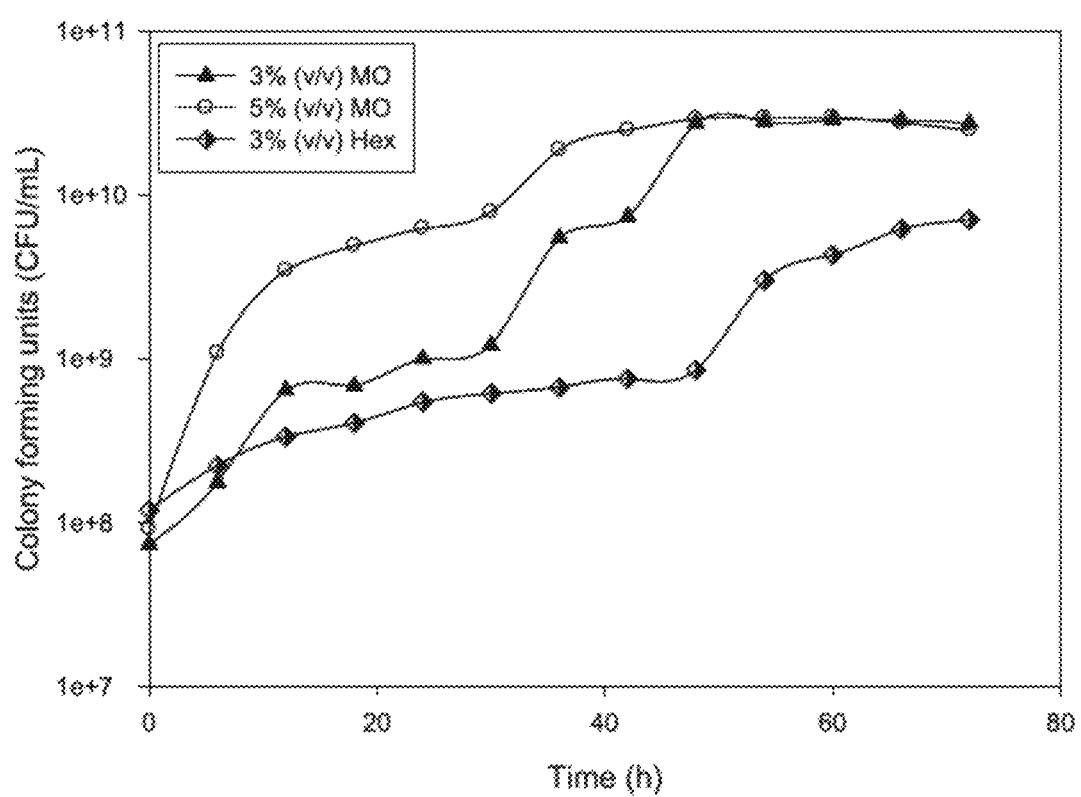
FIG. 21. Profiles of total cell count (CFU/mL) during fermentation of *A. borkumensis* using 3% n-hexadecane and 3% motor oil and 5% motor oil.
Figure 22:
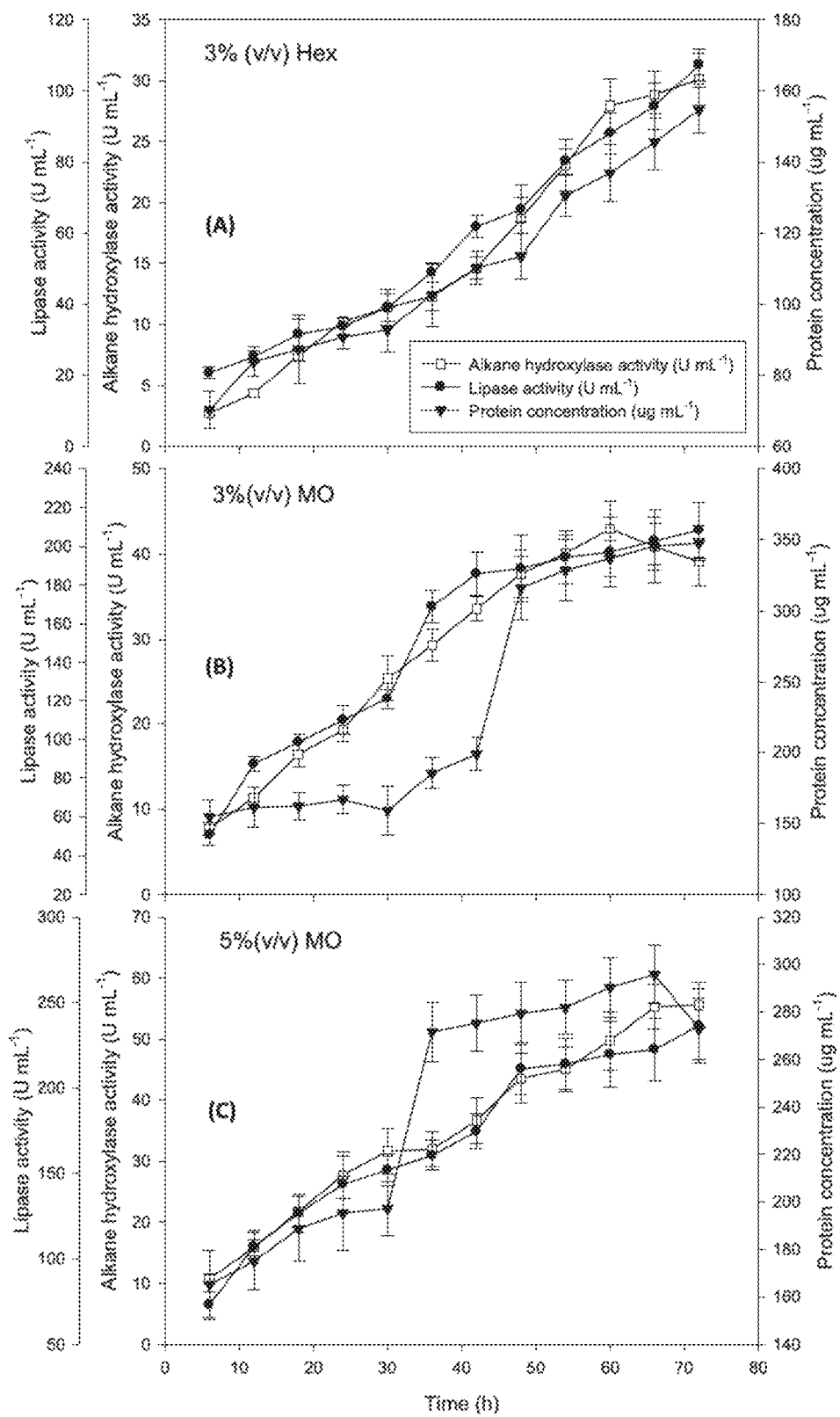
FIG. 22. Profiles of protein concentration, alkane hydroxylase activity and lipase activity during fermentation using: (a) 3% (v/v) n-Hexadecane, (b) 3% (v/v) Motor oil and; (c) 5% (v/v) Motor oil.

Profiles of colonies forming units per mL (CFU mL$^{-1}$), during growth of $A.$ $borkumensis$ in different media are presented in FIG. 21 and the maximum values of growth parameters (maximum cell counts and maximum specific growth rates) are mentioned in Table 10. And, protein concentration, alkane hydroxylase activity, and lipase activity during the fermentation of the three media were determined and their profiles, as well as their maximum values, are presented in FIG. 22 and Table 10, respectively.

Results showed that with 3 and 5% (v/v) of motor oil concentration a significant increase in the cell growth (p=0.024705) was observed as compared to the standard media with increasing turbidity. At the end of fermentation (starting from 48 h), total cells reached the same values for both concentrations of motor oil. The cell growth started immediately after inoculation of the bioreactor reaching its maximum value at 60 h for both media with motor oil (2.9×10$^{10}$ and 3×10$^{10}$ CFU mL$^{-1}$) and at 72 h for the media with n-hexadecane (7.1×10$^{9}$). These results were confirmed with Tukey post-hoc analysis where the media containing 3% and 5% (v/v) of motor oil were statistically comparable in term of cell growth and the values were significantly higher than the standard media (p>0.05).

The total cells of the media with motor oil were followed by a decelerating growth phase and subsequently, the culture entered stationary phase. Nevertheless, maximum alkane hydroxylase and moreover maximum lipase activities were secreted during the decelerating growth phase and subsequent stationary phase signifying non-growth associated production phase. Liu et al., (2014) studied the growth of $Acinetobacter$ sp. LS-1 on hexadecane and found that the utilization of hexadecane was closely related to the strain's growth with the increasing cell turbidity. The growth of this strain was very slow until 12 h incubation with only 5% hexadecane degradation, and then the log phase continued until 24 h, the stationary phase until 30 h with eventual decline phase. The same strain LS-1 was grown with 1% crude oil for one week reaching a cell turbidity of 0.35 OD$_{600}$.

For the lipase and alkane hydroxylase enzymes, the increase in concentration of motor oil from 3% (v/v) to 5% (v/v) caused an increase in the amount of available nutrients, which induced synthesis of the enzymes to convert these substrates into easily consumable nutrients for $A.$ $borkumensis$ growth and synthesis and for degradation of petroleum hydrocarbons. The lipase and alkane hydroxylase production increased significantly with the use of motor oil (p=0.018418 and 0.020087) for lipase and alkane hydroxylase, respectively). The secretion of lipase and alkane hydroxylase was observed only after 3 h for both motor oil and standard medium. This relative delay might be due to a requirement of a critical cell mass level for starting enzymes synthesis. From FIG. 22, it can be clearly observed that alkane hydroxylase and lipase activities increased with an increase in cell mass and seemed to be growth associated. In fact, Sharma et al., (2014) have claimed that if the changes in bacterial population had the same pattern as the soil enzyme activities over the experience, this reflects the role of these microbiological properties in the bioremediation of diesel-contaminated soils.

Tukey post-hoc analysis showed that lipase production in 3% and 5% (v/v) of motor oil were statistically comparable (p=0.588790). For the alkane hydroxylase production, the highest significant production was achieved with media containing 5% motor oil in comparison to 3% motor oil (p=0.036746) and the standard media (p=0.018821).

A maximum of 347 µg mL$^{-1}$ of protein was observed with 3% (v/v) of motor oil after 72 h. Mishra and Singh, (2012) observed similar protein concentration range between 0.11 and 0.65 mg/mL with the strains, $Pseudomonas$ $aeruginosa$ PSA5, Ochrobactrum intermedium P2 and $Rhodococcus$ sp. NJ2 when using n-hexadecane as a carbon source. The protein concentration started to decrease after 72 h from 295.8 to 272.8 µg/mL in the case of 5% motor oil but continued increasing when using the standard media and 3% motor oil. Similar behavior was also noticed in the case of bacterial strain, $O.$ $intermedium$ P2 which showed a continuous increase in protein content till 8th day of incubation and it was not growth associated (Mishra and Singh, 2012). The protease production was not affected by the increase in motor oil concentration (p=0.0648) as was observed in shake flasks experiments.

For hydrocarbons degradation using $Alcanivorax$ $borkumensis$, two degradative enzymes are mainly involved viz. alkane hydroxylase and lipase. Therefore, their production profile during $A.$ $borkumensis$ growth was investigated to understand their role in the biodegradation. In this study alkane hydroxylase and lipase activities exhibited different pattern during the incubation period and this can be explained by the simple reason that not all enzymes are produced by a cell in the same amounts and some are produced more than the others. When these enzymes will be applied for soil decontamination, it will be difficult to distinguish since both intracellular and extracellular enzyme contributes to the overall process (Andreoni et al., 2004).

The alkane hydroxylase was induced during both n-hexadecane and motor oil degradation, but at different incubation periods reaching the maximum between 60 and 72 h. The highest alkane hydroxylase production was observed with 5% motor oil (55.6 U mL$^{-1}$). Several other strains have been reported in the literature to produce alkane hydroxylase with a genetically well-characterized enzymatic complex, such as $Rhodococcus$ sp., $Pseudomonas$ sp and $Acinetobacter$ sp. (Wentzel et al., 2007). Mishra and Singh, (2012) demonstrated the induction of alkane hydroxylase production by $P.$ $aeruginosa$ PSA5, $O.$ $intermedium$ P2 and $Rhodococcus$ sp. NJ2 when using n-hexadecane but at different incubation times ranging from 2 to 8 days.

The highest lipase production was induced by the usage of motor oil rather than n-hexadecane with 208 U mL$^{-1}$ obtained from 3% motor oil and 236 U/mL with 5% motor oil after 72 h incubation. Comparable results were found by Mishra and Singh, (2012), who reported the least induction of lipase enzyme compared to other degradative enzymes during the degradation of n-hexadecane with three different bacterial strains ($O.$ $intermedium$ P2, $P.$ $aeruginosa$ PSA5, $Rhodococcus$ sp. NJ2). Kanwar et al., (2002) used different n-alkane substrates as a carbon source for the growth of $Pseudomonas$ sp. G6 and reported a maximum of only 25 U mL$^{-1}$ of lipase using 2% (v v$^{-1}$) n-hexadecane.

Biodegradation Tests

To evaluate the efficiency of the produced enzymes, two different groundwaters contaminated with PAHs were used and the PAHs composition was analyzed before and after enzymatic degradation in 5 and 10 days. Results presented in Table 11 showed that for the $1^{st}$ site 37.4% of total PAHs were removed after 5 days with a degradation rate of 196.6 µg $L^{-1}$ $day^{-1}$ and that 82.8% were removed after 10 days with a degradation rate of 217.54 µg $L^{-1}$ $day^{-1}$. Removal of anthracene, naphthalene, phenanthrene, and pyrene were 77.55%, 86.58%, 81.78% and 98.52%, respectively after 10 days of enzymatic degradation. The removal of PAHs was also determined for the $2^{nd}$ site contaminated groundwater. Enzymatic biodegradation was almost complete with 95% removal and 499.02 µg $L^{-1}$ $day^{-1}$ removal rate after only 5 days and a slight further removal after 10 days with a slower degradation rate (95.1% and 249.81 µg $L^{-1}$ $day^{-1}$, respectively). Results presented in Table 11 showed the first-order kinetic model using the linear regression. For the $1^{st}$ site, about 10 days biodegradation had the highest k value (0.176 $day^{-1}$) compared to the 5 days treatment (0.093 $day^{-1}$). Moreover, for the $2^{nd}$ site k values were higher (0.598 and 0.301 $days^{-1}$ for the treatment of 5 and 10 days, respectively). These observations demonstrate that 10 days treatment is more efficient than 5 days treatment.

TABLE 11

Specific degradation rate constant (k) and correlation coefficient ($R^2$) during enzymatic degradation of PAHs.

| Enzymatic treatment $1^{st}$ site | k ($day^{-1}$) | $R^2$ | Enzymatic treatment $2^{nd}$ site | k ($day^{-1}$) | $R^2$ |
|---|---|---|---|---|---|
| 5 days | 0.093 | 0.932 | 5 days | 0.598 | 0.949 |
| 10 days | 0.176 | 0.981 | 10 days | 0.301 | 0.915 |

Comparable results were also reported by previous studies. Malik and Ahmed, (2012) studied the removal of petroleum hydrocarbons using a bacterial consortium and found a 51 to 68% degradation efficiency on polyaromatic fractions (anthracene, naphthalene, phenanthrene, and pyrene) with a total concentration of 14784 µg $L^{-1}$ after 24 days (Malik and Ahmed, 2012). Also, Patel et al., (2016) used the strain *Anabaena fertilissima* for 16 days and found a removal of 46% for anthracene and 33% for pyrene, at concentrations of 5 mg $L^{-1}$ and 3 mg $L^{-1}$, respectively (Patel et al., 2016). Obayori et al., (2014) studied the degradation of two different grades of engine oil namely SAE 40W and SAE 20W 50 by *Pseudomonas aeruginosa* LP5 and observed higher degradation rate in the first 12 days than the last 9 days. The values for fresh SAE 40W, used SAE 40W, fresh SAE 20W-50 and used SAE 20W-50 were 177.42, 75.23, 207.14 and 74.37 (mg $L^{-1}$ $d^{-1}$) respectively in the first 12 days. The percentage of removal in this period of time ranged between 92% and 96% (Obayori et al., 2014). Basuki et al., (2015) reported the removal of 35 components out of 47 components of oil by *Acinetobacter junii* TBC 1.2 (Basuki et al., 2015).

Studies on other similar strains, such as *Pseudomonas* sp. have shown that the presence of mono- and dioxygenases enzymes allow the oxidative degradation of some aromatic hydrocarbons, such as phenanthrene through two possible degradation pathways: salicylate or protocatechuate (Chebbi et al., 2017). These pathways share the same common upper route and are initiated by the double hydroxylation of the aromatic ring. However, further studies are needed to explore the mechanisms and modes of action of this promising bacterial strain and the produced enzymes.

Conclusion

Scaling-up enzymes production in optimized conditions and inexpensive media is crucial to commercializing the process. The present study was an attempt in this direction. Alkane hydroxylase and lipase production pattern varied with the type of carbon source as well as its concentration and diverse petroleum sources could be used by the organism as a sole carbon source for enzyme production. The enzymes production was scaled-up to 5 L fermenter using 3% and 5% (v/v) motor oil and 3% (v/v) n-hexadecane as control. The agitation speed, as well as the aeration, influenced the extent of mixing in the bioreactor and the nutrients availability and resulted in high yields of alkane hydroxylase and lipase activities. Enzymatic degradation tested on two different PAHs contaminated groundwaters showed 82.8% removal after only 10 days with a degradation rate of 217.54 µg $L^{-1}$ $day^1$ for the $1^{st}$ site and 95% removal was observed after only 5 days for the $2^{nd}$ site. Thus, *Alcanivorax borkumensis* showed the potential for use in petroleum-contaminated areas. Further studies on the formulation of these produced enzymes need to be made for further applied technique.

Example 5—Large-Scale Production of Enzymes from the Hydrocarbonoclastic Bacteria *Alcanivorax borkumensis*

Abstract

Pilot-scale *Alcanivorax borkumensis* production in 150 L bioreactor was conducted using motor oil as a substrate using optimized operational parameters obtained in previous works in Erlenmeyers and in 5 L bioreactor. In pilot scale fermentation process the oxygen transfer rate is a major limiting factor for high product yield. Thus, the volumetric mass transfer coefficient ($K_La$) remains a tool to determine the oxygen transfer capacity (oxygen uptake rate (OUR) and oxygen transfer rate (OTR)) to obtain better bacterial growth and higher alkane hydroxylase and lipase activity in new bioreactor process optimization and scale-up.

Results showed that the maximum values of $K_La$, OUR, OTR, total cell count, alkane hydroxylase and lipase activity are 196.95 $h^{-1}$, 0.92 mmol $O_2$/L/h, 1.8 mmol $O_2$/L/h, $8.6 \times 10^{10}$ CFU/mL, 222.49 U/mL and 325 U/mL, respectively. Compared with the 5 L bioreactor, the 150 L fermenter showed better oxygen transfer rate which had an effect on the cell growth that doubled the number and enzymes production that increased. This study result corroborates the feasibility of industrial-scale operation of enzymes production using motor oil as a substrate.

Materials and Methods

Bacterial Strain and Culture Medium

*Alcanivorax borkumensis* (SK2) strain was ordered from DSMZ (Braunschweig, Germany). The *A. borkumensis* strain was cultivated and sub-cultured on agar plates using Bacto agar (Difco, Fisher Scientific, Mississauga, Ontario) (18 g/L) and incubated at 30° C. for 72 h. The grown pure bacterial culture was kept at 4° C. for the next step which is the inoculum preparation. The growth medium is composed of (per liter of distilled water): 23 g NaCl, 0.75 g KCl, 1.47 g $CaCl_2 \cdot 2H_2O$, 5.08 g $MgCl_2 \cdot 6H_2O$, 6.16 g $MgSO_4 \cdot 7H_2O$, 0.89 g $Na_2HPO_4 \cdot 2H_2O$, 5.0 g $NaNO_3$, and 0.03 g $FeSO_4 \cdot 7H_2O$. To prevent precipitation, four solutions were prepared, autoclaved separately, cooled at room temperature and then mixed together. Solutions are the following: 1) $Na_2HPO_4$ and $NaNO_3$ (the pH of medium was adjusted to 7.5 using 10% (w/v) of NaOH), 2) NaCl, KCl and $CaCl_2$, 3) $MgCl_2$ and $MgSO_4$, and; 4) $FeSO_4$. The pH value of medium was adjusted to 7.5 with 10% solution of NaOH, and the growth was conducted in a shaking incubator at 30±1° C., 150 rpm for 72 h (Yakimov et al., 1998). Commercial motor oil was used as sole carbon and energy source for inoculum preparation and for *A. borkumensis* growth. Motor oil was characterized and the composition (in mg/L) is the following: 69.8 of $C_{10}$-$C_{50}$, 1.83 of naphthalene, ≤44 of benzene, ≤30 of toluene, ≤44 of ethyl-benzene and ≤84 of xylene (Kadri et al., 2018).

Fermentation in 150 L Computer-Controlled Bioreactor

Fermentations were conducted in 150 stirred tank bioreactors with an operational volume of 100 L. The bioreactor was equipped with accessories and programmable logic control (PLC) board to control dissolved oxygen (DO), pH, anti-foam agent, aeration rate, temperature, and agitation. The iFix 3.5 software (Intellution, Foxborough, MA, USA) was used for automatic control of all parameters via the PLC. Before each sterilization cycle, pH probes (Mettler Toledo, Columbus, OH, USA) were calibrated using two buffers of pH 4 and pH 7 (VWR, Canada). Sodium thiosulfate was used to calibrate the oxygen probe to zero then air saturated water to calibrate it to 100%. The calibration was performed prior to a sterilization cycle.). Polypropylene glycol (PPG, Sigma Canada) (0.01% v/v) solution was used as an anti-foaming component. The bioreactor and the media were sterilized at 121° C. for 20 minutes and cooled down to 30° C. The maximum air was sparged with agitation to calibrate the DO probe at 0 and 100%.

The 150 L (100 L working volume) bioreactor was inoculated with 3 L inoculum (3% v/v) with a CFU/mL of $4 \times 10^{10}$ at sterile conditions (in the presence of flame and alcohol) with *A. borkumensis* pre-culture. The 3 L inoculum was produced in two 4 L Erlenmeyer Flasks with a working volume of 1 L and inoculated with 3% (v/v) of a pre-culture of *A. borkumensis* that was itself produced in 250 mL Erlenmeyer flasks with a working volume of 50 mL and incubation time of 24 h.

To maintain a concentration of dissolved oxygen above 25%, the airflow and agitation rate was maintained between 20-90%. The temperature was maintained at 30° C. by circulating water inside the fermenter jacket. The pH was maintained at 7.5 using a computer-controlled operating system. Samples were collected periodically to determine the colony forming units per mL.

A part of each sample was used for enzymes activity. For this purpose, the broth was centrifuged at 8000 rpm for 10 min at 4° C. and the cell-free supernatant was used to determine extracellular lipase activity. The pellet was resuspended in phosphate buffer (0.1 M, pH 8), ultrasonicated at two different frequencies of 22 kHz and 30 kHz for 6 min (30 s on and 30 s off) in the presence of ice bath. The mixture was then centrifuged at 13 000×g for 20 min to extract the intracellular crude enzyme served to measure alkane hydroxylase activity.

The extraction of alkane hydroxylase for field test was done using pilot plant continuous mode sonicator (1500 w, 20 kHz). For that we kept the broth overnight at 4° C. to start the sonication at low temperature and avoid heating. Then we optimized the contact time (30 s, 1 min, 1.5 min, 2 min, 2.5 min and 3 min) by measuring the enzyme activity. The best activity was obtained for 30 s sonication. Further contact time resulted in decreased activity.

Analysis Parameters
Volumetric Oxygen Transfer Coefficient ($K_La$), Oxygen Transfer Rate (OTR) and Oxygen Uptake Rate (OUR).

The $k_La$ was determined to evaluate *A. borkumensis* performance during the fermentation process. The $k_La$ was calculated based on the dynamic gassing out method (Stanbury et al., 2013) in which the air input was interrupted and then reinstated. When the air flow valve was closed, DO decrease was recorded every 10 s. Then the air flow valve was reopened and the increase of DO was recorded at 10 s intervals until the DO plateaus. The $k_La$ was determined each 3 h.

The following equations were used for kLa calculation:

$$C_L = \left(C^* - \frac{1}{k_La}\right) \times \left(Q_{O_2}X + \frac{dC_L}{dt}\right)$$

$$\frac{dC_L}{dt} = OTR - OUR$$

$$OTR = k_La(C^* - C_L)$$

$$OUR = Q_{O_2}X$$

OTR: the oxygen transfer rate from the gas phase to the liquid phase:
OUR: the oxygen uptake rate by the microorganism
$K_La$: the volumetric oxygen transfer coefficient
$C^*$: the oxygen concentration at saturation
$C_L$: the dissolved oxygen concentration in the medium
$Q_{O2}$: the specific oxygen uptake rate of the microorganism employed
X: the biomass concentration.

The DO electrode in the medium was calibrated at 30±1° C. and then shifted to air-saturated distilled water at a known temperature and ambient pressure to transform the concentration of oxygen in the broth from percentage air saturation to mmol $O_2$ $L^{-1}$. This reading was used with the known saturation concentration of oxygen at saturation in distilled water (0.07559 mmol/L) (100%), to determine the saturation concentration of oxygen in the media at 30° C.

Total Cell Count

The viable cells count was determined by counting colonies grown on agar medium with different dilutions. For all tested dilutions, the mean value of triplicate plates was considered for the counting of CFU for each tested dilution and the results were expressed as colony forming units per mL (CFU $mL^{-1}$). Also, biomass (mg/L), as well as OD600, was determined.

Total Protein and Enzyme Assays
Alkane Hydroxylase Assay

Alkane hydroxylase activity was measured by determining NADPH depletion. The assay mixture was composed of the supernatant containing the enzyme, the phosphate buffer (0.1 M, pH 8), hexadecane (0.5-1 mM), and the dimethyl sulfoxide (DMSO; 1%, vol/vol). Alkanes were added to the buffer using alkane stock solutions in DMSO. The reaction starts by adding NADPH (200 μM), and the oxidation of NADPH was estimated spectrophotometrically at 340 nm (Glieder et al., 2002). One unit of enzyme activity is defined as the amount of enzyme required for consumption of 1 nmol of NADPH per min. The alkane hydroxylase substrate used was n-hexadecane.

Exolipase Assay

Lipase activity was evaluated by spectrophotometer using p-nitrophenyl palmitate as the substrate (M. Thoner, Diploma-Thesis, University of Bochum, Bochum, Germany, 1973). The substrate solution was prepared as follows: 30 mg of p-nitrophenyl palmitate diluted in 10 mL of isopropanol was mixed with a solution composed of 90 mL of 0.05 M Sorensen phosphate buffer, pH 8.0, 207 mg of sodium deoxycholate and 100 mg of gum Arabic. 2.4 mL of this pre-warmed substrate solution (37° C.) was mixed with 0.1 mL of the enzyme. After 15 min of incubation at 37° C., the enzyme activity was evaluated at 410 nm against an enzyme-free control. One unit of enzyme activity is defined as the amount of enzyme needed to liberate 1 nmol of p-nitrophenol per minute.

Statistical Analysis

All the experiments were performed in triplicates. Data presented are the mean values with standard deviation (±SD).

Results and Discussion

The scale-up is an attempt to achieve a promising process for an industrial scale with the aim to satisfy economic and technological implementation. The *A. borkumensis* based motor oil production, as well as its enzymes synthesis, were carried out at laboratory scale and it has been successfully achieved. Now that the operating variables and the physical properties are known or can be easily determined, we aimed for larger scales, so we have started and investigated the production in 5 L bioreactors using different substrate media with different concentrations (Kadri et al., 2018), so the bioprocess conditions such as the temperature, pH, pressure, mixing, concentrations of biomass and inoculum size were already optimized and fixed, with an operational mode previously selected (batch) and also with a selected substrate (5% (v/v) of motor oil). Thus, this study a larger scale of 150 L bioreactor will be carried out and discussed. The 150 L is considered as a pilot plant scale (usually the pilot plant scales are from 50 to 300 L volumes (Garcia-Ochoa and Gomez, 2009) where the operational conditions and the hydrodynamic and mixing are comparable to those employed in the production scale. So, at first place, we will be discussing the results obtained in the 150 L bioreactor then a comparison with our previous study in 5 L fermenter will be held.

OUR, OTR, and $K_La$

The oxygen is a key player in the aerobic bioprocess; for this reason, a particular attention must be paid to study it especially that it has a low solubility in the broth and in aqueous solutions in general, so it has to be supplied continuously. For these reasons, investigating the Oxygen Transfer Rate (OTR) is crucial to reach the most efficient bioreactor scale-up that can be used for industrial production (Hsu and Wu, 2002). The oxygen transfer is dependent on several parameters such as the type of the sparger which will affect the bubbles size and impeller number and structure. Also, agitation speed, aeration rate, fermenter geometry, characteristics of the medium used (the microorganism, the substrate, total cells . . . ) highly affect the oxygen transfer (Parakulsuksatid, 2000). The dissolved oxygen concentrations depend on several factors such as the rate of oxygen transfer from gas to liquid phase, the rate of transportation of oxygen inside the cells, and on the oxygen uptake rate (OUR) by the aerobic microorganism for growth, preservation, and production.

Figure 23:
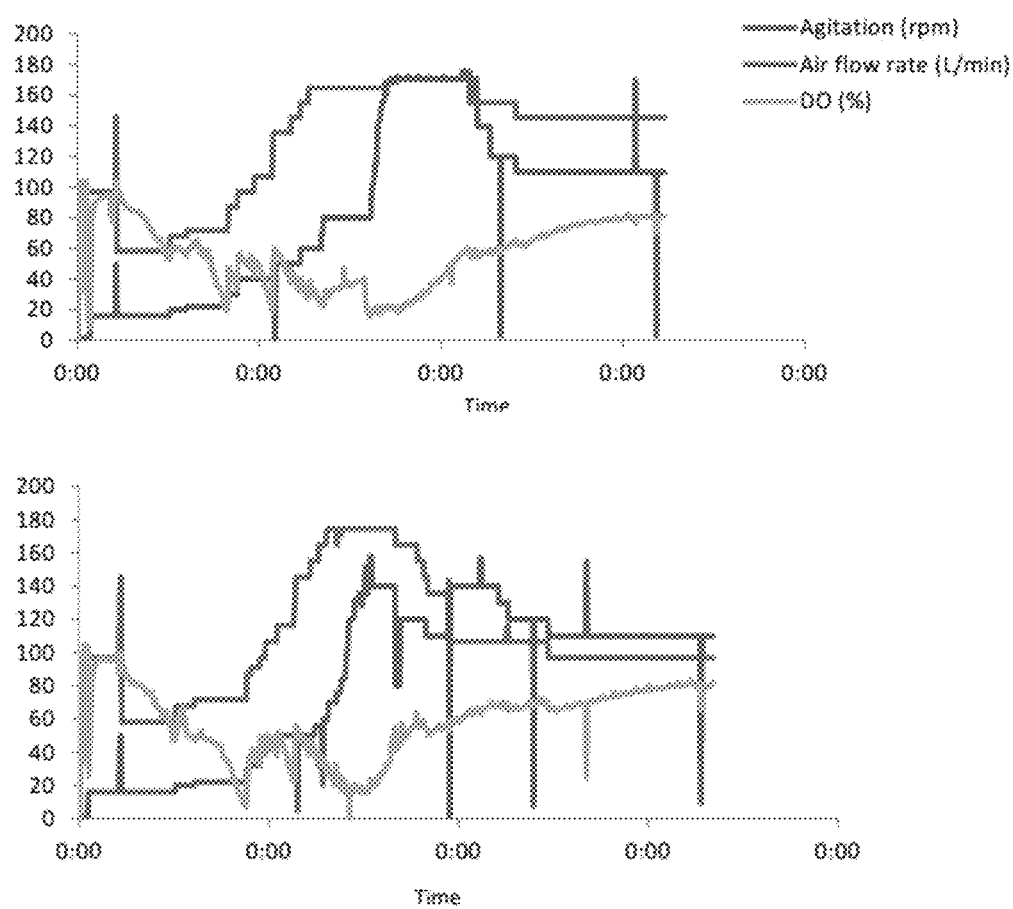
FIG. 23. Data of different batches carried out in 150 L fermenters for 48 hrs, at 30° C. and pH 7.5.
Figure 23:
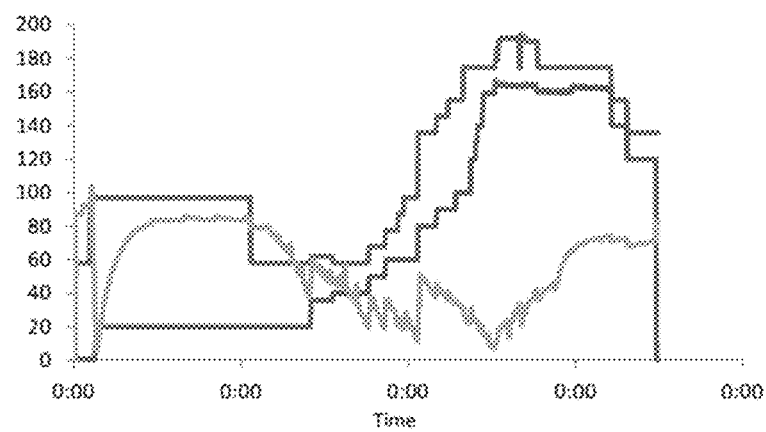
Figure 23:
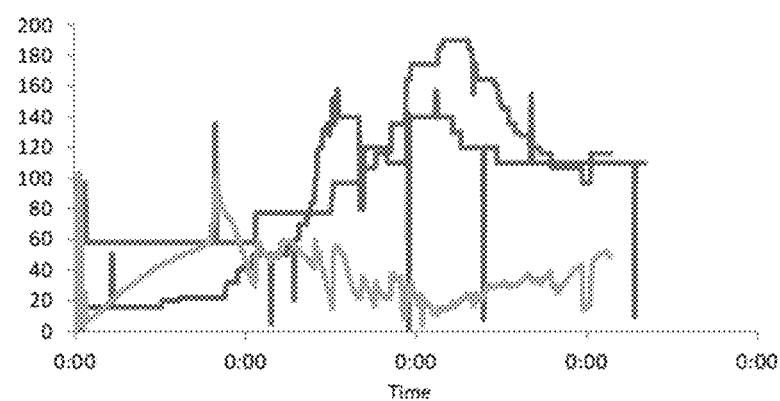
Figure 23:
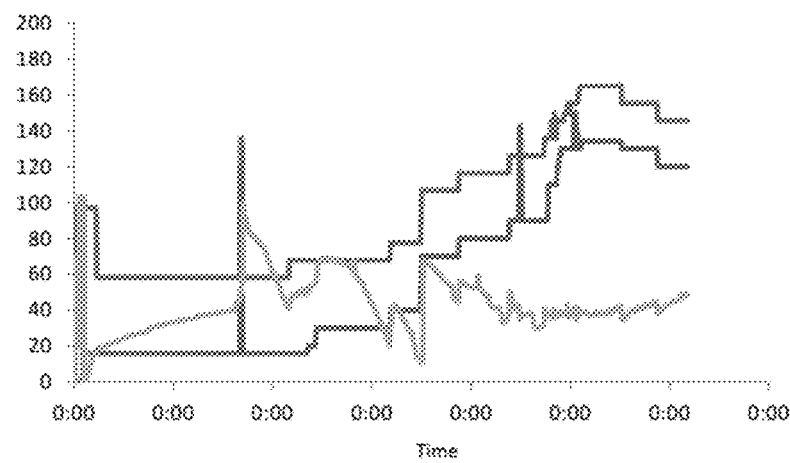
Figure 23:
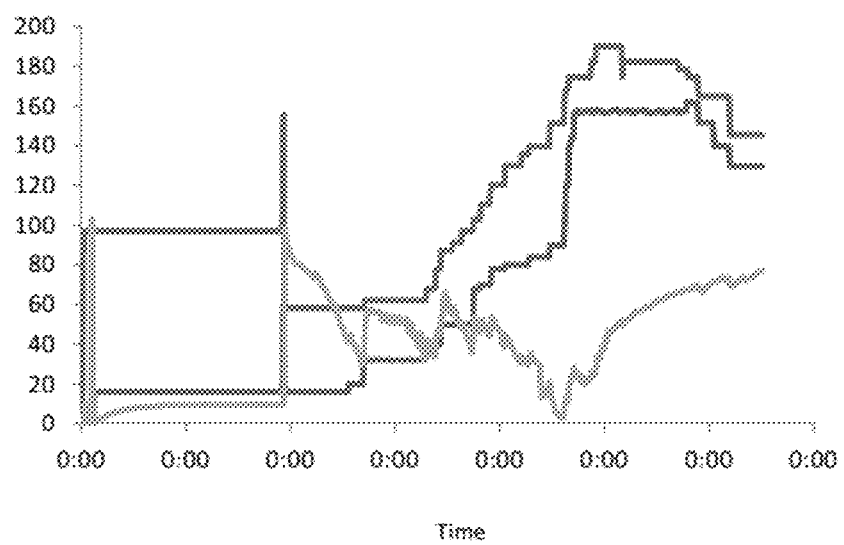
Figure 23:
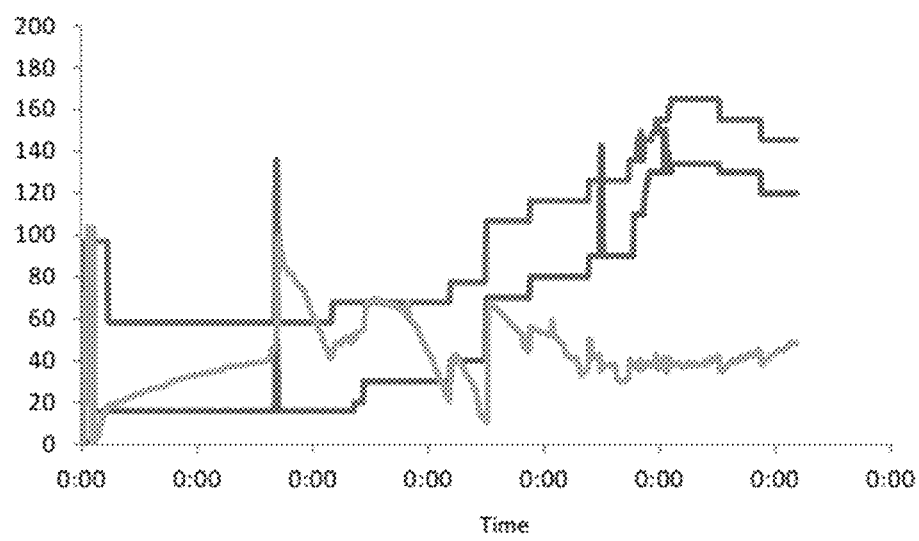

Profiles of fermentation parameters, namely, dissolved oxygen concentration DO, agitation, aeration, volumetric oxygen transfer coefficient (kLa), oxygen uptake rate (OUR) and oxygen transfer rate (OTR) are presented in FIG. 23 and the maximum values of these studied parameters are shown in Table 12, with constant values of pH and temperature (7.5 and 30° C., respectively). Agitation rate (maximum value is 200 rpm) and air flow rate (maximum value is 200 L/min) were varied to control the DO value and maintain it above the critical required level (>25% saturation based on previously reported works).

Results revealed that during the first stage of fermentation (from 0 to 48 h), a decrease in the DO values was detected. Therefore, a higher agitation reaching 85% (170 rpm) and a higher aeration rate reaching 87.5% (175 L/min) were adopted to maintain high dissolved oxygen greater than the minimum required for bacterial cells (25%). This decrease was followed by an increase, until the end of the fermentation. Thus, the agitation and the aeration were preserved at the same level.

The decrease in DO observed corresponded to the exponential growth phase of *A. borkumensis* which required higher oxygen consumption. On the other side, the increase in DO and decrease in oxygen uptake rate are the consequence of the stationary growth phase reached by *A. borkumensis*. Results also showed that the trend of oxygen consumption rate exhibited the maximum value at 15 and 40 h of fermentation and nearly stabilized from 40 to 64 h.

The limiting factor in the aerobic process is the solubility of oxygen in the fermented broth which interferes with the transfer of oxygen from the gas bubbles to cells from one fermentation scale to another. In the present study (150 L bioreactor) and the previously investigated study in 5 L bioreactor, the stirring speed, aeration rate, and the oxygen concentration changed from a bioreactor to another. Nevertheless, the inoculum fermentation time (48 h), the inoculum percentage (3% v/v), the minimum maintained values of dissolved oxygen (25%) were the same in both bioreactors.

Both the $K_La$ and the OTR provide information about oxygen transfer efficiency from a bioreactor to another and oxygen uptake rate in the bioreactors. Table 13 represents a comparison between the 5 L and the 150 L bioreactors in term of agitation, aeration, and height: diameter ratio. The 150 L bioreactor in comparison with the 5 L bioreactor allows more aeration rate, a low agitation speed and larger size of the impeller, as a consequence, the oxygen diffusion in the 150 L bioreactor is better and the size of the air bubbles is smaller (Parakulsuksatid, 2000). Moreover the height:diameter ratio is greater (2:1) which means that the residence time of the gas phase is more significant, the oxygen transfer rate is higher and the power input supplied for the establishment of gas is lower with uniform power dissipation and as a consequence of increased biomass production and increase oxygen consumption (Chandrashekhar and Rao, 2010). Consequently, relatively higher oxygen consumption was observed in the 150 L reactor, compared to the 5 L one with the maximum values of 0.9 mmol/L/min and 0.21 mmol/L/min, respectively. This high oxygen consumption is due to effective oxygen transfer and this leads to better growth and high cell and enzyme production.

Margaritis and Zajic, (1978) have stated that the scale-up can be accomplished following one of these four methods: 1) fundamental procedures 2) semi fundamental procedures 3) dimensional analysis 4) and rules of thumb. The most widely used among these four is the rules of thumb, in which the standards for scale up and percentage of each standard used in the production scale are: constant specific power input, PN, (30% of use); constant volumetric mass transfer coefficient, $K_La$ (30%); constant impeller tip speed of the agitator or shear (20%); and constant dissolved oxygen concentration, DO (25%). The consequence of these standards is a completely different and new process condition on a production scale. So usually, it is unfeasible to keep all the parameters in the same ratio to one another.

*Alcanivorax borkumensis* Growth and Enzyme Production During Fermentation

Figure 24:
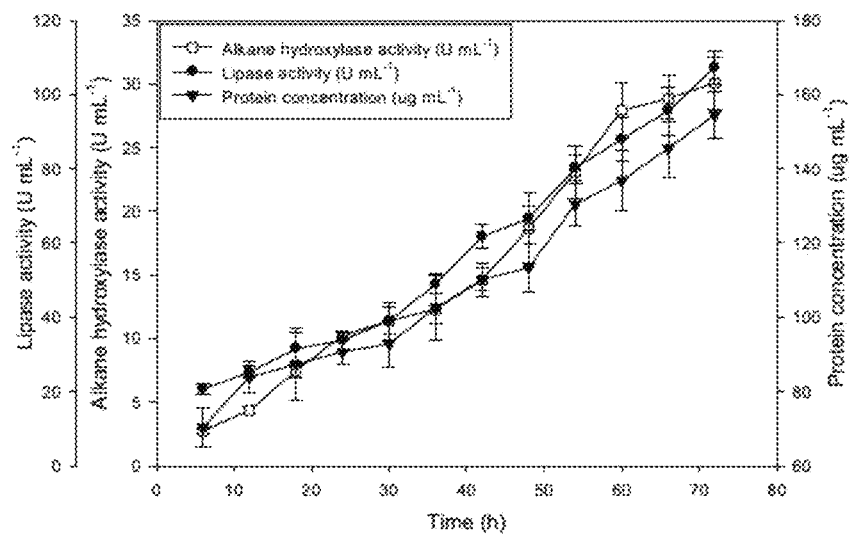
FIG. 24. Profiles of protein concentration, alkane hydroxylase activity and lipase activity during fermentation of A. *Borkumensis* using (a) 3% (v/v) Hexadecane as a substrate.

Profiles of colonies forming units per mL (CFU/mL), during growth of *A. borkumensis* in different media are presented in FIG. 24 and the maximum values of growth parameters (maximum cell counts and maximum specific growth rates) are mentioned in Table 12. Also, the alkane hydroxylase activity and lipase activity over the fermentation process were investigated and their profiles, as well as their maximum values, are presented in FIG. 24 and Table 12, respectively.

The cell growth started immediately after inoculation of the bioreactor reaching its maximum value at 52 h ($8.6 \times 10^{10}$ CFU/mL). The cells were followed by a decelerating growth phase and subsequently, the culture entered stationary phase.

Despite the similar operational conditions in the 5 L and in 150 L fermenters (similar nutrients, similar substrate and substrate concentration with the same minimum oxygen concentration that was maintained), The CFU/mL was obviously higher in 150 L bioreactor than the 5 L bioreactor with a maximum value of $8.6 \times 10^{10}$ CFU/mL and $3 \times 10^{10}$ CFU/mL, respectively. These results correlate well with the tendency of $k_L a$, OUR and OTR detected in both reactors. In fact, the 150 L bioreactor provide better oxygenation related to better aeration, agitation, impeller size, and the ratio height/diameter. These results demonstrate the sensitivity of *A. borkumensis* towards oxygen limitation. comparable results were found by Boniolo et al., (2012) who demonstrated the effect of high aeration (50% DO) on the high number of cells produced by of *Bacillus thuringiensis* and also on the enhanced entomotoxicity of the broth which was 9 folds higher than the one obtained with only 5% DO. Also, Ndao et al., (2017) compared the cell count of the strain *Bacillus thuringiensis* when grown in 3 different scale bioreactors (15 L, 150 L and 2000 L) and have found that whenever there are more oxygen transfer and supply there is more growth and better performance with more cell counts which was found in the 2000 L fermenter.

The enzymes production ability and the bioremediation application at the contaminated sites depends on the scale-up studies (Priya et al., 2015). The degradation of petroleum-contaminated sites depends on the catalyzing and metabolic activity of enzymes. The details on the enzyme activity during the fermentation will determine the degradation ability of the enzyme at the petroleum-contaminated sites. The motor oil was easily consumed during the *A. borkumensis* growth and synthesis of lipase and alkane hydroxylase enzymes. The release of lipase and alkane hydroxylase into the fermentation media was observed at 3 h using motor oil in case of 5 L fermenter (Kadri et al., 2018). However, in case of 150 L bioreactor, the release of enzymes was observed at 12 h, suggesting a necessary delay required for growth of cell mass level for enzyme syntheses (Kadri et al., 2018). The reason for the delay is justified in comparison to the growth curve; an increase in the growth of microorganisms increased the cell mass resulting in the increase in the production of alkane hydroxylase and lipase enzyme. The production and activity of alkane hydroxylase and lipase enzyme are growth associated. The profile of enzyme activity in the bioreactor coincides with the growth of the microorganisms and also with the OUR (El-Bakry et al., 2016). These might be due to the biodegradation of motor oil depending on OUR reaching maximum value along with the growth of microorganisms (El-Bakry et al., 2016). Liu et al., (2014) studied the growth of *Acinetobacter* sp. LS-1 on hexadecane and found that the utilization of hexadecane and the production of enzymes were closely related to the strain's growth.

The results obtained at shake flask scale differ from the scale-up study, suggesting that the changes in temperature gradient profile result in increased heterogeneity affecting microorganism's growth and performance at flask scale (El-Bakry et al., 2016). However, in the case of the scale-up bioreactor, the temperature is controlled to minimize any temperature gradients for highly consistent microorganism's growth delivering high reproducibility (El-Bakry et al., 2016).

The production of alkane hydroxylase was observed from 12 h and reached a maximum activity of 222.49 U/mL at 42 h, suggesting logarithm production of 200 U/mL in 30 h. In comparison to 5 L, the maximum production of alkane hydroxylase was around 55.6 U/mL requiring a fermentation time of 60 to 72 h (Kadri et al., 2018). Similarly to enzyme activity, the CFU/mL in 150 L bioreactor was around $8.6 \times 10^{10}$ CFU/mL in comparison to 5 L around $3 \times 10^{10}$ CFU/mL, respectively. The scale-up system helped in the increased production of enzyme along with decreasing the fermentation time from 72 to 42 h. A decrease in 30 h of fermentation time at commercial scale production will help to run more batch runs/year and will be economical in decreasing the operating and production cost (Laxman Pachapur et al., 2015; Pachapur et al., 2017). The scale-up bioreactor generates higher hydro-mechanical stress around the impellers and propeller affecting the activity of enzymes in comparison to shake flasks (Vasco-Correa and Zapata 2017). Increased performance is normally expected in scale-up bioreactor due to an increase in the dimension of the stirred-tank requiring an additional mixing time (Vasco-Correa and Zapata, 2017).

Similar to the production profile of alkane hydroxylase, the lipase activity was observed from 12 h and reached the maximum of 325 U/mL at 42 h. In comparison to 5 L fermenter, delivered highest lipase production of 236 U/mL after 72 h incubation. The profile of lipase production matched the production profile of alkane hydroxylase, with a gradual decrease in activity after 42 h. During the fermentation, the OUR reached the maximum value suggesting the biodegradation of the substrate and decreased to the minimum values at the end of the fermentation (El-Bakry et al., 2016). During the stationary phase of the *A. borkumensis* growth, the death of microorganisms releases the protease into the fermentation media. The presence of protease acts on the alkane hydroxylase and lipase enzymes, suggesting a decrease in activity after 42 h. The decrease in OUR during the fermentation period (40 h) suggests the decreased growth of *A. borkumensis* with decreased CFU count resulting in the release of protease affecting the activity of enzymes. The scale-up study resulted in the increased production of enzymes and also helped to bring down the fermentation time from 72 h to 42 h for the maximum enzyme activity.

Conclusion

Scaling-up enzymes production in optimized conditions and inexpensive media is crucial to commercializing the process. The present study was an attempt in this direction. Alkane hydroxylase and lipase production was scaled-up to 150 L fermenter using 5% (v/v) motor oil. The agitation speed, as well as the aeration, influenced the extent of mixing in the bioreactor and resulted in high yields of alkane hydroxylase and lipase activities compared to our previous work in 5 L bioreactor. Further studies on the application of these produced enzymes need to be made for the further applied process.

TABLE 12

Maximum value of fermentation process parameters in 150 L bioreactor

| Parameters | Values |
|---|---|
| Max. $k_L a$ (h−1) | 196.95 |
| Max. OTR (mmol $O_2$/L/h) | 0.92 |
| Max. OUR (mmol $O_2$/L/h) | 1.8 |
| Max. specific growth rate (µmax/h) | 0.785 |
| Max. total cell count (×$10^{10}$ CFU/mL) | 8.6 |
| Max. alkane hydroxylase activity (U/mL) | 222.49 |
| Max. lipase activity (U/mL) | 325 |

TABLE 13

Technical comparisons between 5 L and 150 L bioreactors

| Bioreactor | 5 L | 150 L |
|---|---|---|
| Working volume | 3 | 100 |
| Height/Diameter ratio | 1.5:1 | 2:1 |
| Aeration | 3.5 L/min (20 psig) | 200 L/min (20 psig) |
| Agitation | 500 | 200 rpm |
| Impeller | 3 (small size) | 3 (small size) |

Screening for the Production of Biosurfactants and Column Tests for the Biodegradation of Diesel-Contaminated Soils Using *Alcanivorax Borkumensis* Enzymes

Example 6—Screening of Biosurfactant Production by *Alcanivorax borkumensis* Grown on Motor Oil Abstract The screening of biosurfactants production by *Alcanivorax borkumensis* grown on 3% (v/v) of motor oil was investigated. Biosurfactant screening tests revealed that parafilm test was positive, surface tension can be reduced to 34.27 dynes/cm and that hexane, hexadecane, and diesel can be emulsified with an emulsification index of 59%, 85% and 83%, respectively. The study of the stability of the biosurfactant at different temperatures (25-70° C.), pH (2-12) and NaCl concentrations (2-10%) showed that the naturally produced surfactant was quite stable and active even under extreme medium conditions with the best emulsification index found at 25° C., neutral pH and with 2% of NaCl. These preliminary results showed the potential of biosurfactant production by our strain in the presence of motor oil as a sole carbon source for the growth and that this surfactant can be used for oil recovery.

Materials and Methods
Microorganism and Culture Conditions

*Alcanivorax borkumensis* strain SK2 (DSM 11573) was used in this study. *A. borkumensis* was subcultured and streaked on agar plates, incubated for 72 h at 30±1° C. and then preserved at 4±1° C. for future use. Standard media consisted of (per liter of distilled water): 23 g NaCl, 0.75 g KCl, 1.47 g $CaCl_2 \cdot 2H_2O$, 5.08 g $MgCl_2 \cdot 6H_2O$, 6.16 g $MgSO_4 \cdot 7H_2O$, 0.89 g $Na_2HPO_4 \cdot 2H_2O$, 5.0 g $NaNO_3$, and 0.03 g $FeSO_4 \cdot 7H_2O$ (Yakimov et al., 1998). The media was supplied with 3% (v/v) motor oil as the carbon and energy source and the growth was monitored at 30° C., 150 rpm for 72 h.

Screening for Biosurfactant Production

Different methods such as parafilm test, emulsification test and surface tension were used for the screening of biosurfactant production during the time course of *A. borkumensis* growth on motor oil.

Parafilm Test

The method was performed on a band of parafilm M (4 in×125 ft). Briefly, a 25 µl of culture supernatant was dropped on the hydrophobic surface of the parafilm and then the diameter of the droplet was measured. Sterile water was used as a negative control. If the drop becomes flat, it indicates the presence of biosurfactant. If it remains in a dome shape, it indicates the absence of biosurfactant (Ilori et al., 2005).

Measurement of Surface Tension

The surface tension of the culture supernatant was measured using a tensiometer which consists of a 250 mm borosilicate long glass capillary tube graduated from 0 to 10 cm, a glass cylinder with tabulation and a rubber stopper. The non-inoculated culture medium was used as a control.

Emulsification Test

The emulsification index (E24) was measured according to a previously described method by (Ilori et al., 2005). 2 mL of diesel was added to 2 mL of cell-free broth. The mixture was vortexed at high speed for 2 min and left at room temperature. Measurements were taken 24 h later when the emulsion is stable. The (E24) is expressed in percentage and it is the height of the emulsion layer divided by the total height multiplied by 100. Hexadecane and hexane were also assayed for their ability to serve as a substrate for emulsification.

Biosurfactant Stability Studies

Stability of biosurfactant was studied under different temperatures, pH and NaCl concentrations to investigate the effect on the biosurfactant activity. Unless defined, the experiments were conducted at room temperature, neutral pH and without salt. For the temperature stability test, the samples were kept in 10 mL serum bottles and were tightly sealed with butyl rubber stoppers and aluminum crimps six solutions of biosurfactant cell-free broth were prepared under different temperatures ranging from 25-80° C. The emulsification index was measured and compared with at room temperature. For the salinity test, five solutions of biosurfactant cell-free broth were mixed with different NaCl concentrations ranging from 2 to 10% (w/v). The emulsification index was measured and compared with a non-saline solution. Finally, for pH stability test, six solutions of biosurfactant cell-free broth were prepared with different pH values: 2, 3, 6, 8, 10, 12. The emulsification index was measured and compared with a solution at pH 7.

Results and Discussion
Screening of Biosurfactant Production

To confirm the biosurfactant production, a drop of the supernatant was deposited on the hydrophobic surface of the Parafilm M. This test was used for qualitative purposes only and a flat drop indicated positive results. Results presented in Table 14 showed that the diameter of the different deposited drops increased with longer incubation time and became flattened. Indeed, higher cell production led to higher biosurfactant concentration. Zheng et al., (2012) used the Parafilm test to screen the production of biosurfactant by *Streptomyces* isolates and found that 37 out of 50 showed biosurfactant activity with a flat drop. Shekhar et al., (2018) has also used this test to demonstrate positive biosurfactant production by the strain *Pseudomonas stutzeri* (SSASM1).

TABLE 14

Parafilm test

| Sample | Diameter (cm) | Bacterial biomass (g/L) |
|---|---|---|
| Control | 0.4 | 0 |
| 6 h | 0.45 | $0.30 \times 10^{-4}$ |
| 18 h | 0.52 | $0.12 \times 10^{-2}$ |
| 24 h | 0.53 | $0.13 \times 10^{-2}$ |
| 42 h | 0.60 | $0.18 \times 10^{-2}$ |
| 48 h | 0.63 | $0.19 \times 10^{-2}$ |
| 66 h | 0.68 | $0.21 \times 10^{-2}$ |
| 72 h | 0.67 | $0.20 \times 10^{-2}$ |

Figure 25:
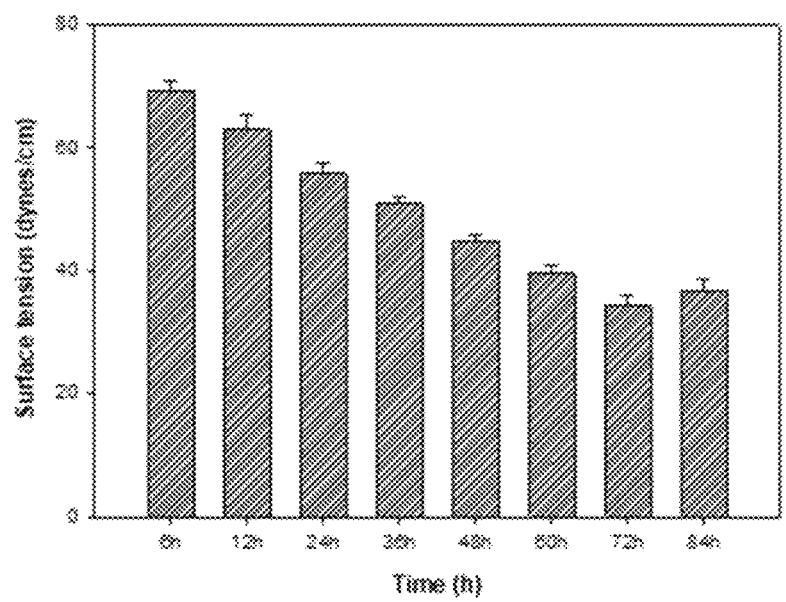
FIG. 25. Surface tension of *Alcanivorax borkumensis* in motor oil media.

Results presented in FIG. 25 showed a reduction of the surface tension measured using a tensiometer from 69.3 dynes/cm to 34.27 dynes/cm when increasing the growth time from 6 h to 72 h, respectively. Similar results were revealed by Sharma et al., (2015) who found that the surface tension reduced with the increase of the dry biomass of *P. aeruginosa* DSVP20 growing on three different substrates: pristane, eicosane, and fluoranthene with values of 27.6 and 32.4 dynes/cm after 3 days for pristane, eicosane, respectively, and 42.43 dynes/cm after 5 days for fluoranthene. Qiao and Shao, (2010) have stated that after 5 days of incubation with n-hexadecane as the sole carbon source in MSM medium, the surface tension of the bacterium *Alcanivorax dieselolei* B-5 reached 29.8-32.8 dynes/cm. *Bacillus licheniformis* JF-2 biosurfactant occurred during active growth but subsequently decreased until disappearance within 6 h and this is due to its internalization by stationary-phase cells (Lin et al., 1993). However, Joshi and Desai, (2013) studied the biosurfactant production by 5 bacterial strains for up to 72 h and reported surface tension values in the range of 28-30 dynes/cm. Ghojavand et al., (2008) and Al-Wahaibi et al., (2014) found that the biosurfactant production by two different species of *B. subtilis* reached the maximum after 10-12 h and continued to be constant even after the exponential phase.

Figure 26:
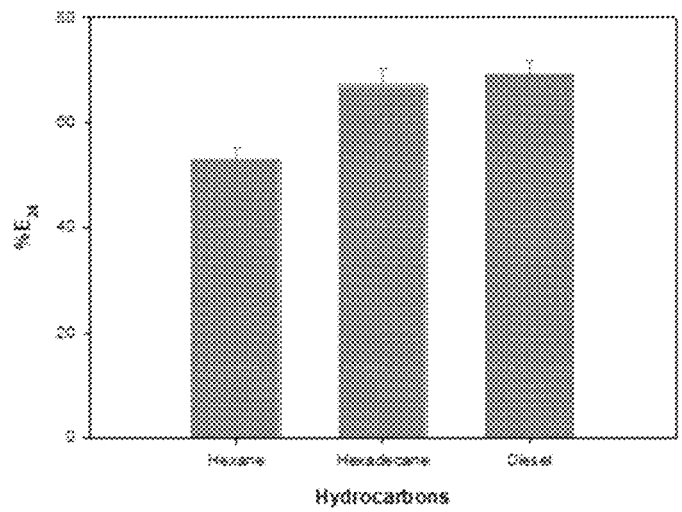
FIG. 26. Emulsification index against different hydrocarbons for *Alcanivorax borkumensis* biosurfactant extracted at the end of fermentation.

The emulsion test presented in FIG. 26 showed the presence of the biosurfactant through the production of emulsion with the supernatant mixed with hexane, hexadecane, and diesel. With hexane as a substrate, the emulsification index was found to be 59%, for hexadecane 85% and for diesel 83%. Al-Wahaibi et al., (2014) have demonstrated that the biosurfactant containing cell-free broth of glucose medium was able to emulsify many hydrocarbons such as tridecane, tetradecane, hexadecane, methylnaphthalene, heavy crude oil and light crude oil. While the biosurfactant containing cell-free broth of date molasses medium gave emulsions with all tested hydrocarbons, except for heavy crude oil. Mukherjee et al., (2008) have also investigated biosurfactant production by a marine strain *Bacillus* sp. in mineral salt media containing different carbon sources (glucose, sucrose, starch or glycerol) with higher emulsification obtained from glycerol and starch than that of the biosurfactant obtained from glucose and sucrose with E24 values in the range of 45-85%. Das et al., (2008) reported biosurfactant production by marine *Bacillus circulans* which emulsified various hydrocarbons such as diesel, hexadecane, kerosene, benzene and petrol in the range of 30-80%. The strain *Klebsiella* sp. FKOD36 isolated by Ahmad et al., (2016) showed an effective biosurfactant production among many other strains with maximum reduction in surface tension of 35.15 dyne/cm and an emulsification index of 66.7%.

Stability Study

Environmental conditions such as pH, temperature, and salinity play a key role in the biosurfactant production both qualitatively and quantitatively. Furthermore, the stability of the biosurfactant at high temperature, a wide range of pH and high salinity ensures the broad application in oil recovery.

Figure 27:
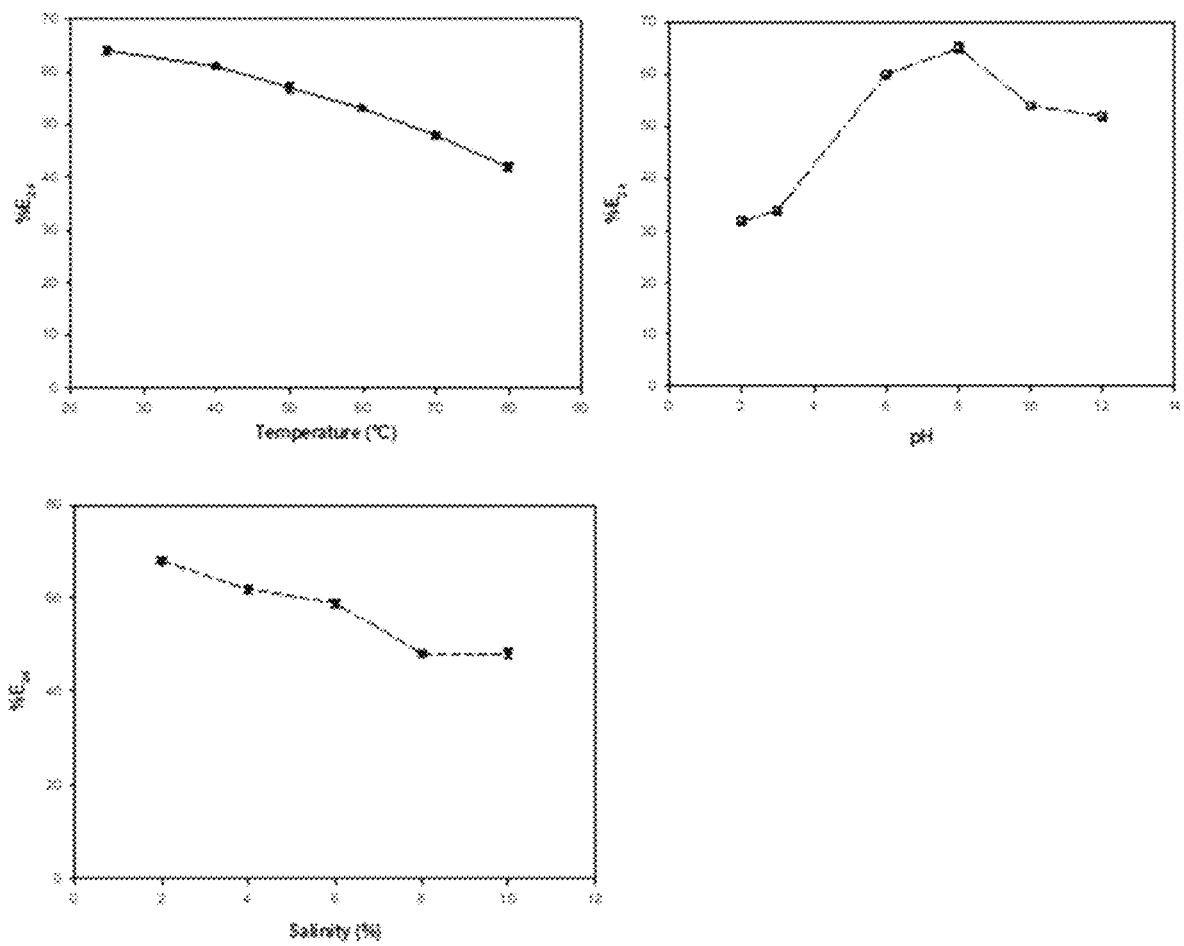
FIG. 27. Stability studies of the biosurfactant produced by *A. borkumensis* grown on 3% (v/v) of motor oil, under different temperature (A), pH (B) and salinity (C) conditions.

The performance of the biosurfactant under different temperature, pH and salinity concentrations are shown in FIG. 27. For different temperatures ranging from moderate (25° C.) to the extreme (80° C.), the biosurfactant exhibited a quite stable behavior with the best emulsification index of 64% obtained at the lowest tested temperatures (at 25° C.). Same results were reported by Al-Wahaibi et al., (2014) who tested the stability of *Bacillus* B10 partially purified biosurfactant and found a good stability under a wide range of temperature going up to 100° C. Joshi and Desai, (2013) stated that under extreme heat conditions, some types of biosurfactants remained intact with no properties modifications even when applying autoclaving (121° C. for 15 min). Almansoory et al., (2017) reported that the growth of *Serratia marcescens* at 30° C. produced higher biosurfactant yield (1.35 g/L) and less surface tension (27.8 mN/m) than at other temperature conditions (20, 25, 35 and 40° C.). Also, Bhardwaj et al., (2013) showed that the preferred temperature for *Candida* species is 30° C. with the best biosurfactant production.

Under extremely acidic conditions at pH 2 and pH 3, the biosurfactant activity decreased and showed lower E24 values of 32% and 34%, respectively. In fact, the biosurfactant was not soluble at acidic pH and have a tendency to precipitate. Some researchers associated the non-stability at acidic medium to the presence of negatively charged groups at the polar ends of the molecules (Batista et al., 2006). However, at alkaline pH conditions, the biosurfactant showed stable behavior even at pH 12 with E24 of 52%. And this stability has been also described by other researchers (Batista et al., 2006; Darvishi et al., 2011).

Finally, the biosurfactant showed fairly stable behaviour with the different NaCl concentrations tested with an emulsification index at 2% NaCl higher than the control in the absence of salt. These results can be explained by the fact that the *Alcanivorax borkumensis* is halophilic strain so some ranges of NaCl concentrations could be effective for the production of biosurfactant. Same results were reported by Al-Wahaibi et al., (2014) who found that the biosurfactant was active at salt concentrations up to 5%. Another report by Almansoory et al., (2017) showed that in the salinity is crucial for biosurfactant production and that in the absence of salt, the growth and the production slow down.

Conclusion

*Alcanivorax borkumensis* produced an effective biosurfactant when cultivated on 3% (v/v) motor oil as a sole carbon source. The biosurfactant showed quite stable behaviour under harsh conditions of temperature, pH and salt with 41%, 32% and 45% emulsification index at 80° C., pH 2 and 10% NaCl concentration, respectively. Furthermore, this biosurfactant offered stable emulsions with a wide range of hydrocarbons; hexane, hexadecane, and diesel with an emulsification index of 59%, 85%, and 83%, respectively. This study is a preliminary investigation that prepares for further experiments at higher scale.

Example 7—Evaluation of the Enzymatic Biodegradation Capacity of Highly Contaminated $C_{10}$-$C_{50}$ Soil in Column Tests Abstract Soil columns were set up to study the biodegradation of soil contaminated with a high concentration of diesel (=19,500 mg/kg) petroleum hydrocarbons with the crude enzyme produced by the hydrocarbonoclastic bacterium, *Alcanivorax borkumensis*. *A. borkumensis* was grown on a media with 3% (v/v) motor oil as sole carbon and energy source. The effects of the enzyme concentration, treatment time and oxidant on the bioremediation of $C_{10}$-$C_{50}$ were investigated. Also, a batch test with the same columns conditions was carried out in parallel to investigate the stability of the enzymes and the effect of the biosurfactants on the desorption and the bioconversion of $C_{10}$-$C_{50}$ in the soil.

Batch tests indicated that these biosurfactants significantly affected the desorption and that alkane hydroxylase and lipase enzymes maintained their catalytic activity during the 20 days of the test, with a half-life of 7.44 days and 8.84 days, respectively. The enzyme concentration X formulated with 40 U/mL of lipase and 10 U/mL of alkane hydroxylase, showed the highest conversion of 57.36% after 12 weeks of treatment with the best degradation rate of 0.0218 day$^{-1}$ compared to values obtained for the concentrations X/2 and X/10.

Materials and Methods

Microorganism and Culture Conditions

*Alcanivorax borkumensis* strain SK2 (DSM 11573) was used in this study for enzyme production. *A. borkumensis* was subcultured and streaked on agar plates, incubated for 72 h at 30±1° C. and then preserved at 4±1° C. for future use. The media consisted of (per liter of distilled water): 23 g NaCl, 0.75 g KCl, 1.47 g $CaCl_2 \cdot 2H_2O$, 5.08 g $MgCl_2 \cdot 6H_2O$, 6.16 g $MgSO_4 \cdot 7H_2O$, 0.89 g $Na_2HPO_4 \cdot 2H_2O$, 5.0 g $NaNO_3$, and 0.03 g $FeSO_4 \cdot 7H_2O$ (Yakimov et al., 1998). The media was supplied with 3% (v/v) motor oil as the carbon and energy source and the growth was monitored at 30±1° C., 150 rpm for 72 h.

Soil Column Tests

Soil

The soils used in the column tests experiments were provided by our industrial collaborator in this work (Laval, QC), and has been collected from a confidential and contaminated industrial site in Quebec, Canada used for petroleum product transfer and storage. The soil originally contaminated with $C_{10}$-$C_{50}$ was spiked in the laboratory with commercial diesel fuel in order to reach a field-representative initial concentration of 19,500 mg/kg. To initiate columns tests, 10 kg of soil was dried at 60° C. for 24 h to remove the moisture. Afterwards, the soil was characterized in terms of grain size distribution and divided accordingly. The grain size distribution is shown in Table 15 following the ASTM D422-63 sieving procedure (ASTM, 2006). The finest and the biggest particle sizes were discarded and the particle sizes between 250 μm and 2 mm were thoroughly remixed and used for column tests. Other soil properties are summarized in Table 16. The total carbon of the soil was 2.6%, pH was 6.5, the porosity once packed in the columns was 0.287 and the hydraulic conductivity was 0.88*10-2 m/s. Column tests were made under full water saturation.

TABLE 15

Grain size distribution of the soil

| Class | Weight (kg) | Percentage (%) | Soil type (AASHTO*) |
|---|---|---|---|
| X > 8 mm | 6.75 | 38.42 | FINE GRAVEL |
| 4 mm > X ≤ 8 mm | 1.99 | 11.33 | |
| 4 mm > X ≤ 2 mm | 1.06 | 6.03 | |
| 1 mm > X ≤ 2 mm | 1.55 | 8.82 | COARSE SAND |
| 500 μm > X ≤ 1 mm | 1.74 | 9.90 | |
| 250 μm > X ≤ 500 μm | 1.71 | 9.73 | FINE SAND |
| 125 μm > X ≤ 250 μm | 1.18 | 6.72 | |
| ≤125 μm | 1.59 | 9.05 | SILT |
| Total | 17.57 | 100.00 | |

*American Association of State Highway and Transportation Officials

TABLE 16

Soil characteristics

| pH | Moisture content (% dry weight) | Total carbon (COT %) | Nitrogen (%) | Flow rate (mL/min) | Porosity | Pore volume (cm$^3$) |
|---|---|---|---|---|---|---|
| 6.5 | 13.5 | 2.6 | 0.2 | 0.41 | 0.287 | 48.08 |

Enzymes

The fermented broth of *A. borkumensis* was centrifuged at 8000 rpm for 10 min at 4° C. The cell-free supernatant represented the crude extracellular enzyme from which lipase activity was estimated. The pellet was re-suspended in phosphate buffer (1 mL, 0.1 M, pH 8.0) and then ultra-sonicated using two frequencies of ultrasounds (22 kHz and 30 kHz) for 6 min at 4° C. and centrifuged at 13,000×g for 20 min. The supernatant was used as a crude intracellular enzyme extract to estimate alkane hydroxylase activity.

Alkane Hydroxylase Assay

Alkane hydroxylase activity was measured using a cofactor (NADPH) depletion assay to determine relative activities. The supernatant containing the enzyme was diluted into phosphate buffer (0.1 M, pH 8), alkane substrate (0.5-1 mM), and dimethyl sulfoxide (DMSO; 1%, v/v). Alkanes were added to the buffer using alkane stock solutions in DMSO. The reaction was initiated by addition of NADPH (200 μM), and the oxidation of NADPH was monitored at 340 nm (Glieder et al., 2002). The alkane substrate used was hexadecane.

Lipase Assay

The lipase activity assay was conducted based on the spectrophotometric method described by Schultz et al., (2007) with some modifications. The stoichiometric release of p-nitrophenol (p-NP) was measured from cleavage of p-nitrophenyl palmitate (p-NPP). p-NPP stock solution at concentration 100 mM was prepared in acetone and 30 μl was added to 2.82 mL of measuring buffer (0.1 M sodium phosphate, 10% v/v acetone, 4% v/w Triton X-100, 0.2% w/v gum arabic, pH 8.0). The prepared solution was incubated for 5 minutes in a 60° C. water bath. Subsequently, it was cooled to 29° C., added to a pre-warmed cuvette (29° C.), containing 150 μl of the lipase solution and placed into the temperature-controlled spectrophotometer (Spectrophotometer CARY 300 UV-VIS). No mixing and no agitation were carried out. The spectrophotometric measurements were conducted at 410 nm.

The concentration X of enzymes that were used in this study for column tests corresponds to the mixture of 10 U/mL of alkane hydroxylase and 40 U/mL of lipase.

Soil Column Experiments
Column Set-Up

Four sets of soil column experiments were carried out in this study. These were identified with alphabetic names B, C, D, and E. Additionally, one control experiment identified as A and one duplicate identified as DUP were also carried out. In each set of experiment, two columns were used (B1, B2, C1, C2, D1, D2, E1, E2). The first column was opened for analysis after 6 weeks of enzymatic treatment and the second one was opened only after 3 months of treatment. A total number of 10 columns were therefore used (more details are provided below). The columns were thoroughly washed with detergent, rinsed many times with distilled water and then dried at room temperature. Column tests were conducted in a permeameter consisting of an acrylic cylinder clamped between Teflon© end plates. One porous nylon disk with a mesh size of 35 μm was inserted at each end of the column, and two O-rings were used to seal the cylinder with the end plates. Viton tubes were used for inflow and outflow. The geometrical characteristics of the columns are summarized in Table 17.

TABLE 17

Geometry of the columns

| Column | Height (cm) | Radius (cm) | Column volume (cm³) | Necessary weight (g) |
|---|---|---|---|---|
| Steel | 14.4 | 1.9 | 155 | 279.5 ± 2.5 |
| Teflon | 15 | 2 | 180.23 | 324.4 ± 2.5 |

The soil columns were prepared using the standard packing procedure presented in Martel and Gélinas, 2016. The soil was added in successive layers of 1 cm in each of the columns and each layer was artificially contaminated with 20 μl of diesel fuel using a micropipette. The soil was compacted to a dry density of 1.8 g/cm³ as shown in Table 17. Each layer of compacted soil was scarified before adding the next layer to prevent preferential flow paths. Finally, the columns were kept entirely sealed until the analysis date.

Figure 28:
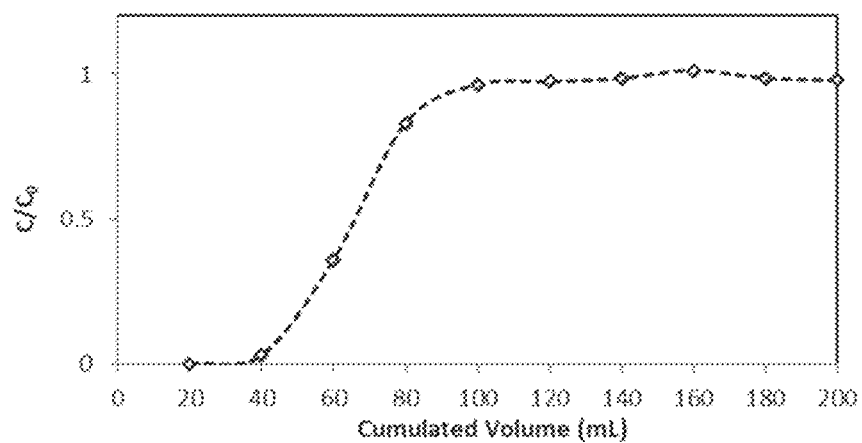
FIG. 28. Output curve of CI−. *For C/C0=0.5, pore volume=48.08 cm3 (this is the volume of enzyme solution needed to saturate one column).

Soil columns were initially saturated from the bottom up with distilled water overnight using a peristaltic pump. And then, 200 mL (which is equivalent to 4 times the pores volume) of enzyme solutions with different concentrations (as detailed in the next section) were flushed through each column. Effluents were collected for characterization after each 20 mL injected. As shown in Table 18 and FIG. 28, Cl—, one of the components of the enzyme solution, was selected as a conservative tracer and used to determine the effective pores volume of the soil columns used for the experiments. The concentration of Cl— collected in the effluent samples was measured using ionic chromatography.

TABLE 18

Output of Cl⁻

| Sample | Volume (mL) | Cumulated volume (mL) | Cl⁻ (mg/L) | C/C₀ |
|---|---|---|---|---|
| V0 | 0 | 0 | 19029.000 | — |
| V1 | 20 | 20 | 0.37 | 1.9681E−05 |
| V2 | 20 | 40 | 590 | 0.03098927 |
| V3 | 20 | 60 | 6844 | 0.35967246 |
| V4 | 20 | 80 | 15812 | 0.83095364 |
| V5 | 20 | 100 | 18332 | 0.96334866 |
| V6 | 20 | 120 | 18524 | 0.97344475 |
| V7 | 20 | 140 | 18734 | 0.98448254 |
| V8 | 20 | 160 | 19269 | 1.01262732 |

TABLE 18-continued

Output of Cl⁻

| Sample | Volume (mL) | Cumulated volume (mL) | Cl⁻ (mg/L) | C/C₀ |
|---|---|---|---|---|
| V9 | 20 | 180 | 18749 | 0.98529961 |
| V10 | 20 | 200 | 18611 | 0.97801145 |

$C_0$: The initial concentration injected;
Pores volume: 48.08 cm³ (This is the volume of enzyme solution needed to saturate one column)

Soil Flushing with Enzyme Solutions

A total of 10 columns were used for these experiments, which were identified with letters A to E, each with varying experimental conditions as detailed below:

Column A: Control without enzyme (Soil+Diesel+Water)
Column B1: enzyme concentration X, a treatment time of 6 weeks with an enzyme injection each 3 weeks
Column B2: enzyme concentration X, a treatment time of 12 weeks with an enzyme injection each 3 weeks
Column C1: enzyme concentration X/2, a treatment time of 6 weeks with an enzyme injection each 3 weeks
Column C2: enzyme concentration X/2, a treatment time of 12 weeks with an enzyme injection each 3 weeks
Column D1: enzyme concentration X/10, a treatment time of 6 weeks with an enzyme injection each 3 weeks
Column D2: enzyme concentration X/10, a treatment time of 12 weeks with an enzyme injection each 3 weeks
Column E1: enzyme concentration X+100 mg/L of $O_2$ (calcium peroxide), a treatment time of 6 weeks with an enzyme injection each 3 weeks
Column E2: enzyme concentration X+100 mg/L of $O_2$ (calcium peroxide), a treatment time of 12 weeks with an enzyme injection each 3 weeks
Column Dup (this is the duplicate of the column D2): enzyme concentration X/10, a treatment time of 12 weeks with an enzyme injection each 3 weeks As mentioned earlier, X corresponds to a concentration of crude alkane Hydroxylase of about 10 U/mL+/−40 U/mL of crude lipase.

The column tests were carried out over a period of 3 months, and the injections were done every 3 weeks for all the columns. Columns (B1, C1, D1, E1) were opened after 6 weeks in order to determine the concentration of degraded diesel after 2 injections. The rest of the columns (B2, C2, D2, E2) were opened after 3 months of treatment to measure the diesel concentration.

Batch Test for Enzyme Stability and Effect of Biosurfactant on Soil Desorption and Biodegradation Batch tests were held separately from the columns in sealed flasks where the conditions were the same as within the columns. 10 g of homogeneous diesel-contaminated soil was mixed with an aqueous medium in a flask and the content was thoroughly mixed. Three different experiments were carried out: (1) a control sample of diesel-contaminated soil was mixed with water only; (2) Another sample of soil contaminated diesel was mixed with the biosurfactant only; and (3), another contaminated soil sample was mixed with the enzyme at a concentration X including the biosurfactant. For each test, a sample was taken each 2 days to determine the lipase and alkane hydroxylase stability over a period of 3 weeks. The extent of biodegradation was estimated from the total diesel content of the soil. The extent of desorption was estimated from the total diesel content in the contaminated soil before treatment and that present in the soil as well as in the liquid dispersion after the treatment.

Diesel analysis
Extraction

For the extraction of $C_{10}$-$C_{50}$ from the soil the protocol of CEAEQ, 2007 was followed. After opening the column, the soil was thoroughly homogenized. Afterwards, 6 to 8 g was weighed into 43 mL glass vials (to have at least 5 g of dry soil). In parallel, the % of moisture content was determined by weighing 5 g of soil in a pre-weighed aluminum cup and placing it in a 105° C. oven for at least 4 hours. Later on, 5 mL of acetone were added and the mixture was shacked on a vortex for a few seconds (10-15 sec). Another 5 mL of hexane were also added and vortexed for a few seconds. The mixture was then ultrasonicated for 30 minutes in an ultrasound bath. Finally, 25 mL of water was added, the mixture was agitated with a vortex and centrifuged for 5 minutes. 2 mL of the upper phase containing hexane was transferred to a glass tube and 150 mg of silica gel was added to purify the sample. The sample was then shaken and settled. 1 mL (minimum 0.5 mL) was finally transferred in a gas chromatography vial of 2 mL for subsequent analysis. 5 replicates were performed to avoid the large difference in results.

Gas Chromatography

GC analysis of petroleum hydrocarbons biodegradation was performed using Hewlett-Packard 6890/5973 chromatograph equipped with flame ionization detector (FID). Analyses were carried out with helium as the carrier gas at a flow rate of 2 mL/min on a DB-1 column (30 m, 0.53 mm i.d., 1.0 mm film thickness). Oven temperature was programmed from 60±1° C. 260° C. at a rate of 4±1° C./min. Split/Splitless injector and detector (FID) temperatures were 260±1° C. and 260±1° C., respectively, and 1 mL of the sample was injected.

Statistical Analysis

Data in this study were summarized as the mean±standard deviation (SD).

Results and Discussion

In general, laboratory pan microcosm and/or column tests are conducted to determine the kinetics of biodegradation, depending on whether an ex- or in situ approach is desired. Alternately, a microcosm test can be used to model essential characteristics of the environment to predict the consequences of bioremediation treatment.

In this section, production of key players enzymes, their stability and their efficacy for contaminant degradation, surfactant effect in contaminant solubilization and biodegradation determined from laboratory shake flask experiments have been documented. Results from a complementary laboratory microcosm study are also presented in order to draw inferences regarding biodegradation potential from a technological perspective.

Effect of Biosurfactants on Soil Desorption and Biodegradation

As hydrocarbons are mostly insoluble in water, bacterial cultures producing biosurfactant such as A. borkumensis (Yakimov et al., 1998) plays a key role in the solubilization and/or emulsification of hydrocarbons. These mechanisms lead to desorption and, by increasing the availability of hydrocarbons in the aqueous phase, ultimately enhance the biodegradation rate (Gogoi et al., 2003). Moreover, biosurfactants are an alternative to chemical surfactant because of their properties as eco-friendly, least toxic, biodegradable and exhibiting high specificity (Ahmad et al., 2016).

Based on results from previous work (unpublished data) which studied the tension and emulsification index of aqueous biosurfactant solution produced by A. borkumensis grown on motor oil, oil solubilization and consequent desorption from the soil matrix is expected to be high.

The effects of the biosurfactant on desorption and degradation were separately studied in a batch test carried out for 3 weeks using the same soil with the same diesel concentration at room temperature. Results of desorption and biodegradation of the different samples are shown in Table 19 from which it is apparent that, the biosurfactant had a significant effect on the desorption process, however the effect on the biodegradation was only marginal. It may be possible, based upon the hypothesis that mass transfer limitations dominate contaminant fate in the soil matrix, to determine the treatment end-point of the hydrocarbons. Under the ideal conditions of the slurry reactor, desorption and solubilization with cultured microorganisms are maximal which, in turn, maximizes the extent of biodegradation. Same biosurfactant behavior was found by Gogoi et al., (2003) who found a description of 71% of oil and a biodegradation percentage of 28%.

TABLE 19

Batch test of the effect of biosurfactant on soil desorption and biodegradation

| Sample no. | Treatment | Desorption (% oil) | % Biodegradation |
|---|---|---|---|
| 1 | Control (Soil + water) | 21.94 ± 1.4 | — |
| 2 | Soil + Biosurfactant | 73.85 ± 3.7 | — |
| 4 | Soil + enzyme + biosurfactant | — | 27 ± 4.6 |

Stability of Enzymes in Batch Test

Figure 29:
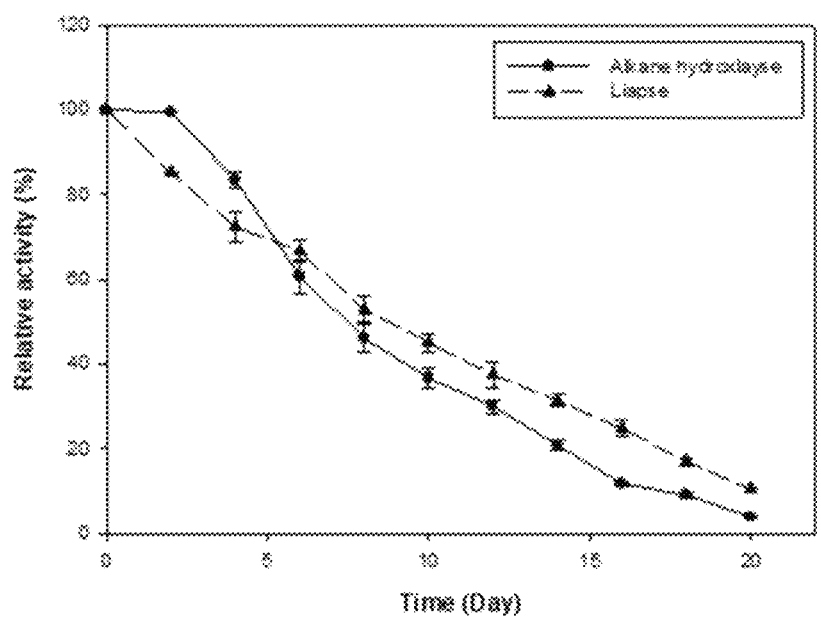
FIG. 29. Stability test of alkane hydroxylase and lipase in soil batch experiment.

Stability tests for alkane hydroxylase and lipase were conducted in batch to determine the necessary period required to re-inject a fresh enzyme in the column tests to maximize the degradation efficiency. FIG. 29 shows the profiles feature of the relative activity of alkane hydroxylase and lipase relatively to the activity of the first day which is the highest. Both enzymes were kept at room temperature for 3 weeks and their activities were determined periodically to evaluate their stability. The results demonstrated that both alkane hydroxylase and lipase enzymes showed the presence of activity until 3 weeks with a half-life of 7.44 days and 8.84 days, respectively. During the first 5 days of experience, free alkane hydroxylase lost 40% of its activity while lipase lost 34% of the activity. After 20 days, alkane hydroxylase and lipase maintained 4% and 10.4% of their catalytic activity, respectively.

Previous studies on oxidoreductase type of enzymes, such as laccase showed no activity after 10 days (Xu et al., 2013). Chiou and Wu, (2004) observed that the activity of lipase decreased more than 50% in 5 days at 25° C. (Chiou and Wu, 2004).

HP $C_{10}$-$C_{50}$ degradation Four sets of experiments were performed with a soil procured from a confidential site in Quebec with the same initial concentration of HP $C_{10}$-$C_{80}$ (19,500 mg/kg) and four different enzymes concentrations or composition. The first set B was performed with an enzyme concentration X (X corresponds to 10 U/mL of alkane hydroxylase and 40 U/mL of lipase). The second set C was performed with an enzyme concentration X/2. The third set D was performed with an enzyme concentration X/10 and the final set was carried out with a concentration X of enzyme and 100 mg/L of $O_2$. For each set of experiment, two different degradation times were tested in two columns, one column was opened after 6 weeks of treatment and the $2^{nd}$ one after 3 months during which freshly produced enzymes were injected every 3 weeks.

Figure 30:
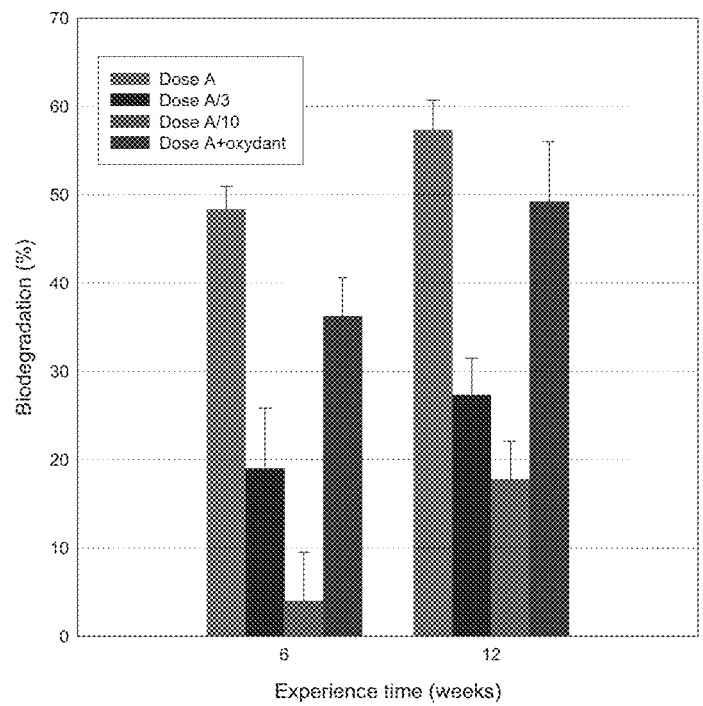
FIG. 30. Global degradation results in soil columns (initial concentration of diesel=19,500 mg/kg).
Figure 31:
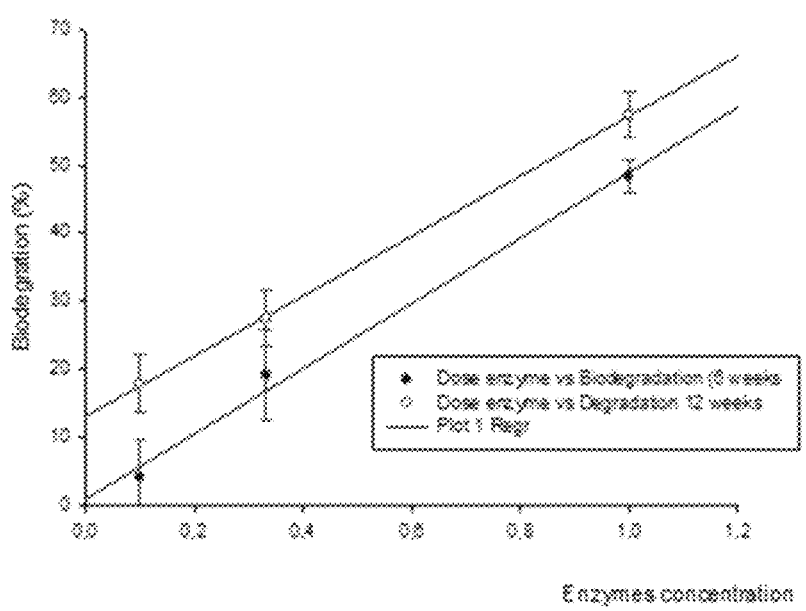
FIG. 31. Correlation between biodegradation and enzymes concentration in columns test.

Results presented in Table 20 have shown that the best degradation percentages for all the sets of experiments were detected in the treatment time period of 3 months, however, the degradation between 6 weeks and 3 months started to decrease. In fact, as shown in FIG. 30 only about 10% increment was detected for the set B, with 48.35% degradation after 6 weeks and 57.36% degradation after 3 months. This indicates that the speed of the reaction started to slow down and will reach an apparent plateau after a certain time. Admon et al., (2001) reported that the degradation pattern is commonly distinguished by a decrease in the degradation rate during the time and this is due to the persistence of oil residue in the soil, usually at a 10 to 25% concentration. Another hypothesis that was set by Namkoong et al., (2002) has related the Difference in TPH degradation rate in time to the rapid degradation of n-alkanes in TPH at the early stage and the resistance of heavier molecular weight followed by a slower conversion. Also from FIG. 30 we can observe that the highest degradation obtained from 3 months treatment (57.36%) was noticed in the column B2 treated with the highest enzyme concentration X, followed by the column E2 in which the oxidant was added at a concentration of 100 mg/L with 49.26% degradation, and from here we can conclude that the source of oxygen has inhibited the degradation and this can be due to the optimal pH of the function of calcium peroxide which was demonstrated to be 11. The lowest degradation was observed in columns C2 and D2 with a degradation percentage of 27.38 and 17.77% respectively. In this same context, FIG. 31 presented the correlation between the concentration of the enzyme and the degradation percentage in 6 weeks and 12 weeks showing an increase in both cases.

TABLE 20

Degradation percentage of $C_{10}$-$C_{50}$

| Sample (5 replc$^{rs}$) | Total diesel concentration (mg/kg soil) | Degradation Percentage (%) | Mean value of degradation Pourcentage (%) |
|---|---|---|---|
| A1 | 19458.848 | — | 19500.32 ± 35.07 |
| A2 | 19542.2736 | — | |
| A3 | 19469.613 | — | |
| A4 | 19519.980 | — | |
| A5 | 19510.926 | — | |
| B11 | 9980.1472 | 48.82114256 | 48.35% ± 2.57 |
| B12 | 9644.432 | 50.54275897 | |
| B13 | 10891.6048 | 44.14700103 | |
| B14 | 9959.424 | 48.92741538 | |
| B15 | 9698.44 | 50.26579487 | |
| B21 | 7454.5984 | 61.77129026 | 57.36% ± 3.33 |
| B22 | 8238.5488 | 57.75103179 | |
| B23 | 8567.5552 | 56.06381949 | |
| B24 | 8993.9632 | 53.87711179 | |
| B25 | — | — | |
| C11 | 14182.7552 | 27.2675445 | 19.05 ± 6.79 |
| C12 | 15102.6896 | 22.54999751 | |
| C13 | 15336.2944 | 21.35204077 | |
| C14 | 17021.6528 | 12.70929685 | |
| C15 | 17285.8816 | 11.35429612 | |
| C21 | 13697.1496 | 29.75779515 | 27.38 ± 4.095 |
| C22 | — | — | |
| C23 | — | — | |
| C24 | 13701.3336 | 29.73633904 | |
| C25 | 15082.5944 | 22.65304839 | |
| D11 | 19184.3328 | 1.61878374 | 3.99 ± 0.39 |
| D12 | 19250.5856 | 1.279030495 | |
| D13 | 19338.4256 | 0.828575194 | |
| D14 | — | — | |
| D15 | — | — | |
| D21 | 15459.4136 | 20.720669 | 17.78 ± 4.31 |
| D22 | 16287.0632 | 16.47637084 | |
| D23 | 16177.2216 | 17.0396533 | |
| D24 | 15025.6632 | 22.94499922 | |
| D25 | 17215.7016 | 11.71418857 | |
| E11 | 11180.4784 | 42.66362261 | 36.31 ± 6.36 |
| E12 | 11490.664 | 41.07294925 | |
| E13 | 12173.8896 | 37.56927673 | |
| E14 | 12991.2704 | 33.37763836 | |
| E15 | 14256.336 | 26.89021229 | |
| E21 | 10686.12 | 45.19875879 | 49.26 ± 6.75 |
| E22 | 10241.8832 | 47.47686468 | |
| E23 | 10094.272 | 48.23383471 | |
| E24 | 7603.8752 | 61.00492352 | |
| E25 | 10841.4576 | 44.40216674 | |
| DUP1 | — | — | 12.60 ± 4.90 |
| DUP2 | 16124.552 | 17.30998974 | |
| DUP3 | 18033.064 | 7.522748718 | |
| DUP4 | — | — | |
| DUP5 | 16968.2464 | 12.98335179 | |

To the best of our knowledge, most of the reports on soil columns tests for hydrocarbons degradation reported treatments using a sole strain or microbial consortia but there are no reports about enzymatic treatment. Suja et al., (2014) found 80% degradation of total TPH in soil microcosm experiments with an initial concentration of 10,000 mg/kg using different microbial consortia for 70 days. This same author investigated the degradation of TPH fractions such as residual oil fractions, gasoline, and diesel, by three different microbial consortia and demonstrated that the diesel fraction is the most degraded fraction. Ueno et al., (2006) tested the degradation of 1% (w/w) of diesel oil in 2 g of soil microcosms using the strain *Pseudomonas aeruginosa* WatG and found a degradation of 51% in a time period of one week. Das and Mukherjee, (2007) used *Pseudomonas aeruginosa* M and NM consortia and *Bacillus subtilis* to treat contaminated soil in a microcosm experiment and showed effective bioremediation when compared to the control set after 120 days.

Degradation Kinetics

The biodegradation rate conceives the progress and the rapidity of the reaction which facilitates the choice of the most suitable treatment among others which is the case in this study. In fact, in laboratory and field-scale experiments, the study of the degradation kinetics is crucial to predicting the fate of petroleum hydrocarbons in the soil (Admon et al., 2001). For the biodegradation of organic compounds, a first-order kinetics model is commonly used (Namkoong et al., 2002), and this is due to the possibility of prediction of concentrations. Specifically, degradation of hydrocarbons was studied in laboratory experiments at different scales and the overall trend of hydrocarbon reduction follows first-order kinetics as observed before by other authors (Van Gestel et al., 2003).

First-order rate constants (k) for all columns experiments are presented in Table 21. The high correlation coefficients ($R^2$) indicated that first-order kinetic model fitted well hydrocarbon degradation in the different column tests with different enzyme concentrations. The first order kinetic model was linearly regressed with the relationship between the reaction time and natural log value of diesel concentration. The kinetic parameters showed that the highest degradation rate was obtained with the highest enzyme concentration (X) in column B with a degradation rate of 0.0218 day$^1$ followed by E, C, and D with a degradation rate of 0.0175, 0.0124 and 0.0050 day$^{-1}$ respectively. The lowest rate was obtained when using the lowest enzyme concentration of X/10. The rate constants for different petroleum hydrocarbons have been identified by previous studies and summarized by the study done by Rončević et al., (2005) and (Admon et al., 2001). In these studies, the rate constants have been divided as follows: n-alkanes, 0.14 to 0.61 day$^{-1}$; crude oil, 0.0051 to 0.0074 day$^{-1}$ and diesel and crude oil, 0.015 to 0.089 day$^{-1}$. Other studies have also investigated the rate of biodegradation such as the study by Suja et al., (2014) in which the fastest rate constant was 0.039 day$^{-1}$ using microbial consortia for the bioremediation of TPH in soil column setups. And the study by Namkoong et al., (2002) who found that the first-order degradation rate of n-alkanes was significantly higher than TPH regardless of the type and the mass of organic amendments that were used.

TABLE 21

Parameter values and coefficients of determination for first-order degradation in columns tests

| Experiment | Enzyme concentration | Coefficient of determination $R^2$ | First-order rate constant k (day$^{-1}$) |
|---|---|---|---|
| B | X | 0.906 | 0.0218 |
| C | X/2 | 0.995 | 0.0124 |
| D | X/10 | 0.850 | 0.0050 |
| E | X/10 + $O_2$ | 0.965 | 0.0175 |

Conclusion

The focus of this study was to evaluate the biodegradation performance of enzymes produced by the hydrocarbonoclastic bacteria *A. borkumensis* grown on motor oil when applied on column diesel-contaminated soil at different concentrations to provide the maximum of information on potential limitations at reasonable costs and time. Results showed that the enzyme concentration X formulated with 40 U/mL of lipase and 10 U/mL of alkane hydroxylase, showed the highest degradation of 57.36% of the intial HP C10-C50 concentration after 12 weeks of treatment with the best degradation rate of 0.0218/day. These tests degradation performance can be improved by increasing enzymes concentration. All of these results yielded important estimation of C10-C50 hydrocarbon degradability in soils. Furthermore, results are in accordance with different contamination types and site histories, despite rates slightly overestimating field rates. Thus, column tests provide substantial information for the choice of suitable technology to clean-up the site of concern, by spotting limitations to biodegradation, predicting remediation performance and provide design parameters for full scale remediation applications.

Figure 32:
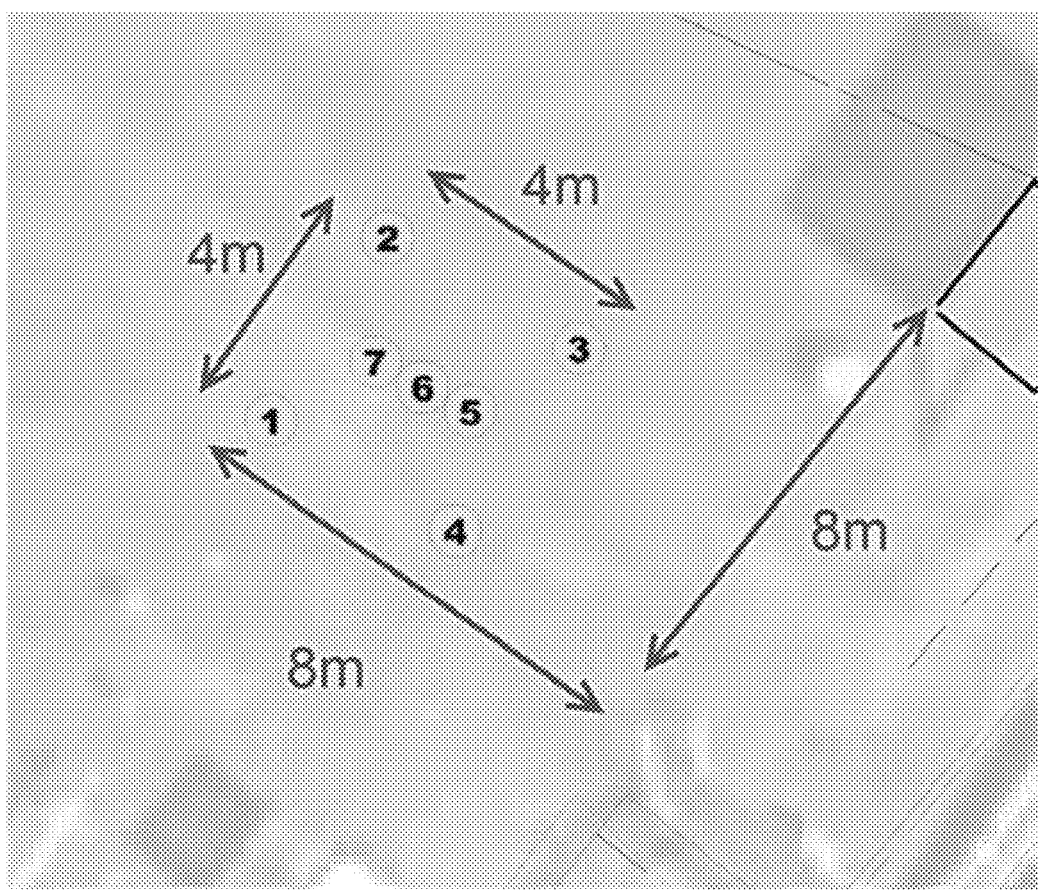
FIG. 32. Testing cell localization map. Note: well no. 6 is the injection well.

Example 8—Protocol for Pilot Testing at the Experimental Site and Preliminary Analysis of Results Following the First Injection Testing Cell Layout The objective of this test is to set up a typical testing cell of a 5-point injection/extraction pattern (standard), i.e. 4 extraction wells at the 4 corners of the cell and an injection well in the centre. The addition of monitoring wells midway between the injection and extraction wells was established (FIG. 32).

Methodology: the wells were set up using a drill. Soil samples were sampled continuously within the zone targeted for the injection of the enzyme solution. After the establishment of the wells, groundwater samples were collected for HP C10-C50 analysis (Table 22).

Preparation of the Equipment Required for Testing
At least two tote containers of 1 m$^3$ each for the preparation of enzyme solutions
Injection line:
  Connectors for the containers' base and injection lines to the bottom of the well;
  Diaphragm pump to avoid pressure drop (optional) and power supply (compressed air);
  1 flow adjustment valve type "tap";
  Provide an air inlet in the highest part of the assembly with an on/off valve (for priming).
1 low speed mixer with a power source (electricity) or recirculation pump.
2 to 3 peristaltic pumps for sampling monitoring wells with a power source (batteries) with black casing and connectors.
¼ tubing for sampling in wells.
1 multiparameter probe (YSI or Hanna): CE, pH, OD, ORP.
Masson jars 250 ml (high) for tracking with YSI.
Water level probe (interface if free phase).

Enzyme Solution Injection:
The objective was to maximize a homogeneous radial distribution of the diluted enzyme solution.
Methodology (Injection #1):
  It was planned that the injection of 5,000 litres of diluted solution should allow to reach the wells located at the 4 corners of the cell.
  Take readings of water levels and phase thickness in all wells.
  Take readings for measuring the electrical conductivity in the wells.
  the crude enzyme crude brew was diluted in 5,000 litres of solution (5 times the following mixture: 960 litres of water+2 broth boilers)—and, once mixed, the electrical conductivity of the tote containers was measured.
  5,000 litres were injected through the action of gravity by not forcing the solution into the formation.
Follow-up during injection:
  Injection rate was controlled by start and stop every 1,000 L;
  The electrical conductivity was monitored in the two wells located at 1 m from the injection well depending on time (one measurement per 250 litres injected if possible).
At the end, a 50 ml sample was taken from each well (injection, 2 monitoring wells and 4 wells at the 4 corners of the cell), were labeled, refrigerated and sent in a cooler with icepacks ASAP for enzymatic activity analysis.

Verification Drilling
The objective was to measure the impact of the enzyme solution injection at least 3 weeks after the end of the injection and before the next injection.
Methodology: Two wells were drilling at 1 m distance from the injection well and the soils located in (and near) the vertical layers targeted by the injection were continuously sampled. HP C10-C50 was analysed. The holes were filled with bentonite.

Summary of the Results Obtained after the Injection #1
Distribution of the Injected Solution
The initially high electrical conductivity values made it difficult to establish a connection between the electrical conductivity measured in the wells and the entrance of the solution. However, the injected solution was opaque (visual tracer) and the observations made after the end of the injection indicated that the water had become opaque in all wells.

The "true" distribution was given by the analysis of the enzymatic activity on the samples taken from wells after the injection of 5,000 litres of diluted solution (Table 23).

Table 23 shows that the activity observed at wells 6, 7 and 3 is similar to the injected solution, and that there is 18 to 31 times more enzymatic activity than the reference observed during the column tests. However, at wells 4 and 1, there was a dilution of 1/10 and 1/20 of the injected solution, respectively. However, the activity observed in these wells remained close to that measured in the column tests.

Observation: the injection of 5,000 litres was partially sufficient to reach the wells located at the 4 corners of the cell.

Soil Characterization

Table 26 presents the results of the verification drilling conducted near the injection well (at 1 m distance) after the first injection. Comparing these results with those obtained on the whole cell, there is a significant reduction in concentrations of $C_{10}$-C50 (from 36% to >99%) following this first injection, mainly for the contaminated soils located in the saturated zone of the unconfined aquifer. When we only compared to the results obtained from wells 3, 5 and 7, then the percentage of reduction was higher. As it can be observed, the magnitude of the reduction increased with depth. This phenomenon could be associated with a density effect that induced a downward movement of the injected solution. This will be verified by complementary density measurements.

Finally, it should be noted that, independently of the degradation associated with the enzymatic activity, two other factors that are difficult to quantify must be considered in the analysis of these results: the heterogeneity of the initial concentrations of HP C10-C50 in the cell, and the presence of potential mobile free phase observed locally on the site.

Proposed Strategy for the Next Phase

In subsequent injections, two experimental variables were verified: the impact of a second injection on the reduction rates (injection No. 2), and the impact of the increased injected volume associated with a reduction in the density of the solution (injection No. 3). The enzymatic activity results obtained following the first injection suggest that even with this dilution, the activity should be sufficient to degrade the hydrocarbons in place. Injections 2 and 3 allowed verification of these experimental variables.

Protocol Specific to Injection #2: Same as for Injection #1

Protocol Specific to Injection #3

200 L of the supplied enzyme crude brew was evenly distributed in 10,000 litres of water (20 litres per tote container).

Injection: the flow rate was controlling between 12 and 14 L/min to favour a slower distribution of the solution in the environment and thus potentially favour a better distribution in the less permeable layers of soils Groundwater characterization (front): All cell wells were sampled prior to injection for enzymatic activity analysis.

Follow-up during the injection: the CE was followed in a few wells using the probes (same approach as the second injection) and tracked manually every 500 L injected (day 1) and 1,000 litres injected (day 2). the 4 corners of the cell were visually checked every 1,000 litres injected to note the appearance of the enzyme solution. The injection totes were sampled for enzymatic activity analysis and CE.

Characterization of groundwater (after): All cell wells were sampled after injection for enzymatic activity analysis.

Soil characterization: Planned for drilling 1 m from the injection well (2) and 1 meter from the 4 corners wells towards the interior of the cell.

TABLE 22

HP C10-C50 concentration in the cell groundwater

| PETROLEUM HYDROCARBONS | Units | RD18-01 | RD18-03 | RD18-05 | RD18-07 | LDR | Lot CQ |
|---|---|---|---|---|---|---|---|
| Petroleum Hydrocarbons (C10-C50) | ug/L | 1300 | 1600 | 1200 | 1600 | 100 | 1929349 |

TABLE 23

Enzymatic activity monitoring in the injection tank (tote) and in the wells after injection of 5,000 liters of solution - first injection

| Sample | ABS (340 nm) | Activity (U/mL) |
|---|---|---|
| RD18-01 | 0.0498 | 24.01929 |
| RD18-02 | 0 | 0 |
| RD18-03 | 0.0564 | 27.20257 |
| RD18-04 | 0.0703 | 33.90675 |
| RD18-05 | 0.015 | 7.234727 |
| RD18-06 | 0.6026 | 290.6431 |
| RD18-07 | 0.4105 | 197.9904 |
| Tote 03 | 0.3145 | 151.6881 |
| Tote 04 | 0.3937 | 189.8875 |
| Tote 05 | 0.3016 | 145.4662 |

TABLE 24

Enzymatic activity monitoring in the injection tank (tote) and in the wells after injection of 5,000 liters of solution - second injection

| | Before Injection | | | After Injection | |
|---|---|---|---|---|---|
| Sample | ABS 340 nm | Activity (U/mL) | Sample | ABS 340 nm | Activity (U/mL) |
| 1 | 0 | 0 | RD18-01 | 0 | 0 |
| 2 | 0 | 0 | RD18-02 | 0 | 0 |
| 3 | 0 | 0 | RD18-03 | 0 | 0 |
| 4 | 0 | 0 | RD18-04 | 0 | 0 |
| 5 | 0 | 0 | RD18-05 | 0.0996 | 48.03859 |
| 6 | 0 | 0 | RD18-06 | 0.0668 | 32.21865 |
| 7 | 0 | 0 | RD18-07 | 0.1961 | 94.58199 |
| 8 | 0 | 0 | Tote01 | 0.189 | 91.15756 |
| | | | Tote02 | 0.2447 | 118.0225 |
| | | | Tote03 | 0.4468 | 215.4984 |
| | | | Tote04 | 0.2679 | 129.2122 |
| | | | Tote05 | 0.3403 | 164.1318 |

TABLE 25

Enzymatic activity monitoring in the injection tank (tote) and in the wells after injection of 5,000 liters of solution - third injection

| Before Injection 21 Nov. 2018 | | | After Injection 29 Nov. 2018 | | |
|---|---|---|---|---|---|
| Sample | ABS 340 nm | Activity (U/mL) | Sample | ABS 340 nm | Activity (U/mL) |
| RD18-01 | 0.027 | 13.022508 | RD18-01 | 0.0262 | 12.6366559 |
| RD18-01 | 0 | 0 | RD18-02 | 0.0668 | 32.2186495 |
| RD18-02 | 0 | 0 | RD18-03 | 0.0679 | 32.7491961 |
| RD18-02 | 0 | 0 | RD18-04 | 0.0374 | 18.0385852 |
| RD18-03 | 0 | 0 | RD18-05 | 0.0045 | 2.17041801 |
| RD18-03 | 0 | 0 | RD18-07 | 0.00249 | 1.20096463 |
| RD18-04 | 0.0034 | 1.63987138 | RD18-070 | 0.0039 | 1.88102894 |
| RD18-04 | 0 | 0 | Tote1 (28 Nov. 2018) | 0.0187 | 9.0192926 |
| RD18-04 | 0.0035 | 1.68810289 | Tote2 (28 Nov. 2018) | 0.0084 | 4.05144695 |
| RD18-04 | 0.0024 | 1.15755627 | Tote3 (28 Nov. 2018) | 0.0249 | 12.0096463 |
| RD18-04 | 0.0034 | 1.63987138 | Tote4 | 0.0401 | 19.340836 |
| RD18-05 | 0.0024 | 1.15755627 | Tote5 | 0.0475 | 22.9099678 |
| RD18-05 | 0.00163 | 0.78617363 | Tote6 | 0.1185 | 57.1543408 |
| RD18-06 | 0 | 0 | Tote7 | 0 | 0 |
| RD18-06 | 0 | 0 | Tote8 | 0.0086 | 4.14790997 |
| RD18-07 | 0 | 0 | Tote9 | 0 | 0 |
| RD18-07 | 0.0025 | 1.20578778 | Tote10 | 0 | 0 |

CONCLUSION OF PILOT TESTING

Results shown in Table 26 clearly indicate that the pilot scale testing "on site" was conclusive and that certain conditions can provide up to 99% reduction of $C_{10}$-$C_{50}$ hydrocarbons from contaminated sites.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. All such modifications are intended to be included within the scope of the appended claims.

All publications and patent applications cited in this specification are herein incorporated by reference as if each individual publication or patent application were specifically and individually indicated to be incorporated by reference.

REFERENCES

Abbassi, B. E., Shquirat, W. D., 2008. Kinetics of indigenous isolated bacteria used for ex-situ bioremediation of petroleum contaminated soil. Water. Air. Soil Pollut. 192, 221-226.

Abraham, W. R., Meyer, H., Yakimov, M., 1998. *Novel glycine containing glucolipids from the alkane using bacterium Alcanivorax borkumensis*. Biochim. Biophys. Acta BBA—Lipids Lipid Metab. 1393, 57-62.

Admon, S., Green, M., Avnimelech, Y., 2001. Biodegradation kinetics of hydrocarbons in soil during land treatment of oily sludge. Biorernediation J. 5, 193-209.

Ahmad, Z., Arshad, M., Asghar, H. N., Sheikh, M. A., Crowley, D. E., 2016. Isolation, screening and functional characterization of biosurfactant producing bacteria isolated from crude oil contaminated site. Int. J. Agric. Biol. 18.

Aichberger, H., Hasinger, M., Braun, R., Loibner, A. P., 2005. Potential of preliminary test methods to predict biodegradation performance of petroleum hydrocarbons in soil. Biodegradation 16, 115-125.

Ajun, W., Yan, S., Li, G., Huili, L., 2009. Preparation of aspirin and probucol in combination loaded chitosan nanoparticles and in vitro release study. Carbohydr. Polym. 75, 566-574.

Alcalde, M., Ferrer, M., Plou, F. J., Ballesteros, A., 2006. *Environmental biocatalysis: from remediation with enzymes to novel green processes*. Trends in Biotechnology 24, 281-287.

Andreoni, V., Cavalca, L., Rao, M. A., Nocerino, G., Bernasconi, S., Dell'Amico, E., Colombo, M., Gianfreda, L., 2004. *Bacterial communities and enzyme activities of PAHs polluted soils*. Chemosphere 57, 401-412.

Anwar, M. Z., Kim, D. J., Kumar, A., Patel, S. K., Otari, S., Mardina, P., Jeong, J.-H., Sohn, J.-H., Kim, J. H., Park, J. T., 2017. *SnO 2 hollow nanotubes: a novel and efficient support matrix for enzyme immobilization*. Sci. Rep. 7, 15333.

Aparna, A., Srinikethan, G., Hedge, S., 2011. Effect of addition of biosurfactant produced by *Pseudomonas* ssp. on biodegradation of crude oil. Int. Proc. Chem. Biol. Environ. Eng. 71-75.

ASTM, C., 2006. Standard test method for sieve analysis of fine and coarse aggregates.

Austin, R. N., Groves, J. T., 2011. *Alkane-oxidizing metalloenzymes in the carbon cycle*. Metallomics 3, 775-787.

Bahreini, E., Aghaiypour, K., Abbasalipourkabir, R., Mokarram, A. R., Goodarzi, M. T., Saidijam, M., 2014. *Preparation and nanoencapsulation of I-asparaginase II in chitosan-tripolyphosphate nanoparticles and in vitro release study*. Nanoscale Res. Lett. 9, 340.

Bamard, E., Bulle, C., Deschênes, L., 2011. Method development for aquatic ecotoxicological characterization factor calculation for hydrocarbon mixtures in life cycle assessment. Environ. Toxicol. Chem. 30, 2342-2352.

Basuki, W., Syahputra, K., Suryani, A. T., Pradipta, I., 2015. *Biodegradation of Used Engine Oil by Acinetobacter junii TBC 1.2*. Indones. J. Biotechnol. 16.

Bisht, D., Yadav, S. K., Darmwal, N. S., 2013. An oxidant and organic solvent tolerant alkaline lipase by *P. aeruginosa* mutant: downstream processing and biochemical characterization. Braz. J. Microbiol. 44, 1305-1314.

Boniolo, F. S., Rodrigues, R. C., Prata, A. M. R., López, M. L., Jacinto, T., da Silveira, M. M., Berbert-Molina, M. A., 2012. Oxygen supply in *Bacillus thuringiensis* fermentations: bringing new insights on their impact on sporulation and δ-endotoxin production. Appl. Microbiol. Biotechnol. 94, 625-636.

Bookstaver, M., Godfrin, M. P., Bose, A., Tripathi, A., 2015. *An insight into the growth of Alcanivorax borkumensis under different inoculation conditions*. J. Pet. Sci. Eng. 129, 153-158.

Boopathy, R., 2000. *Factors limiting bioremediation technologies*. Bioresour. Technol. 74, 63-67.

Borkar, P. S., Bodade, R. G., Rao, S. R., Khobragade, C. N., 2009. Purification and characterization of extracellular lipase from a new strain: *Pseudomonas aeruginosa* SRT 9. Braz. J. Microbiol. 40, 358-366.

Bradford, M. M., 1976. A rapid and sensitive method for the quantitation of microgram quantities of protein utilizing the principle of protein-dye binding. Anal. Biochem. 72, 248-254.

Breuil, C., Shindler, D. B., Sijher, J. S., Kushner, D. J., 1978. *Stimulation of lipase production during bacterial growth on alkanes*. J. Bacteriol. 133, 601-606.

Calvo, P., Remuñan-López, C., Vila-Jato, J. L., Alonso, M. J., 1997. Chitosan and chitosan/ethylene oxide-propylene oxide block copolymer nanoparticles as novel carriers for proteins and vaccines. Pharm. Res. 14, 1431-1436.

Chandrashekhar, H., Rao, J. V., 2010. An Overview of fermenter and the design considerations to enhance its productivity. Pharmacologyonline 1, 261-301.

Chebbi, A., Hentati, D., Zaghden, H., Baccar, N., Rezgui, F., Chalbi, M., Sayadi, S., Chamkha, M., 2017. Polycyclic aromatic hydrocarbon degradation and biosurfactant production by a newly isolated *Pseudomonas* sp. strain from used motor oil-contaminated soil. Int. Biodeterior. Biodegrad. 122, 128-140.

Chénier, M. R., Beaumier, D., Roy, R., Driscoll, B. T., Lawrence, J. R., Greer, C. W., 2003. Impact of seasonal variations and nutrient inputs on nitrogen cycling and degradation of hexadecane by replicated river biofilms. Appl. Environ. Microbiol. 69, 5170-5177.

Chiou, S.-H., Wu, W.-T., 2004. Immobilization of *Candida rugosa* lipase on chitosan with activation of the hydroxyl groups. Biomaterials 25, 197-204.

Choo, D.-W., Kurihara, T., Suzuki, T., Soda, K., Esaki, N., 1998. A cold-adapted lipase of an Alaskan psychrotroph, *Pseudomonas* sp. strain B11-1: gene cloning and enzyme purification and characterization. Appl. Environ. Microbiol. 64, 486-491.

Colombo, J. C., Cabello, M., Arambarri, A. M., 1996. Biodegradation of aliphatic and aromatic hydrocarbons by natural soil microflora and pure cultures of imperfect and lignolitic fungi. Environ. Pollut. 94, 355-362.

Costa, A. S., Romão, L. P. C., Araujo, B. R., Lucas, S. C. O., Maciel, S. T. A., Wisniewski Jr, A., Alexandre, M. da R., 2012. *Environmental strategies to remove volatile aromatic fractions (BTEX) from petroleum industry wastewater using biomass*. Bioresource Technology 105, 31-39.

Costa, P., Lobo, J. M. S., 2001. *Modeling and comparison of dissolution profiles*. Eur. J. Pharm. Sci. 13, 123-133.

Cyplik, P., Schmidt, M., Szulc, A., Marecik, R., Lisiecki, P., Heipieper, H. J., Owsianiak, M., Vainshtein, M., Chrzanowski, \Lukasz, 2011. *Relative quantitative PCR to assess bacterial community dynamics during biodegradation of diesel and biodiesel fuels under various aeration conditions*. Bioresour. Technol. 102, 4347-4352.

Dados, A., Omirou, M., Demetriou, K., Papastephanou, C., Ioannides, I. M., 2014. *Rapid remediation of soil heavily contaminated with hydrocarbons: a comparison of different approaches*. Ann. Microbiol. 65, 241-251.

Dang Vu, K., Tyagi, R. D., Brar, S. K., Valero, J. R., Surampalli, R. Y., 2009. Starch industry wastewater for production of biopesticides—Ramifications of solids concentrations. Environ. Technol. 30, 393-405.

Das, K., Mukherjee, A. K., 2007. Crude petroleum-oil biodegradation efficiency of *Bacillus subtilis* and *Pseudomonas aeruginosa* strains isolated from a petroleum-oil contaminated soil from North-East India. Bioresour. Technol. 98, 1339-1345.

Das, N., Chandran, P., 2010. Microbial degradation of petroleum hydrocarbon contaminants: an overview. Biotechnol. Res. Int. 2011.

Dastgheib, S. M. M., Amoozegar, M. A., Khajeh, K., Ventosa, A., 2011. *A halotolerant Alcanivorax sp. strain with potential application in saline soil remediation*. Appl. Microbiol. Biotechnol. 90, 305-312.

Davis, C., Cort, T., Dai, D., Illangasekare, T. H., Munakata-Marr, J., 2003. *Effects of heterogeneity and experimental scale on the biodegradation of diesel*. Biodegradation 14, 373-384.

De Carvalho, C. C., Parreño-Marchante, B., Neumann, G., Da Fonseca, M. M. R., Heipieper, H. J., 2005. *Adaptation of Rhodococcus erythropolis DCL14 to growth on n-alkanes*, alcohols and terpenes. Appl. Microbiol. Biotechnol. 67, 383-388.

de Lourdes Moreno, M., Perez, D., Garcia, M. T., Mellado, E., 2013. *Halophilic bacteria as a source of novel hydrolytic enzymes*. Life 3, 38-51.

De Queiroz, A. A., Passos, E. D., De Brito Alves, S., Silva, G. S., Higa, O. Z., Vitolo, M., 2006. *Alginate-poly (vinyl alcohol) core-shell microspheres for lipase immobilization*. J. Appl. Polym. Sci. 102, 1553-1560.

Diaz-Ramírez, I. J., 2000. Biodegradación de hidrocarburos por un consorcio microbia-no de la rizósfera de una planta nativa de pantano. Tesis de Maestría, Universidad Autónoma Metropolitana-Iztapalapa, México.

Dou, J., Liu, X., Hu, Z., 2008. Substrate interactions during anaerobic biodegradation of BTEX by the mixed cultures under nitrate reducing conditions. J. Hazard. Mater. 158, 264-272.

Dutta, T. K., Harayama, S., 2001. Biodegradation of n-alkylcycloalkanes and n-alkylbenzenes via new pathways in *Alcanivorax* sp. strain MBIC 4326. Appl. Environ. Microbiol. 67, 1970-1974.

Dzionek, A., Wojcieszyńska, D., Guzik, U., 2016. *Natural carriers in bioremediation: A review*. Electron. J. Biotechnol. 23, 28-36.

El-Bakry, M., Gea, T., Sánchez, A., 2016a. Inoculation effect of thermophilic microorganisms on protease production through solid-state fermentation under non-sterile conditions at lab and bench scale (SSF). Bioprocess Biosyst. Eng. 39, 585-592.

El-Bakry, M., Gea, T., Sánchez, A., 2016b. Inoculation effect of thermophilic microorganisms on protease production through solid-state fermentation under non-sterile conditions at lab and bench scale (SSF). Bioprocess Biosyst. Eng. 39, 585-592.

Faustorilla, M. V., Chen, Z., Dharmarajan, R., Naidu, R., 2017. Determination of Total Petroleum Hydrocarbons in Australian Groundwater through the Improvised Gas Chromatography-Flame Ionization Detection Technique. J. Chromatogr. Sci. 1-9.

Federation, W. E., Association, A. P. H., others, 2005. *Standard methods for the examination of water and wastewater*. Am. Public Health Assoc. APHA Wash. DC USA.

Fedorak, P. M., Westlake, D. W. S., 1981. *Degradation of aromatics and saturates in crude oil by soil enrichments*. Water. Air. Soil Pollut. 16, 367-375.

Feller, G., Thiry, M., Arpigny, J.-L., Mergeay, M., Gerday, C., 1990. *Lipases from psychrotropic Antarctic bacteria*. FEMS Microbiol. Lett. 66, 239-243.

Flores-Flores, T. C., Gutierrez-Rojas, M., Revah, S., Favela-Torres, E., 2011. Comparative study for oxygenases produced by *Aspergillus niger*, ATCC 9642, in solid-state and submerged fermentation. Rev. Mex. Ing. Quim. 10, 189-207.

Freijer, J. I., De Jonge, H., Bouten, W., Verstraten, J. M., 1996. Assessing mineralization rates of petroleum hydrocarbons in soils in relation to environmental factors and experimental scale. Biodegradation 7, 487-500.

Gan, Q., Wang, T., 2007. Chitosan nanoparticle as protein delivery carrier-systematic examination of fabrication conditions for efficient loading and release. Colloids Surf. B Biointerfaces 59, 24-34.

Gan, Q., Wang, T., Cochrane, C., McCarron, P., 2005. Modulation of surface charge, particle size and morphological properties of chitosan-TPP nanoparticles intended for gene delivery. Colloids Surf. B Biointerfaces 44, 65-73.

Garcia-Ochoa, F., Gomez, E., 2009. Bioreactor scale-up and oxygen transfer rate in microbial processes: an overview. Biotechnol. Adv. 27, 153-176.

Gianfreda, L., Bollag, J.-M., 2002. Isolated enzymes for the transformation and detoxification of organic pollutants. Marcel Dekker: New York.

Gianfreda, L., Rao, M. A., 2004. Potential of extra cellular enzymes in remediation of polluted soils: a review. Enzyme Microb. Technol. 35, 339-354.

Gianfreda, L., Rao, M. A., Gennari, M., Trevisan, M., 2008. *Bonifica di suoli contaminati e depurazione dell'acqua*. Agrofarmaci. Conoscenze per un Uso Sostenibile. Oasi Alberto Perdisa, Bologna, Italy 521-564.

Gill, J., Orsat, V., Kermasha, S., 2017. Optimization of encapsulation of a microbial laccase enzymatic extract using selected matrices. Process Biochem.

Glieder, A., Farinas, E. T., Arnold, F. H., 2002. Laboratory evolution of a soluble, self-sufficient, highly active alkane hydroxylase. Nat. Biotechnol. 20, 1135-1139.

Gogoi, B. K., Dutta, N. N., Goswami, P., Mohan, T. K., 2003. A case study of bioremediation of petroleum-hydrocarbon contaminated soil at a crude oil spill site. Adv. Environ. Res. 7, 767-82.

Golyshin, P. N., Martins Dos Santos, V. A. P., Kaiser, O., Ferrer, M., Sabirova, Y. S., Lünsdorf, H., Chernikova, T. N., Golyshina, O. V., Yakimov, M. M., Pühler, A., Timmis, K. N., 2003. *Genome sequence completed of Alcanivorax borkumensis, a hydrocarbon-degrading bacterium that plays a global role in oil removal from marine systems*. J. Biotechnol. 106, 215-220.

Graham, D. W., Smith, V. H., Cleland, D. L., Law, K. P., 1999. *Effects of nitrogen and phosphorus supply on hexadecane biodegradation in soil systems*. Water. Air. Soil Pollut. 111, 1-18.

Gupta, R., Beg, Q., Khan, S., Chauhan, B., 2002. An overview on fermentation, downstream processing and properties of microbial alkaline proteases. Appl. Microbiol. Biotechnol. 60, 381-395.

Guzik, U., Hupert-Kocurek, K., Wojcieszyńska, D., 2014. Immobilization as a strategy for improving enzyme properties-application to oxidoreductases. Molecules 19, 8995-9018.

Haines, J. R., Alexander, M., 1974. *Microbial degradation of high-molecular-weight alkanes*. Appl. Microbiol. 28, 1084.

Hamed, T. A., Bayraktar, E., Mehmetoğlu, T., Mehmetoğlu, Ü., 2003. *Substrate interactions during the biodegradation of benzene, toluene and phenol mixtures*. Process Biochem. 39, 27-35.

Hanstveit, A. O., 1992. Biodegradability of petroleum waxes and beeswax in an adapted $CO_2$ evolution test. Chemosphere 25, 605-620.

Hara, A., Syutsubo, K., Harayama, S., 2003. *Alcanivorax which prevails in oil-contaminated seawater exhibits broad substrate specificity for alkane degradation*. Environ. Microbiol. 5, 746-753.

Haritash, A. K., Kaushik, C. P., 2009. Biodegradation aspects of Polycyclic Aromatic Hydrocarbons (PAHs): A review. J. Hazard. Mater. 169, 1-15.

Hassanshahian, M., Emtiazi, G., Caruso, G., Cappello, S., 2014. Bioremediation (bioaugmentation/biostimulation) trials of oil polluted seawater: a mesocosm simulation study. Mar. Environ. Res. 95, 28-38.

Hatch, R. T., 1974. *Biochemical engineering*, S. Aiba, AE Humphrey, and NF Millis, Academic Press, Inc., New York (1973). 434 pages $28.50. Also publ. in English by Univ. Tokyo Press, Japan, 6000 yen. AIChE J. 20, 831-831.

Hsu, Y.-L., Wu, W.-T., 2002. *A novel approach for scaling-up a fermentation system*. Biochem. Eng. J. 11, 123-130.

Higuchi, T., 1963. Mechanism of sustained-action medication. Theoretical analysis of rate of release of solid drugs dispersed in solid matrices. J. Pharm. Sci. 52, 1145-1149.

Horowitz, A., Atlas, R. M., 1977. Response of microorganisms to an accidental gasoline spillage in an arctic freshwater ecosystem. Appl. Environ. Microbiol. 33, 1252-1258.

Ijah, U. J. J., 1998. Studies on relative capabilities of bacterial and yeast isolates from tropical soil in degrading crude oil. Waste Manag. 18, 293-299.

Ivshina, I. B., Kuyukina, M. S., Krivoruchko, A. V., Elkin, A. A., Makarov, S. O., Cunningham, C. J., Peshkur, T. A., Atlas, R. M., Philp, J. C., 2015. *Oil spill problems and sustainable response strategies through new technologies*. Environ. Sci. Process. Impacts 17, 1201-1219.

Izrael-Zivkovic, L. T., Gojgic-Cvijovic, G. D., Gopcevic, K. R., Vrvic, M. M., Karadzic, I. M., 2009. *Enzymatic characterization of 30 kDa lipase from Pseudomonas aeruginosa ATCC 27853*. J. Basic Microbiol. 49, 452-462.

Jaeger, K.-E., Ransac, S., Dijkstra, B. W., Colson, C., van Heuvel, M., Misset, O., 1994. *Bacterial lipases*. FEMS Microbiol. Rev. 15, 29-63.

Jo, M.-S., Rene, E. R., Kim, S.-H., Park, H.-S., 2008. An analysis of synergistic and antagonistic behavior during BTEX removal in batch system using response surface methodology. J. Hazard. Mater. 152, 1276-1284.

Jonassen, H., Kjøniksen, A. L., Hiorth, M., 2012a. *Stability of chitosan nanoparticles cross-linked with tripolyphosphate*. Biomacromolecules 13, 3747-3756.

Jonassen, H., Kjøniksen, A. L., Hiorth, M., 2012b. *Effects of ionic strength on the size and compactness of chitosan nanoparticles*. Colloid Polym. Sci. 290, 919-929.

Kadri, T., Magdouli, S., Rouissi, T., Brar, S. K., Daghrir, R., Lauzon, J.-M., 2018. Bench-scale production of enzymes from the hydrocarbonoclastic bacteria *Alcanivorax borkumensis* and biodegradation tests. J. Biotechnol.

Kadri, T., Rouissi, T., Magdouli, S., Brar, S. K., Hegde, K., Khiari, Z., Daghrir, R., Lauzon, J.-M., 2018. *Production and characterization of novel hydrocarbon degrading enzymes from Alcanivorax borkumensis*. Int. J. Biol. Macromol. 112, 230-240.

Kadri, T., Rouissi, T., Kaur Brar, S., Cledon, M., Sarma, S., Verma, M., 2017. *Biodegradation of polycyclic aromatic hydrocarbons (PAHs) by fungal enzymes: A review*. J. Environ. Sci. 51, 52-74.

Kanaly, R. A., Harayama, S., 2000. Biodegradation of High-Molecular-Weight Polycyclic Aromatic Hydrocarbons by Bacteria. J. Bacteriol. 182, 2059-2067.

Kanwar, L., Gogoi, B. K., Goswami, P., 2002. Production of a *Pseudomonas* lipase in n-alkane substrate and its isolation using an improved ammonium sulfate precipitation technique. Bioresour. Technol. 84, 207-211.

Karamalidis, A. K., Evangelou, A. C., Karabika, E., Koukkou, A. I., Drainas, C., Voudrias, E. A., 2010. Laboratory scale bioremediation of petroleum-contaminated soil by indigenous microorganisms and added *Pseudomonas aeruginosa* strain Spet. Bioresour. Technol. 101, 6545-6552.

Kasai, Y., Kishira, H., Sasaki, T., Syutsubo, K., Watanabe, K., Harayama, S., 2002. *Predominant growth of Alcanivorax strains in oil-contaminated* and *nutrient-supplemented sea water*. Environ. Microbiol. 4, 141-147.

Kennedy, J., O'leary, N. D., Kiran, G. S., Morrissey, J. P., O'Gara, F., Selvin, J., Dobson, A. D. W., 2011. Functional metagenomic strategies for the discovery of novel enzymes and biosurfactants with biotechnological applications from marine ecosystems. J. Appl. Microbiol. 111, 787-799.

Kvenvolden, K. A., Cooper, C. K., 2003. *Natural seepage of crude oil into the marine environment*. Geo-Mar Lett 23, 140-146.

Knaul, J. Z., Hudson, S. M., Creber, K. A., 1999. *Improved mechanical properties of chitosan fibers*. J. Appl. Polym. Sci. 72, 1721-1732.

Korsmeyer, R. W., Gurny, R., Doelker, E., Buri, P., Peppas, N. A., 1983. *Mechanisms of solute release from porous hydrophilic polymers*. Int. J. Pharm. 15, 25-35.

Koukaras, E. N., Papadimitriou, S. A., Bikiaris, D. N., Froudakis, G. E., 2012a. *Insight on the formation of chitosan nanoparticles through ionotropic gelation with tripolyphosphate*. Mol. Pharm. 9, 2856-2862.

Koukaras, E. N., Papadimitriou, S. A., Bikiaris, D. N., Froudakis, G. E., 2012b. *Insight on the formation of chitosan nanoparticles through ionotropic gelation with tripolyphosphate*. Mol. Pharm. 9, 2856-2862.

Kumar, A., Kim, I.-W., Patel, S. K., Lee, J.-K., 2018. Synthesis of Protein-Inorganic Nanohybrids with Improved Catalytic Properties Using Co 3 (PO 4) 2. Indian J. Microbiol. 58, 100-104.

Kumar, R., Das, A. J., Juwarkar, A. A., 2015. Reclamation of petrol oil contaminated soil by rhamnolipids producing PGPR strains for growing Withania somnifera a medicinal shrub. World J. Microbiol. Biotechnol. 31, 307-313.

Kumari, N., Vashishtha, A., Saini, P., Menghani, E., 2013. Isolation, identification and characterization of oil degrading bacteria isolated from the contaminated sites of Barmer, Rajasthan. Int J Biotechnol Bioeng Res 4, 429-436.

Laemmli, U. K., 1970. Cleavage of structural proteins during the assembly of the head of bacteriophage T4. Nature 227, 680-685.

La Presse (2013). 100 000 *litres de pétrole sur la rivière Chaudière*. Available at https://www.lapresse.ca/actualites/dossiers/tragedie-a-lac-megantic/201307/09/01-4669087-100-000-litres-de-petrole-sur-la-riviere-chaudiere.php.

Laxman Pachapur, V., Jyoti Sarma, S., Kaur Brar, S., Le Bihan, Y., Ricardo Soccol, C., Buelna, G., Verma, M., 2015. *Co-culture strategies for increased biohydrogen production*. Int. J. Energy Res. 39, 1479-1504.

Lee, D.-W., Powers, K., Baney, R., 2004. Physicochemical properties and blood compatibility of acylated chitosan nanoparticles. Carbohydr. Polym. 58, 371-377.

Li, H., Liu, Y. H., Luo, N., Zhang, X. Y., Luan, T. G., Hu, J. M., Wang, Z. Y., Wu, P. C., Chen, M. J., Lu, J. Q., 2006. *Biodegradation of benzene and its derivatives by a psychrotolerant and moderately haloalkaliphilic Planococcus* sp. *strain ZD22*. Res. Microbiol. 157, 629-636.

Li, P., Wang, L., Feng, L., 2013. Characterization of a novel Rieske-type alkane monooxygenase system in *Pusillimonas* sp. strain T7-7. J. Bacteriol. 195, 1892-1901.

Liu, C., Wang, W., Wu, Y., Zhou, Z., Lai, Q., Shao, Z., 2011. *Multiple alkane hydroxylase systems in a marine alkane degrader, Alcanivorax dieselolei B-5*. Environ. Microbiol. 13, 1168-1178.

Liu, H., Yao, J., Yuan, Z., Shang, Y., Chen, H., Wang, F., Masakorala, K., Yu, C., Cai, M., Blake, R. E., Choi, M. M. F., 2014. *Isolation and characterization of crude-oil-degrading bacteria from oil-water mixture in Dagang oilfield*, China. Int. Biodeterior. Biodegrad. 87, 52-59.

Liu, W., Luo, Y., Teng, Y., Li, Z., Ma, L. Q., 2010. *Bioremediation of oily sludge-contaminated soil by stimulating indigenous microbes*. Environ. Geochem. Health 32, 23-29.

Lopes, D. B., Fraga, L. P., Fleuri, L. F., Macedo, G. A., 2011. *Lipase and esterase: to what extent can this classification be applied accurately?* Food Sci. Technol. Camp. 31, 603-613.

López-León, T., Carvalho, E. L. S., Seijo, B., Ortega-Vinuesa, J. L., Bastos-González, D., 2005. *Physicochemical characterization of chitosan nanoparticles: electrokinetic and stability behavior*. J. Colloid Interface Sci. 283, 344-351.

Lu, L., Zeng, G., Fan, C., Ren, X., Wang, C., Zhao, Q., Zhang, J., Chen, M., Chen, A., Jiang, M., 2013a. Characterization of a laccase-like multicopper oxidase from newly isolated *Streptomyces* sp. C1 in agricultural waste compost and enzymatic decolorization of azo dyes. Biochem. Eng. J. 72, 70-76.

Lu, L., Zeng, G., Fan, C., Ren, X., Wang, C., Zhao, Q., Zhang, J., Chen, M., Chen, A., Jiang, M., 2013b. Characterization of a laccase-like multicopper oxidase from newly isolated *Streptomyces* sp. C1 in agricultural waste compost and enzymatic decolorization of azo dyes. Biochem. Eng. J. 72, 70-76.

Lubna Tahir, M. I. A., 2013. *Production and Characterization of Esterase in Lantinus tigrinus for Degradation of Polystyrene*. Pol. J. Microbiol. Pol. Tow. Mikrobiol. Pol. Soc. Microbiol. 62, 101-8.

Luo, Y., Zhang, B., Cheng, W.-H., Wang, Q., 2010. Preparation, characterization and evaluation of selenite-loaded chitosan/TPP nanoparticles with or without zein coating. Carbohydr. Polym. 82, 942-951.

Mahmoud, G. A.-E., Koutb, M. M., Morsy, F. M., Bagy, M. M., 2015. Characterization of lipase enzyme produced by hydrocarbons utilizing fungus *Aspergillus terreus*. Eur. J. Biol. Res. 5, 70-77.

Maletić, S., Dalmacija, B., Rončević, S. jan, 2013. *Petroleum Hydrocarbon Biodegradability in Soil-Implications for Bioremediation*. Ed. Vladimir Kutcherov 43.

Malik, Z., Ahmed, S., 2012. Degradation of petroleum hydrocarbons by oil field isolated bacterial consortium. Afr. J. Biotechnol. 11, 650-658.

Mao, H.-Q., Roy, K., Troung-Le, V. L., Janes, K. A., Lin, K. Y., Wang, Y., August, J. T., Leong, K. W., 2001. *Chitosan-DNA nanoparticles as gene carriers: synthesis, characterization and transfection efficiency*. J. Controlled Release 70, 399-421.

Marchut-Mikolajczyk, O., Kwapisz, E., Wieczorek, D., Antczak, T., 2015. *Biodegradation of diesel oil hydrocarbons enhanced with Mucor circinelloides enzyme preparation*. Int. Biodeterior. Biodegrad. 104, 142-148.

Margaritis, A., Zajic, J. E., 1978. Mixing, mass transfer, and scale-up of polysaccharide fermentations. Biotechnol. Bioeng. 20, 939-1001.

Margesin, R., Feller, G., Hämmerle, M., Stegner, U., Schinner, F., 2002. *A colorimetric method for the determination of lipase activity in soil*. Biotechnol. Lett. 24, 27-33.

Margesin, R., Hammerle, M., Tscherko, D., 2007. Microbial activity and community composition during bioremediation of diesel-oil-contaminated soil: effects of hydrocarbon concentration, fertilizers, and incubation time. Microb. Ecol. 53, 259-269.

Margesin, R., Labbe, D., Schinner, F., Greer, C. W., Whyte, L. G., 2003. *Characterization of hydrocarbon-degrading microbial populations in contaminated and pristine alpine soils*. Appl. Environ. Microbiol. 69, 3085-3092.

Martínez-Martínez, M., Lores, I., Peña-García, C., Bargiela, R., Reyes-Duarte, D., Guazzaroni, M.-E., Peláez, A. I., Sánchez, J., Ferrer, M., 2014. *Biochemical studies on a versatile esterase that is most catalytically active with polyaromatic esters*. Microb. Biotechnol. 7, 184-191.

Mathur, A. K., Majumder, C. B., 2010. Kinetics modelling of the biodegradation of benzene, toluene and phenol as single substrate and mixed substrate by using *Pseudomonas putida*. Chem. Biochem. Eng. Q. 24, 101-109.

Matturro, B., Frascadore, E., Cappello, S., Genovese, M., Rossetti, S., 2016. *In situ detection of alkB2 gene involved in Alcanivorax borkumensis SK2T hydrocarbon biodegradation*. Mar. Pollut. Bull. 110, 378-382.

McGenity, T. J., 2014. Hydrocarbon biodegradation in intertidal wetland sediments. Curr. Opin. Biotechnol. 27, 46-54.

Miastkowska, M., Sikora, E., Ogonowski, J., Zielina, M., \Ludzik, A., 2016. *The kinetic study of isotretinoin release from nanoemulsion*. Colloids Surf. Physicochem. Eng. Asp. 510, 63-68.

Miles, A. A., Misra, S. S., Irwin, J. O., 1938. *The estimation of the bactericidal power of the blood*. Epidemiol. Infect. 38, 732-749.

Millioli, V. S., Servulo, E. L. C., Sobral, L. G. S., De Carvalho, D. D., others, 2009. Bioremediation of crude oil-bearing soil: evaluating the effect of rhamnolipid addition to soil toxicity and to crude oil biodegradation efficiency. Global NEST Journal 11, 181-188.

Mishra, S., Sarma, P. M., Lal, B., 2004. Crude oil degradation efficiency of a recombinant *Acinetobacter baumannii* strain and its survival in crude oil-contaminated soil microcosm. FEMS Microbiol. Lett. 235, 323-331.

Mishra, S., Singh, S. N., 2012. Microbial degradation of n-hexadecane in mineral salt medium as mediated by degradative enzymes. Bioresour. Technol. 111, 148-154.

Morán, A. C., Olivera, N., Commendatore, M., Esteves, J. L., Siñeriz, F., 2000. *Enhancement of hydrocarbon waste biodegradation by addition of a biosurfactant from Bacillus subtilis O9*. Biodegradation 11, 65-71.

Naether, D. J., Slawtschew, S., Stasik, S., Engel, M., Olzog, M., Wick, L. Y., Timmis, K. N., Heipieper, H. J., 2013. Adaptation of the Hydrocarbonoclastic Bacterium *Alcanivorax borkumensis* SK2 to Alkanes and Toxic Organic Compounds: a Physiological and Transcriptomic Approach. Appl. Environ. Microbiol. 79, 4282-4293.

Naghdi, M., Taheran, M., Brar, S. K., Kermanshahi-pour, A., Verma, M., Surampalli, R. Y., 2017. *Immobilized laccase on oxygen functionalized nanobiochars through mineral acids treatment for removal of carbamazepine*. Sci. Total Environ. 584, 393-401.

Naing, S.-H., Parvez, S., Pender-Cudlip, M., Groves, J. T., Austin, R. N., 2013. Substrate specificity and reaction mechanism of purified alkane hydroxylase from the hydrocarbonoclastic bacterium *Alcanivorax borkumensis* (AbAlkB). J. Inorg. Biochem. 121, 46-52.

Namkoong, W., Hwang, E.-Y., Park, J.-S., Choi, J.-Y., 2002. *Bioremediation of diesel-contaminated soil with composting*. Environ. Pollut. 119, 23-31.

Ndao, A., Sellamuthu, B., Gnepe, J. R., Tyagi, R. D., Valero, J. R., 2017. Pilot-scale biopesticide production by *Bacillus thuringiensis* subsp. kurstaki using starch industry wastewater as raw material. J. Environ. Sci. Health Part B 52, 623-630.

Nievas, M. L., Commendatore, M. G., Esteves, J. L., Bucalá, V., 2008. Biodegradation pattern of hydrocarbons from a fuel oil-type complex residue by an emulsifier-producing microbial consortium. J. Hazard. Mater. 154, 96-104.

Nikolopoulou, M., Kalogerakis, N., 2009. Biostimulation strategies for fresh and chronically polluted marine environments with petroleum hydrocarbons. J. Chem. Technol. Biotechnol. 84, 802-807.

Nkem, B. M., Halimoon, N., Yusoff, F. M., Johari, W. L. W., Zakaria, M. P., Medipally, S. R., Kannan, N., 2016. Isolation, identification and diesel-oil biodegradation capacities of indigenous hydrocarbon-degrading strains of *Cellulosimicrobium cellulans* and *Acinetobacter baumannii* from tarball at Terengganu beach, Malaysia. Mar. Pollut. Bull. 107, 261-268.

Obayori, O. S., Salam, L. B., Ogunwumi, O. S., 2014. *Biodegradation of fresh and used engine oils by Pseudomonas aeruginosa LP5*. J. Bioremediation Biodegredation 5, 1.

Pachapur, V. L., Das, R. K., Brar, S. K., Le Bihan, Y., Buelna, G., 2017. Valorization of crude glycerol and eggshell biowaste as media components for hydrogen production: A scale-up study using co-culture system. Bioresour. Technol. 225, 386-394.

Parakulsuksatid, P., 2000. Utilization of a Microbubble Dispersion to Increase Oxygen Transfer in Pilot-Scale Bakerâ s Yeast Fermentation Unit (PhD Thesis). Virginia Tech.

Park, D., Oh, H., Heo, S., Jeong, W., Shin, D. H., Bae, K. S., Park, H., others, 2007. *Characterization of an extracellular lipase in Burkholderia sp. HY-10 isolated from a longicorn beetle*. J. Microbiol.-SEOUL-45, 409.

Patel, J. G., Kumar, J. N., Kumar, R. N., Khan, S. R., 2016. Biodegradation capability and enzymatic variation of potentially hazardous polycyclic aromatic hydrocarbons-anthracene and pyrene by *Anabaena fertilissima*. Polycycl. Aromat. Compd. 36, 72-87.

Patel, S. K., Anwar, M. Z., Kumar, A., Otari, S. V., Pagolu, R. T., Kim, S.-Y., Kim, I.-W., Lee, J.-K., 2017a. *Fe 2O3 yolk-shell particle-based laccase biosensor for efficient detection of 2, 6-dimethoxyphenol*. Biochem. Eng. J.

Patel, S. K., Choi, S. H., Kang, Y. C., Lee, J.-K., 2017b. Eco-friendly composite of Fe3O4-reduced graphene oxide particles for efficient enzyme immobilization. ACS Appl. Mater. Interfaces 9, 2213-2222.

Patel, S. K., Choi, S. H., Kang, Y. C., Lee, J. K., 2016. Large-scale aerosol-assisted synthesis of biofriendly Fe 2O3 yolk-shell particles: a promising support for enzyme immobilization. Nanoscale 8, 6728-6738.

Patel, S. K., Kondaveeti, S., Otari, S. V., Pagolu, R. T., Jeong, S. H., Kim, S. C., Cho, B.-K., Kang, Y. C., Lee, J.-K., 2017c. *Repeated batch methanol production from a simulated biogas mixture using immobilized Methylocystis bryophila*. Energy.

Patel, S. K., Otari, S. V., Kang, Y. C., Lee, J.-K., 2017d. Protein-inorganic hybrid system for efficient his-tagged enzymes immobilization and its application in L-xylulose production. RSC Adv. 7, 3488-3494.

Patel, S. K., Otari, S. V., Li, J., Kim, D. R., Kim, S. C., Cho, B.-K., Kalia, V. C., Kang, Y. C., Lee, J.-K., 2018. Synthesis of cross-linked protein-metal hybrid nanoflowers and its application in repeated batch decolorization of synthetic dyes. J. Hazard. Mater.

Patel, S. K., Singh, R. K., Kumar, A., Jeong, J.-H., Jeong, S. H., Kalia, V. C., Kim, I.-W., Lee, J.-K., 2017e. *Biological methanol production by immobilized Methylocella tundrae using simulated biohythane as a feed*. Bioresour. Technol. 241, 922-927.

Peng, C., Lee, J.-W., Sichani, H. T., Ng, J. C., 2015. *Toxic effects of individual and combined effects of BTEX on Euglena gracilis*. J. Hazard. Mater. 284, 10-18.

Pitol, L. O., Biz, A., Mallmann, E., Krieger, N., Mitchell, D. A., 2016. *Production of pectinases by solid-state fermentation in a pilot-scale packed-bed bioreactor*. Chem. Eng. J. 283, 1009-1018.

Prim, N., Sánchez, M., Ruiz, C., Pastor, F. J., Diaz, P., 2003. *Use of methylumbeliferyl-derivative substrates for lipase activity characterization*. J. Mol. Catal. B Enzym. 22, 339-346.

Priya, A., Mandal, A. K., Ball, A. S., Manefield, M., Lal, B., Sarma, P. M., 2015. Mass culture strategy for bacterial yeast co-culture for degradation of petroleum hydrocarbons in marine environment. Mar. Pollut. Bull. 100, 191-199.

Pulicharla, R., Marques, C., Das, R. K., Rouissi, T., Brar, S. K., 2016. *Encapsulation and release studies of strawberry polyphenols in biodegradable chitosan nanoformulation*. Int. J. Biol. Macromol. 88, 171-178.

Qiao, N., Shao, Z., 2010. Isolation and characterization of a novel biosurfactant produced by hydrocarbon-degrading bacterium *Alcanivorax dieselolei* B-5. J. Appl. Microbiol. 108, 1207-1216.

Rampino, A., Borgogna, M., Blasi, P., Bellich, B., Cesaro, A., 2013. *Chitosan nanoparticles: preparation, size evolution and stability*. Int. J. Pharm. 455, 219-228.

Rojo, F., 2009. *Degradation of alkanes by bacteria*. Environ. Microbiol. 11, 2477-2490.

Ron, E. Z., Rosenberg, E., 2014. *Enhanced bioremediation of oil spills in the sea*. Curr. Opin. Biotechnol. 27, 191-194.

Rončević, S., Dalmacija, B., Ivančev-Tumbas, I., Tričković, J., Petrović, O., Klašnja, M., Agbaba, J., 2005. *Kinetics of degradation of hydrocarbons in the contaminated soil layer*. Arch. Environ. Contam. Toxicol. 49, 27-36.

Ryu, H.-W., Joo, Y.-H., An, Y.-J., Cho, K.-S., 2006. *Isolation and characterization of psychrotrophic and halotolerant Rhodococcus sp. YHLT*-2. J. Microbiol. Biotechnol. 16, 605-612.

Sabirova, J. S., Becker, A., Lunsdorf, H., Nicaud, J.-M., Timmis, K. N., Golyshin, P. N., 2011. *Transcriptional profiling of the marine oil-degrading bacterium Alcanivorax borkumensis during growth on n-alkanes*. FEMS Microbiol. Lett. 319, 160-168.

Sadighi, A., Faramarzi, M. A., 2013. Congo red decolorization by immobilized laccase through chitosan nanoparticles on the glass beads. J. Taiwan Inst. Chem. Eng. 44, 156-162.

Sajna, K. V., Sukumaran, R. K., Gottumukkala, L. D., Pandey, A., 2015. *Crude oil biodegradation aided by biosurfactants from Pseudozyma sp. NII 08165 or its culture broth*. Bioresource technology 191, 133-139.

Salvachúa, D., Prieto, A., Martinez, Á. T., Martínez, M. J., 2013. Characterization of a novel dye-decolorizing peroxidase (DyP)-type enzyme from *Irpex lacteus* and its application in enzymatic hydrolysis of wheat straw. Appl. Environ. Microbiol. 79, 4316-4324.

Schneiker, S., dos Santos, V. A. M., Bartels, D., Bekel, T., Brecht, M., Buhrmester, J., Chernikova, T. N., Denaro, R., Ferrer, M., Gertler, C., Goesmann, A., Golyshina, O. V., Kaminski, F., Khachane, A. N., Lang, S., Linke, B., McHardy, A. C., Meyer, F., Nechitaylo, T., Puhler, A., Regenhardt, D., Rupp, O., Sabirova, J. S., Selbitschka, W., Yakimov, M. M., Timmis, K. N., Vorholter, F.-J., Weidner, S., Kaiser, O., Golyshin, P. N., 2006. *Genome sequence of the ubiquitous hydrocarbon-degrading marine bacterium Alcanivorax borkumensis*. Nat. Biotechnol. 24, 997-1004.

Schoefs, O., Perrier, M., Samson, R., 2004. Estimation of contaminant depletion in unsaturated soils using a reduced-order biodegradation model and carbon dioxide measurement. Appl. Microbiol. Biotechnol. 64, 53-61.

Schultz, N., Hobley, T. J., Syldatk, C., 2007. Spectrophotometric assay for online measurement of the activity of lipase immobilised on micro-magnetic particles. Biotechnol. Lett. 29, 365-371.

Scoma, A., Barbato, M., Borin, S., Daffonchio, D., Boon, N., 2016a. An impaired metabolic response to hydrostatic pressure explains *Alcanivorax borkumensis* recorded distribution in the deep marine water column. Sci. Rep. 6.

Scoma, A., Barbato, M., Hernandez-Sanabria, E., Mapelli, F., Daffonchio, D., Borin, S., Boon, N., 2016b. Microbial oil-degradation under mild hydrostatic pressure (10 MPa): which pathways are impacted in piezosensitive hydrocarbonoclastic bacteria? Sci. Rep. 6.

Setti, L., Lanzarini, G., Pifferi, P. G., Spagna, G., 1993. Further research into the aerobic degradation of n-alkanes in a heavy oil by a pure culture of a *Pseudomonas* sp. Chemosphere 26, 1151-1157.

Sharma, A., Kumar, P., Rehman, M. B., 2014. Biodegradation of diesel hydrocarbon in soil by bioaugmentation of *Pseudomonas aeruginosa*: A laboratory scale study. Int. J. Environ. Bioremediation Biodegrad. 2, 202-212.

Sheldon, R. A., Rantwijk, F. van, 2004. *Biocatalysis for Sustainable Organic Synthesis*. Aust. J. Chem. 57, 281-289.

Shu, X. Z., Zhu, K. J., 2002. Controlled drug release properties of ionically cross-linked chitosan beads: the influence of anion structure. Int. J. Pharm. 233, 217-225.

Shu, X. Z., Zhu, K. J., 2000. A novel approach to prepare tripolyphosphate/chitosan complex beads for controlled release drug delivery. Int. J. Pharm. 201, 51-58.

Singh, R., Celin, S. M., 2010. Biodegradation of BTEX (benzene, toluene, ethyl benzene and xylene) compounds by bacterial strain under aerobic conditions. J. Ecobiotechnology 2.

Stanbury, P. F., Whitaker, A., Hall, S. J., 2013. *Principles of fermentation technology*. Elsevier.

Suja, F., Rahim, F., Taha, M. R., Hambali, N., Razali, M. R., Khalid, A., Hamzah, A., 2014. Effects of local microbial bioaugmentation and biostimulation on the bioremediation of total petroleum hydrocarbons (TPH) in crude oil contaminated soil based on laboratory and field observations. Int. Biodeterior. Biodegrad. 90, 115-122.

Taheran, M., Naghdi, M., Brar, S. K., Knystautas, E. J., Verma, M., Surampalli, R. Y., 2017. *Degradation of chlortetracycline using immobilized laccase on Polyacrylonitrile-biochar composite nanofibrous membrane*. Sci. Total Environ. 605, 315-321.

The Globe and Mail. *PQ picks old Conservative ally as its new envoy to Ottawa*, n.d. Available at http://www.theglobeandmail.com/news/politics/pq-picks-old-conservative-ally-as-its-new-envoy-to-ottawa/article14819514/ (accessed 7 Nov. 2016).

Thenmozhi, R., Nagasathya, A., Thajuddin, N., 2011. *Studies on biodegradation of used engine oil by consortium cultures*. Adv. Environ. Biol. 1051-1058.

Topakas, E., Vafiadi, C., Christakopoulos, P., 2007. *Microbial production, characterization and applications of feruloyl esterases*. Process Biochem. 42, 497-509.

Ueda, S., Fujio, Y., Lim, J. Y., 1982. Production and some properties of pectic enzymes from *Aspergillus oryzae* A-3. J. Appl. Biochem. 4, 524-532.

Ueno, A., Hasanuzzaman, M., Yumoto, I., Okuyama, H., 2006. Verification of degradation of n-alkanes in diesel oil by *Pseudomonas aeruginosa* strain WatG in soil microcosms. Curr. Microbiol. 52, 182-185.

Van Beilen, J. B., Funhoff, E. G., 2007. Alkane hydroxylases involved in microbial alkane degradation. Appl. Microbiol. Biotechnol. 74, 13-21.

Van Beilen, J. B., Marin, M. M., Smits, T. H. M., Röthlisberger, M., Franchini, A. G., Witholt, B., Rojo, F., 2004. *Characterization of two alkane hydroxylase genes from the marine hydrocarbonoclastic bacterium Alcanivorax borkumensis*. Environ. Microbiol. 6, 264-273.

Vasco-Correa, J., Zapata, A. D. Z., 2017. Enzymatic extraction of pectin from passion fruit peel (*Passiflora edulis* f. *flavicarpa*) at laboratory and bench scale. LWT-Food Sci. Technol. 80, 280-285.

Van Beilen, J. B., Funhoff, E. G., 2007. *Alkane hydroxylases involved in microbial alkane degradation*. Appl. Microbiol. Biotechnol. 74, 13-21.

Van Gestel, K., Mergaert, J., Swings, J., Coosemans, J., Ryckeboer, J., 2003. *Bioremediation of diesel oil-contaminated soil by composting with biowaste*. Environ. Pollut. 125, 361-368.

Volke-Sepulveda, T. L., Gutierrez-Rojas, M., Favela-Torres, E., 2003. *Biodegradation of hexadecane in liquid and solid-state fermentations by Aspergillus niger*. Bioresour. Technol. 87, 81-86.

Wang, L., Wang, W., Lai, Q., Shao, Z., 2010. Gene diversity of CYP153A and AlkB alkane hydroxylases in oil-degrading bacteria isolated from the Atlantic Ocean. Environ. Microbiol. 12, 1230-1242.

Wang, W., Shao, Z., 2014. The long-chain alkane metabolism network of *Alcanivorax dieselolei*. Nat. Commun. 5.

Wang, W., Shao, Z., 2012. Diversity of flavin-binding monooxygenase genes (almA) in marine bacteria capable of degradation long-chain alkanes. FEMS Microbiol. Ecol. 80, 523-533.

Wang, W., Wang, L., Shao, Z., 2010. Diversity and abundance of oil-degrading bacteria and alkane hydroxylase (alkB) genes in the subtropical seawater of Xiamen Island. Microb. Ecol. 60, 429-439.

Wu, Y., Teng, Y., Li, Z., Liao, X., Luo, Y., 2008. Potential role of polycyclic aromatic hydrocarbons (PAHs) oxidation by fungal laccase in the remediation of an aged contaminated soil. Soil Biol. Biochem. 40, 789-796.

Wu, Y., Yang, W., Wang, C., Hu, J., Fu, S., 2005. *Chitosan nanoparticles as a novel delivery system for ammonium glycyrrhizinate*. Int. J. Pharm. 295, 235-245.

Xu, R., Zhou, Q., Li, F., Zhang, B., 2013. Laccase immobilization on chitosan/poly (vinyl alcohol) composite nanofibrous membranes for 2, 4-dichlorophenol removal. Chem. Eng. J. 222, 321-329.

Xu, Y., Du, Y., 2003. Effect of molecular structure of chitosan on protein delivery properties of chitosan nanoparticles. Int. J. Pharm. 250, 215-226.

Yakimov, M. M., Golyshin, P. N., Lang, S., Moore, E. R., Abraham, W.-R., Lunsdorf, H., Timmis, K. N., 1998. *Alcanivorax borkumensis gen. nov., sp. nov., a new, hydrocarbon-degrading and surfactant-producing marine bacterium*. Int. J. Syst. Evol. Microbiol. 48, 339-348.

Yakimov, M. M., Timmis, K. N., Golyshin, P. N., 2007. *Obligate oil-degrading marine bacteria*. Curr. Opin. Biotechnol. 18, 257-266.

Zaak, H., Siar, E.-H., Kornecki, J. F., Fernandez-Lopez, L., Pedrero, S. G., Virgen-Ortíz, J. J., Fernandez-Lafuente, R., 2017. Effect of immobilization rate and enzyme crowding on enzyme stability under different conditions. The case of lipase from *Thermomyces lanuginosus* immobilized on octyl agarose beads. Process Biochem. 56, 117-123.

Zeynalov, E., Nagiev, T., 2015. Enzymatic catalysis of hydrocarbons oxidation "in vitro" (review).

Zhang, H., Oh, M., Allen, C., Kumacheva, E., 2004. *Monodisperse chitosan nanoparticles for mucosal drug delivery*. Biomacromolecules 5, 2461-2468.

Zhang, S., Wu, G., Liu, Zhixiang, Shao, Z., Liu, Ziduo, 2014. Characterization of EstB, a novel cold-active and organic solvent-tolerant esterase from marine microorganism *Alcanivorax dieselolei* B-5 (T). Extremophiles 18, 251-259.

The invention claimed is:

1. A composition comprising at least one selected from the group consisting of:
   i) a cell free supernatant of *Alkanivorax borkumensis* (*A. borkumensis*) comprising an extracellular enzyme extract;
   ii) a supernatant of sonicated cells of *A. borkumensis* comprising an intracellular enzyme extract and an extracellular enzyme extract; and
   iii) combinations thereof; and
   between about 0.5% (v/v) and about 12% (v/v) of petroleum-derived hydrocarbons;
   wherein the composition comprises a plurality of polypeptides that exhibit at least two enzymatic activities selected from the group consisting of lipase activity, esterase activity, and alkane hydroxylase activity.

2. The composition of claim 1, wherein the plurality of polypeptides comprises one or more polypeptides that exhibit lipase activity.

3. The composition of claim 1, wherein the plurality of polypeptides comprises at least one polypeptide that exhibits alkane hydroxylase activity.

4. The composition of claim 1, wherein the *A. borkumensis* comprises *Alakanivorax borkumensis* strain SK2 (DSM 11573).

5. The composition of claim 1, wherein the *A. borkumensis* is grown in a culture medium comprising the petroleum-derived hydrocarbons.

6. The composition of claim 1, wherein the plurality of polypeptides exhibit lipase activity, esterase activity, and alkane hydroxylase activity.

7. The composition of claim 6, wherein the composition retains more than 70% of its original activity after one month when stored at low temperature between −20±1° C. and 4±1° C.

8. The composition of claim 1, wherein the plurality of polypeptides comprises at least one of a concentration of polypeptides exhibiting esterase activity from about 10 U/mL to about 500 U/mL, a concentration of lipase from about 10 to about 250 U/mL, and a concentration of alkane hydroxylase from about 1 U/mL to about 1000 U/mL.

9. The composition of claim 1, wherein the composition further comprises a biosurfactant produced from *A. borkumensis* and obtained from a culture supernatant thereof.

10. A method for treating a petroleum-hydrocarbon polluted-system, comprising the steps of:
   contacting the composition as defined in claim 1, with the petroleum-hydrocarbon polluted-system to form an inoculated medium; and
   incubating the inoculated medium for at least about 24 hours at a temperature of at least about 8° C. to achieve biodegradation of at least a portion of the petroleum-hydrocarbon.

11. The method of claim 10, wherein the petroleum-hydrocarbon comprises $C_{10}$-$C_{50}$ hydrocarbons, BTX, PAH, polychlorinated organic compounds, or mixtures thereof.

12. The method of claim 10, wherein the treating of the petroleum-hydrocarbon polluted-system comprises removing between about 30% and about 80% of total petroleum hydrocarbons (TPH).

13. A method for producing a composition as defined in claim 1, comprising the steps of:
   obtaining a crude culture medium comprising *A. borkumensis* cells grown on a medium comprising the about 0.5% (v/v) to about 12% (v/v) of petroleum-derived hydrocarbons;
   sonicating the crude culture medium to obtain a sonicated crude culture medium; and
   centrifuging the sonicated crude culture medium to recover the supernatant of sonicated cells.

14. The method of claim 13, further comprising incubating the cells under conditions comprising about 2% to about 10% of salt to achieve production of a biosurfactant.

15. The method of claim 14, wherein the medium comprises petroleum-derived hydrocarbons at a concentration of 3% (v/v), the petroleum-derived hydrocarbon being selected from the group consisting of hexane, hexadecane, motor oil, and mixtures thereof.

16. The composition of claim 1, wherein at least a portion of the polypeptides of the plurality of polypeptides is provided in admixture with chitosan.

17. The composition of claim 16, further comprising a polyanion to form nanoparticles with the chitosan.

18. The composition of claim 17, wherein the polyanion is tripolyphosphate (TPP) to form chitosan-TPP nanoparticles (CSNP).

19. The composition of claim 18, wherein the at least a portion of the polypeptides of the plurality of polypeptides exhibiting enzymatic activity is entrapped into the CSNP.

20. The composition of claim 18, comprising a polypeptide-to-CSNP ratio of between 1:1 to 7:1.

21. The composition of claim 18, wherein the at least a portion of polypeptides of the plurality of polypeptides exhibiting enzymatic activity comprises a polypeptide that exhibits alkane hydroxylase activity and a polypeptide that exhibits lipase activity, and wherein the polypeptide that exhibits alkane hydroxylase activity and the polypeptide that exhibits lipase activity are immobilized on the CSNP and exhibit more than a two-fold increase in in vitro half-life in comparison with free polypeptide.

22. The composition of claim 1, wherein the petroleum-derived hydrocarbons are selected from the group comprising hexane, hexadecane, motor oil, and mixtures thereof.

23. The composition of claim 1, further comprising a carrier, wherein the carrier comprises at least one selected from the group consisting of: sodium phosphate buffer and dimethyl sulfoxide.

* * * * *